US009873690B2

(12) United States Patent
Ninkovic et al.

(10) Patent No.: US 9,873,690 B2
(45) Date of Patent: Jan. 23, 2018

(54) 3-INDOL SUBSTITUTED DERIVATIVES, PHARMACEUTICAL COMPOSITIONS AND METHODS FOR USE

(71) Applicants: Pfizer Inc., New York, NY (US); iTeos Therapeutics, Charleroi (BE)

(72) Inventors: Sacha Ninkovic, La Jolla, CA (US); Stefano Crosignani, Nivelles (BE); Indrawan James McAlpine, San Diego, CA (US); Michael Raymond Collins, San Diego, CA (US); Stephanie Anne Scales, San Diego, CA (US); Andreas Maderna, Stony Point, NY (US); Martin Wythes, Solana Beach, CA (US)

(73) Assignees: Pfizer Inc, New York, NY (US); iTeos Therapeutics, Charleroi (BE)

( * ) Notice: Subject to any disclaimer, the term of this patent is extended or adjusted under 35 U.S.C. 154(b) by 0 days.

(21) Appl. No.: 15/072,534

(22) Filed: Mar. 17, 2016

(65) Prior Publication Data
US 2016/0272628 A1 Sep. 22, 2016

Related U.S. Application Data

(63) Continuation-in-part of application No. PCT/IB2015/051957, filed on Mar. 17, 2015.

(60) Provisional application No. 62/203,032, filed on Aug. 10, 2015.

(51) Int. Cl.
C07D 417/04 (2006.01)
C07D 417/14 (2006.01)
A61K 31/404 (2006.01)
C07D 417/12 (2006.01)

(52) U.S. Cl.
CPC ......... C07D 417/04 (2013.01); A61K 31/404 (2013.01); C07D 417/12 (2013.01); C07D 417/14 (2013.01)

(58) Field of Classification Search
None
See application file for complete search history.

(56) References Cited

U.S. PATENT DOCUMENTS

| 7,151,108 | B2 | 12/2006 | Prudhomme et al. |
| 8,008,481 | B2 | 8/2011 | Ericsson et al. |
| 9,126,984 | B2 | 9/2015 | Crosignani et al. |
| 2003/0109550 | A1 | 6/2003 | Clare et al. |
| 2005/0165005 | A1 | 7/2005 | Genevois et al. |
| 2009/0118292 | A1 | 5/2009 | Deng et al. |
| 2010/0160303 | A1 | 6/2010 | Liu et al. |
| 2010/0305133 | A1 | 12/2010 | Colon et al. |
| 2010/0317863 | A1 | 12/2010 | Kuzmich et al. |
| 2011/0046370 | A1 | 2/2011 | Sim et al. |
| 2011/0166143 | A1 | 7/2011 | Bretschneider et al. |
| 2012/0053345 | A1 | 3/2012 | Ericson et al. |
| 2015/0225367 | A1 | 8/2015 | Crosignani et al. |
| 2015/0266857 | A1* | 9/2015 | Crosignani .......... C07D 405/04 514/234.5 |
| 2015/0328228 | A1 | 11/2015 | Crosignani et al. |
| 2015/0329525 | A1 | 11/2015 | Crosignani et al. |
| 2016/0263087 | A1 | 9/2016 | Crosignani et al. |

FOREIGN PATENT DOCUMENTS

| CN | 101265259 A | 9/2008 |
| EP | 1411057 A1 | 4/2004 |
| JP | 2000-095759 A | 4/2000 |
| WO | WO-1997/043230 A1 | 11/1997 |
| WO | WO-2000/043393 A1 | 7/2000 |

(Continued)

OTHER PUBLICATIONS

Beevers, Low molecular weight indole fragments as IMPDH inhibitors, Bioorganic & Medicinal Chemistry Letters, vol. 16(9):2535-2538, May 2006.
Bennett & Plum (EDS), Cecil Textbook of Medicine (20th Ed., vol. 2), W.B. Saunders Company, Philadelphia, pp. 1992-1996 and 2050-2057, Jan. 1996.
Cavallo et al., "The Immune Hallmarks of Cancer", Cancer Immunology Immunotherapy, vol. 60(3):319-326, Nov. 26, 2011.
Chemical Abstract Service, Database Registry Accession No. 1309341-94-3 RN, Jun. 14, 2011.
Chemical Abstracts Service, Database Registry Accession No. 1125444-69-0, Mar. 23, 2009.
Chemical Abstracts Service, Database Registry Accession No. 859666-30-1, Aug. 11, 2005.

(Continued)

Primary Examiner — Dennis Heyer
(74) Attorney, Agent, or Firm — Howson & Howson LLP; Cathy Kodroff; David Rubin

(57) ABSTRACT

A compound of Formula I is provided:

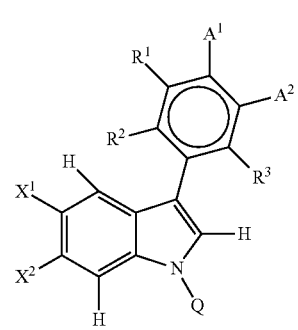

or pharmaceutically acceptable enantiomers, salts or solvates thereof. The invention further relates to the use of the compounds of Formula I as TDO2 inhibitors. The invention also relates to the use of the compounds of Formula I for the treatment and/or prevention of cancer, neurodegenerative disorders such as Parkinson's disease, Alzheimer's disease and Huntington's disease, chronic viral infections such as HCV and HIV, depression, and obesity. The invention also relates to a process for manufacturing compounds of Formula I.

9 Claims, No Drawings

(56) References Cited

FOREIGN PATENT DOCUMENTS

| WO | WO-2003/082869 | | 10/2003 |
|---|---|---|---|
| WO | WO-2003/101981 | A1 | 12/2003 |
| WO | WO-2005/058035 | A1 | 6/2005 |
| WO | WO-2006/005608 | A1 | 1/2006 |
| WO | WO-2006/086484 | A1 | 8/2006 |
| WO | WO2007/039580 | A1 | 4/2007 |
| WO | WO2007/045622 | A1 | 4/2007 |
| WO | WO-2007/050963 | A1 | 5/2007 |
| WO | WO-2007/087488 | A2 | 8/2007 |
| WO | WO-2007/117465 | A2 | 10/2007 |
| WO | WO-2007/124252 | | 11/2007 |
| WO | WO-2008/068621 | | 6/2008 |
| WO | WO-2008/073306 | A1 | 6/2008 |
| WO | WO-2008/094992 | A2 | 8/2008 |
| WO | WO-2008/115804 | A1 | 9/2008 |
| WO | WO-2009/015067 | A2 | 1/2009 |
| WO | WO-2009/073497 | A2 | 6/2009 |
| WO | WO-2009/118292 | A1 | 10/2009 |
| WO | WO-2010/008427 | A1 | 1/2010 |
| WO | WO-2010/046013 | A1 | 4/2010 |
| WO | WO2010/096389 | A1 | 8/2010 |
| WO | WO-2010/136491 | A1 | 12/2010 |
| WO | WO-2011/038163 | A1 | 3/2011 |
| WO | WO-2011/046954 | A1 | 4/2011 |
| WO | WO-2012/068406 | A2 | 5/2012 |
| WO | WO-2012/129338 | A1 | 9/2012 |
| WO | WO-2012/161877 | A1 | 11/2012 |
| WO | WO-2013/025883 | A1 | 2/2013 |
| WO | WO-2015/140717 | A1 | 9/2015 |
| WO | WO-2015/173764 | | 11/2015 |

OTHER PUBLICATIONS

Chen et al. Synthesis and antiproliferative activity of novel 2-aryl-4-benzoyl-imidazole derivatives targeting tubulin polymerization. Bioorganic & Medicinal Chemistry. vol. 19(16):4782-4795. Aug. 2011.
FDA mulls drug to slow late-stage Alzheimer's [online], [retrieved on Sep. 23, 2003]. Retrieved form the Internet, URL: http://www.cnn.com/2003/HEALTH/conditions/09/24/alzheimers.drug.ap/index.html.
Galon et al. Cancer classification using the immunoscore: a worldwide task force, J Transl Med, vol. 10(205):1-9, Oct. 2012.
Godin-Ethier et al., Indoleamine 2, 3-dioxygenase expression in human cancers: clinical and immunologic perspectives, Clin Cancer Res, vol. 17:6985-6991, Nov. 2011.
Guo et al. Solubility-Driven Optimization of (Pyridin-3-yl) Benzoxazinyl-oxazolidinones Leading to a Promising Antibacterial Agent. Journal of Medicinal Chemistry. vol. 56(6):2642-2650. Feb. 2013.
Gupton et al., "Preparation of indole containing building blocks for the regiospecific construction of indole appended pyrazoles and pyrroles", Tetrahedron, vol. 69(69):5829-5840, May 2013.
Hanahan et al., "The hallmarks of cancer", Cell, vol. 100(1):57-70, Jan. 2000.
Hanahan, et al., "Hallmarks of Cancer: The Next Generation", Cell, vol. 144:646-674, Mar. 4, 2011.
Henon, Expedited Synthesis of Substituted Dipyrrolo [3,4-a:3,4-c] carbazole-1,3,4,6-tetraones Structrually Related to Granulatimide, Synthesis, vol. 2006(4):711-715, Jan. 1, 2006.
Henon, Synthesis and biological evaluation of new dipyrrolo [3,4-a:3,4-c] carbazole-1,3,4,6-tetraones, substituted with various saturated and unsaturated side chains via palladium catalyzed cross-coupling reactions, Bioorganic & Medicinal Chemistry, vol. 14(11):3825-3834, Jun. 1, 2006.
Jakse et al., "Application of alkyl 3-dimethylamino-2-(1H-indol-3-yl)propenoates in the synthesis of 3-heteroarylindoles", Tetrahedron, Vol, 60:4601-4608, Mar. 2004.
Jimenez et al., "4-(1-Phenyl-1H-pyrazol-4-yl)quinolones as novel, selective and brain penetrant metabotropic glutamate receptor 4 positive allosteric modulators", Bioorg. Med. Chem. Let., vol. 22(9):3235-3239, Mar. 7, 2012.

Kyrgidia et al., "Melanoma: Stem cells, sun exposure and hallmarks for carcinogenesis, molecular concepts and future clinical implications", Journal of Carcinogenesis, vol. 9(1):1-16, Feb. 16, 2010.
Macor, A Direct Synthesis of 3-(Pyrrolidin-3-yl) Indoles for Use as Conformationally Restricted Analogs of Tryptamines, Synthesis, 1997(4):443-449, Apr. 4, 1007.
Mahboobi, 3-Bromo-4-(1H-3-indolyl)-2, 5-dihydro-1H-2, 5-pyrroledione derivatives as new lead compounds for antibacterially active substances, European Journal of Medicinal Chemistry, vol. 41(2):176-191, Feb. 1, 2006.
Martin et al. Synthesis of Novel Analogs of Acetyl Coenzyme A: Mimics of Enzyme Reaction Intermediates. Journal of the American Chemical Society. vol. 116(11):4660-4668. Jun. 1994.
Motz et al., Deciphering and Reversing Tumor Immune Suppression, Immunity, vol. 39(1):61-73. Jul. 25, 2013.
Muller et al., "Chronic inflammation that facilitates tumor progression creates local immune suppression by inducing indoleamine 2,3-dioxygenase", PNAS, vol. 105(44):17073-17078, Nov. 2008.
Munn et al., Indoleamine 2, 3-dioxygenase and metabolic control of immune responses, Trends Immunol, vol. 34(3):137-143, Mar. 2013.
Munn, Blocking IDO activity to enhance anti-tumor immunity, Front Biosci Elite, vol. 4:734-745, Jan. 2012.
Shigemitsu, Synthesis of 3-Methylthio-4-aryl-3-pyrroline-2, 5-diones and 3-Arylpyrrolidine-2, 5-diones by Reaction of Nitroketene Dithioacetal with Arylacetonitriles, Heterocycles, vol. 55(12):2257-2260, Jan. 1, 2001.
Tominaga et al., Synthesis of Methylthiomaleimides for the Preparation of Pyridazines and Related Compounds, J Heterocyclic Chem, vol. 39(3):571-591, May 2002.
Turiso et al. Discovery and in Vivo Evaluation of Dual PI3Kβ/δ Inhibitors. Journal of Medicinal Chemistry. vol. 55(17):7667-7685. Aug. 2012.
Lala, et al. "Role of nitric oxide in tumor progression: lessons from experimental tumors." Cancer and Metastasis Reviews 17.1 (1998): 91-106.
Vippagunta, et al. "Crystalline solids." Advanced drug delivery reviews 48.1 (2001): 3-26.
Golub et al., "Molecular classification of cancer: class discovery and class prediction by gene expression monitoring." science 286. 5439 (1999): 531-537.
Cancer [Online], [Retrieved on Jul. 6, 2007], Retrieved from the internet, URL http://www.nlm.nih.gov/medlineplus/cancer.html.
Cancer [Online], [Retrieved on Jul. 6, 2007], Retrieved from the internet, URL http://en.wikipedia.org/wiki/Cancer.
U.S. Appl. No. 15/331,446, filed Oct. 21, 2016.
Office Action dated Oct. 14, 2016 issued in U.S. Appl. No. 14/660,082, filed Mar. 17, 2015.
Baroni et al., Synthesis of 3-Heteroaryloxindoles through t-BuOCl-Mediated Oxidation of 3-Heteroarylindoles, Synthesis, vol. 2010(23):4075-4081, Oct. 2010.
Comings et al., Exon and intron variants in the human tryptophan 2,3-dioxygenase gene: potential association with Tourette syndrome, substance abuse and other disorders, Pharmacogenetics, vol. 6(4):307-318, Aug. 1996.
Davies et al., Tryptophan, Neurodegeneration and HIV-Associated Neurocognitive Disorder, Int J Tryptophan Res, vol. 3: 121-140, Jun. 2010.
Dolusic et al., Indoleamine 2,3-dioxygenase inhibitors: a patent review (2008-2012), Expert Opin Ter Pat., vol. 23(10):1367-1381, Oct. 2013 (ePub Aug. 2013).
Dolusic et al., Tryptophan 2,3-dioxygenase (TDO) inhibitors. 3-(2-(pyridyl)ethenyl)indoles as potential anticancer immunomodulators, J Med Chem., vol. 54(15):5320-5334, Aug. 2011 (ePub Jul. 2011).
Fallarino et al., T cell apoptosis by tryptophan catabolism, Cell Death Differ, vol. 9 (10):1069-1077, Oct. 2002.
Forrest et al., Blood levels of kynurenines, interleukin-23 and soluble human leucocyte antigen-G at different stages of Hunting-ton's disease, J Neurochem, vol. 112(1):112-122, Jan. 2010.

(56) References Cited

OTHER PUBLICATIONS

Fuvesi et al., The role of kynurenines in the pathomechanism of amyotrophic lateral sclerosis and multiple sclerosis: therapeutic implications, J Neural Transm (Vienna), vol. 119(2):225-234, Feb. 2012 (ePub Jan. 2012).

Holmgaard et al., Indoleamine 2,3-dioxygenase is a critical resistance mechanism in antitumor T cell immunotherapy targeting CTLA-4, J Exp Med., vol. 210(7):1389-1402, Jul. 2013 (ePub Jun. 2013).

Lahdou et al., Increased serum levels of quinolinic acid indicate enhanced severity of hepatic dysfunction in patients with liver cirrhosis, Hum Immunol, vol. 74(1):60-66, Jan. 2013.

Manna et al., UPLC-MS-based urine metabolomics reveals indole-3-lactic acid and phenyllactic acid as conserved biomarkers for alcohol-induced liver disease in the Ppara-null mouse model, J Proteome Res, vol. 10(9):4120-4133, Sep. 2011.

Mellor et al., Creating immune privilege: active local suppression that benefits friends, but protects foes, Nat Rev Immunol, vol. 8(1):74-80, Jan. 2008.

Miller et al., Expression of the kynurenine pathway enzyme tryptophan 2,3-dioxygenase is increased in the frontal cortex of individuals with schizophrenia, Neurobiol Dis., vol. 15(3):618-629, Apr. 2004.

Munn et al., Inhibition of T cell proliferation by macrophage tryptophan catabolism, J Exp Med, vol. 189(9):1363-1372, May 1999.

Munn et al., Prevention of allogeneic fetal rejection by tryptophan catabolism, Science, vol. 281(5380):1191-1193, Aug. 1998.

Ohta et al., Relationship between the level of serum L-tryptophan and its hepatic uptake and metabolism in rats with carbon tetrachloride-induced liver cirrhosis, Amino Acids, vol. 10(4):369-378, Dec. 1996.

Opitz et al., An endogenous tumour-promoting ligand of the human aryl hydrocarbon receptor, Nature, vol. 478(7368):197-203, Oct. 2011.

Pilotte et al., Reversal of tumoral immune resistance by inhibition of tryptophan 2,3-dioxygenase, PNAS, vol. 109(7):2497-2502, Feb. 2012.

Sahm et al., The endogenous tryptophan metabolite and NAD+ precursor quinolinic acid confers resistance of gliomas to oxidative stress, Cancer Res, vol. 73(11):3225-3234, Jun. 2013 (ePub Apr. 2013).

Sperner-Unterweger et al., Enhanced tryptophan degradation in patients with ovarian carcinoma correlates with several serum soluble immune activation markers, Immunobiology, vol. 216(3):296-301, Mar. 2011.

Stone et al., The kynurenine pathway as a therapeutic target in cognitive and neurodegenerative disorders, Br J Pharmacol, vol. 169(6):1211-1227, Jul. 2013.

Tilman et al., Human periostin gene expression in normal tissues, tumors and melanoma: evidences for periostin production by both stromal and melanoma cells, Mol Cancer, vol. 6:80, pp. 1-13, Dec. 2007.

Uyttenhove et al., Evidence for a tumoral immune resistance mechanism based on tryptophan degradation by indoleamine 2,3-dioxygenase, Nat Med., vol. 9(10):1269-1274, Oct. 2003 (ePub Sep. 2003).

Widner et al., Increased neopterin production and tryptophan degradation in advanced Parkinson's disease, J Neural Transm (Vienna), vol. 109(2):191-189, Feb. 2002.

Wu et al., Expression of Tryptophan 2,3-Dioxygenase and Production of Kynurenine Pathway Metabolites in Triple Transgenic Mice and Human Alzheimer's Disease Brain, PLOS One, vol. 8(4):e59749, Apr. 2013.

International Search Report and Written Opinion issued on priority International Patent Application No. PCT/IB2016/051509, dated Apr. 21, 2016.

U.S. Appl. No. 15/034,380, filed May 4, 2016.

Communication dated Jul. 21, 2016 issued on related European Patent Application No. 14796082.7 with corresponding response dated Jan. 16, 2017.

Communication dated Sep. 22, 2016 issued on related European Patent Application No. 15706941.0 with corresponding response dated Feb. 17, 2017.

Communication dated Dec. 7, 2016 issued on related European Patent Application No. 15714653.1.

Response to Office Action dated Oct. 14, 2016 issued in U.S. Appl. No. 14/660,082, filed Jan. 17, 2017.

\* cited by examiner

– INDOL SUBSTITUTED DERIVATIVES, PHARMACEUTICAL COMPOSITIONS AND METHODS FOR USE

CROSS-REFERENCE TO RELATED APPLICATIONS

This application claims the benefit of the priority of U.S. Provisional Application No. 62/203,032, filed Aug. 10, 2015 and International Patent Application No. PCT/IB2015/051957, filed Mar. 17, 2015, both of which are incorporated herein by reference.

FIELD OF INVENTION

The present invention relates to novel 3-(indol-3-yl)-pyridine derivatives, including pharmaceutically acceptable enantiomers, salts and solvates thereof. Compounds of the invention are inhibitors of TDO2 (tryptophan 2,3-dioxygenase) and are useful as therapeutic compounds, particularly in the treatment and/or prevention of cancers.

BACKGROUND OF INVENTION

Two decades after the importance of tryptophan catabolism for maintaining the immune privilege of the placenta was discovered (Munn, D. H. et al., Science, 1998, 281, 1191-1193), increasing evidence is extending its biological relevance beyond immune tolerance to non-self. According to the generally accepted concept, tryptophan, an essential amino acid, is catabolized in the local microenvironment of tumors, immune-privileged sites, or sites of inflammation (Mellor A L and Munn D H., Nat Rev Immunol, 2008, 8, 74-80). In these tissues, cancer cells, immune cells, or specialized epithelial cells (e.g., syncytiotrophoblasts in the placenta) create an immunosuppressive environment in tumors that shuts down antitumor immune responses in tumors and in tumor-draining lymph nodes by inducing T-cell anergy and apoptosis through depletion of tryptophan and accumulation of immunosuppressive tryptophan catabolites (Munn D H et al., J Exp Med., 1999, 189, 1363-1372; Fallarino F et al., Cell Death Differ., 2002, 9, 1069-1077).

It has recently been discovered that a key enzyme in tryptophan catabolism, tryptophan 2,3-dioxygenase (TDO2), which is considered responsible for regulating systemic tryptophan levels in the liver, is constitutively expressed in a wide variety of cancers, such as for example in bladder carcinoma, hepatocarcinoma, melanoma, mesothelioma, neuroblastoma, sarcoma, breast carcinoma, leukemia, renal cell carcinoma, colorectal carcinoma, head and neck carcinoma, lung carcinoma, brain tumor, glioblastoma, astrocytoma, myeloma, and pancreatic carcinoma (Pilotte L et al., Proc Natl Acad Sci USA, 2012, 109(7), 2497-502). TDO2 expression in tumor cells prevents tumor surveillance by the immune system and thus prevents tumor rejection by locally degrading tryptophan (Opitz C A et al., Nature, 2011, 478(7368), 197-203). The first evidence for this was provided through inhibition of TDO2 by a small molecule which inhibited tumor growth in a P815 mastocytoma tumor model with a prophylactic vaccination approach (Pilotte L et al., Proc Natl Acad Sci USA, 2012, 109(7), 2497-502). P815mTDO2 expressing tumors were rejected less in comparison to P815 tumors transfected with an empty vector, clearly demonstrating a growth benefit for TDO2 expressing tumors. Inhibition with a TDO2 inhibitor strongly decreased tumor growth in P815mTDO2 implanted tumors. Antitumor activity with the TDO2 inhibitor was equally observed in the P815 control implanted tumors negative for TDO2, thus providing evidence for an effect of TDO2 expressed in the immune system of the animal. These experiments for the first time provided clear evidence for a role of TDO2 in regulating tumor growth through expression in the cancer cell as well as immune compartment.

In line with its expression profile in liver, TDO2 was found predominantly in hepatocellular carcinoma (HCC) (Pilotte L et al., Proc Natl Acad Sci USA, 2012, 109(7), 2497-502). Inhibition of tryptophan catabolism and thus restoration of tryptophan concentration and decreased production of downstream metabolites could prove beneficial in the context of liver disease progressing to the stage of liver carcinoma. More particularly: (i) several reports have shown evidence that increased availability of tryptophan through supplementation is beneficial for example, cirrhotic livers, allowing the direct use of tryptophan for protein synthesis (Ohta et al., Amino Acids, 1996, 10(4), 369-78); (ii) there is a correlation between increased downstream serum tryptophan metabolites, such as quinolinic acid, and hepatic dysfunction in patients with liver cirrhosis (Landou et al., Hum Immunol, 2013, 74(1), 60-6) and (iii) increased secretion of another tryptophan metabolite, indole-3-lactic acid, has been associated with alcohol-induced liver disease in mice (Manna et al., J Proteome Res, 2011, 10(9), 4120-33). In the context of liver carcinoma itself, very high RNA expression is a good indication for therapeutic evaluation of TDO2 inhibitors (Pilotte L et al., Proc Natl Acad Sci USA, 2012, 109(7), 2497-502). The above thus provides a clear rationale for TDO2 activity modulation in the control of liver tumor development.

In addition to expression in liver, TDO2 is expressed in neurons, microglia and astrocytes and the potential benefit of TDO2 inhibition in the context of glioma was shown in another animal model. Platten and collaborators demonstrated that the tryptophan catabolite kynurenine produced by TDO expressed in the tumor cells suppresses antitumour immune responses and promotes tumor-cell survival and motility through the AHR in an autocrine/paracrine fashion (Opitz C A et al., Nature, 2011, 478(7368), 197-203).

The TDO-AHR pathway is active in human brain tumors and is associated with malignant progression and poor survival. Further evidence came from the accumulation of a downstream metabolite, quinolinic acid which accumulates in human gliomas and was associated with a malignant phenotype (Sahm et al., Cancer Res, 2013, 73(11), 3225-34). Here tryptophan catabolism was shown to occur in microglia cells as well. The above data thus provides evidence for TDO2 targeting in glioma with brain-penetrant small molecules.

Other tumor types in which TDO2 mRNA was found are breast carcinoma, bladder, renal cell, pancreatic, colorectal, head & neck carcinoma and lung carcinoma as well as melanoma thus broadening the scope of TDO2 targeting beyond HCC and glioma (Pilotte L et al., Proc Natl Acad Sci USA, 2012, 109(7), 2497-502).

The enhanced Tryptophan degradation observed in patients with gynecological cancers (ovarian carcinoma, cervical cancer, endometrial cancer) provides additional rationale for TDO2 targeting in those cancers (Sperner-Unterweger B et al, Immunology, 2011, 216 (3); 296-301).

The tryptophan catabolism in some cancers might be also increased by the expression of indoleamine 2,3-dioxygenase (IDO1) by tumor cells (Uyttenhove, C. et al., Nat. Med., 2003, 9, 1269-1274).

Because tryptophan catabolism is induced by inflammatory mediators, notably IFN-gamma, it is thought to represent an endogenous mechanism that restricts excessive immune responses, thereby preventing immunopathology. However in the context of cancer, there is strong evidence that suppression of antitumor immune responses in precancerous lesions and established cancers by tryptophan catabolism promotes tumor growth, which would make such catabolism an attractive target for therapeutic intervention (Dolušić E and Frederick R., Expert Opin Ther Pat., 2013, 23(10), 1367-81). Hence, a considerable effort is being made to identify selective and efficient inhibitors of tryptophan catabolism to enhance the efficacy of conventional chemotherapy, immune checkpoints (Holmgaard R B et al., J Exp Med., 2013, 210(7), 1389-402) or therapeutic vaccines.

In the context of neurological brain disorders, TDO2 expression has been demonstrated in neurons, brain vasculature and additionally in the case of schizophrenia in astroglial cells (Miller C et al., 2004, Neurobiology Dis, 15(3):618-29). The kynurenine pathway is now considered as a therapeutic target in cognitive diseases like bipolar disorder or Tourette syndrome and neurodegenerative disorders like Alzheimer, motor neuron disease like Amyotrophic lateral sclerosis, Multiple sclerosis, Huntington or Parkinson's disease (Stone T W, 2013, Br J of Pharmacol, 169(6): 1211-27; Wu et al, 2013, Plos One, 8(4):e59749; Fuvesi et al, 2012, J Neural Transm, 119(2):225-34, Widner et al, 2002, J Neural Transm, 109(2):181-9; Comings et al, 1996, Pharmacogenetics, 6(4):307-18, Forrest 2010, J Neurochem, 112(1):112-22).

Cognitive changes related to Tryptophan catabolism have also been shown in patients infected with human immunodeficiency virus type-1 (HIV), called HIV-associated neurocognitive disorder (HAND) (Davies et al, 2010, Int J of Tryptophan Res, 3:121-40). In addition, T cell hyporesponsiveness has been recently associated with the Tryptophan catabolic pathway in HIV-infected patients with possibly extension to other chronic infectious diseases like e.g. Hepatitis C.

Some TDO2 inhibitors were proposed in WO2010/008427 and by Dolusic, E. et al. (Dolusic et al., J. Med. Chem., 2011, 54, 5320-5334), however either their affinity for the target is limited, or their pharmacokinetic properties are not suitable for development as a drug for human use.

Therefore, there is a need for new TDO2 inhibitors with improved efficacy for cancer treatment and/or prevention.

SUMMARY OF THE INVENTION

The present invention provides new TDO2 inhibitors which may be administered to a mammalian subject having a condition or disease where it is desirable to modulate, and in particular decrease, activity of TDO2, including, without limitation, patients diagnosed with cancer, or any subject being at risk of developing a cancer. Also provided are compositions containing these compounds and uses thereof.

In one aspect, a compound of Formula I is provided or a pharmaceutically acceptable salt, solvent or solvate thereof, where $A^1$, $A^2$, Q, $R^1$, $R^2$, $R^3$, $X^1$ and $X^2$ are as defined herein.

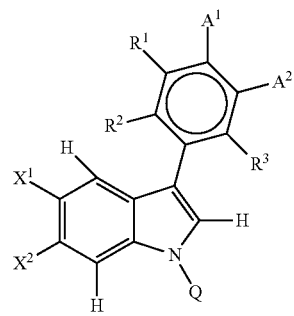

In a further aspect, a pharmaceutical composition is provided which comprises a compound according to Formula I is provided, or a pharmaceutically acceptable enantiomer, salt or solvate thereof, and at least one pharmaceutically acceptable carrier, diluent, excipient and/or adjuvant.

In yet another aspect, a medicament is provided which comprises a compound according to Formula I, or a pharmaceutically acceptable enantiomer, salt or solvate thereof.

In yet a further aspect, a compound of Formula I, or a pharmaceutically acceptable enantiomer, salt or solvate thereof is provided, for use in the treatment and/or prevention of cancer, neurodegenerative disorders such as Parkinson's disease, Alzheimer's disease and Huntington's disease, chronic viral infections such as HCV and HIV, depression, and obesity, or for use as TDO2 inhibitor.

In still another aspect, a method of treating and/or preventing of cancer, neurodegenerative disorders such as Parkinson's disease, Alzheimer's disease and Huntington's disease, chronic viral infections such as HCV and HIV, depression, and obesity, or inhibiting TDO2 is provide. The method comprises administering a compound of Formula I, or a pharmaceutically acceptable salt thereof.

In a further aspect, a process for manufacturing a compound of Formula I or a pharmaceutically acceptable enantiomer, salt or solvate thereof is provide. The process comprises:

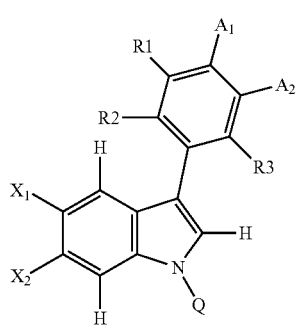

and pharmaceutically acceptable enantiomers, salts and solvates thereof, wherein $X^1$, $X^2$, $R^1$, $R^2$, $R^3$, $A^1$, $A^2$ and Q are as defined in Formula I;

comprising:
(a1) reacting a compound of Formula (i)

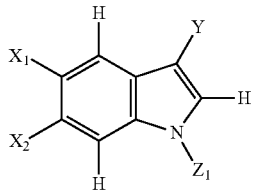

wherein
$X^1$ and $X^2$ are as defined in Formula I;
$Z^1$ represents Q or an amino protecting group such as for example an arylsulphonyl, a tert-butoxy carbonyl, a methoxymethyl, a para-methoxy benzyl, a benzyl or any other suitable protecting group known to those skilled in the art Y represents an halogen (preferably iodine, bromine or chlorine), an alkylsulfonyloxy having 1-6 carbon atoms (preferably methylsulfonyloxy or trifluoromethylsulfonyloxy) or arylsulfonyloxy having 6-10 carbon atoms (preferably phenyl- or p-tolylsulfonyloxy), or any leaving group known to those skilled in the art with a compound of Formula (ii)

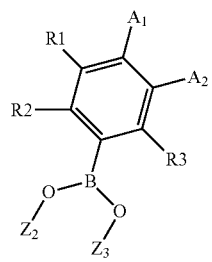

wherein
$R^1$, $R^2$, $R^3$, $A^1$, $A^2$ and $A^3$ are as defined in Formula I;
$Z^2$ and $Z^3$ represent H or alkyl groups, with the possibility for $Z^2$ and $Z^3$ to form a ring;
so as to obtain a compound of Formula (iii),

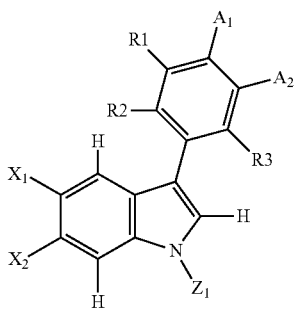

wherein $X^1$, $X^2$, $R^1$, $R^2$, $R^3$, $A^1$, $A^2$ and $Z^1$ are as defined above;
and
(b1) in the case wherein $Z^1$ is not Q, deprotecting the indole amine of compound of Formula (iii), to afford compound of Formula I.

Still other aspects and advantages of the invention will be apparent from the following detailed description of the invention.

DETAILED DESCRIPTION OF THE INVENTION

Compounds

Provided herein are Compounds of Formula I, or a pharmaceutically acceptable enantiomer, salt, or solvate therein. Unless otherwise specified, while reference is made to Formula I and its uses and methods of production for convenience, it will be understood that its subformula: Formula II are encompassed within these descriptions. Formula I has the structure:

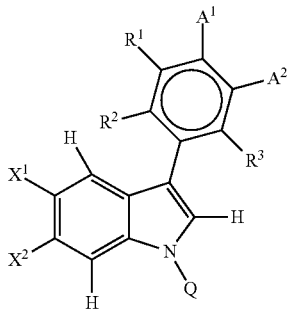

or a pharmaceutically acceptable enantiomer, salt, or solvate thereof, wherein:
$X^1$ and $X^2$ represent each independently H, halogen, OH, OR7, or C1-C4 alkyl;
$R^1$, $R^2$, and $R^3$ are independently: H, halogen, cyano, $R^7$, OH, $OR^7$, $NR^7R^8$, $CONR^7$, $N(R^7)COR^8$, $SO_2R^7$, or alkyl$NR^7R^8$;
Q is H or COW or $CONR^7R^8$;
$R^7$ and $R^8$ are independently (i) H, (ii) $NH_2$, (iii) C1 to C6 branched or unbranched alkyl, optionally substituted with one to three substituents selected from oxo, amino, OH, halogen, C1 to C4 alkyl, (iv) a C1-C3 alkyl-heterocycle or a heterocycle, an optionally substituted five or six-membered heterocycle in which the substituent is oxo, OH, NH2, or a C1 to C3 alkyl, which is optionally substituted;
$A^1$ and $A^2$ together form a 5-membered fused ring structure comprising $SO_2NR^5CR^9$, wherein $R^9$ is a hydrogen atom or a group, optionally substituted, selected from C1-C6 alkyl, aryl, arylalkyl, alkylaryl, heteroaryl, heteroarylalkyl, alkylheteroaryl, or amino;
$R^5$ and $R^6$ are independently: (i') H, (ii') oxo, (iii') amino, (iv') halogen or a group, optionally substituted, selected from:
(v') C1-C6 alkyl, linear or branched; optionally substituted with up to three substituents selected from halogen, hydroxyl, $OR^9$, $COOR^9$, $CONR^9R^{10}$, $NR^9COR^{10}$, $NR^9R^{10}$, $SO_2R^9$, $SO_2NR^9R^{10}$, $NR^9SO_2R^{10}$, $SOR^9$, aryl, or CO-alkyl, wherein $R^9$ and $R^{10}$ represent each independently a hydrogen atom or a group, optionally substituted, selected from C1-C6 alkyl, heterocyclyl, aryl, arylalkyl, alkylaryl, heteroaryl, heteroarylalkyl, alkylheteroaryl, or amino;
(vi') heterocyclyl or C1-C2 alkyl-heterocyclyl. the heterocyclyl being optionally substituted with up to three substituents which are independently halogen, hydroxyl, oxo, $OR^9$, $COOR^9$, $CONR^9R^{10}$, $NR^9COR^{10}$, $NR^9R^{10}$, $SO_2R^9$, $SO_2NR^9R^{10}$, $NR^9SO_2R^{10}$, $SO_2R^9$, aryl, CO-alkyl, or alkyl, the alkyl group being optionally substituted by one or more groups selected from halogen, hydroxyl, amino or COOK wherein $R^9$ and $R^{10}$ represent each independently a hydrogen atom or a group, optionally substituted, selected from C1-C6 alkyl, aryl, arylalkyl, alkylaryl, heteroaryl, heteroarylalkyl, alkylheteroaryl, or amino;

(vii') cycloalkyl, optionally substituted with up to three substituents selected from halogen, hydroxyl, $OR^9$, $COOR^9$, $CONR^9R^{10}$, $NR^9COR^{10}$, $NR^9R^{10}$, $SO_2R^9$, $SO_2NR^9R^{10}$, $NR^9SO_2R^{10}$, $SO_2R^9$, aryl, CO-alkyl, or C1-C6 alkyl which is optionally substituted by one or more groups selected from halogen, hydroxyl, amino or COOK wherein $R^9$ and $R^{10}$ represent each independently a hydrogen atom or a group, optionally substituted, selected from C1-C6 alkyl, aryl, arylalkyl, alkylaryl, heteroaryl, heteroarylalkyl, alkylheteroaryl, or amino In certain embodiments of Formula I, Q is H. In certain embodiments of Formula I, $X^1$ and $X^2$ are independently H, F or Cl, preferably F. In certain embodiments, in a compound of Formula I, $A^2$ is H, halogen, or OH, preferably H.

In certain embodiments of Formula I, wherein $X^1$ is H and $X^2$ is F.

In certain embodiments of Formula I, $A^1$ and $A^2$ together form a 5-membered fused ring structure comprising $SO_2NR^5CR^9$, wherein $R^9$ is a hydrogen atom or a group, optionally substituted, selected from C1-C6 alkyl, aryl, arylalkyl, alkylaryl, heteroaryl, heteroarylalkyl, alkylheteroaryl, or amino. In a further embodiment, $A^1$ and $A^2$ together form a 5-membered fused ring structure comprising $SO_2NR^5CR^{9'}$, wherein $R^{9'}$ is a $C_1$-$C_4$ alkyl, OH, or halogen.

In another embodiment, $X^1$ and $X^2$ represent each independently H, halogen, OH, OR'; or C1-C4 alkyl; $R^1$, $R^2$, and $R^3$ are independently: H, halogen, cyano, $R^7$, $OR^7$, $NR^7R^8$, $CONR^7$, $N(R^7)COR^8$, $SO_2R^7$, or alkyl$NR^7R^8$, Q is H or COW or $CONR^7R^8$, $R^7$ and $R^8$ are independently (i) H, (ii) $NH_2$, (iii) C1 to C6 branched or unbranched alkyl, optionally substituted with one to three substituents selected from one or more of oxo, amino, OH, halogen, or C1 to C4 alkyl, (iv) a C1-C3 alkyl-heterocycle or (v) a heterocycle, wherein the heterocycle of (iv) or (v) is an optionally substituted five or six-membered heterocycle in which the substituent is oxo, OH, $NH_2$, or a C1 to C3 alkyl which is optionally substituted with one to three substitutents selected from one or more of a halogen, alkyl, OH, oxo, or amino.

In certain embodiments, $A^1$ and $A^2$ together form a 5-membered fused ring structure comprising $SO_2NR^5CR^{9'}R^9$, wherein $R^{9'}$ is H, or $R^{9'}$ and $R^9$ are each methyl, wherein when $R^{9'}$ is H, $R^9$ is a hydrogen atom, cyclopropyl, or a group, optionally substituted, selected from C1-C6 alkyl, aryl, arylalkyl, alkylaryl, heteroaryl, heteroarylalkyl, or alkylheteroaryl, wherein the optionally substituted group has one, two or three substituents selected from one or more of a halogen, 01-C4 alkyl, OH, oxo, or amino.

In certain embodiments, $R^5$ and $R^6$ are independently: (I') H, (ii') oxo, (iii') amino, (iv') halogen or a group, optionally substituted, selected from:
(v') C1-C6 alkyl, linear or branched, optionally substituted with up to three substituents selected from one or more of halogen, hydroxyl, $OR^9$, $COOR^9$, $CONR^9R^{10}$, $NR^9COR^{10}$, $NR^9R^{10}$, $SO_2R^9$, $SO_2NR^9R^{10}$, $NR^9SO_2R^{10}$, $SOR^9$, aryl, or CO-alkyl, (vi') heterocyclyl or C1-C3 alkyl-heterocyclyl, the heterocyclyl being optionally substituted with up to three substituents which are selected from one or more of halogen, hydroxyl, oxo, $OR^9$, $COOR^9$, $CONR^9R^{10}$, $NR^9COR^{10}$, $NR^9R^{10}$, $SO_2R^9$, $SO_2NR^9R^{10}$, $NR^9SO_2R^{10}$, $SO_2R^9$, aryl, CO-alkyl, a five or six membered heterocycle having 2 N atoms in its backbone; a piperidine substituted with F and three OH, or alkyl, the alkyl group being optionally substituted by one to three groups selected from one or more of halogen, hydroxyl, oxo, amino or COOK (vii') cycloalkyl, optionally substituted with up to three substituents selected from halogen, hydroxyl, $OR^9$, $COOR^9$, $CONR^9R^{10}$, $NR^9COR^{10}$, $NR^9R^{10}$, $SO_2R^9$, $SO_2NR^9R^{10}$, $NR^9SO_2R^{10}$, $SO_2R^9$, aryl, CO-alkyl, or C1-C6 alkyl which is optionally substituted by one or more groups selected from halogen, hydroxyl, amino or COOK $R^9$ and $R^{10}$ represent each independently a hydrogen atom or a group, optionally substituted, selected from C1-C6 alkyl, wherein when substituted, the C1-C6 alkyl has one, two or three groups selected from one or more halogen, hydroxyl, oxo, amino or COOH, heterocyclyl, aryl, arylalkyl, alkylaryl, heteroaryl, heteroarylalkyl, or alkylheteroaryl, wherein when substituted, the aryl, arylalkyl, alkylaryl, heteroaryl, heteroarylalkyl, alkylheteroaryl has up to three substituents which are one or more of halogen, hydroxyl, oxo, $OR^9$, $COOR^9$, $CONR^9R^{10}$, $NR^9COR^{10}$, $NR^9R^{10}$, $SO_2R^9$, $SO_2NR^9R^{10}$, $NR^9SO_2R^{10}$, $SO_2R^9$, CO-alkyl, or amino In other embodiments, $A^1$ or $A^2$ together form a 5-membered fused ring structure comprising $SO_2NR^5CR^9$. In certain embodiments, $R^5$ is the C1-C3 alkyl-heterocyclyl optionally substituted with up to three substituents which are independently halogen, C1-C6 alkyl, hydroxyl, oxo, $OR^9$, $COOR^9$, $CONR^9R^{10}$, $NR^9COR^{10}$, $NR^9R^{10}$, $SO_2R^9$, $SO_2NR^9R^{10}$, $NR^9SO_2R^{10}$, or $SO_2R^9$.

In other embodiments, when $SO_2NR^5CR^9$, $R^9$ is a $C_1$-$C_4$ alkyl which is optionally substituted with OH or halogen.

In certain embodiments, a compound of Formula I is in a salt form. In another embodiment, the free base (non-salt) form of a compound of Formula I is provided.

Further provided herein is a compound of Formula II:

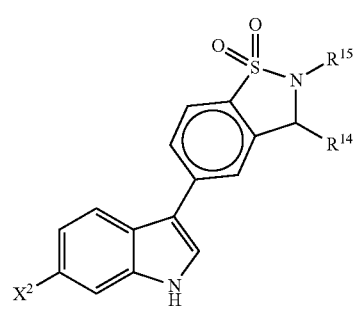

II or a pharmaceutically acceptable enantiomer, salt or solvate thereof, wherein:
$X^2$ is H, halogen, OH, OR'; or C1-C4 alkyl;
$R^7$ is: (i) H; (ii) $NH_2$; (iii) C1 to C6 branched or unbranched alkyl, optionally substituted with one to three substituents selected from oxo, amino, OH, halogen, or C1 to C4 alkyl; (iv) a C1-C3 alkyl-heterocycle, or (v) an optionally substituted five or six-membered heterocycle, in which the substituent is a C1 to C3 alkyl, which is itself optionally substituted with a group selected from oxo, OH, or $NH_2$; $R^{14}$ and $R^{15}$ are independently H or a group, optionally substituted, selected from C1-C6 alkyl, aryl, arylalkyl, alkylaryl, heteroaryl, heteroarylalkyl, alkylheteroaryl, or amino. In certain embodiments, $R^{14}$ is H, C1 to C3 alkyl, or OH. In still other embodiments, $R^{15}$ is defined as $R^5$ and $R^{14}$ is defined as $R^9R^{9'}$ of Formula I in the 5-membered fused ring structure comprising $SO_2NR^5CR^{9'}R^9$ of Formula I, wherein R9' is H, or R9' and R9 are each methyl, wherein when R9' is H, R9 is a hydrogen atom, cyclopropyl, or a group, optionally substituted, selected from C1-C6 alkyl, aryl, arylalkyl, alkylaryl, heteroaryl, heteroarylalkyl, or alkylheteroaryl, wherein the optionally substituted group has one, two or three substituents selected from one or more of a halogen, C1-C4 alkyl, OH, oxo, or amino.

In certain embodiments, the optionally substituted group has one, two or three substituents selected from one or more of a halogen, C1-C4 alkyl, OH, oxo, or amino.

In certain embodiments of Formula II, $X^2$ is halogen.

In certain embodiments of Formula II, $R^{14}$ is $CH_3$.

In certain embodiments, a compound of Formula II is in a salt form. In another embodiment, the free base (non-salt) form of a compound of Formula II is provided.

Illustrative compounds of Formula I are those listed in Table 1 hereafter.

| Compound-IUPAC name | Structure |
| --- | --- |
| (+)-5-(6-fluoro-1H-indol-3-yl)-3-methyl-2,3-dihydro-1,2-benzothiazole 1,1-dioxide | 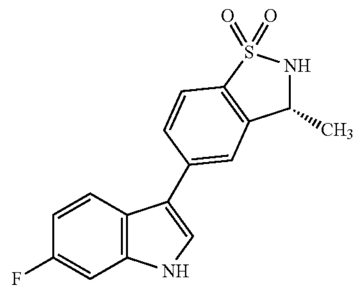 [SMILES: C[C@H]1NS(=O)(=O)c2ccc(-c3c[nH]c4cc(F)ccc34)cc21] |
| (−)-5-(6-fluoro-1H-indol-3-yl)-3-methyl-2,3-dihydro-1,2-benzothiazole 1,1-dioxide | 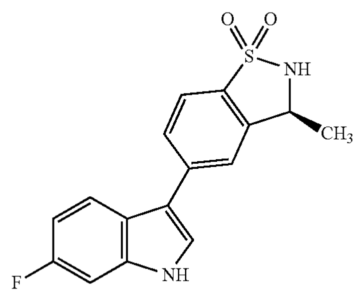 [SMILES: C[C@@H]1NS(=O)(=O)c2ccc(-c3c[nH]c4cc(F)ccc34)cc21] |
| (+)-3-ethyl-5-(6-fluoro-1H-indol-3-yl)-2,3-dihydrobenzo[d]isothiazole 1,1-dioxide | 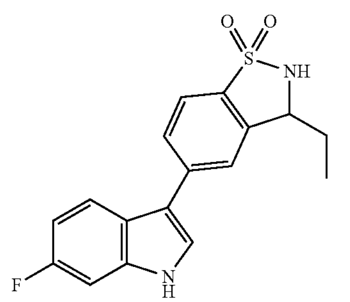 [SMILES: CCC1NS(=O)(=O)c2ccc(-c3c[nH]c4cc(F)ccc34)cc21] |
| (−)-3-ethyl-5-(6-fluoro-1H-indol-3-yl)-2,3-dihydrobenzo[d]isothiazole-1,1-dioxide | 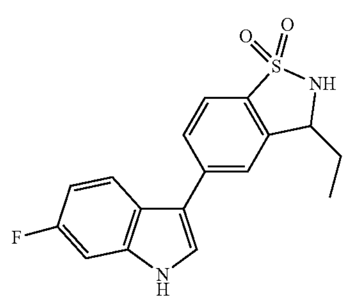 [SMILES: CCC1NS(=O)(=O)c2ccc(-c3c[nH]c4cc(F)ccc34)cc21] |

-continued

| Compound-IUPAC name | Structure |
|---|---|
| 5-(6-fluoro-1H-indol-3-yl)-3,3-dimethyl-2,3-dihydrobenzo[d]isothiazole-1,1-dioxide | 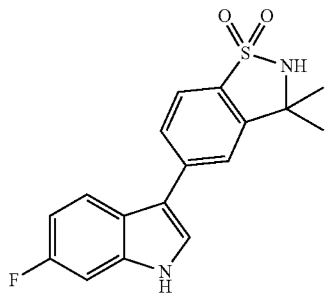 [SMILES: CC1(C)NS(=O)(=O)c2ccc(-c3c[nH]c4cc(F)ccc34)cc21] |
| (+)-5-(6-fluoro-1H-indol-3-yl)-3-propyl-2,3-dihydrobenzo[d]isothiazole 1,1-dioxide | 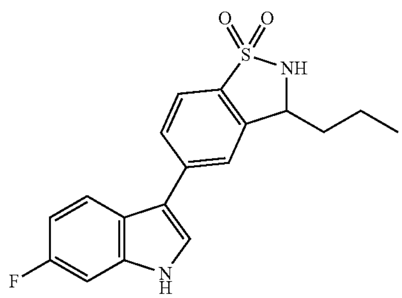 [SMILES: CCCC1NS(=O)(=O)c2ccc(-c3c[nH]c4cc(F)ccc34)cc21] |
| (−)-5-(6-fluoro-1H-indol-3-yl)-3-propyl-2,3-dihydrobenzo[d]isothiazole-1,1-dioxide | 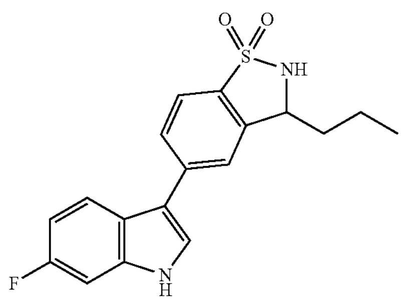 [SMILES: CCCC1NS(=O)(=O)c2ccc(-c3c[nH]c4cc(F)ccc34)cc21] |
| (+)-5-(6-fluoro-1H-indol-3-yl)-3-isopropyl-2,3-dihydrobenzo[d]isothiazole 1,1-dioxide | 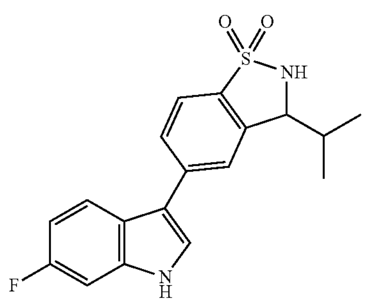 [SMILES: CC(C)C1NS(=O)(=O)c2ccc(-c3c[nH]c4cc(F)ccc34)cc21] |
| (−)-5-(6-fluoro-1H-indol-3-yl)-3-isopropyl-2,3-dihydrobenzo[d]isothiazole 1,1-dioxide | 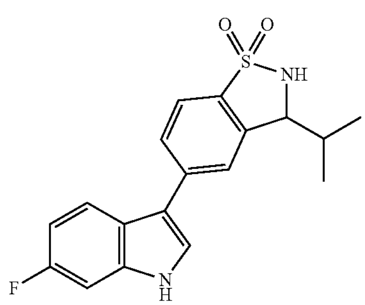 [SMILES: CC(C)C1NS(=O)(=O)c2ccc(-c3c[nH]c4cc(F)ccc34)cc21] |

| Compound-IUPAC name | Structure |
|---|---|
| (+)-3-cyclopropyl-5-(6-fluoro-1H-indol-3-yl)-2,3-dihydrobenzo[d]isothiazole 1,1-dioxide | 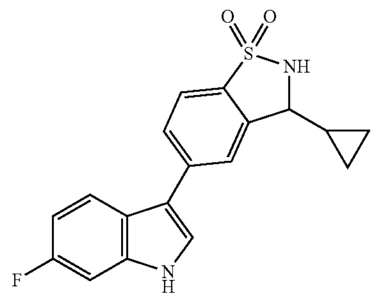 [SMILES: O=S1(=O)NC(C2CC2)c2cc(-c3c[nH]c4cc(F)ccc34)ccc21] |
| (−)-3-cyclopropyl-5-(6-fluoro-1H-indol-3-yl)-2,3-dihydrobenzo[d]isothiazole 1,1-dioxide | 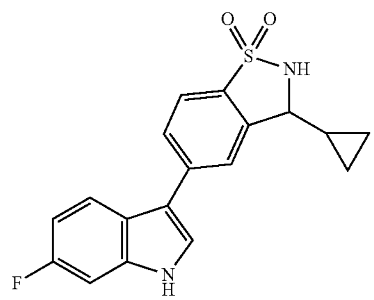 [SMILES: O=S1(=O)NC(C2CC2)c2cc(-c3c[nH]c4cc(F)ccc34)ccc21] |
| (−)-5-(6-fluoro-1H-indol-3-yl)-3-(hydroxylmethyl)-2,3-dihydrobenzo[d]isothiazole 1,1-dioxide | |
| (+)-5-(6-fluoro-1H-indol-3-yl)-3-(hydroxymethyl)-2,3-dihydrobenzo[d]isothiazole 1,1-dioxide | |
| methyl 5-(6-fluoro-1H-indol-3-yl)-2,3-dihydrobenzo[d]isothiazole-3-carboxylate 1,1-dioxide | 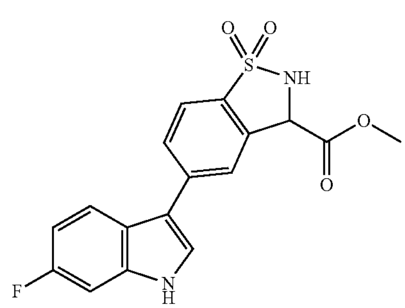 [SMILES: COC(=O)C1NS(=O)(=O)c2ccc(-c3c[nH]c4cc(F)ccc34)cc21] |

| Compound-IUPAC name | Structure |
|---|---|
| (−)-5-(6-fluoro-1H-indol-3-yl)-2,3-dihydro-benzo[d]isothiazole-3-carboxamide 1,1-dioxide | 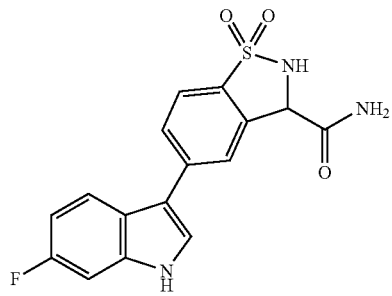 |
| (+)-5-(6-fluoro-1H-indol-3-yl)-2,3-dihydro-benzo[d]isothiazole-3-carboxamide 1,1-dioxide | 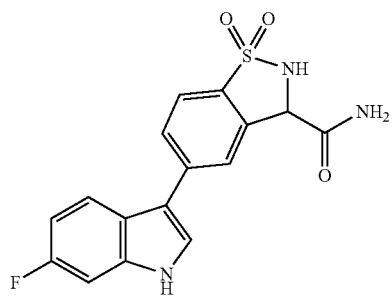 |
| (−)-5-(6-fluoro-1H-indol-3-yl)-N-methyl-2,3-dihydrobenzo[d]isothiazole-3-carboxamide 1,1-dioxide | 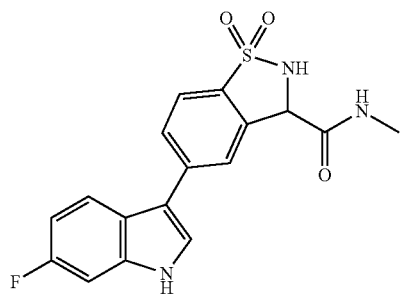 [SMILES: CNC(=O)C1NS(=O)(=O)c2ccc(-c3c[nH]c4cc(F)ccc34)cc21] |
| (+)-5-(6-fluoro-1H-indol-3-yl)-N-methyl-2,3-dihydrobenzo[d]isothiazole-3-carboxamide 1,1-dioxide | 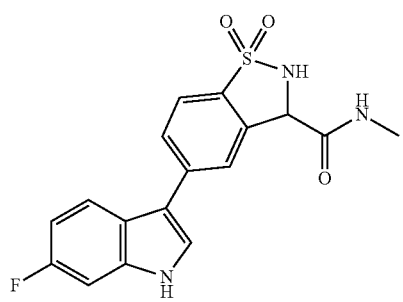 |
| (+)-3-(aminomethyl)-5-(6-fluoro-1H-indol-3-yl)-2,3-dihydrobenzo[d]isothiazole 1,1-dioxide | 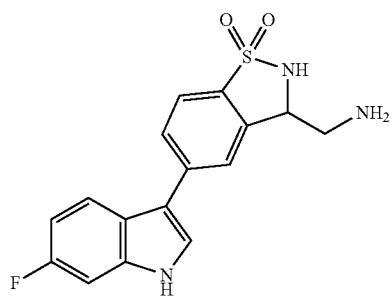 [SMILES: NCC1NS(=O)(=O)c2ccc(-c3c[nH]c4cc(F)ccc34)cc21] |

| Compound-IUPAC name | Structure |
|---|---|
| (−)-3-(aminomethyl)-5-(6-fluoro-1H-indol-3-yl)-2,3-dihydrobenzo[d]isothiazole 1,1-dioxide | 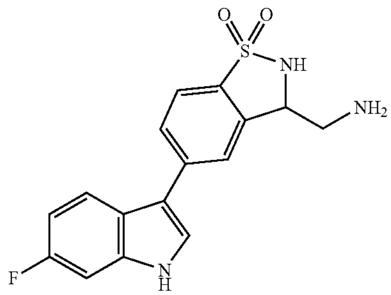 [SMILES: NCC1NS(=O)(=O)c2ccc(-c3c[nH]c4cc(F)ccc34)cc21] |
| (−)-methyl ((5-(6-fluoro-1H-indol-3-yl)-1,1-dioxido-2,3-dihydrobenzo[d]isothiazol-3-yl)methyl) carbamate | 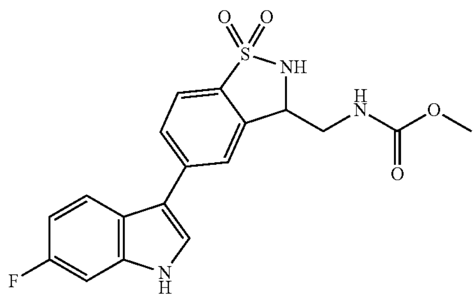 [SMILES: COC(=O)NCC1NS(=O)(=O)c2ccc(-c3c[nH]c4cc(F)ccc34)cc21] |
| (+)-methyl ((5-(6-fluoro-1H-indol-3-yl)-1,1-dioxido-2,3-dihydrobenzo[d]isothiazol-3-yl)methyl) carbamate | 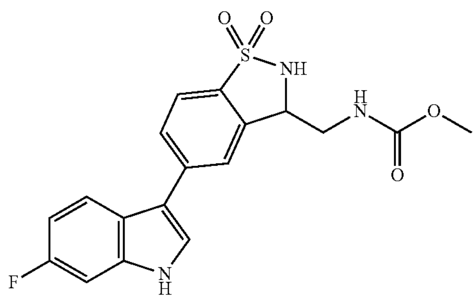 [SMILES: COC(=O)NCC1NS(=O)(=O)c2ccc(-c3c[nH]c4cc(F)ccc34)cc21] |
| (−)-N-((5-(6-fluoro-1H-indol-3-yl)-1,1-dioxido-2,3-dihydrobenzo[d]isothiazol-3-yl)methyl)acetamide | 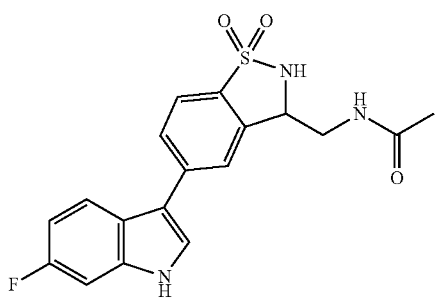 [SMILES: CC(=O)NCC1NS(=O)(=O)c2ccc(-c3c[nH]c4cc(F)ccc34)cc21] |
| (+)-N-((5-(6-fluoro-1H-indol-3-yl)-1,1-dioxido-2,3-dihydrobenzo[d]isothiazol-3-yl)methyl)acetamide | 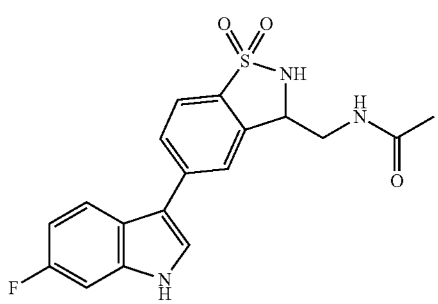 |

-continued

| Compound-IUPAC name | Structure |
|---|---|
| (−)-3-((dimethylamino)methyl)-5-(6-fluoro-1H-indol-3-yl)-2,3-dihydrobenzo[d]isothiazole 1,1-dioxide | 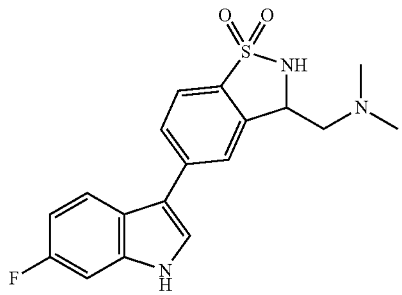 [SMILES: CN(C)CC1NS(=O)(=O)c2ccc(-c3c[nH]c4cc(F)ccc34)cc21] |
| (+)-3-((dimethylamino)methyl)-5-(6-fluoro-1H-indol-3-yl)-2,3-dihydrobenzo[d]isothiazole 1,1-dioxide | 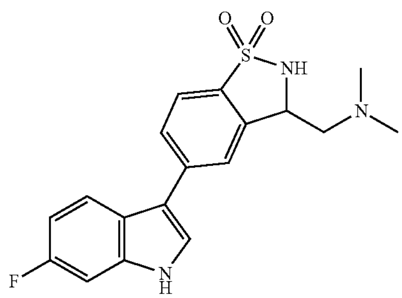 [SMILES: CN(C)CC1NS(=O)(=O)c2ccc(-c3c[nH]c4cc(F)ccc34)cc21] |
| (+)-N-((5-(6-fluoro-1H-indol-3-yl)-1,1-dioxido-2,3-dihydrobenzo[d]isothiazol-3-yl)methyl)-N-methylacetamide | 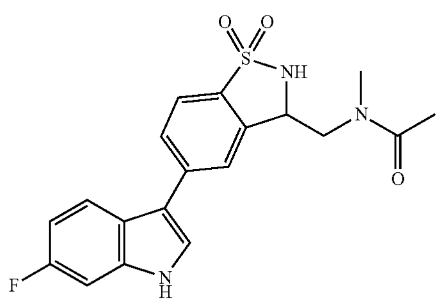 |
| (−)-N-((5-(6-fluoro-1H-indol-3-yl)-1,1-dioxido-2,3-dihydrobenzo[d]isothiazol-3-yl)methyl)-N-methylacetamide | 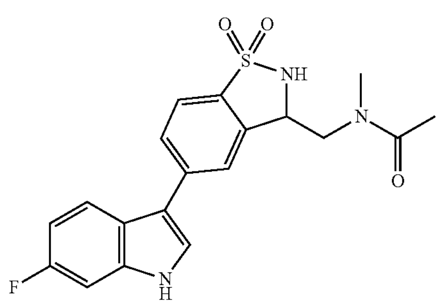 [SMILES: CC(=O)N(C)CC1NS(=O)(=O)c2ccc(-c3c[nH]c4cc(F)ccc34)cc21] |
| (−)-5-(6-fluoro-1H-indol-3-yl)-3-(2-hydroxyethyl)-2,3-dihydrobenzo[d]isothiazole 1,1-dioxide | 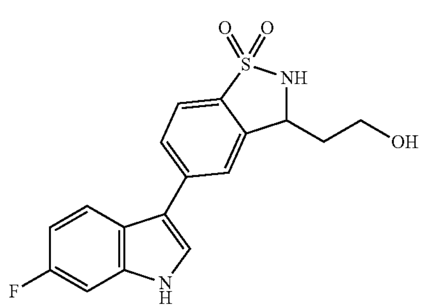 [SMILES: O=S1(=O)NC(CCO)c2cc(-c3c[nH]c4cc(F)ccc34)ccc21] |

| Compound-IUPAC name | Structure |
|---|---|
| (+)-5-(6-fluoro-1H-indol-3-yl)-3-(2-hydroxyethyl)-2,3-dihydrobenzo[d]isothiazole 1,1-dioxide | |
| 2-(2-aminoethyl)-5-(6-fluoro-1H-indol-3-yl)-2,3-dihydrobenzo[d]isothiazole 1,1-dioxide | 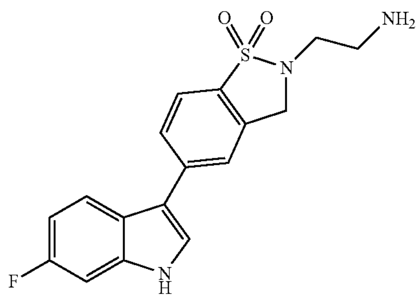 [SMILES: NCCN1Cc2cc(-c3c[nH]c4cc(F)ccc34)ccc2S1(=O)=O] |
| 2-(2-(dimethylamino)ethyl)-5-(6-fluoro-1H-indol-3-yl)-2,3-dihydrobenzo[d]isothiazole 1,1-dioxide | 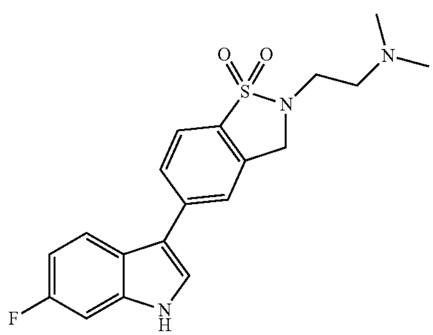 [SMILES: CN(C)CCN1Cc2cc(-c3c[nH]c4cc(F)ccc34)ccc2S1(=O)=O] |
| 5-(6-fluoro-1H-indol-3-yl)-2-(2-hydroxyethyl)-2,3-dihydrobenzo[d]isothiazole 1,1-dioxide | |
| (S)-2-(2,3-dihydroxypropyl)-5-(6-fluoro-1H-indol-3-yl)-2,3-dihydrobenzo[d]isothiazole 1,1-dioxide | 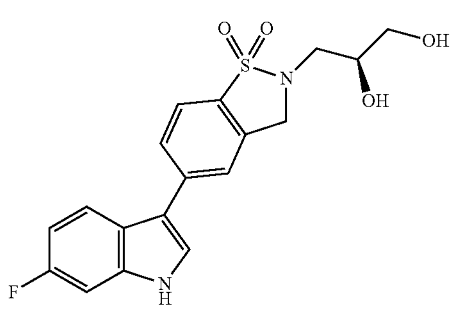 [SMILES: O=S1(=O)c2ccc(-c3c[nH]c4cc(F)ccc34)cc2CN1C[C@H](O)CO] |

-continued
| Compound-IUPAC name | Structure |
|---|---|
| (R)-2-(2,3-dihydroxypropyl)-5-(6-fluoro-1H-indol-3-yl)-2,3-dihydrobenzo[d]isothiazole 1,1-dioxide | 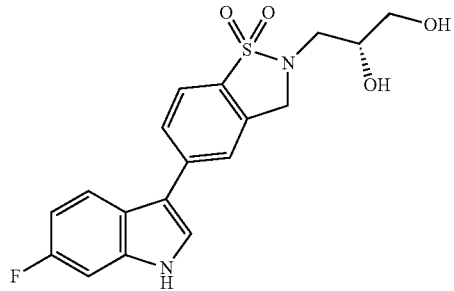 [SMILES: O=S1(=O)c2ccc(-c3c[nH]c4cc(F)ccc34)cc2CN1C[C@@H](O)CO] |
| 5-(6-fluoro-1H-indol-3-yl)-2-(piperidin-4-yl)-2,3-dihydrobenzo[d]isothiazole 1,1-dioxide | 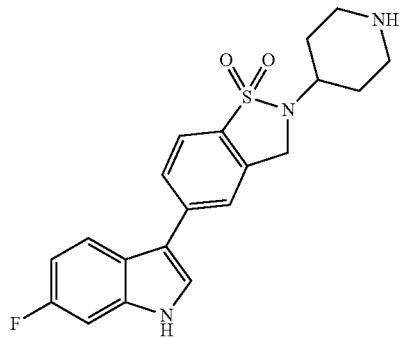 [SMILES: O=S1(=O)c2ccc(-c3c[nH]c4cc(F)ccc34)cc2CN1C1CCNCC1] |
| 5-(6-fluoro-1H-indol-3-yl)-2-(1-methylpiperidin-4-yl)-2,3-dihydrobenzo[d]isothiazole 1,1-dioxide | 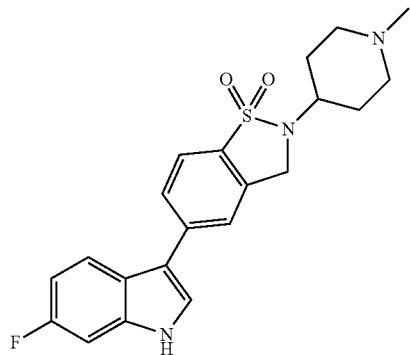 [SMILES: CN1CCC(N2Cc3cc(-c4c[nH]c5cc(F)ccc45)ccc3S2(=O)=O)CC1] |
| (R)-5-(6-fluoro-1H-indol-3-yl)-2-(tetrahydrofuran-3-yl)-2,3-dihydrobenzo[d]isothiazole 1,1-dioxide | 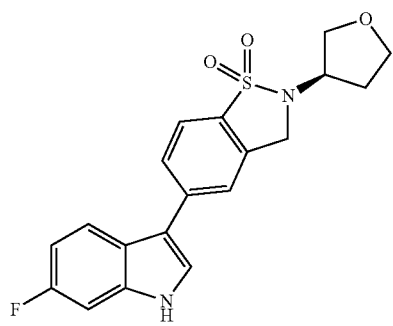 [SMILES: O=S1(=O)c2ccc(-c3c[nH]c4cc(F)ccc34)cc2CN1[C@@H]1CCOC1] |

| Compound-IUPAC name | Structure |
|---|---|
| (S)-5-(6-fluoro-1H-indol-3-yl)-2-(tetrahydro-furan-3-yl)-2,3-dihydrobenzo[d]isothiazole 1,1-dioxide | 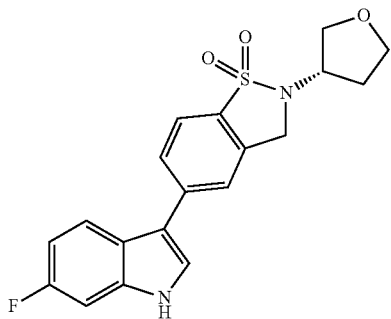 [SMILES: O=S1(=O)c2ccc(-c3c[nH]c4cc(F)ccc34)cc2CN1[C@H]1CCOC1] |
| 2-(azetidin-3-yl)-5-(6-fluoro-1H-indol-3-yl)-2,3-dihydrobenzo[d]isothiazole 1,1-dioxide | 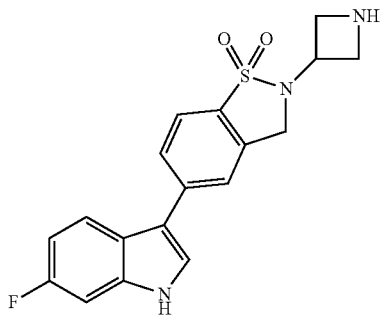 [SMILES: O=S1(=O)c2ccc(-c3c[nH]c4cc(F)ccc34)cc2CN1C1CNC1] |
| 5-(6-fluoro-1H-indol-3-yl)-2-(1-methyl-azetidin-3-yl)-2,3-dihydrobenzo[d]isothiazole 1,1-dioxide | 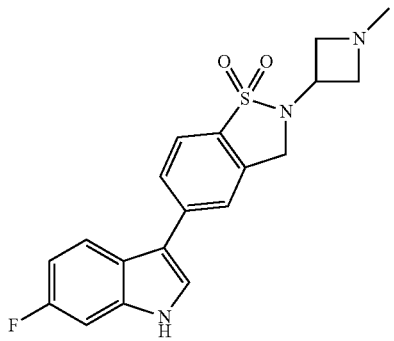 [SMILES: CN1CC(N2Cc3cc(-c4c[nH]c5cc(F)ccc45)ccc3S2(=O)=O)C1] |
| (+)-5-(6-fluoro-1H-indol-3-yl)-2-(2-(methyl-sulfinyl)ethyl)-2,3-dihydrobenzo[d]isothiazole 1,1-dioxide | 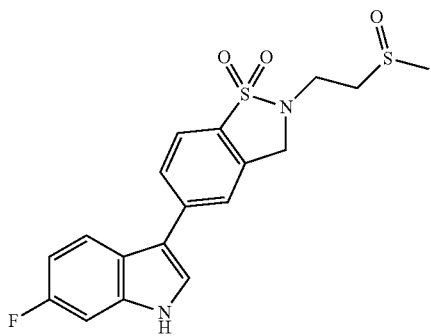 [SMILES: CS(=O)CCN1Cc2cc(-c3c[nH]c4cc(F)ccc34)ccc2S1(=O)=O] |

-continued
| Compound-IUPAC name | Structure |
|---|---|
| 3-(5-(6-fluoro-1H-indol-3-yl)-1,1-dioxido-benzo[d]isothiazol-2(3H)-yl)-N-methyl-propanamide | 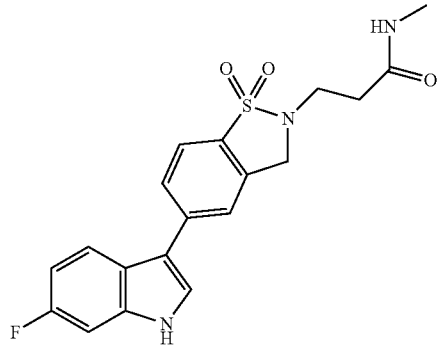 |
| 3-(5-(6-fluoro-1H-indol-3-yl)-1,1-dioxido-benzo[d]isothiazol-2(3H)-yl)propanamide | 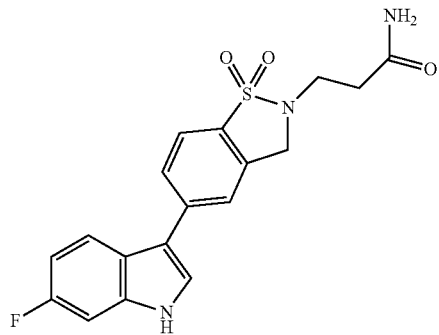 |
| (+)-3-(5-(6-fluoro-1H-indol-3-yl)-3-methyl-1,1-dioxidobenzo[d]isothiazol-2(3H)-yl)-N-methylpropanamide | 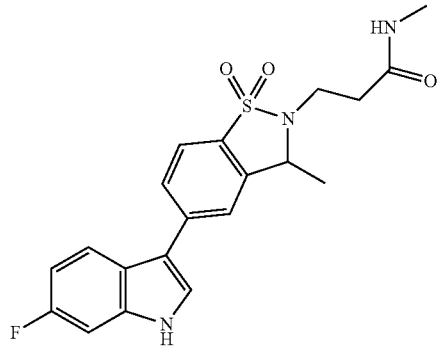 |
| (−)-3-(5-(6-fluoro-1H-indol-3-yl)-3-methyl-1,1-dioxidobenzo[d]isothiazol-2(3H)-yl)-N-methylpropanamide | 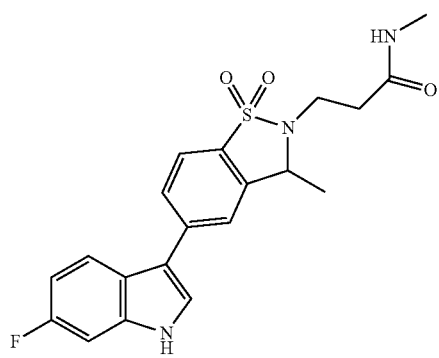 |

| Compound-IUPAC name | Structure |
|---|---|
| (+)-3-(5-(6-fluoro-1H-indol-3-yl)-3-methyl-1,1-dioxidobenzo[d]isothiazol-2(3H)-yl)propanamide | 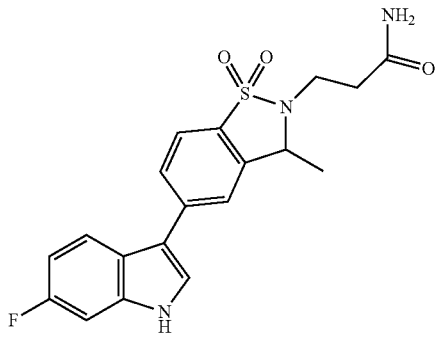 |
| (−)-3-(5-(6-fluoro-1H-indol-3-yl)-3-methyl-1,1-dioxidobenzo[d]isothiazol-2(3H)-yl)propanamide | 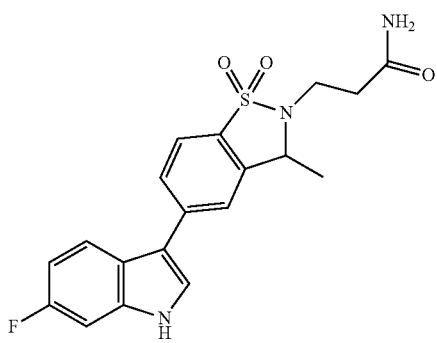 |
| (+)-3-(5-(6-fluoro-1H-indol-3-yl)-3-methyl-1,1-dioxidobenzo[d]isothiazol-2(3H)-yl)-1-(piperazin-1-yl)propan-1-one | 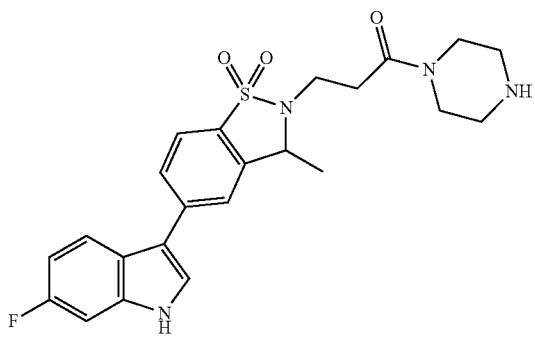 [SMILES: CC1c2cc(-c3c[nH]c4cc(F)ccc34)ccc2S(=O)(=O)N1CCC(=O)N1CCNCC1] |
| (−)3-(5-(6-fluoro-1H-indol-3-yl)-3-methyl-1,1-dioxidobenzo[d]isothiazol-2(3H)-yl)-1-piperazin-1-yl)propan-1-one | 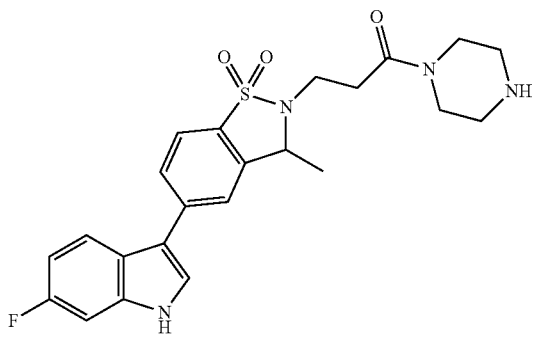 [SMILES: CC1c2cc(-c3c[nH]c4cc(F)ccc34)ccc2S(=O)(=O)N1CCC(=O)N1CCNCC1] |

| Compound-IUPAC name | Structure |
|---|---|
| (−)-5-(6-fluoro-1H-indol-3-yl)-3-methyl-2-(piperidin-4-yl)-2,3-dihydrobenzo[d]isothiazole 1,1-dioxide | 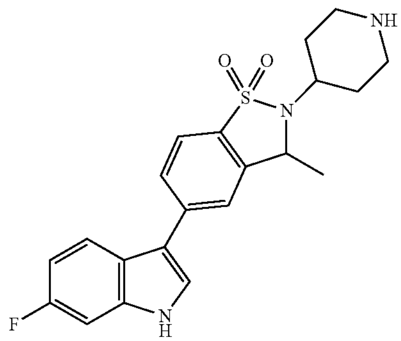 [SMILES: CC1c2cc(-c3c[nH]c4cc(F)ccc34)ccc2S(=O)(=O)N1C1CCNCC1] |
| (+)-5-(6-fluoro-1H-indol-3-yl)-3-methyl-2-(piperidin-4-yl)-2,3-dihydrobenzo[d]isothiazole 1,1-dioxide | 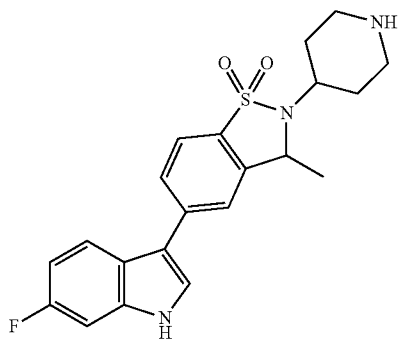 [SMILES: CC1c2cc(-c3c[nH]c4cc(F)ccc34)ccc2S(=O)(=O)N1C1CCNCC1] |
| (+)-5-(6-fluoro-1H-indol-3-yl)-3-methyl-2-(2-(methylsulfonyl)ethyl)-2,3-dihydrobenzo[d]isothiazole 1,1-dioxide | 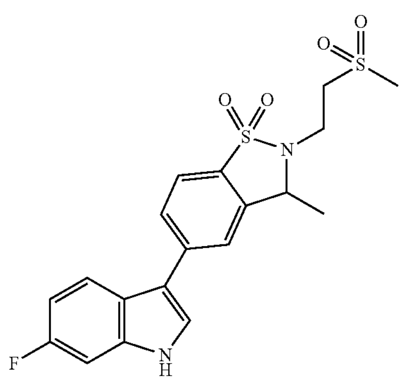 [SMILES: CC1c2cc(-c3c[nH]c4cc(F)ccc34)ccc2S(=O)(=O)N1CCS(C)(=O)=O] |
| (−)-5-(6-fluoro-1H-indol-3-yl)-3-methyl-2-(2-(methylsulfonyl)ethyl)-2,3-dihydrobenzo[d]isothiazole 1,1-dioxide | 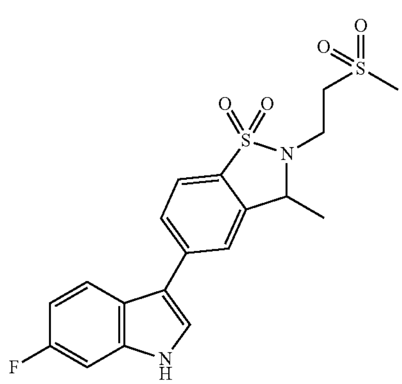 [SMILES: CC1c2cc(-c3c[nH]c4cc(F)ccc34)ccc2S(=O)(=O)N1CCS(C)(=O)=O] |

| Compound-IUPAC name | Structure |
|---|---|
| (+)-5-(6-fluoro-1H-indol-3-yl)-3-methyl-2-(2-(methylsulfinyl)ethyl)-2,3-dihydrobenzo[d]isothiazole 1,1-dioxide | |
| (−)-5-(6-fluoro-1H-indol-3-yl)-3-methyl-2-(2-(methylsulfinyl)ethyl)-2,3-dihydrobenzo[d]isothiazole 1,1-dioxide | |
| (−)-5-(6-fluoro-1H-indol-3-yl)-3-methyl-2-(2-(methylsulfinyl)ethyl)-2,3-dihydrobenzo[d]isothiazole 1,1-dioxide | |
| (+)-5-(6-fluoro-1H-indol-3-yl)-3-methyl-2-(2-(methylsulfinyl)ethyl)-2,3-dihydrobenzo[d]isothiazole 1,1-dioxide | |

-continued

| Compound-IUPAC name | Structure |
|---|---|
| (−)-2-(5-(6-fluoro-1H-indol-3-yl)-3-methyl-1,1-dioxidobenzo[d]isothiazol-2(3H)-yl)-N-methylethane-1-sulfonamide | 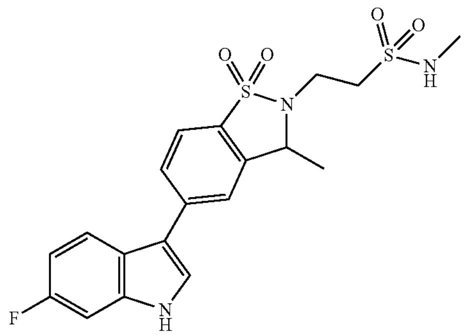 [SMILES: CNS(=O)(=O)CCN1C(C)c2cc(-c3c[nH]c4cc(F)ccc34)ccc2S1(=O)=O] |
| (+)-2-(5-(6-fluoro-1H-indol-3-yl)-3-methyl-1,1-dioxidobenzo[d]isothiazol-2(3H)-yl)-N-methylethane-1-sulfonamide | 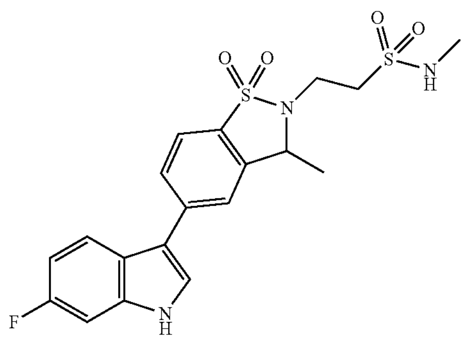 [SMILES: CNS(=O)(=O)CCN1C(C)c2cc(-c3c[nH]c4cc(F)ccc34)ccc2S1(=O)=O] |
| (+)-2-(5-(6-fluoro-1H-indol-3-yl)-3-methyl-1,1-dioxidobenzo[d]isothiazol-2(3H)-yl)ethane-1-sulfonamide | 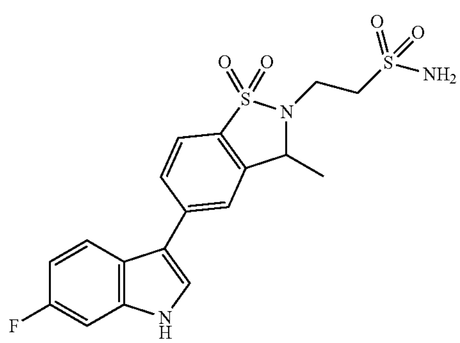 [SMILES: CC1c2cc(-c3c[nH]c4cc(F)ccc34)ccc2S(=O)(=O)N1CCS(N)(=O)=O] |
| (−)-2-(5-(6-fluoro-1H-indol-3-yl)-3-methyl-1,1-dioxidobenzo[d]isothiazol-2(3H)-yl)ethane-1-sulfonamide | 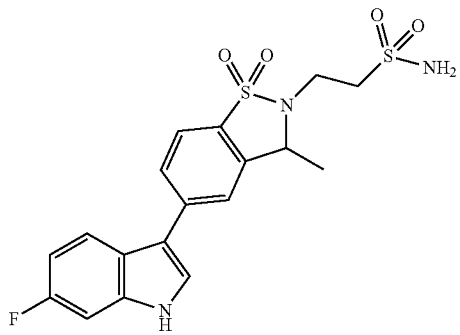 [SMILES: CC1c2cc(-c3c[nH]c4cc(F)ccc34)ccc2S(=O)(=O)N1CCS(N)(=O)=O] |

| Compound-IUPAC name | Structure |
|---|---|
| (+)-5-(6-fluoro-1H-indol-3-yl)-2-(2-hydroxyethyl)-3-methyl-2,3-dihydrobenzo[d]isothiazole 1,1-dioxide | 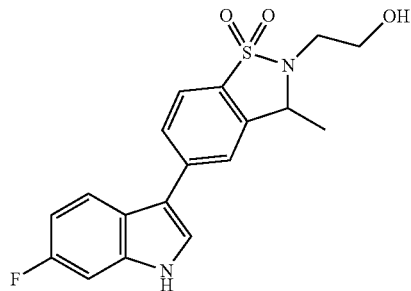 [SMILES: CC1c2cc(-c3c[nH]c4cc(F)ccc34)ccc2S(=O)(=O)N1CCO] |
| (−)-5-(6-fluoro-1H-indol-3-yl)-2-(2-hydroxyethyl)-3-methyl-2,3-dihydrobenzo[d]isothiazole 1,1-dioxide | 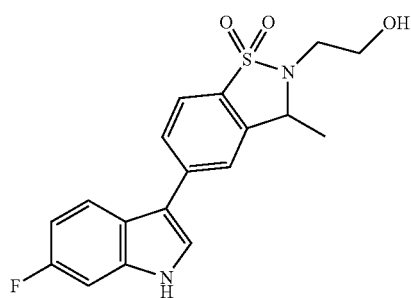 |
| (−)1-(2-(5-(6-fluoro-1H-indol-3-yl)-3-methyl-1,1-dioxidobenzo[d]isothiazol-2(3H)-yl)ethyl)piperazin-2-one | 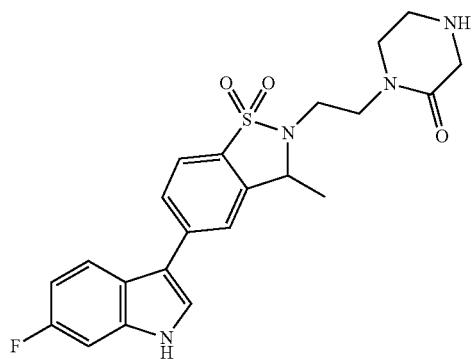 [SMILES: CC1c2cc(-c3c[nH]c4cc(F)ccc34)ccc2S(=O)(=O)N1CCN1CCNCC1=O] |
| (+)1-(2-(5-(6-fluoro-1H-indol-3-yl)-3-methyl-1,1-dioxidobenzo[d]isothiazol-2(3H)-yl)ethyl)piperazin-2-one | 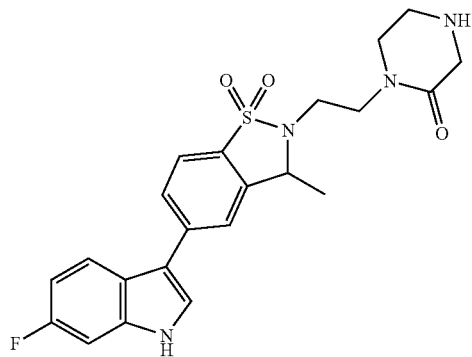 [SMILES: CC1c2cc(-c3c[nH]c4cc(F)ccc34)ccc2S(=O)(=O)N1CCN1CCNCC1=O] |

-continued

| Compound-IUPAC name | Structure |
|---|---|
| (+)-5-(6-fluoro-1H-indol-3-yl)-2-(2-(5-hydroxy-3-methyl-1H-pyrazol-1-yl)ethyl)-3-methyl-2,3-dihydrobenzo[d]isothiazole 1,1-dioxide | 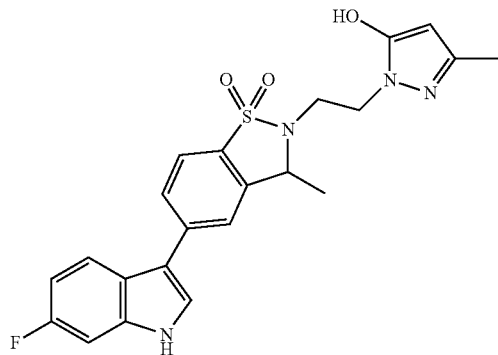 [SMILES: Cc1cc(O)n(CCN2C(C)c3cc(-c4c[nH]c5cc(F)ccc45)ccc3S2(=O)=O)n1] |
| (−)-5-(6-fluoro-1H-indol-3-yl)-2-(2-(5-hydroxy-3-methyl-1H-pyrazol-1-yl)ethyl)-3-methyl-2,3-dihydrobenzo[d]isothiazole 1,1-dioxide | 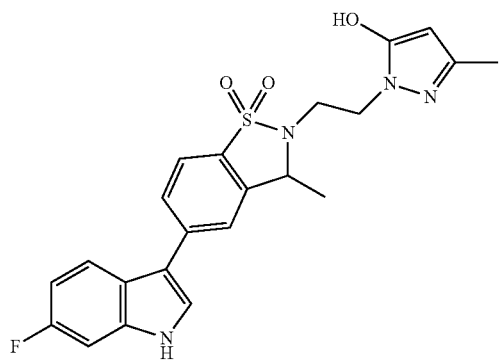 [SMILES: Cc1cc(O)n(CCN2C(C)c3cc(-c4c[nH]c5cc(F)ccc45)ccc3S2(=O)=O)n1] |
| (+)-3-(2-(5-(6-fluoro-1H-indol-3-yl)-3-methyl-1,1-dioxidobenzo[d]isothiazol-2(3H)-yl)ethyl)oxazolidin-2-one | 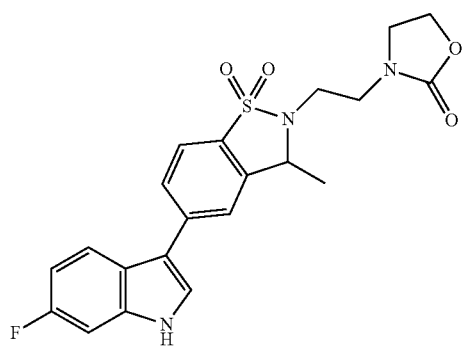 [SMILES: CC1c2cc(-c3c[nH]c4cc(F)ccc34)ccc2S(=O)(=O)N1CCN1CCOC1=O] |
| (−)-3-(2-(5-(6-fluoro-1H-indol-3-yl)-3-methyl-1,1-dioxidobenzo[d]isothiazol-2(3H)-yl)ethyl)oxazolidin-2-one | 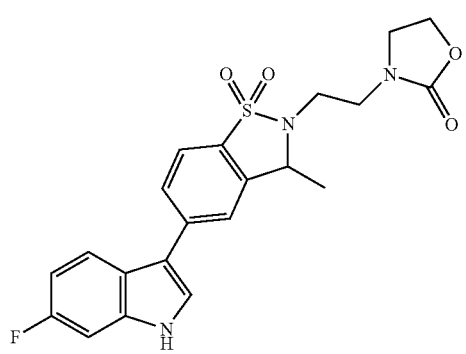 |

| Compound-IUPAC name | Structure |
|---|---|
| (+)-1-(4-(5-(6-fluoro-1H-indol-3-yl)-3-methyl-1,1-dioxidobenzo[d]isothiazol-2(3H)-yl)piperidin-1-yl)ethanone | 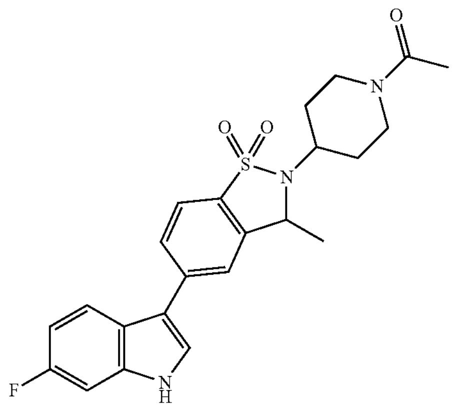 [SMILES: CC(=O)N1CCC(N2C(C)c3cc(-c4c[nH]c5cc(F)ccc45)ccc3S2(=O)=O)CC1] |
| (−)-1-(4-(5-(6-fluoro-1H-indol-3-yl)-3-methyl-1,1-dioxidobenzo[d]isothiazol-2(3H)-yl)piperidin-1-yl)ethanone | 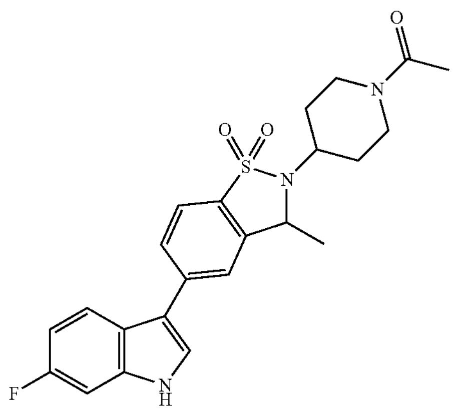 [SMILES: CC(=O)N1CCC(N2C(C)c3cc(-c4c[nH]c5cc(F)ccc45)ccc3S2(=O)=O)CC1] |
| (+)-1-(3-(5-(6-fluoro-1H-indol-3-yl)-3-methyl-1,1-dioxidobenzo[d]isothiazol-2(3H)-yl)pyrrolidin-1-yl)ethanone | |
| (+)-1-(3-(5-(6-fluoro-1H-indol-3-yl)-3-methyl-1,1-dioxidobenzo[d]isothiazol-2(3H)-yl)pyrrolidin-1-yl)ethanone | |

| Compound-IUPAC name | Structure |
|---|---|
| (−)-1-(3-(5-(6-fluoro-1H-indol-3-yl)-3-methyl-1,1-dioxidobenzo[d]isothiazol-2(3H)-yl)pyrrolidin-1-yl)ethanone | 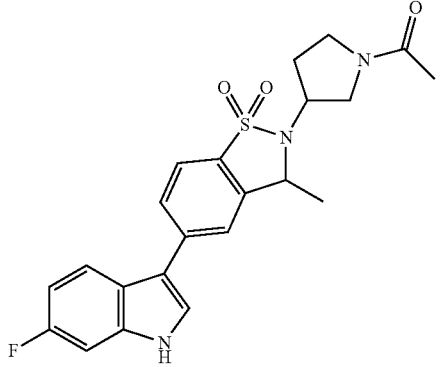 [SMILES: CC(=O)N1CCC(N2C(C)c3cc(-c4c[nH]c5cc(F)ccc45)ccc3S2(=O)=O)C1] |
| (−)-1-(3-(5-(6-fluoro-1H-indol-3-yl)-3-methyl-1,1-dioxidobenzo[d]isothiazol-2(3H)-yl)pyrrolidin-1-yl)ethanone | 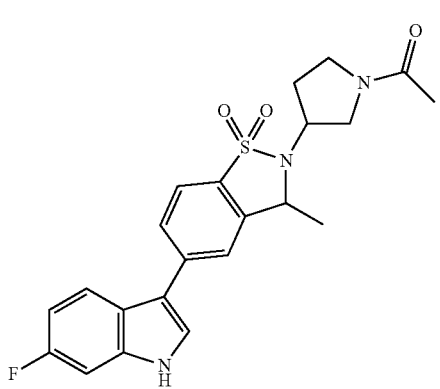 [SMILES: CC(=O)N1CCC(N2C(C)c3cc(-c4c[nH]c5cc(F)ccc45)ccc3S2(=O)=O)C1] |
| (−) 5-(6-fluoro-1H-indol-3-yl)-3-methyl-2-(piperidin-4-ylmethyl)-2,3-dihydrobenzo[d]isothiazole 1,1-dioxide | 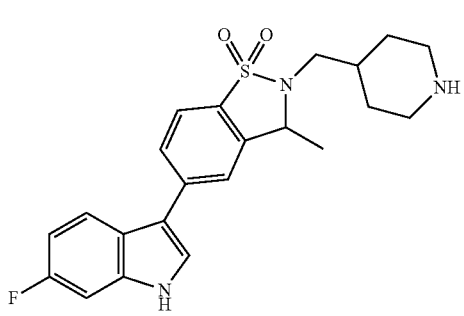 [SMILES: CC1c2cc(-c3c[nH]c4cc(F)ccc34)ccc2S(=O)(=O)N1CC1CCNCC1] |
| (+)-5-(6-fluoro-1H-indol-3-yl)-3-methyl-2-(piperidin-4-ylmethyl)-2,3-dihydrobenzo[d]isothiazole 1,1-dioxide | 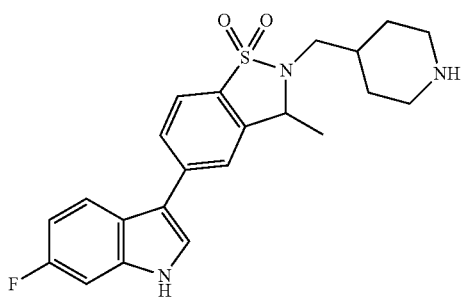 [SMILES: CC1c2cc(-c3c[nH]c4cc(F)ccc34)ccc2S(=O)(=O)N1CC1CCNCC1] |

| Compound-IUPAC name | Structure |
|---|---|
| (−)-5-(6-fluoro-1H-indol-3-yl)-3-methyl-2-((1-methylpiperidin-4-yl)methyl)-2,3-dihydro-benzo[d]isothiazole 1,1-dioxide | 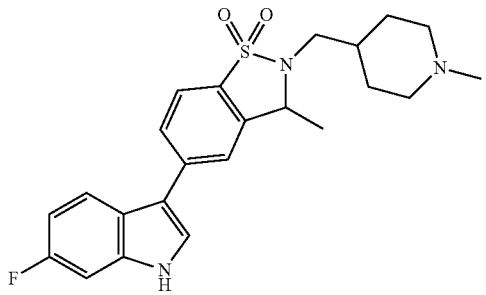 [SMILES: CC1c2cc(-c3c[nH]c4cc(F)ccc34)ccc2S(=O)(=O)N1CC1CCN(C)CC1] |
| (+)-5-(6-fluoro-1H-indol-3-yl)-3-methyl-2-((1-methylpiperidin-4-yl)methyl)-2,3-dihydro-benzo[d]isothiazole 1,1-dioxide | 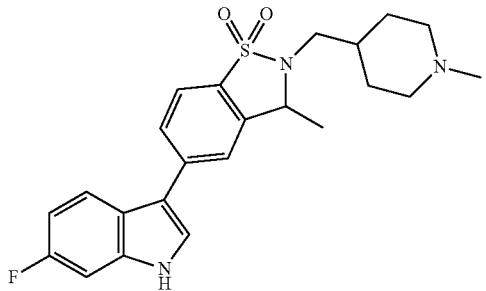 [SMILES: CC1c2cc(-c3c[nH]c4cc(F)ccc34)ccc2S(=O)(=O)N1CC1CCN(C)CC1] |
| (+)-(5S)-5-((5-(6-fluoro-1H-indol-3-yl)-3-methyl-1,1-dioxidobenzo[d]isothiazol-2(3H)-yl)methyl)-5-methylpyrrolidin-2-one | 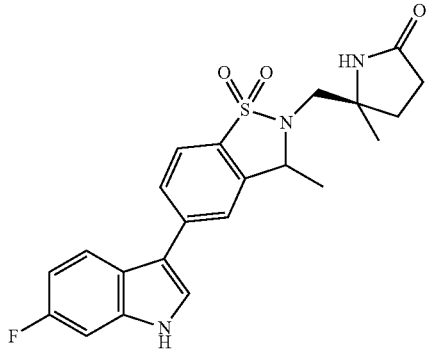 |
| (+)-(5S)-5-((5-(6-fluoro-1H-indol-3-yl)-3-methyl-1,1-dioxidobenzo[d]isothiazol-2(3H)-yl)methyl)-5-methylpyrrolidin-2-one | 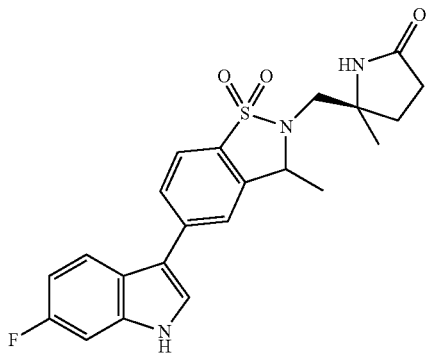 |

| Compound-IUPAC name | Structure |
|---|---|
| (−)-(5R)-5-((5-(6-fluoro-1H-indol-3-yl)-3-methyl-1,1-dioxidobenzo[d]isothiazol-2(3H)-yl)methyl)-5-methylpyrrolidin-2-one | 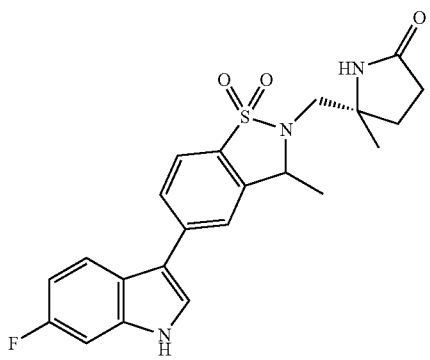 |
| (−)-5-(6-fluoro-1H-indol-3-yl)-3-methyl-2-((1-methyl-1H-1,2,4-triazol-3-yl)methyl)-2,3-dihydrobenzo[d]isothiazole 1,1-dioxide | 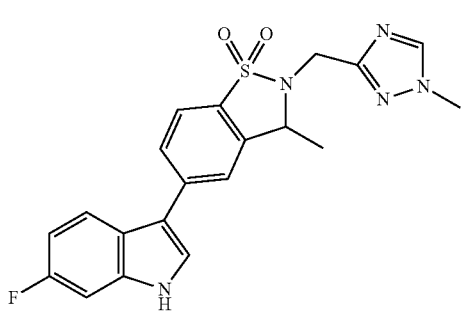 [SMILES: CC1c2cc(-c3c[nH]c4cc(F)ccc34)ccc2S(=O)(=O)N1Cc1ncn(C)n1] |
| (+)-5-(6-fluoro-1H-indol-3-yl)-3-methyl-2-((1-methyl-1H-1,2,4-triazol-3-yl)methyl)-2,3-dihydrobenzo[d]isothiazole 1,1-dioxide | 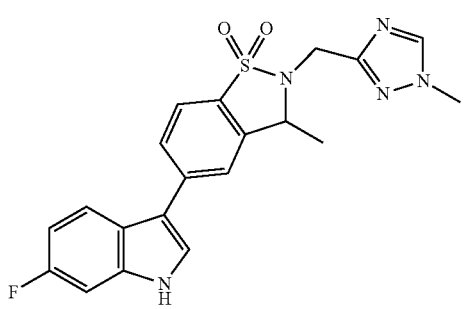 [SMILES: CC1c2cc(-c3c[nH]c4cc(F)ccc34)ccc2S(=O)(=O)N1Cc1ncn(C)n1] |
| :<br>(−)-4-((5-(6-fluoro-1H-indol-3-yl)-3-methyl-1,1-dioxidobenzo[d]isothiazol-2(3H)-yl)methyl)-4-methyloxazolidin-2-one | 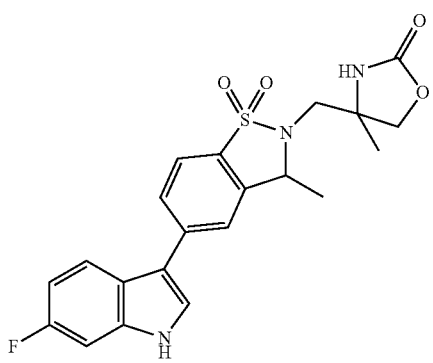 [SMILES: CC1c2cc(-c3c[nH]c4cc(F)ccc34)ccc2S(=O)(=O)N1CC1(C)COC(=O)N1] |

-continued

| Compound-IUPAC name | Structure |
|---|---|
| (+)-4-((5-(6-fluoro-1H-indol-3-yl)-3-methyl-1,1-dioxidobenzo[d]isothiazol-2(3H)-yl)methyl)-4-methyloxazolidin-2-one | 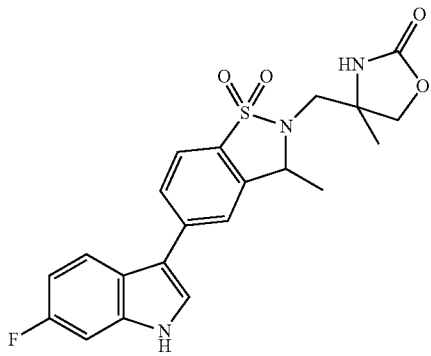 [SMILES: CC1c2cc(-c3c[nH]c4cc(F)ccc34)ccc2S(=O)(=O)N1CC1(C)COC(=O)N1] |
| (+)-4-((5-(6-fluoro-1H-indol-3-yl)-3-methyl-1,1-dioxidobenzo[d]isothiazol-2(3H)-yl)methyl)-4-methyloxazolidin-2-one | 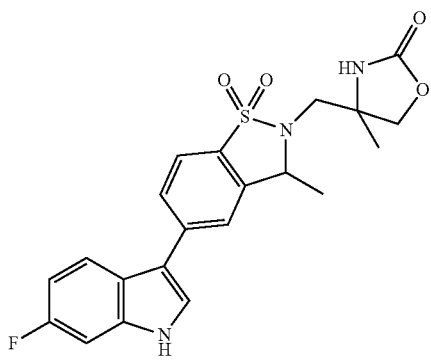 [SMILES: CC1c2cc(-c3c[nH]c4cc(F)ccc34)ccc2S(=O)(=O)N1CC1(C)COC(=O)N1] |
| (−)-2-(azetidin-3-yl)-5-(6-fluoro-1H-indol-3-yl)-3-methyl-2,3-dihydrobenzo[d]isothiazole 1,1-dioxide | 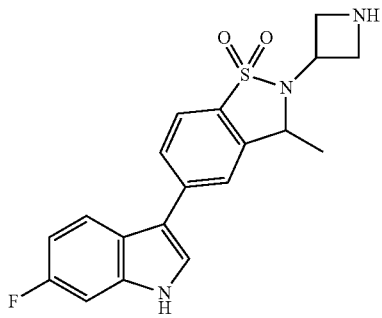 |
| (+)-2-(azetidin-3-yl)-5-(6-fluoro-1H-indol-3-yl)-3-methyl-2,3-dihydrobenzo[d]isothiazole 1,1-dioxide | 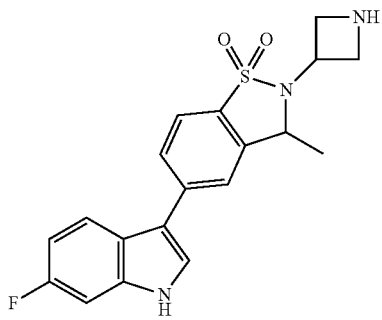 [SMILES: CC1c2cc(-c3c[nH]c4cc(F)ccc34)ccc2S(=O)(=O)N1C1CNC1] |

| Compound-IUPAC name | Structure |
|---|---|
| (−)-2-((R)-2,3-dihydroxypropyl)-5-(6-fluoro-1H-indol-3-yl)-3-methyl-2,3-dihydrobenzo[d]isothiazole 1,1-dioxide | 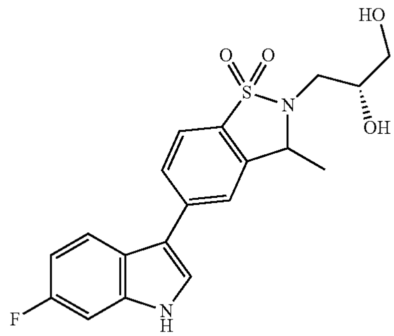 [SMILES: CC1c2cc(-c3c[nH]c4cc(F)ccc34)ccc2S(=O)(=O)N1C[C@@H](O)CO] |
| (+)-2-((R)-2,3-dihydroxypropyl)-5-(6-fluoro-1H-indol-3-yl)-3-methyl-2,3-dihydrobenzo[d]isothiazole 1,1-dioxide | 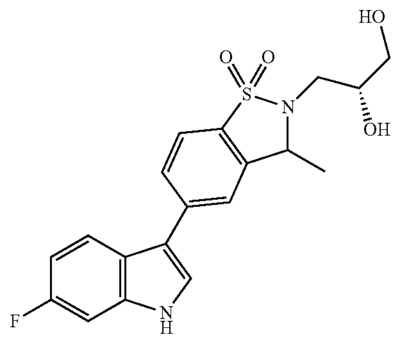 [SMILES: CC1c2cc(-c3c[nH]c4cc(F)ccc34)ccc2S(=O)(=O)N1C[C@@H](O)CO] |
| (−)-2-((S)-2,3-dihydroxypropyl)-5-(6-fluoro-1H-indol-3-yl)-3-methyl-2,3-dihydrobenzo[d]isothiazole 1,1-dioxide | 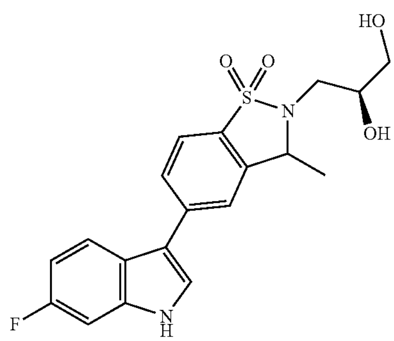 [SMILES: CC1c2cc(-c3c[nH]c4cc(F)ccc34)ccc2S(=O)(=O)N1C[C@H](O)CO] |
| (+)-2-((S)-2,3-dihydroxypropyl)-5-(6-fluoro-1H-indol-3-yl)-3-methyl-2,3-dihydrobenzo[d]isothiazole 1,1-dioxide | 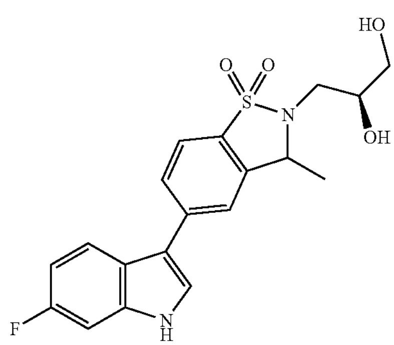 [SMILES: CC1c2cc(-c3c[nH]c4cc(F)ccc34)ccc2S(=O)(=O)N1C[C@H](O)CO] |

| Compound-IUPAC name | Structure |
|---|---|
| (+)-3-(5-(6-fluoro-1H-indol-3-yl)-3-methyl-1,1-dioxidobenzo[d]isothiazol-2(3H)-yl)-2-hydroxy-N-methylpropanamide | 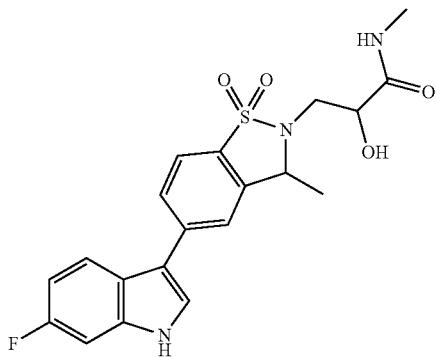 |
| (−)-3-(5-(6-fluoro-1H-indol-3-yl)-3-methyl-1,1-dioxidobenzo[d]isothiazol-2(3H)-yl)-2-hydroxy-N-methylpropanamide | 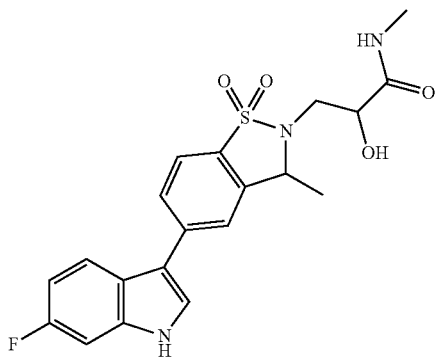 |
| (+)-3-(5-(6-fluoro-1H-indol-3-yl)-3-methyl-1,1-dioxidobenzo[d]isothiazol-2(3H)-yl)-2-hydroxy-N-methylpropanamide | 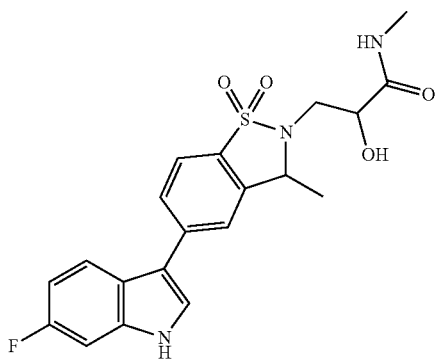 |
| (−)-2-amino-3-(5-(6-fluoro-1H-indol-3-yl)-3-methyl-1,1-dioxidobenzo[d]isothiazol-2(3H)-yl)-N-methylpropanamide | 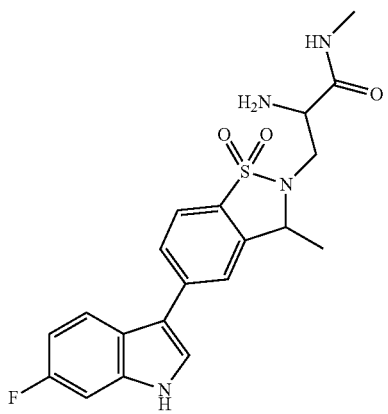 [SMILES: CNC(=O)C(N)CN1C(C)c2cc(-c3c[nH]c4cc(F)ccc34)ccc2S1(=O)=O] |

| Compound-IUPAC name | Structure |
|---|---|
| (+)-2-amino-3-(5-(6-fluoro-1H-indol-3-yl)-3-methyl-1,1-dioxidobenzo[d]isothiazol-2(3H)-yl)-N-methylpropanamide | 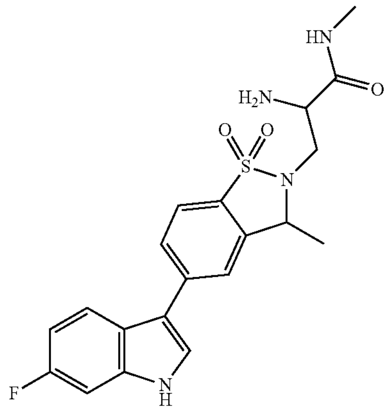 [SMILES: CNC(=O)C(N)CN1C(C)c2cc(-c3c[nH]c4cc(F)ccc34)ccc2S1(=O)=O] |
| (+)-3-(5-(6-fluoro-1H-indol-3-yl)-3-methyl-1,1-dioxidobenzo[d]isothiazol-2(3H)-yl)-2-methoxy-N-methylpropanamide | 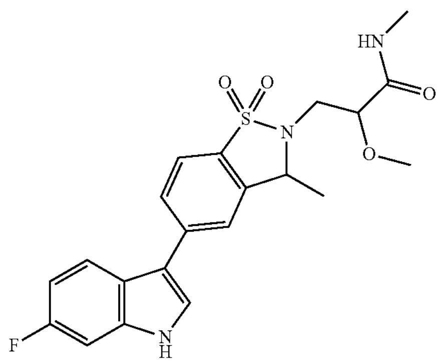 |
| (−)-3-(5-(6-fluoro-1H-indol-3-yl)-3-methyl-1,1-dioxidobenzo[d]isothiazol-2(3H)-yl)-2-methoxy-N-methylpropanamide | 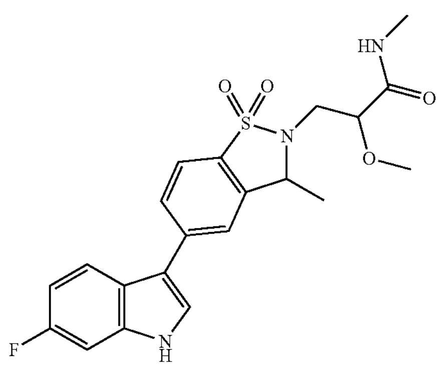 |
| (−)-ethyl (2-(5-(6-fluoro-1H-indol-3-yl)-3-methyl-1,1-dioxidobenzo[d]isothiazol-2(3H)-yl)ethyl)carbamate | 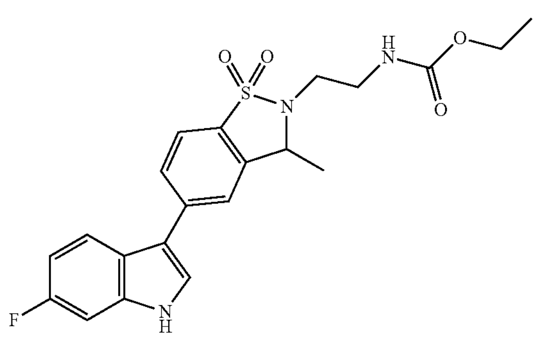 [SMILES: CCOC(=O)NCCN1C(C)c2cc(-c3c[nH]c4cc(F)ccc34)ccc2S1(=O)=O] |

-continued
| Compound-IUPAC name | Structure |
|---|---|
| (+)-ethyl (2-(5-(6-fluoro-1H-indol-3-yl)-3-methyl-1,1-dioxidobenzo[d]isothiazol-2(3H)-yl)ethyl)carbamate | 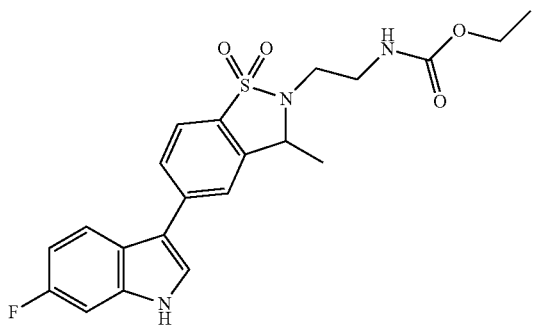 [SMILES: CCOC(=O)NCCN1C(C)c2cc(-c3c[nH]c4cc(F)ccc34)ccc2S1(=O)=O] |
| (−)-2-(5-(6-fluoro-1H-indol-3-yl)-3-methyl-1,1-dioxidobenzo[d]isothiazol-2(3H)-yl)-N-methylacetamide | 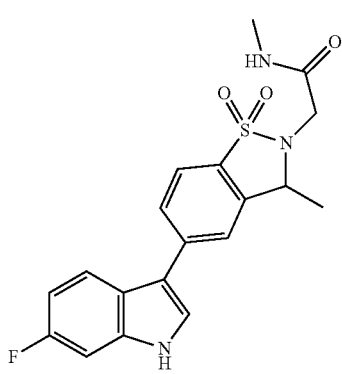 [SMILES: CNC(=O)CN1C(C)c2cc(-c3c[nH]c4cc(F)ccc34)ccc2S1(=O)=O] |
| (+)-2-(5-(6-fluoro-1H-indol-3-yl)-3-methyl-1,1-dioxidobenzo[d]isothiazol-2(3H)-yl)-Nmethylacetamide | 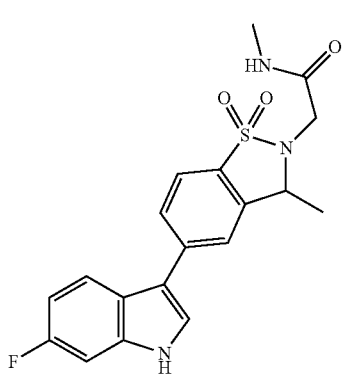 [SMILES: CNC(=O)CN1C(C)c2cc(-c3c[nH]c4cc(F)ccc34)ccc2S1(=O)=O] |
| (−)-2-(5-(6-fluoro-1H-indol-3-yl)-3-methyl-1,1-dioxido-benzo[d]isothiazol-2(3H)-yl)-N,N-dimethyl-acetamide | 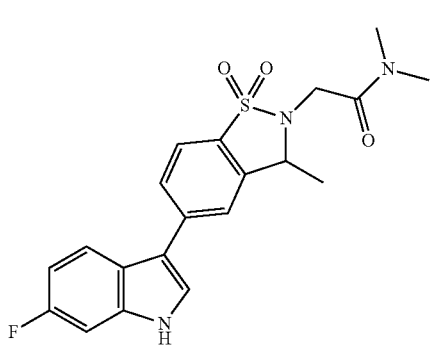 |

| Compound-IUPAC name | Structure |
|---|---|
| (+) 2-(5-(6-fluoro-1H-indol-3-yl)-3-methyl-1,1-dioxidobenzo[d]isothiazol-2(3H)-yl)-N,N-dimethylacetamide | 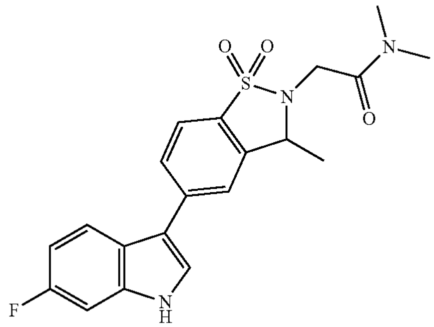 [SMILES: CC1c2cc(-c3c[nH]c4cc(F)ccc34)ccc2S(=O)(=O)N1CC(=O)N(C)C] |
| (+) 2-(5-(6-fluoroindolin-3-yl)-3-methyl-1,1-dioxidobenzo[d]isothiazol-2(3H)-yl)acetamide | |
| (−)-2-(5-(6-fluoroindolin-3-yl)-3-methyl-1,1-dioxidobenzo[d]isothiazol-2(3H)-yl)acetamide | 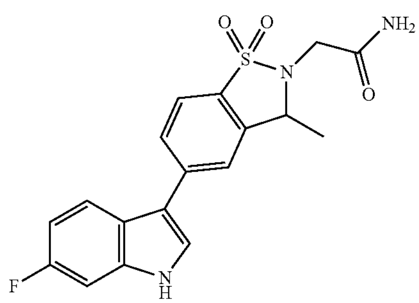 [SMILES: CC1c2cc(-c3c[nH]c4cc(F)ccc34)ccc2S(=O)(=O)N1CC(N)=O] |
| (−)-5-(6-fluoro-1H-indol-3-yl)-3-methyl-2-(2-morpholinoethyl)-2,3-dihydrobenzo[d]isothiazole 1,1-dioxide | 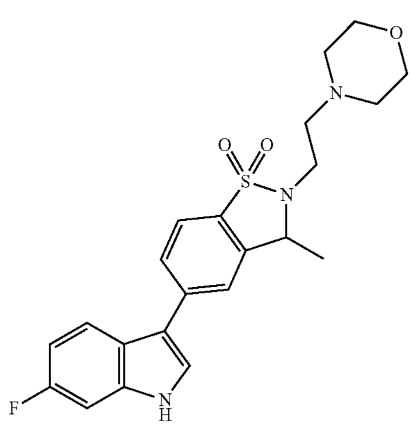 [SMILES: CC1c2cc(-c3c[nH]c4cc(F)ccc34)ccc2S(=O)(=O)N1CCN1CCOCC1] |

| Compound-IUPAC name | Structure |
|---|---|
| (+)-5-(6-fluoro-1H-indol-3-yl)-3-methyl-2-(2-morpholinoethyl)-2,3-dihydrobenzo[d]isothiazole 1,1-dioxide | 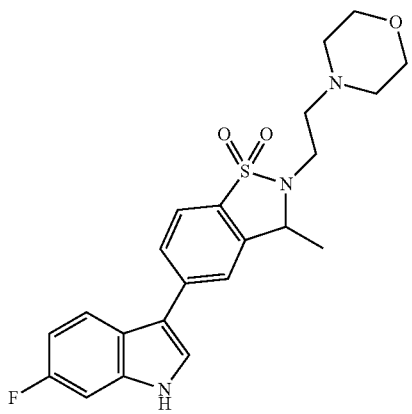 [SMILES: CC1c2cc(-c3c[nH]c4cc(F)ccc34)ccc2S(=O)(=O)N1CCN1CCOCC1] |
| (−)-4-(-5-(6-fluoro-1H-indol-3-yl)-3-methyl-1,1-dioxidobenzo[d]isothiazol-2(3H)-yl)piperidin-2-one | 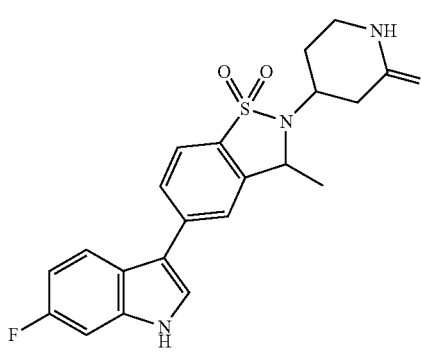 |
| (+)-4-((S)-5-(6-fluoro-1H-indol-3-yl)-3-methyl-1,1-dioxidobenzo[d]isothiazol-2(3H)-yl)piperidin-2-one | 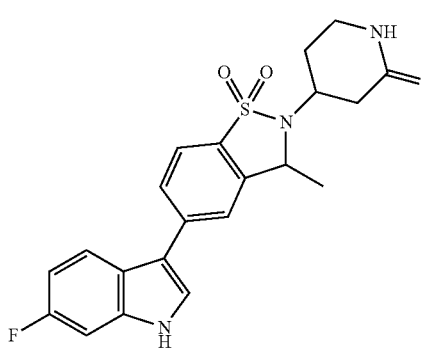 |
| (+)4-(5-(6-fluoro-1H-indol-3-yl)-3-methyl-1,1-dioxidobenzo[d]isothiazol-2(3H)-yl)pyrrolidin-2-one | 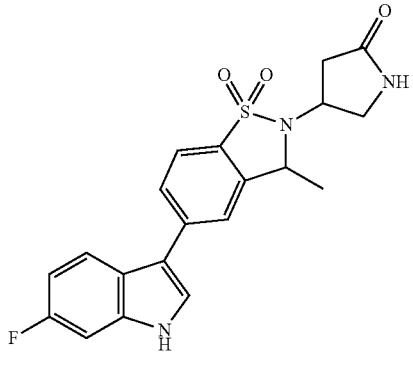 [SMILES: CC1c2cc(-c3c[nH]c4cc(F)ccc34)ccc2S(=O)(=O)N1C1CNC(=O)C1] |

| Compound-IUPAC name | Structure |
|---|---|
| (−)-4-(5-(6-fluoro-1H-indol-3-yl)-3-methyl-1,1-dioxidobenzo[d]isothiazol-2(3H)-yl)pyrrolidin-2-one | |
| (−)-2-(5-(6-fluoro-1H-indol-3-yl)-3-(hydroxymethyl)-1,1-dioxidobenzo[d]isothiazol-2(3H)-yl)-N-methylacetamide | |
| (+)-2-(5-(6-fluoro-1H-indol-3-yl)-3-(hydroxymethyl)-1,1-dioxidobenzo[d]isothiazol-2(3H)-yl)-N-methylacetamide | |
| (−)-5-(6-fluoro-1H-indol-3-yl)-3-(hydroxymethyl)-2-((1-methyl-1H-1,2,4-triazol-3-yl)methyl)-2,3-dihydrobenzo[d]isothiazole 1,1-dioxide | |

| Compound-IUPAC name | Structure |
|---|---|
| (+)-5-(6-fluoro-1H-indol-3-yl)-3-(hydroxymethyl)-2-((1-methyl-1H-1,2,4-triazol-3-yl)methyl)-2,3-dihydrobenzo[d]isothiazole 1,1-dioxide | 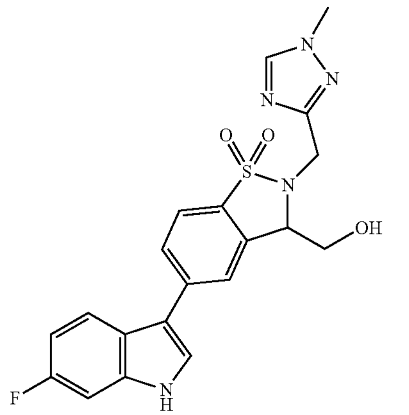 [SMILES: Cn1cnc(CN2C(CO)c3cc(-c4c[nH]c5cc(F)ccc45)ccc3S2(=O)=O)n1] |
| (+)-5-(6-fluoro-1H-indol-3-yl)-2-(2-hydroxyethyl)-3-(hydroxymethyl)-2,3-dihydrobenzo[d]isothiazole 1,1-dioxide | 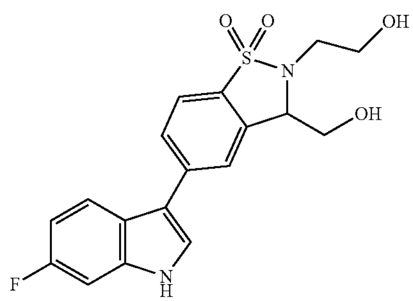 [SMILES: O=S1(=O)c2ccc(-c3c[nH]c4cc(F)ccc34)cc2C(CO)N1CCO] |
| (−)-5-(6-fluoro-1H-indol-3-yl)-2-(2-hydroxyethyl)-3-(hydroxymethyl)-2,3-dihydrobenzo[d]isothiazole 1,1-dioxide | 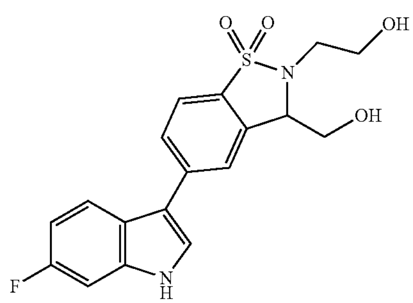 [SMILES: O=S1(=O)c2ccc(-c3c[nH]c4cc(F)ccc34)cc2C(CO)N1CCO] |
| (−)-5-(2-(5-(6-fluoro-1H-indol-3-yl)-3-methyl-1,1-dioxidobenzo[d]isothiazol-2(3H)-yl)ethyl)-1,3,4-oxadiazol-2(3H)-one | 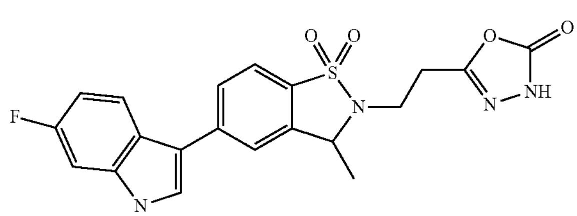 [SMILES: CC1c2cc(-c3c[nH]c4cc(F)ccc34)ccc2S(=O)(=O)N1CCc1n[nH]c(=O)o1] |
| (+)-5-(2-(5-(6-fluoro-1H-indol-3-yl)-3-methyl-1,1-dioxidobenzo[d]isothiazol-2(3H)-yl)ethyl)-1,3,4-oxadiazol-2(3H)-one | 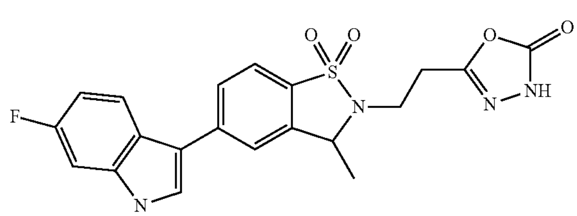 [SMILES: CC1c2cc(-c3c[nH]c4cc(F)ccc34)ccc2S(=O)(=O)N1CCc1n[nH]c(=O)o1] |

| Compound-IUPAC name | Structure |
|---|---|
| 5-(6-fluoro-1H-indol-3-yl)-3-methylbenzo[d]isothiazole 1,1-dioxide | 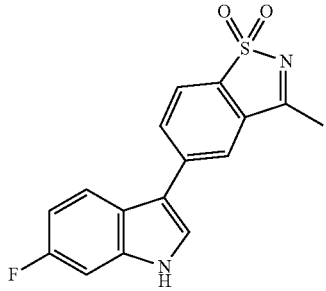 [SMILES: CC1=NS(=O)(=O)c2ccc(-c3c[nH]c4cc(F)ccc34)cc21] |
| 5-(6-fluoro-1H-indol-3-yl)-2H-spiro[benzo[d]isothiazole-3,1'-cyclopropane] 1,1-dioxide | 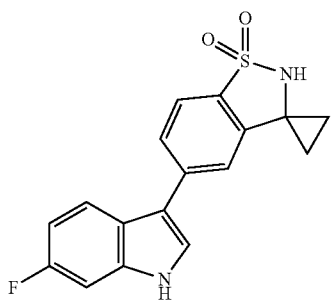 [SMILES: O=S1(=O)NC2(CC2)c2cc(-c3c[nH]c4cc(F)ccc34)ccc21] |
| 5-(6-fluoro-1H-indol-3-yl)-3-((methylamino)methyl)-2,3-dihydrobenzo[d]isothiazole 1,1-dioxide | 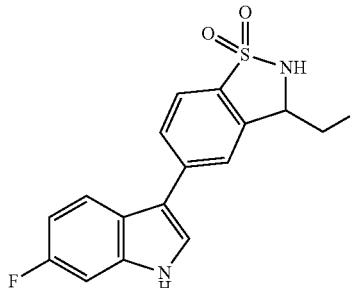 |
| (+)-5-(6-fluoro-1H-indol-3-yl)-3-((methylamino)methyl)-2,3-dihydrobenzo[d]isothiazole 1,1-dioxide | 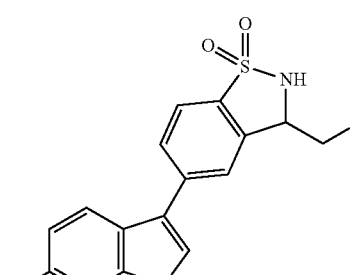 |
| (−)-N-((5-(6-fluoro-1H-indol-3-yl)-1,1-dioxido-2,3-dihydrobenzo[d]isothiazol-3-yl)methyl)methanesulfonamide | 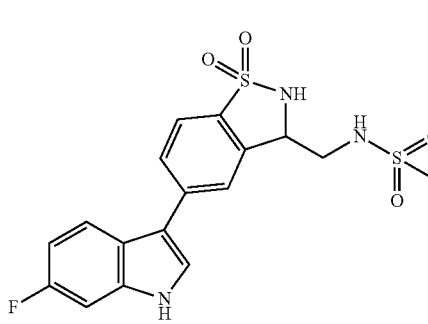 |

-continued

| Compound-IUPAC name | Structure |
|---|---|
| (+)-N-((5-(6-fluoro-1H-indol-3-yl)-1,1-dioxido-2,3-dihydrobenzo[d]isothiazol-3-yl)methyl)methanesulfonamide | 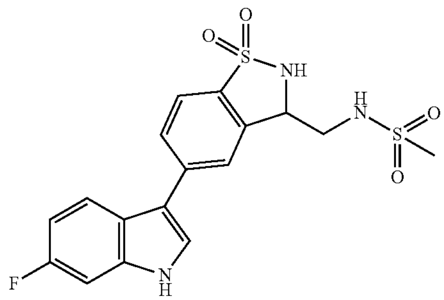 [SMILES: CS(=O)(=O)NCC1NS(=O)(=O)c2ccc(-c3c[nH]c4cc(F)ccc34)cc21] |
| 3-((2-(2,2-difluoroethyl)-4-(6-fluoro-1H-indol-3-yl)phenyl)sulfonamido)propanamide | 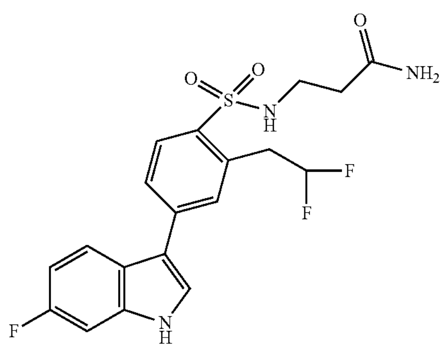 [SMILES: NC(=O)CCNS(=O)(=O)c1ccc(-c2c[nH]c3cc(F)ccc23)cc1CC(F)F] |
| (−)-2-(2,3-dihydroxypropyl)-5-(6-fluoro-1H-indol-3-yl)-3-(hydroxymethyl)-2,3-dihydro-benzo[d]isothiazole 1,1-dioxide | |
| (−)-2-(2,3-dihydroxypropyl)-5-(6-fluoro-1H-indol-3-yl)-3-(hydroxymethyl)-2,3-dihydro-benzo[d]isothiazole 1,1-dioxide | |

-continued

| Compound-IUPAC name | Structure |
|---|---|
| (+)-2-(2,3-dihydroxypropyl)-5-(6-fluoro-1H-indol-3-yl)-3-(hydroxymethyl)-2,3-dihydro-benzo[d]isothiazole 1,1-dioxide | 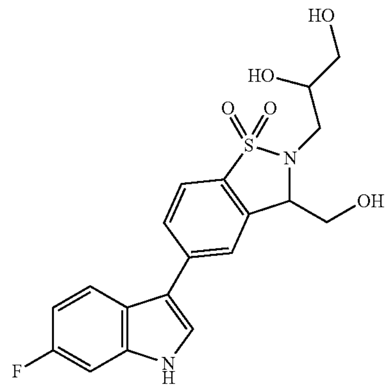 [SMILES: O=S1(=O)c2ccc(-c3c[nH]c4cc(F)ccc34)cc2C(CO)N1CC(O)CO] |
| (−)-2-(5-(6-fluoro-1H-indol-3-yl)-3-methyl-1,1-dioxidobenzo[d]isothiazol-2(3H)-yl)-N-methylpropanamide | 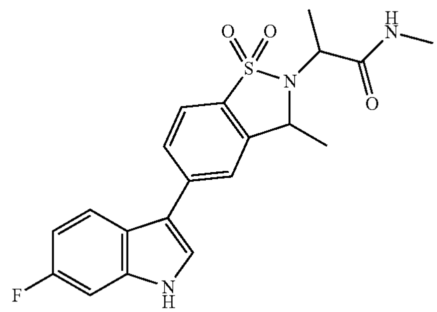 [SMILES: CNC(=O)C(C)N1C(C)c2cc(-c3c[nH]c4cc(F)ccc34)ccc2S1(=O)=O] |
| (+)-2-(5-(6-fluoro-1H-indol-3-yl)-3-methyl-1,1-dioxidobenzo[d]isothiazol-2(3H)-yl)-N-methylpropanamide | 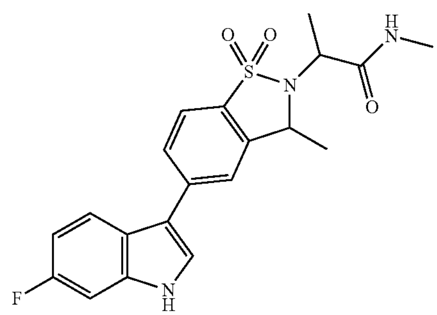 [SMILES: CNC(=O)C(C)N1C(C)c2cc(-c3c[nH]c4cc(F)ccc34)ccc2S1(=O)=O] |
| 2-(5-(6-fluoro-1H-indol-3-yl)-3-methyl-1,1-dioxidobenzo[d]isothiazol-2(3H)-yl)-N-methylpropanamide | 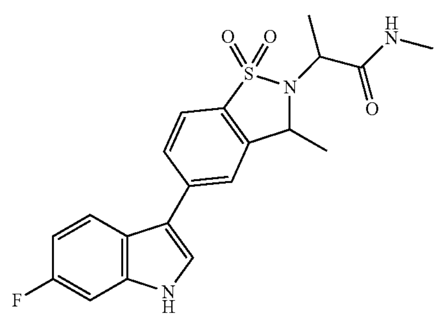 [SMILES: CNC(=O)C(C)N1C(C)c2cc(-c3c[nH]c4cc(F)ccc34)ccc2S1(=O)=O] |

| Compound-IUPAC name | Structure |
| --- | --- |
| (−)-2-(5-(6-fluoro-1H-indol-3-yl)-3-methyl-1,1-dioxidobenzo[d]isothiazol-2(3H)-yl)-N-methylpropanamide | 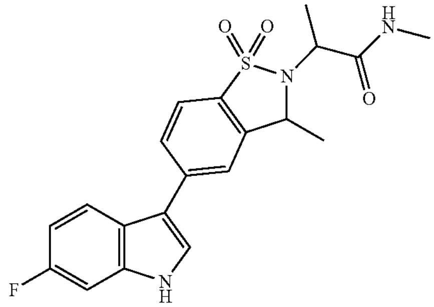 [SMILES: CNC(=O)C(C)N1C(C)c2cc(-c3c[nH]c4cc(F)ccc34)ccc2S1(=O)=O] |
| 5-(6-fluoro-1H-indol-3-yl)-3-methyl-2-(pyridin-2-ylmethyl)-2,3-dihydrobenzo[d]isothiazole 1,1-dioxide | 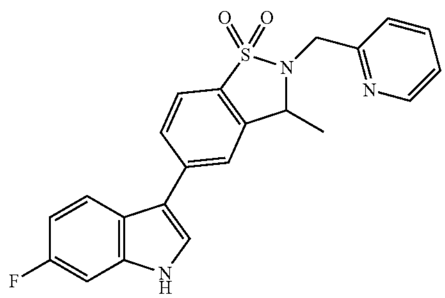 [SMILES: CC1c2cc(-c3c[nH]c4cc(F)ccc34)ccc2S(=O)(=O)N1Cc1ccccn1] |
| 5-(6-fluoro-1H-indol-3-yl)-3-methyl-2-((6-methylpyridin-2-yl)methyl)-2,3-dihydrobenzo[d]isothiazole 1,1-dioxide | 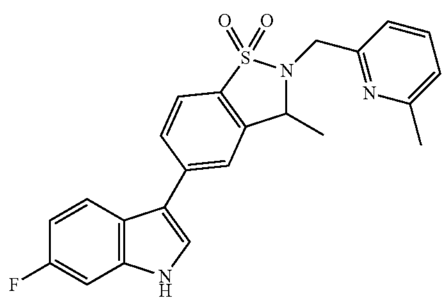 [SMILES: Cc1cccc(CN2C(C)c3cc(-c4c[nH]c5cc(F)ccc45)ccc3S2(=O)=O)n1] |
| (R)-5-(6-fluoro-1H-indol-3-yl)-3-methyl-2-(pyridin-2-ylmethyl)-2,3-dihydrobenzo[d]isothiazole 1,1-dioxide | 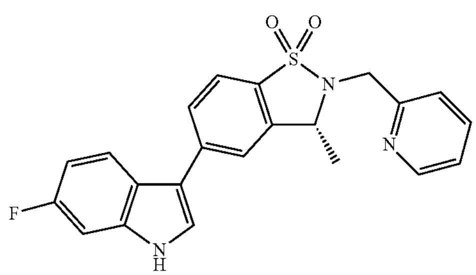 [SMILES: C[C@@H]1c2cc(-c3c[nH]c4cc(F)ccc34)ccc2S(=O)(=O)N1Cc1ccccn1] |
| (R)-5-(6-fluoro-1H-indol-3-yl)-3-methyl-2-((6-methylpyridin-2-yl)methyl)-2,3-dihydrobenzo[d]isothiazole 1,1-dioxide | 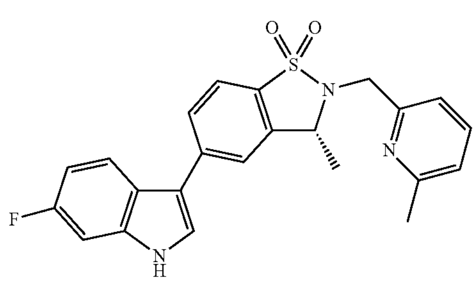 [SMILES: Cc1cccc(CN2[C@H](C)c3cc(-c4c[nH]c5cc(F)ccc45)ccc3S2(=O)=O)n1] |

| Compound-IUPAC name | Structure |
|---|---|
| (R)-5-(6-fluoro-1H-indol-3-yl)-3-methyl-2-((2-methyl-2H-tetrazol-5-yl)methyl)-2,3-dihydrobenzo[d]isothiazole 1,1-dioxide | 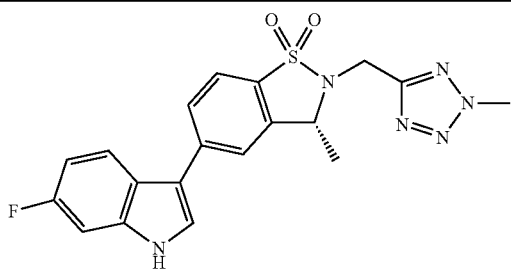 | or pharmaceutically acceptable enantiomers, salts and solvates thereof. In one embodiment, a compound which is an enantiomer is selected. In another embodiment, a compound which is a salt is selected. In further embodiment, a compound which is a solvate is selected. In still another embodiment, a compound of Table 1, Formula I (or its subformulae) is selected which is a free base (non-salt). Also encompassed herein are salts of the given Formulae, salts of enantiomers, and solvates of such salts.

The compounds of Table 1 were named using ChemBioDraw® Ultra version 12.0 (PerkinElmer).

The compounds of Formula I and subformulae thereof may contain an asymmetric center and thus may exist as different stereoisomeric forms. Accordingly, the present invention includes all possible stereoisomers and includes not only racemic compounds but the individual enantiomers and their non-racemic mixtures as well. When a compound is desired as a single enantiomer, such may be obtained by stereospecific synthesis, by resolution of the final product or any convenient intermediate, or by chiral chromatographic methods as each are known in the art. Resolution of the final product, an intermediate, or a starting material may be performed by any suitable method known in the art.

The compounds of the invention may be in the form of "pharmaceutically acceptable salts". Pharmaceutically acceptable salts of the compounds of Formula I include the acid addition and base salts thereof. Suitable acid addition salts are formed from acids which form non-toxic salts. Examples include the acetate, lactobionate, benzenesulfonate, laurate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mandalate, bitartrate, methylbromide, bromide, methylnitrate, calcium edetate, mucate, napsylate, chloride, clavulanate, Butyl(N) oleate, edetate, estolate, pantothenate, polygalacuronate, salicylate, glutamate, glycollylarsanilate, sulfate, hexylrosorcinate, subacetate, hydrabamine, hydroxynaphthaloate, etolate, triethiodide, valerate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminum, arginine, benzathine, calcium, choline, diethylamine, diolamine, glycine, lysine, magnesium, meglumine, olamine, ornithine, N,N-dibenzyethelenediamine, piperazine, tris(hydroxymethyl)aminomethane, tetramethylammonium hydroxide, methylglucamine, ammonium salt, potassium, sodium, tromethamine, 2-(diethylamino)ethanol, ethanolamine, morpholine, 4-(2-hydroxyethyl)-morpholine and zinc salts. Hemisalts of acids and bases may also be formed, for example, hemisulphate and hemicalcium salts. Preferred, pharmaceutically acceptable salts include hydrochloride/chloride, hydrobromide/bromide, bisulphate/sulphate, nitrate, citrate, and acetate.

When the compounds of the invention contain an acidic group as well as a basic group the compounds of the invention may also form internal salts, and such compounds are within the scope of the invention. When the compounds of the invention contain a hydrogen-donating heteroatom (e.g. NH), the invention also covers salts and/or isomers formed by transfer of said hydrogen atom to a basic group or atom within the molecule.

Pharmaceutically acceptable salts of compounds of Formula I may be prepared by one or more of these methods:

(i) by reacting the compound of Formula I with the desired acid;

(ii) by reacting the compound of Formula I with the desired base;

(iii) by removing an acid- or base-labile protecting group from a suitable precursor of the compound of Formula I or by ring-opening a suitable cyclic precursor, for example, a lactone or lactam, using the desired acid; or (iv) by converting one salt of the compound of Formula I to another by reaction with an appropriate acid or by means of a suitable ion exchange column.

All these reactions are typically carried out in solution. The salt, may precipitate from solution and be collected by filtration or may be recovered by evaporation of the solvent. The degree of ionization in the salt may vary from completely ionized to almost non-ionized.

The compounds of the present invention may be administered in the form of pharmaceutically acceptable salts, which are as defined above. These salts may be prepared by standard procedures, e.g. by reacting a free acid with a suitable organic or inorganic base. Where a basic group is present, such as amino, an acidic salt, i.e. hydrochloride, hydrobromide, acetate, palmoate, and the like, can be used as the dosage form.

Also, in the case of an alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

Process for Manufacturing

The compounds of Formula I can be prepared by different ways with reactions known to a person skilled in the art.

The invention further relates to a first process for manufacturing of compounds of Formula I

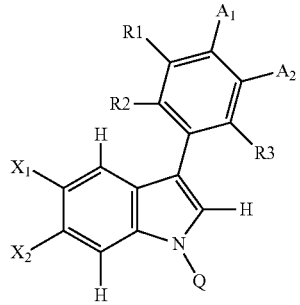

and pharmaceutically acceptable enantiomers, salts and solvates thereof, wherein $X^1$, $X^2$, $R^1$, $R^2$, $R^3$, $A^1$, $A^2$ and Q are as defined in Formula I;
comprising:
(a1) reacting a compound of Formula (i)

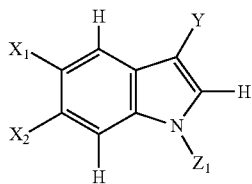

wherein
$X^1$ and $X^2$ are as defined in Formula I;
$Z^1$ represents Q or an amino protecting group such as for example an arylsulphonyl, a tert-butoxy carbonyl, a methoxymethyl, a para-methoxy benzyl, a benzyl or any other suitable protecting group known to those skilled in the art
Y represents an halogen (preferably iodine, bromine or chlorine), an alkylsulfonyloxy having 1-6 carbon atoms (preferably methylsulfonyloxy or trifluoromethylsulfonyloxy) or arylsulfonyloxy having 6-10 carbon atoms (preferably phenyl- or p-tolylsulfonyloxy), or any leaving group known to those skilled in the art
with a compound of Formula (ii)

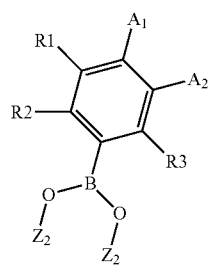

wherein
$R^1$, $R^2$, $R^3$, $A^1$, $A^2$ and $A^3$ are as defined in Formula I;
$Z^2$ and $Z^3$ represent H or alkyl groups, with the possibility for $Z^2$ and $Z^3$ to form a ring;

so as to obtain a compound of Formula (iii),

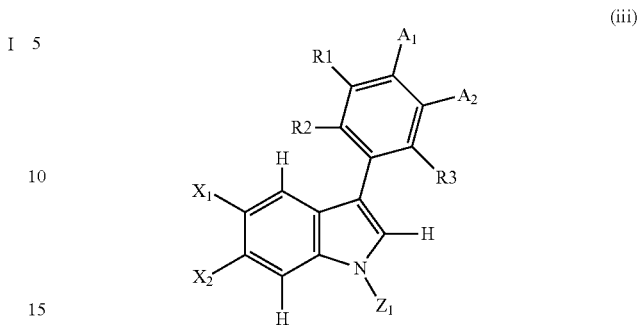

wherein $X^1$, $X^2$, $R^1$, $R^2$, $R^3$, $A^1$, $A^2$ and $Z^1$ are as defined above;
and
(b1) in the case wherein $Z^1$ is not Q, deprotecting the indole amine of compound of Formula (iii), to afford compound of Formula I.

According to one embodiment, step (a1) may be performed with or without a catalyst such as but not limited to $Pd_2(dba)_3$, $Pd(PPh_3)_4$, dichlorobis-(triphenylphosphine)palladium(II) or 1,1'-bis(diphenylphosphino)ferrocene-dichloro palladium(II), $Pd(OAc)_2$, or Pd/C in the presence or absence of an additional ligand, such as but not limited to X-Phos, S-Phos, $P(oTol)_3$, $PPh_3$, BINAP, $P(tBu)_3$ or any other suitable phosphine ligand known to those skilled in the art.

According to one embodiment, step (a1) may be performed in the presence of bases such as but not limited to $K_3PO_4$, $K_2CO_3$, $Na_2CO_3$.

According to one embodiment, step (a1) may be performed in the presence of a suitable solvent such as but not limited to dioxane, THF, DMF, water or mixtures thereof, preferably in a mixture of dioxane or THF and water.

According to one embodiment, step (a1) may be performed at a temperature ranging from 20° C. to about 180° C., with or without microwave irradiation, for a period ranging from 10 minutes to a few hours, e.g. 10 minutes to 24 h.

According to one embodiment, the deprotection (b1) may be performed, depending on the nature of the group $Z^1$, by treatment with bases, such as but not limited to sodium hydroxide, potassium hydroxide, potassium carbonate. According to one embodiment, the deprotection may be performed in the presence or absence of a suitable solvent such as but not limited to methanol, ethanol, isopropanol, tert-butanol, THF, DMF, Dioxane, water or a mixture thereof. According to one embodiment, the deprotection may be performed at a temperature ranging from 20° C. to 100° C., preferably at about 85° C., for a few hours, e.g. one hour to 24 h.

According to an alternative embodiment, the deprotection (b1) may be performed, depending on the nature of the group $Z^1$ in the presence of strong acids, such as but not limited to HCl, TFA, HF, HBr. According to one embodiment, the deprotection may be performed in the presence or absence of a suitable solvent such as methanol, ethanol, isopropanol, tert-butanol, THF, DMF, Dioxane, water or a mixture thereof. According to one embodiment, the deprotection may be performed at a temperature between about 20° C. to about 100° C., for a period comprised between 10 minutes and a few hours, e.g. 10 minutes to 24 h.

Also provided is a second process of manufacturing of compounds of Formula I

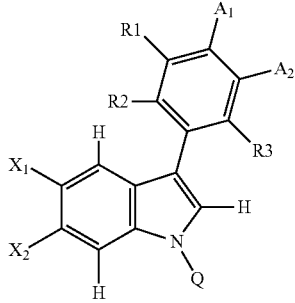

and pharmaceutically acceptable enantiomers, salts and solvates thereof, wherein $X^1$, $X^2$, $R^1$, $R^2$, $R^3$, $A^1$, $A^2$ and Q are as defined in Formula I;
comprising:
(a2) reacting a compound of Formula (iv)

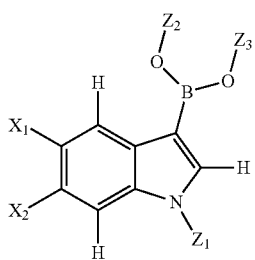

wherein
$X^1$ and $X^2$ are as defined in Formula I;
$Z^1$ represents Q or an amino protecting group such as for example an arylsulphonyl, a tert-butoxy carbonyl, a methoxymethyl, a para-methoxy benzyl, a benzyl or any other suitable protecting group known to those skilled in the art
$Z^2$ and $Z^3$ represent H or alkyl groups, with the possibility for $Z^2$ and $Z^3$ to form a ring;
with a compound of Formula (v)

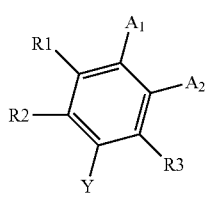

wherein
$R^1$, $R^2$, $R^3$, $A^1$ and $A^2$ are as defined in Formula I;
Y represents an halogen (preferably iodine, bromine or chlorine), an alkylsulfonyloxy having 1-6 carbon atoms (preferably methylsulfonyloxy or trifluoromethylsulfonyloxy) or arylsulfonyloxy having 6-10 carbon atoms (preferably phenyl- or p-tolylsulfonyloxy), or any leaving group known to those skilled in the art so as to obtain a compound of Formula (vi),

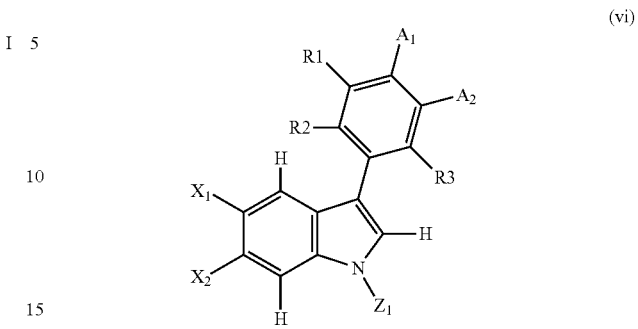

wherein $X^1$, $X^2$, $R^1$, $R^2$, $R^3$, $A^1$, $A^2$ and $Z^1$ are as defined above;
and
(b2) in the case wherein $Z^1$ is not Q, deprotecting the indole amine of compound of Formula (xii), to afford compound of Formula I (or its subformulae).

According to one embodiment, step (a2) may be performed with or without a catalyst such as but not limited to $Pd_2(dba)_3$, $Pd(PPh_3)_4$, dichlorobis-(triphenylphosphine)palladium(II) or 1,1'-bis(diphenylphosphino)ferrocene-dichloro palladium(II), $Pd(OAc)_2$, or Pd/C in the presence or absence of an additional ligand, such as but not limited to X-Phos, S-Phos, $P(oTol)_3$, $PPh_3$, BINAP, $P(tBu)_3$ or any other suitable phosphine ligand known to those skilled in the art.

According to one embodiment, step (a2) may be performed in the presence of bases such as but not limited to $K_3PO_4$, $K_2CO_3$, $Na_2CO_3$.

According to one embodiment, step (a2) may be performed in the presence of a suitable solvent such as but not limited to dioxane, THF, DMF, water or mixtures thereof, preferably in a mixture of dioxane or THF and water.

According to one embodiment, step (a2) may be performed at a temperature ranging from 20° C. to about 180° C., with or without microwave irradiation, for a period ranging from 10 minutes to a few hours, e.g. 10 minutes to 24 h.

According to one embodiment, the deprotection step (b2) may be performed in conditions described above for deprotection (b1).

In general, the synthesis pathways for any individual compound of Formula (I) will depend on the specific substituents of each molecule and upon the ready availability of intermediates necessary; again such factors being appreciated by those of ordinary skill in the art.

According to a further general process, compounds of Formula I can be converted to alternative compounds of Formula I, employing suitable interconversion techniques well known by a person skilled in the art.

Compounds of the Formula I and related formulae can furthermore be obtained by liberating compounds of the Formula I from one of their functional derivatives by treatment with a solvolysing or hydrogenolysing agent.

Preferred starting materials for the solvolysis or hydrogenolysis are those which conform to the Formula I and related formulae, but contain corresponding protected amino and/or hydroxyl groups instead of one or more free amino and/or hydroxyl groups, preferably those which carry an amino-protecting group instead of an H atom bonded to an N atom, in particular those which carry an R*—N group, in which R* denotes an amino-protecting group, instead of an HN group, and/or those which carry a hydroxyl-protecting group instead of the H atom of a hydroxyl group, for example those which conform to the Formula I, but carry a —COOR group, in which R denotes a hydroxyl-protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxy¬carbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC (tert-butoxycarbonyl) and 2-iodoethoxycarbonyl; aralkoxycarbonyl, such as CBZ ("carbobenzoxy"), 4-methoxybenzyloxycarbonyl and FMOC, and arylsulfonyl, such as Mtr. Preferred amino-protecting groups are BOC and Mtr, CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the Formula I and related formulae are liberated from their functional derivatives—depending on the protecting group used—for example strong inorganic acids, such as hydrochloric acid, perchloric acid or sulfuric acid, strong organic carboxylic acids, such as trichloroacetic acid, TFA or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (room temperature).

The BOC, OtBu and Mtr groups can, for example, preferably be cleaved off using TFA in dichloromethane or using approximately 3 to 5N HCl in dioxane at 15–30° C., and the FMOC group can be cleaved off using an approximately 5 to 50% solution of dimethylamine, diethylamine or piperidine in DMF at 15–30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Examples of suitable inert solvents are hydrocarbons, such as hexane, petroleum ether, benzene, toluene or xylene, chlorinated hydrocarbons, such as trichloroethylene, 1,2-dichloroethane, tetrachloromethane, trifluoromethylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane, glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be hydrolysed, for example, using HCl, $H_2SO_4$, or using LiOH, NaOH or KOH in water, water/THF, water/THF/ethanol or water/dioxane, at temperatures between 0 and 100° C.

Free amino groups can furthermore be acylated in a conventional manner using an acyl chloride or anhydride or alkylated using an unsubstituted or substituted alkyl halide, advantageously in an inert solvent, such as dichloromethane or THF and/or in the presence of a base, such as triethylamine or pyridine, at temperatures between −60° C. and +30° C.

For all the protection and deprotection methods, see Philip J. Kocienski, in "Protecting Groups", Georg Thieme Verlag Stuttgart, N.Y., 1994 and, Theodora W. Greene and Peter G. M. Wuts in "Protective Groups in Organic Synthesis", Wiley Interscience, 3rd Edition 1999.

Reaction schemes as described in the example section are illustrative only and should not be construed as limiting the invention in any way.

Applications

A compound of Formula I (inclusive of its subformulae, e.g., Formulae Ia, Ib, and II) or pharmaceutically acceptable enantiomers, salts and solvates are useful as the active ingredient in a pharmaceutical composition or preparation. In one embodiment, a compound is used as a TDO2 inhibitor.

Accordingly, in a particularly preferred embodiment, the compounds of Formula I and subformulae, including without limitation, those of Table 1 above, or pharmaceutically acceptable enantiomers, salts and solvates thereof, are used as TDO2 inhibitors.

Accordingly, in another aspect, these compounds or enantiomers, salts and solvates thereof are used in the synthesis of pharmaceutical active ingredients, such as TDO2 inhibitors.

In one embodiment, compounds of Formula I and subformulae in particular those of Table 1 above, or pharmaceutically acceptable enantiomers, salts and solvates thereof, are used for increasing immune recognition and destruction of the cancer cells.

The compounds of Formula I and subformulae are useful as medicaments, in particular in the prevention and/or treatment of cancer.

In one embodiment, the compounds described herein or pharmaceutically acceptable enantiomers, salts or solvates thereof are for use in the treatment and/or prevention of cancer, neurodegenerative disorders such as Parkinson's disease, Alzheimer's disease and Huntington's disease, chronic viral infections such as HCV and HIV, depression, and obesity.

Also provided is a method for treatment or prevention of cancer, neurodegenerative disorders such as Parkinson's disease, Alzheimer's disease and Huntington's disease, chronic viral infections such as HCV and HIV, depression, and obesity, which comprises administering to a mammalian species in need thereof a therapeutically effective amount of the compound according to the invention or a pharmaceutically acceptable enantiomers, salts or solvates thereof.

Various cancers are known in the art. The cancer may be metastatic or non-metastatic. The cancer may be may be familial or sporadic. In some embodiments, the cancer is selected from the group consisting of: leukemia and multiple myeloma. Additional cancers that can be treated using the methods of the invention include, for example, benign and malignant solid tumors and benign and malignant non-solid tumors.

Examples of solid tumors include, but are not limited to: biliary tract cancer, brain cancer (including glioblastomas and medulloblastomas), breast cancer, cervical cancer, choriocarcinoma, colon cancer, endometrial cancer, esophageal cancer, gastric cancer, intraepithelial neoplasms (including Bowen's disease and Paget's disease), liver cancer, lung cancer, neuroblastomas, oral cancer (including squamous cell carcinoma), ovarian cancer (including those arising from epithelial cells, stromal cells, germ cells and mesenchymal cells), pancreatic cancer, prostate cancer, rectal cancer, renal cancer (including adenocarcinoma and Wilms tumour), sarcomas (including leiomyosarcoma, rhabdomyosarcoma, liposarcoma, fibrosarcoma and osteosarcoma), skin cancer (including melanoma, Kaposi's sarcoma, basocellular cancer and squamous cell cancer), testicular cancer including germinal tumors (seminomas, and non-seminomas such as teratomas and choriocarcinomas), stromal tumors, germ cell tumors, and thyroid cancer (including thyroid adenocarcinoma and medullary carcinoma).

Examples of non-solid tumors include but are not limited to hematological neoplasms. As used herein, a hematologic neoplasm is a term of art which includes lymphoid disorders, myeloid disorders, and AIDS associated leukemias.

Lymphoid disorders include but are not limited to acute lymphocytic leukemia and chronic lymphoproliferative disorders (e.g., lymphomas, myelomas, and chronic lymphoid leukemias). Lymphomas include, for example, Hodgkin's disease, non-Hodgkin's lymphoma lymphomas, and lymphocytic lymphomas). Chronic lymphoid leukemias include, for example, T cell chronic lymphoid leukemias and B cell chronic lymphoid leukemias.

The invention also provides for a method for delaying in patient the onset of cancer comprising the administration of a pharmaceutically effective amount of a compound of Formula I or pharmaceutically acceptable enantiomer, salt and solvate thereof to a patient in need thereof.

Preferably, the patient is a warm-blooded animal, more preferably a human.

The compounds of the invention are especially useful in the treatment and/or prevention of cancer.

In a specific embodiment, the compounds of the invention are especially useful in the treatment and/or prevention of cancer.

The invention further provides the use of a compound of Formula I or a pharmaceutically acceptable enantiomer, salt and solvate thereof for the manufacture of a medicament for treating and/or preventing cancer.

According to a further feature of the present invention there is provided a method for modulating TDO2 activity, in a patient, preferably a warm blooded animal, preferably a mammal, and even more preferably a human, in need of such treatment, which comprises administering to said patient an effective amount of compound of the present invention, or a pharmaceutically acceptable enantiomer, salt and solvate thereof.

In a further embodiment, the invention provides use of a compound of Formula I (or a subformulae thereof), or a pharmaceutically acceptable enantiomer, salt or solvate thereof for use in the treatment and/or prevention of cancer. In one embodiment, the cancer is bladder carcinoma. In another embodiment, the cancer is hepatocarcinoma. In a further embodiment, the cancer is melanoma. In another embodiment, the cancer is mesothelioma. In a further embodiment, the cancer is a neuroblastoma. In another embodiment, the cancer is a sarcoma. In a further embodiment, the cancer is breast carcinoma. In still another embodiment, the cancer is leukemia. In a further embodiment, the cancer is a renal cell carcinoma. In a further embodiment, the cancer is a colorectal carcinoma. In still another embodiment, the cancer is head & neck carcinoma. In another embodiment, the cancer is lung carcinoma. In still another embodiment, the cancer is a brain tumor. In a further embodiment, the cancer is a glioblastoma. In still another embodiment, the cancer is an astrocytoma. In a further embodiment, the cancer is a myeloma. In yet another embodiment, the cancer is pancreatic carcinoma.

In another embodiment, the invention provides use of a compound of Formula I (or a subformulae thereof), or a pharmaceutically acceptable enantiomer, salt or solvate thereof for use in the treatment of a neurodegenerative disorder. In one embodiment, the disorder is Parkinson's disease. In another embodiment, the disorder is Alzheimer's disease. In a further embodiment, the disorder is Huntington's disease.

In still another embodiment, use of a compound of Formula I (or a subformulae thereof), or a pharmaceutically acceptable enantiomer, salt or solvate thereof) in the treatment of chronic viral infections such as HCV and HIV is provided.

In another embodiment, use of a compound of Formula I (or a subformulae thereof), or a pharmaceutically acceptable enantiomer, salt or solvate thereof) in the treatment of depression is provided.

In another embodiment, use of a compound of Formula I (or a subformulae thereof), or a pharmaceutically acceptable enantiomer, salt or solvate thereof) in the treatment of obesity is provided.

For use in such treatments, the compounds provided herein may be formulated as follows.

Formulations

The invention also provides pharmaceutical compositions comprising one or more compounds of Formula I and/or a subformula thereof, or a pharmaceutically acceptable enantiomer, salt and solvate thereof and at least one pharmaceutically acceptable carrier, diluent, excipient and/or adjuvant. As indicated above, the invention also covers pharmaceutical compositions which contain, in addition to a compound of the present invention, a pharmaceutically acceptable enantiomer, salt and solvate thereof as active ingredient, additional therapeutic agents and/or active ingredients.

Another object of this invention is a medicament comprising at least one compound of the invention, or a pharmaceutically acceptable enantiomer, salt and solvate thereof, as active ingredient.

According to a further feature of the present invention there is provided the use of a compound of Formula I or a pharmaceutically acceptable enantiomer, salt and solvate thereof for the manufacture of a medicament for modulating TDO2 activity in a patient, in need of such treatment, which comprises administering to said patient an effective amount of compound of the present invention, or a pharmaceutically acceptable enantiomer, salt and solvate thereof.

Generally, for pharmaceutical use, the compounds of the invention may be formulated as a pharmaceutical preparation comprising at least one compound of the invention and at least one pharmaceutically acceptable carrier, diluent, excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in pharmaceutical formulations, such as lubricating agents, wetting agents, emulsifying and suspending agents, dispersing agents, disintegrants, bulking agents, fillers, preserving agents, sweetening agents, flavoring agents, flow regulators, release agents, etc. The compositions may also be formulated so as to provide rapid, sustained or delayed release of the active compound(s) contained therein.

In one embodiment, at least one compound of Formula I, its subformulae, or an enantiomer, salt or solvate thereof, is delivered to a subject in an amount ranging from about 0.01 mg/kg to about 600 mg/kg, or a dose of about 1 mg to about 500 mg. However, higher or lower amounts may be selected, e.g., taking consideration such factors as the indication being treated, and/or the age and weight of the patient.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use.

Depending on the condition to be prevented or treated and the route of administration, the active compound of the invention may be administered as a single daily dose, divided over one or more daily doses, or essentially continuously, e.g. using a drip infusion.

Definitions

As used herein, the following terms have the following meanings:

Where groups may be substituted, such groups may be substituted with one or more substituents, and preferably with one, two or three substituents. Substituents may be selected from but not limited to, for example, the group comprising halogen, hydroxyl, oxo, nitro, amido, carboxy, amino, cyano haloalkoxy, and haloalkyl. In certain embodiments, more than one substituent may be on the same atom of a group (e.g., a dimethyl substitution on a N or C). In other embodiments, other substituents may be selected, such as are described and/or illustrated in the examples.

The term "halogen" means fluoro (F), chloro (Cl), bromo (Br), or iodo (I).

The following definitions are used in connection with the compounds described herein. In general, the number of carbon atoms present in a given group is designated "Cx to Cy", where x and y are the lower and upper limits, respectively. The carbon number as used in the definitions herein refers to carbon backbone and carbon branching, but does not include carbon atoms of the substituents, such as alkoxy substitutions and the like. Unless indicated otherwise, the nomenclature of substituents that are not explicitly defined herein are determined by naming from left to right the terminal portion of the functionality followed by the adjacent functionality toward the point of attachment. As used herein, "optionally substituted" means that at least 1 hydrogen atom of the optionally substituted group has been replaced.

The term "alkyl" by itself or as part of another substituent refers to a hydrocarbyl radical of Formula $C_nH_{2n+1}$ wherein n is a number greater than or equal to 1. Alkyl groups may contain 1 to 10 carbons (inclusive), i.e., C1, C2, C3, C4, C5, C6, C7, C8, C9 or C10, i.e., C1-C10 alkyl. In certain embodiments, alkyl groups of this invention comprise from 1 to 6 carbon atoms, preferably from 1 to 4 carbon atoms, more preferably from 1 to 3 carbon atoms. Alkyl groups may be linear or branched and may be substituted as indicated herein. Suitable alkyl groups include methyl, ethyl, n-propyl, i-propyl, n-butyl, i-butyl, s-butyl and t-butyl, pentyl and its isomers (e.g. n-pentyl, iso-pentyl), and hexyl and its isomers (e.g. n-hexyl, iso-hexyl).

The term "haloalkyl" alone or in combination, refers to an alkyl radical having the meaning as defined above wherein one or more hydrogens are replaced with a halogen as defined above. Non-limiting examples of such haloalkyl radicals include fluoromethyl, difluoromethyl, trifluoro methyl and the like. In one example, the haloalkyl is a C1 to C6 alkyl group substituted with at least one halogen. In another example, the haloalkyl is a C1 to C4 alkyl group substituted with at least one halogen. Each halogen substitution may be independently selected.

The term "cycloalkyl" as used herein is a cyclic alkyl group, that is to say, a monovalent, saturated, or unsaturated hydrocarbyl group having 1 or 2 cyclic structures. Cycloalkyl includes monocyclic or bicyclic hydrocarbyl groups. Cycloalkyl groups may comprise 3 or more carbon atoms in the ring and generally, according to this invention comprise from 3 to 10, more preferably from 3 to 8 carbon atoms still more preferably from 3 to 6 carbon atoms. Examples of cycloalkyl groups include but are not limited to cyclopropyl, cyclobutyl, cyclopentyl, cyclohexyl, with cyclopropyl being particularly preferred.

The term "heteroatom" refers to a sulfur, nitrogen or oxygen atom.

Where at least one carbon atom in a cycloalkyl group is replaced with a heteroatom, the resultant ring is referred to herein as "heterocyclyl".

The terms "heterocyclyl" or "heterocycle" as used herein by itself or as part of another group refer to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen, oxygen and/or sulfur atoms, where the nitrogen and sulfur heteroatoms may optionally be oxidized and the nitrogen heteroatoms may optionally be quaternized. The heterocycle may contain 3 to 7 carbon atoms (inclusive), or an integer therebetween. Any of the carbon atoms of the heterocyclic group may be substituted by oxo (for example piperidone, pyrrolidinone). The heterocyclic group may be attached at any heteroatom or carbon atom of the ring or ring system, where valence allows. The rings of multi-ring heterocycles may be fused, bridged and/or joined through one or more Spiro atoms. In one embodiment, a heterocycle is a 4, 5 or 6 membered ring, with 1, 2 or 3 heteroatoms in its backbone selected from one or more N or O. In one embodiment, the heterocycle is a 5-membered ring having 3 N. As used herein, when the number of heteroatoms is specified, the remaining members of the heterocycle backbone are C atoms. Non limiting exemplary heterocyclic groups include piperidinyl, azetidinyl, tetrahydropyranyl, piperazinyl, imidazolinyl, morpholinyl, oxetanyl, pyrazolidinyl imidazolidinyl, isoxazolinyl, oxazolidinyl, isoxazolidinyl, thiazolidinyl, isothiazolidinyl, indolyl, indolinyl, isoindolinyl, tetrahydrofuranyl, tetrahydroquinolinyl, thiomorpholinyl, thiomorpholinylsulfoxide, thiomorpholinylsulfone, pyrrolizinyl.

The term "aryl" as used herein refers to a polyunsaturated, aromatic hydrocarbyl group having a single ring (i.e. phenyl) or multiple aromatic rings fused together (e.g. naphthyl) or linked covalently, typically containing 5 to 12 atoms; preferably 6 to 10, wherein at least one ring is aromatic. The aromatic ring may optionally include one to two additional rings (either cycloalkyl, heterocyclyl or heteroaryl) fused thereto. Aryl is also intended to include the partially hydrogenated derivatives of the carbocyclic (carbon-containing ring) systems enumerated herein. Non-limiting examples of aryl comprise phenyl, biphenylyl, biphenylenylnaphthalenyl, indenyl.

The term "heteroaryl" as used herein by itself or as part of another group refers but is not limited to 5 to 12 carbon-atom aromatic rings or ring systems containing 1 to 2 rings which are fused together or linked covalently, typically containing 5 to 6 atoms; at least one of which is aromatic, in which one or more carbon atoms in one or more of these rings is replaced by oxygen, nitrogen and/or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: pyridazinyl, pyridinyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyrimidyl, pyrazinyl, oxazinyl, dioxinyl, thiazinyl, triazinyl, indolyl, indolizinyl, isoindolyl, benzofuranyl, isobenzofuranyl, benzothiophenyl, isobenzothiophenyl, indazolyl, benzimidazolyl, quinolinyl, isoquinolinyl, cinnolinyl, quinazolinyl, quinoxalinyl.

The term "arylalkyl" refers to any group -alkyl-aryl. The term "alkylaryl" refers to any group -aryl-alkyl.

The term "heteroarylalkyl" refers to any group -alkyl-heteroaryl. The term "alkylheteroaryl" refers to any group -heteroaryl-alkyl.

The term "alkoxy" refers to any group O-alkyl. The term "haloalkoxy" refers to any group O-haloalkyl.

The term "oxo" refers to a =O moiety.

The term "amino" refers to a —$NH_2$ group or any group derived thereof by substitution of one or two hydrogen atom by an organic aliphatic or aromatic group. Preferably, groups derived from —$NH_2$ are "alkylamino" groups, i.e. N-alkyl groups, comprising monoalkylamino and dialkylamino. Non-limited examples of the term "amino" include $NH_2$, NHMe or $NMe_2$, NHCOOH, $NHCOOCH_3$, $NHCOCH_3$, or N(CH3)COCH3.

The term "amino-protecting group" refers to a protecting group for an amine function. According to a preferred embodiment, the amino-protecting group is selected in the groups comprising: arylsulphonyl, tert-butoxy carbonyl, methoxymethyl, para-methoxy benzyl or benzyl.

The term "leaving group" refers to a molecular fragment that departs with a pair of electrons in heterolytic bond cleavage. According to a preferred embodiment, the leaving group is selected in the groups comprising: halogen, preferably iodine, bromine or chlorine; alkylsulfonyloxy having 1-6 carbon atoms, preferably methylsulfonyloxy or trifluoromethylsulfonyloxy; or arylsulfonyloxy having 6-10 carbon atoms, preferably phenyl- or p-tolylsulfonyloxy.

The term "solvate" is used herein to describe a compound in this invention that contains stoichiometric or sub-stoichiometric amounts of one or more pharmaceutically acceptable solvent molecule, e.g., ethanol. Typically, a solvate does not significantly alter the physiological activity or toxicity of the compounds, and as such may function as pharmacological equivalents to non-solvate compounds of Formula I and its subformula as defined herein. The term "solvate" as used herein is a combination, physical association and/or solvation of a compound of the present invention with a solvent molecule. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. "Solvate" may encompass solvates of salts of the compounds of Formula I.

The term "hydrate" refers to when the solvent molecule is water and may be an inorganic salt containing $nH_2O$, wherein n is the number of water molecules per formula unit of the salt. N may be ½, 1½, or an integer from 1 to 10. A hydrate which has lost water The compounds of the invention include compounds of Formula I as hereinbefore defined, including all polymorphs and crystal habits thereof, prodrugs and prodrugs thereof and isotopically-labeled compounds of Formula I.

The invention also generally covers all pharmaceutically acceptable predrugs and prodrugs of the compounds of Formula I.

The term "prodrug" as used herein means the pharmacologically acceptable derivatives of compounds of Formula I, such as for example esters, whose in vivo biotransformation product generates the biologically active drug. Prodrugs are generally characterized by increased bio-availability and are readily metabolized into biologically active compounds in vivo.

The term "predrug", as used herein, means any compound that will be modified to form a drug species, wherein the modification may take place either inside or outside of the body, and either before or after the predrug reaches the area of the body where administration of the drug is indicated.

The term "patient" refers to a warm-blooded animal, more preferably a human, who/which is awaiting the receipt of, or is receiving medical care or is/will be the object of a medical procedure.

The term "human" refers to a subject of both genders and at any stage of development (i.e. neonate, infant, juvenile, adolescent, adult).

The terms "treat", "treating" and "treatment", as used herein, are meant to include alleviating, attenuating or abrogating a condition or disease and/or its attendant symptoms.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "therapeutically effective amount" (or more simply an "effective amount") as used herein means the amount of active agent or active ingredient that is sufficient to achieve the desired therapeutic or prophylactic effect in the patient to which/whom it is administered.

The term "administration", or a variant thereof (e.g. "administering"), means providing the active agent or active ingredient, alone or as part of a pharmaceutically acceptable composition, to the patient in whom/which the condition, symptom, or disease is to be treated or prevented.

By "pharmaceutically acceptable" is meant that the ingredients of a pharmaceutical composition are compatible with each other and not deleterious to the patient thereof.

The term "pharmaceutical vehicle" as used herein means a carrier or inert medium used as solvent or diluent in which the pharmaceutically active agent is formulated and/or administered. Non-limiting examples of pharmaceutical vehicles include creams, gels, lotions, solutions, and liposomes.

The words "comprise", "comprises", and "comprising" are to be interpreted inclusively rather than exclusively. The words "consist", "consisting", and its variants, are to be interpreted exclusively, rather than inclusively.

As used herein, the term "about" means a variability of 10% from the reference given, unless otherwise specified.

EXAMPLES

The present invention will be better understood with reference to the following examples. These examples are intended to representative of specific embodiments of the invention, and are not intended as limiting the scope of the invention.

I. Chemistry Examples

The mass spectrometry (MS) data provided in the examples described below were obtained as followed: Mass spectrum: LC/MS Agilent 6110 (Electron Spray Ionization, ESI) or a Waters Acquity SQD (ESI).

The NMR data provided in the examples described below were obtained as followed: Bruker Ultrashield™ 400 PLUS and Bruker Fourier 300 MHz and TMS was used as an internal standard.

The microwave chemistry was performed on a single mode microwave reactor Initiator Microwave System EU from Biotage.

Preparative High Performance Liquid Chromatography (HPLC) purifications were performed with a mass directed autopurification Fractionlynx from Waters equipped with a Xbridge™ Prep C18 OBD column 19×150 mm 5 µm, unless otherwise reported. All HPLC purifications were performed with a gradient of $CH_3CN/H_2O/NH_4HCO_3$ (5 mM), $CH_3CN/H_2O/TFA$ (0.1%), or $CH_3CN/H_2O/NH_3H_2O$ (0.1%).

The following abbreviations are used herein and have the indicated definitions: ACN is acetonitrile; DMSO is dimethylsulfoxide; DCM is dichloromethane; DIPEA is diisopropylethylamine; DMF is N,N-dimethylformamide, dppf is 1,1'-bis(diphenylphosphino)ferrocene, EtOH is ethanol; HATU is 2-(1H-7-azabenzotriazol-1-yl)-1,1,3,3-tetramethyl uronium hexafluorophosphate methanaminium; Hz is hertz; KOAc is potassium acetate; MeOH is methanol; MeNH2 is methylamide; BH3MeS is borane dimethyl sulfide. BuOK is potassium tert-butoxide. MeI is methylodid. MHz is megahertz; mM is millimolar; mL is milliliter; min is minutes; mol is moles; M+ is molecular ion; [M+H]+ is protonated molecular ion; N is normality; NMR is nuclear magnetic resonance; PE is petrol ether; EA is ethyl acetate. PPh3 is triphenylphosphine; psi is pound per square inch; PPM is parts per million; qd po means daily by mouth; rt is room temperature; RT is retention time; TLC is thin layer chromatography; TFA is trifluoroacetic acid; TEA is trimethylamine; SFC is supercritical fluid chromatography. LCMS (also LC-MS) is liquid chromatography—mass spectrometry. HPLC is High Performance Liquid Chromatography. TBAF is tetra-n-butylammonium fluoride. AIBN is azobisisobutyronitrile; BNS is benzenesulfonic acid; TBDPSCl is tert-butyldiphenylchlorosilane.

Intermediate 1: tert-butyl 6-fluoro-3-(4,4,5,5-tetramethyl-1,3,2-dioxaborolan-2-yl)-1H-indole-1-carboxylate Step 1: tert-butyl 6-fluoro-1H-indole-1-carboxylate To a solution of 6-fluoro-1H-indole (10.0 g, 74.0 mmol) in DCM (200 mL) were added (Boc)$_2$O (19.4 g, 88.9 mmol), TEA (11.2 g, 15.4 mmol) and DMAP (1.81 g, 14.8 mmol). The reaction was stirred at 18° C. for 18 h. The mixture was washed with aq HCl (1 M, 100 mL) and brine. The organic layer was dried, filtered and concentrated to afford 17.4 g of the crude product which was used for next step without purification.

Step 2: tert-butyl 3-bromo-6-fluoro-1H-indole-1-carboxylate

To a solution of tert-butyl 6-fluoro-1H-indole-1-carboxylate (17.4 g, 74.0 mmol) in DCM (200 mL) was added NBS (15.8 g, 88.8 mmol). The reaction was stirred at 40° C. for 6 h. The mixture was washed with water and brine. The organic layer was dried, filtered and concentrated. The residue was purified by silica gel chromatography (PE/EtOAc=10:1) to afford the title compound as a white solid.

Step 3: tert-butyl 6-fluoro-3-(4,4,5,5-tetramethyl-1,3,2-dioxaborolan-2-yl)-1H-indole-1-carboxylate To a solution of tert-butyl 3-bromo-6-fluoro-1H-indole-1-carboxylate (10.0 g, 32.0 mmol) in dioxane (150 mL) were added 4,4,4',4',5,5,5',5'-octamethyl-2,2'-bi(1,3,2-dioxaborolane) (12.0 g, 47.0 mmol), KOAc (9.30 g, 95.0 mmol) and Pd(dppf)Cl$_2$ (2.30 g, 3.10 mmol). The reaction was stirred at 90° C. for 5 h. The solvent was removed and DCM (300 mL) was added. The mixture was washed with brine, dried and filtered. The filtrate was concentrated and purified by silica gel chromatography (PE/EtOAc=10:1) to afford the title compound (6.00 g, 50%) as a white solid.

Example 1

Example 1: (+)-5-(6-fluoro-1H-indol-3-yl)-3-methyl-2,3-dihydro-1,2-benzothiazole 1,1-dioxide

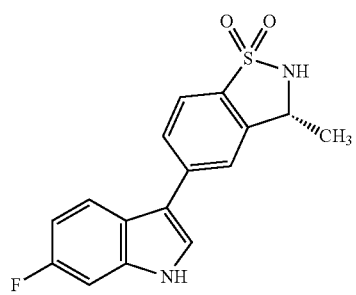 [SMILES: C[C@H]1NS(=O)(=O)c2ccc(-c3c[nH]c4cc(F)ccc34)cc21]

Step 1: 4-bromo-2-ethylbenzenesulfonyl azide

A solution of 4-bromo-2-ethylbenzene-1-sulfonyl chloride (2 g, 7.0 mmol) in water/acetone (1:1, 50 ml) was stirred in a round bottom flask and cooled in an ice bath to 0° C. for 15-20 minutes. Sodium azide (0.92 g, 14.2 mmol) was added in portions to the sulfonyl chloride mixture The pale red solution was stirred at 20° C. for 3 h. The reaction solution was concentrated in vacuum at 25° C. to remove the acetone and the crude product was extracted using ethyl acetate (3×15 ml). The organic phase was then washed with brine (10 ml/mmol), dried over sodium sulfate, and concentrated in vacuum at 25° C. to give the title compound (2.0 g, 98%) as an oil.

Step 2: 5-bromo-3-methyl-2,3-dihydrobenzo[d]isothiazole 1,1-dioxide

A solution of 4-bromo-2-ethylbenzenesulfonyl azide (500 mg, 1.72 mmol) and Co(TPP) (116 mg, 0.172 mmol) in PhCl (5 mL) was degassed with N$_2$ for three times and then stirred at 80-85° C. for 24 h. Additional Co(TPP) (116 mg, 0.172 mmol) was added and the solution stirred at 80-85° C. for another 48 h. The mixture was concentrated to dryness and purified by flash chromatography (SiO$_2$, petroleum ether/EtOAc=1/5 to 1/1) to give crude 5-bromo-3-methyl-2,3-dihydro-benzo[d]isothiazole 1,1-dioxide (380 mg, yield 84.1%) as a red gum. $^1$H NMR (400 MHz, CDCl$_3$) d=7.72-7.62 (m, 2H), 7.58-7.53 (m, 1H), 4.76 (td, J=6.4, 12.3 Hz, 1H), 4.63 (br. s., 1H), 1.63 (d, J=6.5 Hz, 3H).

Step 3. tert-butyl 6-fluoro-3-(3-methyl-1,1-dioxido-2,3-dihydrobenzo[d]isothiazol-5-yl)-1H-indole-1-carboxylate To a light white suspension of tert-butyl 6-fluoro-3-(4,4,5,5-tetramethyl-1,3,2-dioxaborolan-2-yl)-1H-indole-1-carboxylate (524 mg, 1.45 mmol), 5-bromo-3-methyl-2,3-dihydrobenzo[d]isothiazole 1,1-dioxide (380 mg, 1.45 mmol) and K$_3$PO$_4$ (616 mg, 2.9 mmol) in dioxane (15 mL) and H$_2$O (5 mL) was added Pd(dppf)Cl$_2$ (106 mg, 0.145 mmol) under nitrogen atmosphere then the suspension was stirred at 100° C. for 18 hours. The reaction mixture was diluted with EtOAc (60 mL) and water (20 mL). The layers were separated, then the aqueous layer was extracted with EtOAc (30 mL*2). The combined organic layers were washed with brine (20 mL×2), dried over anhydrous Na$_2$SO$_4$, filtered and concentrated to give crude tert-butyl 6-fluoro-3-(3-methyl-1,1-dioxido-2,3-dihydrobenzo[d]isothiazol-5-yl)-1H-indole-1-carboxylate (604 mg) as a black solid, which was used the next step without further purification.

Step 4: 5-(6-fluoro-1H-indol-3-yl)-3-methyl-2,3-dihydro-1,2-benzothiazole 1,1-dioxide To a yellow solution of tert-butyl 6-fluoro-3-(3-methyl-1,1-dioxido-2,3-dihydrobenzo[d]isothiazol-5-yl)-1H-indole-1-carboxylate (0.604 g, 1.45 mmol) in DCM (6 mL) was added TFA (3 mL) at 0° C. After addition, the black solution was stirred at 20° C. for 2 h. The black solution was concentrated and treated with aq. NaHCO$_3$ (10 mL), extracted with DCM (10 mL×5), dried over NaSO4, filtered and concentrated to give the crude product (0.5 g), which was purified by flash chromatography (SiO$_2$, DCM/EtOAc=10/1 to 3/1) to give racemic 5-(6-fluoro-1H-indol-3-yl)-3-methyl-2,3-dihydro-1,2-benzothiazole 1,1-dioxide (0.18 g, 45% yield) as a black solid. 150 mg of the racemic product was separated by Preparative chiral SFC to give (+)-5-(6-fluoro-1H-indol-3-yl)-3-methyl-2,3-dihydro-1,2-benzothiazole 1,1-dioxide as the first eluting peak (70 mg, 47%) as a yellow solid. $^1$H NMR (400 MHz, DMSO-d6) d=11.67 (br. s., 1H), 8.02-7.68 (m, 6H), 7.27 (dd, J=2.3, 10.0 Hz, 1H), 7.02 (dt, J=2.5, 9.3 Hz, 1H), 4.90-4.67 (m, 1H), 1.54 (d, J=6.5 Hz, 3H); LC-MS: m/z 316.9 (M+H)$^+$. [α]$^{20}_D$ +27.0° (c=2 mg/ml, EtOH).

Example 2: (−)-5-(6-fluoro-1H-indol-3-yl)-3-methyl-2,3-dihydro-1,2-benzothiazole 1,1-dioxide

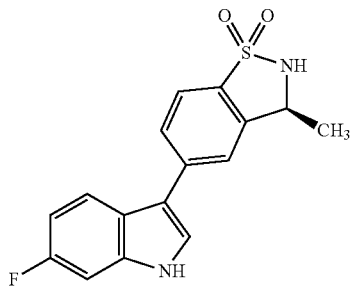 [SMILES: C[C@@H]1NS(=O)(=O)c2ccc(-c3c[nH]c4cc(F)ccc34)cc21]

The Title compound was obtained as the second eluting peak from the chiral separation described for Example 111 (70 mg, 47%, a yellow solid). ¹H NMR (400 MHz, DMSO-d6) d=11.67 (br. s., 1H), 8.05-7.69 (m, 6H), 7.27 (dd, J=2.0, 10.0 Hz, 1H), 7.11-6.86 (m, 1H), 4.91-4.64 (m, 1H), 1.54 (d, J=6.5 Hz, 3H); LC-MS: m/z 316.9 (M+H)⁺. [α]²⁰_D −43.8° (c=1.3 mg/ml, EtOH).

Example 3: (+)-3-ethyl-5-(6-fluoro-1H-indol-3-yl)-2,3-dihydrobenzo[d]-isothiazole 1,1-dioxide

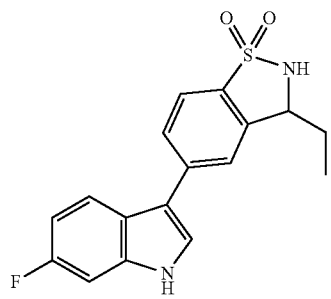 [SMILES: CCC1NS(=O)(=O)c2ccc(-c3c[nH]c4cc(F)ccc34)cc21]

Step 1: 1-bromo-3-propylbenzene

To a suspension of 1-(3-bromophenyl)propan-1-one (5000 mg, 23.5 mmol) and KOH (3.95 g, 70.4 mmol) in (CH₂OH)₂ (28 mL) was added N₂H₄—H₂O (4.15 g, 70.4 mmol). The mixture was stirred under a N₂ atmosphere at 200° C. for 4 h then at 140° C. for 16 h. The reaction was cooled to room temperature and quenched with 1 M HCl (500 mL) (pH 3-4) then extracted with petroleum ether (150 mL). The organic layer was washed with brine (100 mL) then dried over anhydrous Na₂SO₄, filtered and concentrated. The crude residue was purified by column chromatography (silica gel, petroleum ether) to give 1-bromo-3-propylbenzene (4.0 g, 86%) as clear oil. ¹H NMR (400 MHz, CDCl₃)™ [ππμ] 7.37-7.30 (m, 2H), 7.19-7.09 (m, 2H), 2.64-2.52 (m, 2H), 1.69-1.61 (m, 2H), 0.95 (t, J=7.3 Hz, 3H).

Step 2: 4-bromo-2-propylbenzene-1-sulfonyl chloride

A 100 mL round bottom flask was purged with N₂ and charged with 1-bromo-3-propylbenzene (2 g, 10 mmol) and chloroform (25 mL) then cooled in an ice bath to 0° C. Chlorosulfonic acid (7.02 g, 60.3 mmol) was added dropwise over 10 min and the reaction was stirred at 0° C. for 1 hr then at 30° C. for 16 h. The crude reaction was carefully poured into ice-water (60 mL) and extracted with dichloromethane (50 mL×2). The combined organic layers were washed with brine (60 mL×3) then dried over Na₂SO₄, filtered and concentrated. The residue was purified by column chromatography (silica gel, petroleum ether) to give 4-bromo-2-propylbenzene-1-sulfonyl chloride (1.6 g, 53%) as yellow oil. ¹H NMR (400 MHz, CDCl₃)™ [ππμ] 7.93 (d, J=8.5 Hz, 1H), 7.63 (d, J=2.0 Hz, 1H), 7.56 (dd, J=2.1, 8.7 Hz, 1H), 3.15-3.02 (m, 2H), 1.85-1.70 (m, 2H), 1.08 (t, J=7.3 Hz, 3H).

Step 3: 4-bromo-2-propylbenzenesulfonyl azide

A solution of 4-bromo-2-propylbenzene-1-sulfonyl chloride (1.6 g, 3.2 mmol) in water/acetone (16 ml/16 mL) was cooled in an ice bath then sodium azide (523 mg, 8.04 mmol) was added in portions The reaction was stirred at ~10° C. for 1 hr then concentrated and extracted with petroleum ether (30 ml). The organic layer was washed with brine (20 ml) then dried over Na₂SO₄, filtered and concentrated to give 4-bromo-2-propylbenzenesulfonyl azide (1.6 g, 98%) as clear oil. ¹H NMR (400 MHz, CDCl₃)™ [ππμ] 7.90 (d, J=8.5 Hz, 1H), 7.61 (d, J=2.0 Hz, 1H), 7.54 (dd, J=2.0, 8.5 Hz, 1H), 3.00-2.88 (m, 2H), 1.73 (dd, J=7.5, 15.6 Hz, 2H), 1.05 (t, J=7.3 Hz, 3H).

Step 4: 5-bromo-3-ethyl-2,3-dihydrobenzo[d]isothiazole 1,1-dioxide

To a yellow solution of 4-bromo-2-propylbenzenesulfonyl azide (1.63 g, 5.36 mmol) in chlorobenzene (5 mL) was added 5,10,15,20-tetraphenyl-21H, 23H-porphine cobalt (II) (180 mg, 0.268 mmol) under N₂. The reaction was sparged with N₂ for 2 min and heated to 80° C. for 64 h then concentrated. The crude residue was purified by column chromatography (silica gel, 10-20% ethyl acetate/petroleum ether) to give a mixture of 5-bromo-3-ethyl-2,3-dihydrobenzo[d]isothiazole 1,1-dioxide and 6-bromo-3-methyl-3,4-dihydro-2H-benzo[e][1,2]thiazine 1,1-dioxide (1.0 g, 68% mixture) as black gum. ¹H NMR (400 MHz, CDCl₃)™ [ππμ] 7.69-7.59 (m, 3H), 7.56-7.46 (m, 2H), 7.39 (s, 1H), 4.85 (br s, 1H), 4.71-4.56 (m, 1H), 4.45 (d, J=11.3 Hz, 1H), 4.11-3.94 (m, 1H), 3.00-2.88 (m, 1H), 2.84-2.71 (m, 1H), 2.10-1.95 (m, 1H), 1.81 (td, J=7.5, 14.7 Hz, 1H), 1.40 (d, J=6.5 Hz, 3H), 1.08-0.99 (m, 3H).

Step 5: tert-butyl 3-(3-ethyl-1,1-dioxido-2,3-dihydrobenzo[d]isothiazol-5-yl)-6-fluoro-1H-indole-1-carboxylate To a yellow solution of 5-bromo-3-ethyl-2,3-dihydrobenzo[d]isothiazole 1,1-dioxide and 6-bromo-3-methyl-3,4-dihydro-2H-benzo[e][1,2]thiazine 1,1-dioxide (600 mg, 2.17 mmol), tert-butyl 6-fluoro-3-(4,4,5,5-tetramethyl-1,3,2-dioxaborolan-2-yl)-1H-indole-1-carboxylate (872 mg, 2.17 mmol) and K₃PO₄ (922 mg, 4.35 mmol) in Dioxane/H₂O (8 ml/2 mL) was added Pd(dppf)Cl₂ (153 mg, 0.217 mmol) at 25° C. under N₂. The red suspension was stirred at 80° C. for 2 h then diluted with water (10 mL) and extracted with ethyl acetate (15 mL×2). The combined organic layers were washed with brine (10 mL) then dried over anhydrous Na₂SO₄, filtered and concentrated. The crude residue was purified by column chromatography (silica gel, 20% ethyl acetate/petroleum ether) to give a mixture of tert-butyl 3-(3-ethyl-1,1-dioxido-2,3-dihydrobenzo[d]isothiazol-5-yl)-6-fluoro-1H-indole-1-carboxylate and tert-butyl 6-fluoro-3-(3-methyl-1,1-dioxido-3, 4-dihydro-2H-benzo[e][1,2] thiazin-6-yl)-1H-indole-1-carboxylate (570 mg, 61% mixture) as an off-white solid.

Step 6: (+) 3-ethyl-5-(6-fluoro-1H-indol-3-yl)-2,3-dihydrobenzo[d]isothiazole 1,1-dioxide To a clear solution of tert-butyl 3-(3-ethyl-1,1-dioxido-2, 3-dihydrobenzo[d] isothiazol-5-yl)-6-fluoro-1H-indole-1-carboxylate and tert-butyl 6-fluoro-3-(3-methyl-1,1-dioxido-3,4-dihydro-2H-benzo[e][1,2]thiazin-6-yl)-1H-indole-1-carboxylate (570 mg, 1.32 mmol) in dichloromethane (12 mL) was added trifluoroacetic acid (4 mL). The reaction was stirred at 25° C. for 1 h then concentrated. The residue was neutralized to pH>7 with NaHCO$_3$ (sat) and extracted with ethyl acetate (30 mL×2). The combined organic layers were washed with brine (30 mL) then dried over anhydrous Na$_2$SO$_4$, filtered and concentrated. The residue was purified by column chromatography (silica gel, 30% ethyl acetate/petroleum ether) to give a mixture of four products. The mixture was separated by prep-chiral supercritical fluid chromatography (SFC) to give (+)-3-ethyl-5-(6-fluoro-1H-indol-3-yl)-2,3-dihydrobenzo[d] isothiazole 1,1-dioxide as the first eluting peak (38 mg, 9%) as an off-white solid. $^1$H NMR (400 MHz, DMSO-d$_6$)™ [πτμ] 11.66 (br s, 1H), 7.98-7.82 (m, 5H), 7.81-7.73 (m, 1H), 7.26 (dd, J=2.3, 10.0 Hz, 1H), 7.01 (dt, J=2.4, 9.2 Hz, 1H), 4.70-4.61 (m, 1H), 2.08-1.90 (m, 1H), 1.75-1.60 (m, 1H), 0.95 (t, J=7.3 Hz, 3H); LC-MS: m/z, 331.2 (M+H)$^+$, [α]$^{20}_D$ +43.8° (c=0.95 mg/mL, methanol).

Example 4: (−)-3-ethyl-5-(6-fluoro-1H-indol-3-yl)-2,3-dihydrobenzo[d]isothiazole 1,1-dioxide

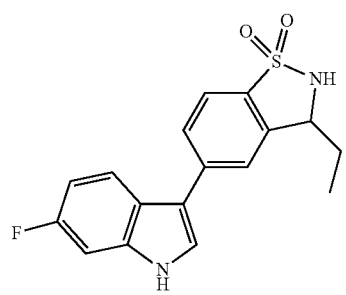 [SMILES: CCC1NS(=O)(=O)c2ccc(-c3c[nH]c4cc(F)ccc34)cc21]

The title compound was isolated as the second eluting peak from the SFC purification described in Example 3 (36 mg, 8%) as an off white solid. $^1$H NMR (400 MHz, DMSO-d$_6$)™ [πτμ] 11.66 (br s, 1H), 8.01-7.81 (m, 5H), 7.80-7.75 (m, 1H), 7.26 (dd, J=2.3, 9.8 Hz, 1H), 7.05-6.95 (m, 1H), 4.72-4.58 (m, 1H), 2.10-1.95 (m, 1H), 1.75-1.58 (m, 1H), 0.95 (t, J=7.3 Hz, 3H); LC-MS: m/z 330.9 (M+H)$^+$, [α]$^{20}_D$ −48° (c=1.0 mg/mL, methanol).

Example 5: 5-(6-fluoro-1H-indol-3-yl)-3,3-dimethyl-2,3-dihydrobenzo[d]isothiazole 1,1-dioxide

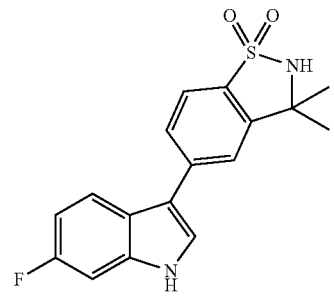 [SMILES: CC1(C)NS(=O)(=O)c2ccc(-c3c[nH]c4cc(F)ccc34)cc21]

Following the general method as outlined in Example 3, starting with 1-bromo-3-isopropylbenzene, the title compound was obtained as a white solid. $^1$H NMR (400 MHz, DMSO-d$_6$)™ [πτμ] 11.68 (br s, 1H), 7.94-7.88 (m, 3H), 7.88-7.81 (m, 2H), 7.75 (d, J=8.0 Hz, 1H), 7.27 (d, J=10.0 Hz, 1H), 7.01 (t, J=9.3 Hz, 1H), 1.60 (s, 6H); LC-MS: m/z 352.9 (M+23)$^+$.

Example 6: (+)-5-(6-fluoro-1H-indol-3-yl)-3-propyl-2,3-dihydrobenzo[d]isothiazole 1,1-dioxide

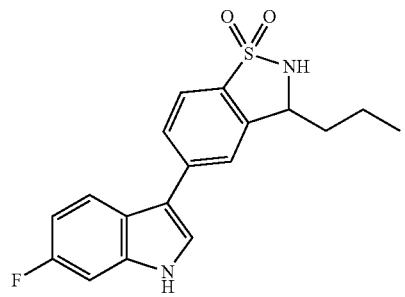

Following the general method as outlined in Example 3, starting with 1-bromo-3-butylbenzene, the title compound was obtained as the first eluting peak as a gray solid. $^1$H NMR (400 MHz, MeOD)™ [πτμ] 7.92-7.81 (m, 2H), 7.80-7.72 (m, 2H), 7.66 (s, 1H), 7.16 (dd, J=2.3, 9.8 Hz, 1H), 6.95 (dt, J=2.4, 9.2 Hz, 1H), 4.74 (dd, J=3.5, 9.0 Hz, 1H), 2.09-1.96 (m, 1H), 1.82-1.69 (m, 1H), 1.63-1.48 (m, 2H), 1.01 (t, J=7.4 Hz, 3H); LC-MS: m/z 344.9 (M+H)$^+$, [α]$^{20}_D$ +34.8° (c=2.3 mg/ml, methanol).

Example 7: (−)-5-(6-fluoro-1H-indol-3-yl)-3-propyl-2,3-dihydrobenzo[d]isothiazole 1,1-dioxide

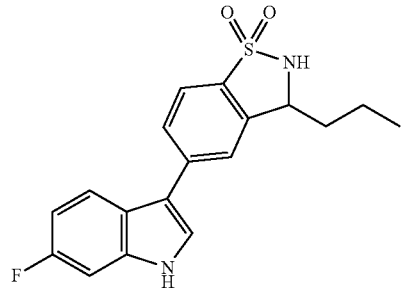 [SMILES: CCCC1NS(=O)(=O)c2ccc(-c3c[nH]c4cc(F)ccc34)cc21]

Following the general method as outlined in Example 3, starting with 1-bromo-3-butylbenzene, the title compound was obtained as the second eluting peak as a gray solid. $^1$H NMR (400 MHz, MeOD)™ [ππμ] 7.89-7.81 (m, 2H), 7.78-7.71 (m, 2H), 7.66 (s, 1H), 7.15 (dd, J=2.4, 9.7 Hz, 1H), 6.94 (dt, J=2.5, 9.2 Hz, 1H), 4.73 (dd, J=3.4, 8.9 Hz, 1H), 2.06-1.96 (m, 1H), 1.81-1.69 (m, 1H), 1.60-1.48 (m, 2H), 1.01 (t, J=7.3 Hz, 3H), LC-MS: m/z 344.9 (M+H)$^+$, $[\alpha]^{20}_D$ −36.4° (c=2.5 mg/ml, methanol).

Example 8: (+)-5-(6-fluoro-1H-indol-3-yl)-3-isopropyl-2,3-dihydrobenzo[d]isothiazole 1,1-dioxide

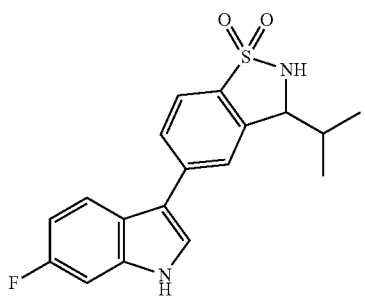 [SMILES: CC(C)C1NS(=O)(=O)c2ccc(-c3c[nH]c4cc(F)ccc34)cc21]

Step 1: 4-bromo-2-isobutylbenzenesulfonamide

A yellow solution of 4-bromo-2-isobutylbenzene-1-sulfonyl chloride (1000 mg, 3.21 mmol) and NH$_4$OH (5 mL) in anhydrous dichloromethane (50 mL) was stirred at 25° C. for 2 h. This reaction was diluted with H$_2$O (10 mL) and the layers were separated. The organic layer was dried over Na$_2$SO$_4$, filtered and concentrated then purified by column chromatography (petroleum ether/ethyl acetate=6/1-3/1) to give 4-bromo-2-isobutylbenzenesulfonamide (900 mg, 96%) as a brown solid.

Step 2: 4-bromo-2-(1-bromo-2-methylpropyl)benzenesulfonamide

A yellow solution of 4-bromo-2-isobutylbenzenesulfonamide (200 mg, 0.684 mmol), N-bromosuccinamide (NBS) (146 mg, 0.820 mmol) and azobisiosbutyronitrile (AIBN) (11 mg, 0.07 mmol) in CCl$_4$ (10 mL) was stirred at 70° C. for 12 h. This reaction was diluted with H$_2$O (10 mL) and the layers were separated. The organic layer was dried over Na$_2$SO$_4$, filtered and concentrated then purified by column chromatography (SiO$_2$, petroleum ether/ethyl acetate=6/1-3/1) to give 4-bromo-2-(1-bromo-2-methylpropyl)benzenesulfonamide (250 mg, 98) as a brown solid.

Step 3: 5-bromo-3-isopropyl-2,3-dihydrobenzo[d]isothiazole 1,1-dioxide

A yellow solution of 4-bromo-2-(1-bromo-2-methylpropyl)benzene-sulfonamide (350 mg, 0.943 mmol) and K$_2$CO$_3$ (261 mg, 1.89 mmol) in H$_2$O/acetone (5 mL/10 mL) was stirred at 50° C. for 12 h then concentrated and extracted with ethyl acetate (20 mL×3). The combined organic layers were dried over Na$_2$SO$_4$, filtered and concentrated then purified by column chromatography (petroleum ether/ethyl acetate=5/1) to give 5-bromo-3-isopropyl-2,3-dihydrobenzo[d]isothiazole 1,1-dioxide (200 mg, 85%) as a yellow gum.

Step 4: tert-butyl 3-(4-(2-(3-ethoxy-3-oxopropyl)-3-methyl-1,1-dioxido-2,3-dihydrobenzo[d]isothiazol-5-yl)phenyl)-6-fluoro-1H-indole-1-carboxylate To a solution of 5-bromo-3-isopropyl-2,3-dihydrobenzo[d]isothiazole 1,1-dioxide (400 mg, 2.21 mmol), tert-butyl 6-fluoro-3-(4,4,5,5-tetramethyl-1,3,2-dioxaborolan-2-yl)-1H-indole-1-carboxylate (498 mg, 1.38 mmol) and K$_3$PO$_4$ (586 mg, 2.76 mmol) in dioxane/H$_2$O(12 mL/4 mL) was added Pd(dppf)Cl$_2$ (101 mg, 0.138 mmol) at 28° C. under N$_2$. The red suspension was stirred at 80° C. for 16 h then diluted with water (8 mL) and extracted with ethyl acetate (15 mL×3). The combined organic layers were dried over anhydrous Na$_2$SO$_4$, filtered and concentrated. The crude residue was purified by column chromatography (silica gel, 5-30% ethyl acetate/petroleum ether) to give tert-butyl 3-(4-(2-(3-ethoxy-3-oxopropyl)-3-methyl-1,1-dioxido-2,3-dihydrobenzo[d]isothiazol-5-yl)phenyl)-6-fluoro-1H-indole-1-carboxylate (300 mg, 24%) as a yellow gum.

Step 5: (+)-5-(6-fluoro-1H-indol-3-yl)-3-isopropyl-2,3-dihydrobenzo-[d]isothiazole 1,1-dioxide A red solution of tert-butyl 3-(4-(2-(3-ethoxy-3-oxopropyl)-3-methyl-1,1-dioxido-2,3-dihydrobenzo[d]isothiazol-5-yl)phenyl)-6-fluoro-1H-indole-1-carboxylate (300 mg, 0.675 mmol) in trifluoroacetic acid and dichloromethane (5 mL/5 mL) was stirred at 20° C. under a N2 atmosphere for 1 h. The yellow suspension was concentrated then diluted with aq. NaHCO$_3$ (10 mL) and extracted ethyl acetate (20 mL×3). The combined organic layers were dried over Na$_2$SO$_4$, filtered and concentrated. The crude residue was purified by column chromatography (SiO$_2$, petroleum ether/ethyl acetate=1/1 to ethyl acetate/methanol=10/1) and prep-HPLC to give racemic5-(6-fluoro-1H-indol-3-yl)-3-isopropyl-2,3-dihydrobenzo[d]isothiazole 1,1-dioxide (30 mg, 13%) as a white solid. The racemic product was separated by prep-chiral SFC to give (+)-5-(6-fluoro-1H-indol-3-yl)-3-isopropyl-2,3-dihydrobenzo[d]isothiazole 1,1-dioxide as the first eluting peak (10 mg, 4%) as a pale yellow solid. $^1$H NMR (400 MHz, MeOD)™ [ππμ] 7.95-7.83 (m, 2H), 7.80-7.75 (m, 2H), 7.69 (s, 1H), 7.18 (dd, J=2.4, 9.7 Hz, 1H), 6.97 (dt, J=2.4, 9.2 Hz, 1H), 4.77 (d, J=3.0 Hz, 1H), 2.48-2.30 (m, 1H), 1.18 (d, J=7.0 Hz, 3H), 0.78 (d, J=6.8 Hz, 3H); LC-MS: m/z 344.9 (M+Na)$^+$, $[\alpha]^{20}_D$ +35.3° (methanol, 0.001 g/mL).

Example 9: (−)-5-(6-fluoro-1H-indol-3-yl)-3-isopropyl-2,3-dihydrobenzo-[d]isothiazole 1,1-dioxide

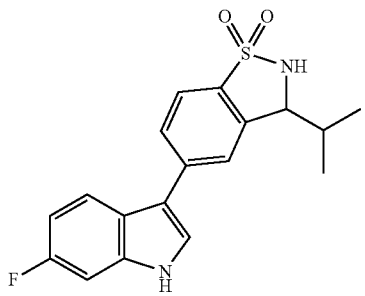 [SMILES: CC(C)C1NS(=O)(=O)c2ccc(-c3c[nH]c4cc(F)ccc34)cc21]

The title compound was obtained as the second eluting peak from the purification described in Example 8 as a pale yellow solid. $^1$H NMR (400 MHz, MeOD)™ [ππμ] 7.94-7.83 (m, 2H), 7.80-7.75 (m, 2H), 7.69 (s, 1H), 7.18 (dd, J=2.4, 9.4 Hz, 1H), 6.97 (dt, J=2.4, 9.2 Hz, 1H), 4.77 (d, J=3.0 Hz, 1H), 2.44-2.32 (m, 1H), 1.18 (d, J=6.8 Hz, 3H), 0.78 (d, J=6.8 Hz, 3H); LC-MS: m/z 344.9 (M+H)$^+$; $[\alpha]^{20}_D$ −25° (methanol, 0.001 g/mL).

Example 10: (+)-3-cyclopropyl-5-(6-fluoro-1H-indol-3-yl)-2,3-dihydrobenzo[d]isothiazole 1,1-dioxide

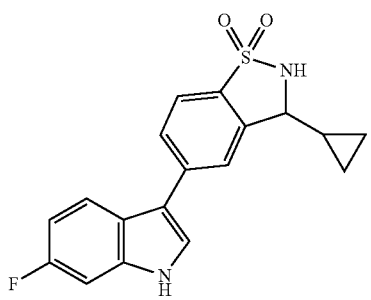 [SMILES: O=S1(=O)NC(C2CC2)c2cc(-c3c[nH]c4cc(F)ccc34)ccc21]

Step 1: 5-bromo-3-cyclopropylbenzo[d]isothiazole 1,1-dioxide

A solution of 5-bromobenzo[d]isothiazol-3(2H)-one 1,1-dioxide (500 mg, 1.91 mmol) in anhydrous THF (5.0 mL) was evacuated and back-filled with nitrogen in four cycles then cyclopropylmagnesium bromide (0.5 M in THF, 15.3 mL) was slowly added. The reaction was heated to 40° C. for 2 h then cooled and quenched with aqueous NH$_4$Cl (sat) (15 mL) and 2M HCl (0.5 mL). The reaction was extracted with EtOAc (20 mL×3) and the combined organic layers were washed with water (15 mL) then concentrated. The crude residue was purified by column chromatography (silica gel, 4-50% EtOAc/Petroleum ether) to afford 5-bromo-3-cyclopropylbenzo[d]isothiazole 1,1-dioxide (270 mg, 50%) as a white solid. $^1$H NMR (400 MHz, DMSO-d$_6$)™ [ππμ] 8.62 (d, J=1.0 Hz, 1H), 8.15-8.07 (m, 2H), 2.91-2.79 (m, 1H), 1.47 (qd, J=3.6, 7.7 Hz, 2H), 1.34 (quin, J=3.9 Hz, 2H).

Step 2: 5-bromo-3-cyclopropyl-2,3-dihydrobenzo[d]isothiazole 1,1-dioxide

To a clear solution of 5-bromo-3-cyclopropylbenzo[d]isothiazole 1,1-dioxide (344 mg, 0.35 mmol) in MeOH (12 mL) was added NaBH$_4$ (68 mg, 1.8 mmol) at 15° C. The reaction was stirred at 15° C. for 1.5 h then quenched with water (1.5 mL) and concentrated. The crude reside was purified by column chromatography (silica gel, 4-50% EtOAc/Petroleum ether) to afford 5-bromo-3-cyclopropyl-2,3-dihydrobenzo[d]isothiazole 1,1-dioxide (222 mg, 64%) as a yellow solid. $^1$H NMR (400 MHz, DMSO-d$_6$) δ [ppm] 8.16 (br s, 1H), 7.93 (s, 1H), 7.79 (d, J=4.5 Hz, 2H), 4.22 (d, J=7.5 Hz, 1H), 1.13 (d, J=16.1 Hz, 1H), 0.71-0.60 (m, 2H), 0.48-0.35 (m, 2H)

Step 3: tert-butyl 3-(3-cyclopropyl-1,1-dioxido-2,3-dihydrobenzo[d]-isothiazol-5-yl)-6-fluoro-1H-indole-1-carboxylate A mixture of 5-bromo-3-cyclopropyl-2,3-dihydrobenzo[d]isothiazole 1,1-dioxide (267 mg, 0.93 mmol), tert-butyl 6-fluoro-3-(4,4,5,5-tetramethyl-1,3,2-dioxaborolan-2-yl)-1H-indole-1-carboxylate (351 mg, 0.97 mmol), PdCl$_2$(dppf) (69 mg, 0.09 mmol) and K$_3$PO$_4$ (590 mg, 2.78 mmol) in 1,4-dioxane (9 mL) was sparged with nitrogen for 1 min then stirred at 85° C. for 2.5 h. The reaction was concentrated and purified by column chromatography (silica gel, 5-60% EtOAc/Petroleum ether) to afford tert-butyl 3-(3-cyclopropyl-1,1-dioxido-2,3-dihydrobenzo[d]isothiazol-5-yl)-6-fluoro-1H-indole-1-carboxylate (330 mg, 81%) as yellow gum. $^1$H NMR (400 MHz, DMSO-d$_6$)™ [ππμ] 8.12-8.05 (m, 2H), 7.97 (s, 1H), 7.94-7.85 (m, 3H), 7.76-7.68 (m, 1H), 7.26 (dt, J=2.5, 9.0 Hz, 1H), 4.32 (dd, J=4.5, 7.5 Hz, 1H), 1.75-1.59 (m, 8H), 1.28-1.19 (m, 1H), 0.76-0.57 (m, 2H), 0.52-0.36 (m, 2H); LC-MS: m/z 443.1 (M+H)$^+$.

Step 4: (+)-3-cyclopropyl-5-(6-fluoro-1H-indol-3-yl)-2,3-dihydrobenzo-[d]isothiazole 1,1-dioxide To a yellow solution of tert-butyl 3-(3-cyclopropyl-1,1-dioxido-2,3-dihydrobenzo[d]isothiazol-5-yl)-6-fluoro-1H-indole-1-carboxylate (330 mg, 0.75 mmol) in CH$_2$Cl$_2$ (8.0 mL) was added TFA (4.0 mL) at 18° C. The reaction was stirred for 3 h then concentrated and re-dissolved in DCM (50 mL). The solution was neutralized with NaHCO$_3$ (sat) (15 mL) and the layers were separated. The aqueous layer was back-extracted with dichloromethane (DCM) (20 mL×2) and the combine organic layers were concentrated and purified by column chromatography (silica gel, 10-65% EtOAc/Petroleum ether) to give racemic 3-cyclopropyl-5-(6-fluoro-1H-indol-3-yl)-2,3-dihydrobenzo[d]isothiazole 1,1-dioxide (190 mg, 74%) as yellow gum. The enantiomers were separated by prep-chiral SFC to give (+)-3-cyclopropyl-5-(6-fluoro-1H-indol-3-yl)-2,3-dihydrobenzo[d]isothiazole 1,1-dioxide as the first eluting peak (55 mg, 29%) as a white solid. $^1$H NMR (400 MHz, DMSO-d$_6$)™ [ππμ] 11.68 (br s, 1H), 8.01-7.83 (m, 5H), 7.81-7.76 (m, 1H), 7.27 (dd, J=2.3, 9.8 Hz, 1H), 7.02 (dt, J=2.5, 9.3 Hz, 1H), 4.28 (dd, J=4.0, 7.5 Hz, 1H), 1.26-1.13 (m, 1H), 0.78-0.59 (m, 2H), 0.52-0.37 (m, 2H); LC-MS: m/z 343.1 (M+H)$^+$, $[\alpha]^{20}_D$ +39.55° (c=0.0015 g/mL, MeOH).

Example 11: (−)-3-cyclopropyl-5-(6-fluoro-1H-indol-3-yl)-2,3-dihydrobenzo[d]isothiazole 1,1-dioxide

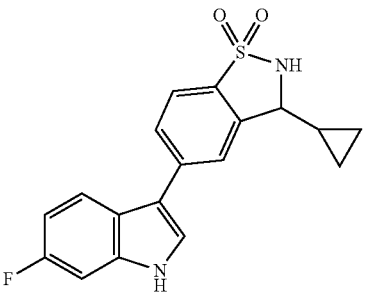 [SMILES: O=S1(=O)NC(C2CC2)c2cc(-c3c[nH]c4cc(F)ccc34)ccc21]

The title compound was obtained as the second eluting peak from the chiral separation described for Example 10 (60 mg, 32%) as a white solid. $^1$H NMR (400 MHz, DMSO-d$_6$) [ppm] 11.68 (br s, 1H), 8.00-7.85 (m, 5H), 7.81-7.76 (m, 1H), 7.27 (dd, J=2.3, 9.8 Hz, 1H), 7.06-6.97 (m, 1H), 4.31-4.24 (m, 1H), 1.25-1.13 (m, 1H), 0.77-0.59

(m, 2H), 0.52-0.37 (m, 2H); LC-MS: m/z 343.1 (M+H)+, $[\alpha]^{20}_D$ −33.46° (c=0.0017 g/mL, MeOH).

Example 12: (−)-5-(6-fluoro-1H-indol-3-yl)-3-(hydroxymethyl)-2,3-dihydrobenzo[d]isothiazole 1,1-dioxide

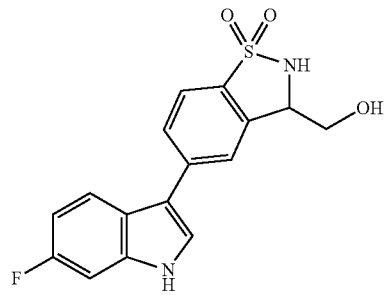 [SMILES: O=S1(=O)NC(CO)c2cc(-c3c[nH]c4cc(F)ccc34)ccc21]

Step 1: methyl 2-(2-(azidosulfonyl)-5-bromophenyl)acetate

A yellow solution of methyl 2-(5-bromo-2-(chlorosulfonyl)phenyl)acetate (10 g, 4.6 mmol) in acetone (100 ml) and H$_2$O (50 mL) was cooled in an ice bath then sodium azide (3 g, 46 mmol) was added in portions. The reaction was stirred at 0° C. for 1 h then concentrated and extracted with MTBE (3×50 ml). The combined organic layers were washed with brine (10 ml) then dried over Na$_2$SO$_4$, filtered and concentrated. The crude product was purified by column chromatography (silica gel, 0-10% ethyl acetate/petroleum ether) to give methyl 2-(2-(azidosulfonyl)-5-bromophenyl) acetate (6 g, 59%) as a white solid. $^1$H NMR (400 MHz, MeOD)™ [ππμ] 7.89-8.01 (m, 1H), 7.59-7.70 (m, 2H), 4.05 (s, 2H), 3.75 (s, 3H).

Step 2: methyl 5-bromo-2,3-dihydrobenzo[d]isothiazole-3-carboxylate 1,1-dioxide

To a solution of methyl 2-(2-(azidosulfonyl)-5-bromophenyl)acetate (6 g, 19 mmol) in chlorobenzene (15 mL) was added 5,10,15,20-tetraphenyl-21H, 23H-porphine cobalt(II) (654 mg, 0.974 mmol) under N$_2$. The brown suspension was sparged with N$_2$ for 2 min and heated to 80° C. for 18 h. The reaction was cooled to ambient temperature and concentrated then purified by column chromatography (silica gel, 0-30% ethyl acetate/petroleum ether) to give methyl 5-bromo-2,3-dihydrobenzo[d]isothiazole-3-carboxylate 1,1-dioxide (3.5 g, 59%) as a light brown solid. $^1$H NMR (400 MHz, CDCl$_3$)™ [ππμ] 7.86 (s, 1H), 7.64-7.75 (m, 1H), 7.58-7.63 (m, 1H), 5.48-5.53 (br, 1H), 5.26 (d, 1H), 3.97 (s, 3H).

Step 3: 5-bromo-2,3-dihydrobenzo[d]isothiazole-3-carboxylic acid 1,1-dioxide

To a solution of methyl 5-bromo-2,3-dihydrobenzo[d]isothiazole-3-carboxylate 1,1-dioxide (2.5 g, 8.2 mmol) in THF (25 mL) was added a solution of LiOH—H$_2$O (857 mg, 20.4 mmol) in water (25 mL). The reaction was stirred at ambient temperature for 10 min then concentrated to remove tetrahydrofuran (THF) and washed with methyl tert-butyl ether (MTBE) (2×50 mL). The aqueous phase was acidified to pH 2 with 2 N HCl and extracted with MTBE (2×50 mL). The combined organic layers were dried over Na$_2$SO$_4$, filtered, and concentrated to give 5-bromo-2,3-dihydrobenzo [d]isothiazole-3-carboxylic acid 1,1-dioxide (1.8 g, 76%) as a light brown solid. $^1$H NMR (400 MHz, MeOD)™ [ππμ] 8.00 (s, 1H), 7.84 (dd, J=8.28, 1.00 Hz, 1H), 7.69-7.76 (m, 1H), 5.38 (s, 1H).

Step 4: 5-bromo-3-(hydroxymethyl)-2,3-dihydrobenzo[d]isothiazole 1,1-dioxide

To a solution of 5-bromo-2,3-dihydrobenzo[d]isothiazole-3-carboxylic acid 1,1-dioxide (1.0 g, 3.4 mmol) in dry THF (20 mL) was added BH$_3$-Me$_2$S (2.1 g, 27 mmol) dropwise at 0° C. The reaction was stirred at ambient temperature for 4 h then carefully poured into ice-water (50 mL) (gas evolution) and extracted with MTBE (3×30 mL). The combined organic layers were dried over Na$_2$SO$_4$, filtered and concentrated. The residue was purified by column chromatography (silica gel, 0-10% methanol/dichloromethane) to give 5-bromo-3-(hydroxymethyl)-2,3-dihydrobenzo[d]isothiazole 1,1-dioxide (650 mg, 68%) as a white solid. $^1$H NMR (400 MHz, MeOD)™ [ππμ] 7.88 (d, J=0.75 Hz, 1H), 7.75-7.82 (m, 1H), 7.64-7.73 (m, 1H), 4.69 (t, J=5.77 Hz, 1H), 3.73-3.87 (m, 2H).

Step 5: tert-butyl 6-fluoro-3-(3-(hydroxymethyl)-1,1-dioxido-2,3-dihydrobenzo[d]isothiazol-5-yl)-1H-indole-1-carboxylate A solution of 5-bromo-3-(hydroxymethyl)-2,3-dihydrobenzo[d]isothiazole 1,1-dioxide (550 mg, 1.98 mmol) and tert-butyl 6-fluoro-3-(4,4,5,5-tetramethyl-1,3,2-dioxaborolan-2-yl)-1H-indole-1-carboxylate (929 mg, 2.57 mmol) in dioxane (10 mL) was added Cs$_2$CO$_3$ (1290 mg, 3.96 mmol) and Pd(dppf)$_2$Cl$_2$ (145 mg, 0.198 mmol). The light brown solution was sparged with N$_2$ for 2 min, sealed and stirred at 80° C. for 2 h. The reaction was cooled to ambient temperature then concentrated and purified by column chromatography (silica gel, 0-45% ethyl acetate/petroleum) to give tert-butyl 6-fluoro-3-(3-(hydroxymethyl)-1,1-dioxido-2,3-dihydrobenzo[d]isothiazol-5-yl)-1H-indole-1-carboxylate (500 mg, 59%) as a light yellow gum.

Step 6: (−)-5-(6-fluoro-1H-indol-3-yl)-3-(hydroxymethyl)-2,3-dihydrobenzo[d]isothiazole 1,1-dioxide Racemic tert-butyl 6-fluoro-3-(3-(hydroxymethyl)-1,1-dioxido-2,3-dihydrobenzo[d]isothiazol-5-yl)-1H-indole-1-carboxylate (200 mg) was purified by chiral SFC to give two enantiomers. To a solution of peak 1 (100 mg, 0.231 mmol) in methanol (5 mL) was added HCl/methanol (10 mL, 4 M) at 0° C. The reaction was warmed to ambient temperature and stirred for 2 h then concentrated. The crude product was purified by prep-HPLC to give (−)-5-(6-fluoro-1H-indol-3-yl)-3-(hydroxymethyl)-2,3-dihydrobenzo[d]isothiazole 1,1-dioxide (45 mg, 59%) as a white solid. $^1$H NMR (400 MHz, DMSO-d$_6$)™ [ππμ] 11.57-11.75 (m, 1H), 7.85-8.00 (m, 5H), 7.77-7.83 (m, 1H), 7.27 (dd, J=9.91, 2.38 Hz, 1H), 7.02 (td, J=9.29, 2.51 Hz, 1H), 5.25 (t, J=5.52 Hz, 1H), 4.67 (t, J=5.90 Hz, 1H), 3.61-3.80 (m, 2H); LC-MS: m/z (M+Na)+ 354.9; $[\alpha]^{20}_D$ −40.3° (c=2.2 mg/ml, DMSO).

Example 13: (+)-5-(6-fluoro-1H-indol-3-yl)-3-(hydroxymethyl)-2,3-dihydrobenzo[d]isothiazole 1,1-dioxide

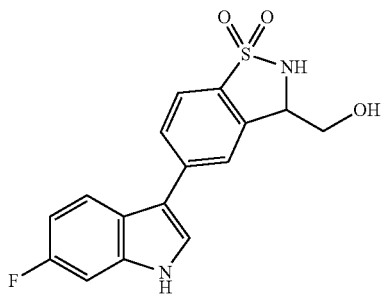 [SMILES: O=S1(=O)NC(CO)c2cc(-c3c[nH]c4cc(F)ccc34)ccc21]

To a solution of the second peak from chiral separation described in Example 12 (100 mg, 0.231 mmol) in methanol (5 mL) was added HCl/methanol (10 mL, 4 M) at 0° C. The reaction was warmed to ambient temperature and stirred for 2 h then concentrated. The crude product was purified by prep-HPLC to give (+)-5-(6-fluoro-1H-indol-3-yl)-3-(hydroxymethyl)-2,3-dihydrobenzo[d]isothiazole 1,1-dioxide (36 mg, 47%) as a white solid. $^1$H NMR (400 MHz, DMSO-$d_6$)™ [πτμ] 11.57-11.75 (m, 1H), 7.85-8.00 (m, 5H), 7.77-7.83 (m, 1H), 7.27 (dd, J=9.91, 2.38 Hz, 1H), 7.02 (td, J=9.29, 2.51 Hz, 1H), 5.25 (t, J=5.52 Hz, 1H), 4.67 (t, J=5.90 Hz, 1H), 3.61-3.80 (m, 2H); LC-MS: m/z (M+Na)$^+$ 354.9; $[\alpha]^{20}_D$ +37.3° (c=3 mg/ml, DMSO).

Example 14: methyl 5-(6-fluoro-1H-indol-3-yl)-2,3-dihydrobenzo-[d]isothiazole-3-carboxylate 1,1-dioxide

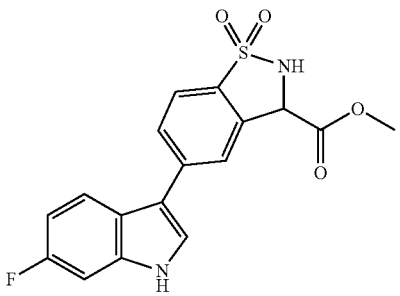 [SMILES: COC(=O)C1NS(=O)(=O)c2ccc(-c3c[nH]c4cc(F)ccc34)cc21]

Step 1: methyl 5-(1-(tert-butoxycarbonyl)-6-fluoro-1H-indol-3-yl)-2,3-dihydrobenzo[d]isothiazole-3-carboxylate 1,1-dioxide To a vial was added methyl 5-bromo-2,3-dihydrobenzo[d]isothiazole-3-carboxylate 1,1-dioxide (Example 12, Step 2, 200 mg, 0.653 mmol), tert-butyl 6-fluoro-3-(4,4,5,5-tetramethyl-1,3,2-dioxaborolan-2-yl)-1H-indole-1-carboxylate (236 mg, 0.653 mmol) and Pd(Amphos)Cl$_2$. The mixture was capped then evacuated and back-filled with N$_2$ in two cycles. Toluene (13 mL) was added followed by CsF (469 mg, 3.27 mmol, 1 M in water) and the reaction was heated to 70° C. with for 17 h. The crude reaction was diluted with EtOAc (20 mL) and water (5 mL) then the layers were separated. The organic phase was dried over Na$_2$SO$_4$, filtered and concentrated then purified by column chromatography to give methyl 5-(1-(tert-butoxycarbonyl)-6-fluoro-1H-indol-3-yl)-2,3-dihydrobenzo[d] isothiazole-3-carboxylate 1,1-dioxide (180 mg, 60%) as light yellow solid. $^1$H NMR (400 MHz, CDCl$_3$)™ [πτμ] 7.93-8.01 (m, 1H), 7.90 (d, J=8.53 Hz, 2H), 7.82-7.86 (m, 1H), 7.79 (s, 1H), 7.65 (dd, J=8.78, 5.27 Hz, 1H), 7.10 (d, J=2.51 Hz, 1H), 5.48 (d, J=4.02 Hz, 1H), 5.36 (d, J=4.27 Hz, 1H), 3.96 (s, 3H), 1.67-1.77 (m, 9H)

Step 2: methyl 5-(6-fluoro-1H-indol-3-yl)-2,3-dihydrobenzo[d]isothiazole-3-carboxylate 1,1-dioxide To a solution of methyl 5-(1-(tert-butoxycarbonyl)-6-fluoro-1H-indol-3-yl)-2,3-dihydrobenzo[d]isothiazole-3-carboxylate 1,1-dioxide (180 mg, 0.391 mmol) in dry DCM (2 mL) was added HCl/MeOH (10 mL, 4 M). The reaction was stirred at room temperature for 2 h then concentrated and purified by column chromatography to give racemic methyl 5-(6-fluoro-1H-indol-3-yl)-2,3-dihydrobenzo[d]isothiazole-3-carboxylate 1,1-dioxide (120 mg, 85%) as white solid. $^1$H NMR (400 MHz, DMSO-$d_6$)™ [πτμ] 11.71 (br s, 1H), 8.36-8.62 (m, 1H), 7.81-8.05 (m, 5H), 7.29 (dd, J=9.79, 2.26 Hz, 1H), 6.95-7.10 (m, 1H), 5.59 (br s, 1H), 3.78 (s, 3H); LC-MS: m/z 383.0 (M+Na)$^+$.

Example 15: (−)-5-(6-fluoro-1H-indol-3-yl)-2,3-dihydrobenzo[d]-Isothiazole-3-carboxamide 1,1-dioxide

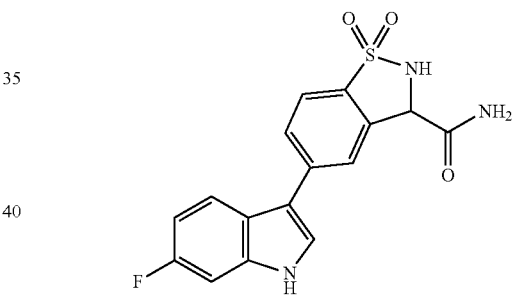

Step 1: tert-butyl 3-(3-carbamoyl-1,1-dioxido-2,3-dihydrobenzo[d]isothiazol-5-yl)-6-fluoro-1H-indole-1-carboxylate A solution of methyl 5-(1-(tert-butoxycarbonyl)-6-fluoro-1H-indol-3-yl)-2,3-dihydrobenzo[d]isothiazole-3-carboxylate 1,1-dioxide (150 mg, 0.326 mmol) in EtOH (15 mL) was sparged with NH$_3$ gas for 10 min at −30° C. The reaction was sealed and stirred at room temperature for 18 h then concentrated to give tert-butyl 3-(3-carbamoyl-1,1-dioxido-2,3-dihydrobenzo[d]isothiazol-5-yl)-6-fluoro-1H-indole-1-carboxylate (150 mg, 100%) as light yellow solid.

Step 2: 5-(6-fluoro-1H-indol-3-yl)-2,3-dihydrobenzo[d]-isothiazole-3-carboxamide 1,1-dioxide To a solution of tert-butyl 3-(3-carbamoyl-1,1-dioxido-2,3-dihydrobenzo[d]-isothiazol-5-yl)-6-fluoro-1H-indole-1-carboxylate (150 mg, 0.337 mmol) in EtOAc (2 mL) was added HCl/EtOAc (10 mL, 4M) at 0° C. The reaction was stirred at room temperature for 18 h then concentrated and neutralized NaHCO$_3$ (sat) (10 mL). The layers were separated and the organic phase was concentrated and purified by column chromatography to give the title compound as a racemic mixture. The enantiomers were separated by prep-chiral SFC to give 5-(6-fluoro-1H-indol-3-yl)-2,3-dihydrobenzo[d]isothiazole-3-carboxamide 1,1-dioxide as the first eluting peak (24 mg, 21%) as yellow solid. $^1$H NMR (400 MHz, DMSO-d$_6$)™ [ππμ] 11.71 (br s, 1H), 8.23 (d, J=5.02 Hz, 1H), 8.03 (s, 1H), 7.88-7.95 (m, 3H), 7.79-7.86 (m, 1H), 7.65 (s, 2H), 7.29 (dd, J=9.79, 2.26 Hz, 1H), 7.04 (td, J=9.22, 2.38 Hz, 1H), 5.19 (d, J=5.02 Hz, 1H), LC-MS: m/z 367.9 (M+Na)$^+$; $[\alpha]^{20}_D$ −31.0 (c=0.004 g/mL, DMSO).

Example 16: (+)-5-(6-fluoro-1H-indol-3-yl)-2,3-dihydrobenzo[d]-isothiazole-3-carboxamide 1,1-dioxide

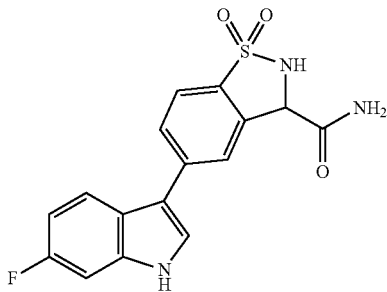 [SMILES: NC(=O)C1NS(=O)(=O)c2ccc(-c3c[nH]c4cc(F)ccc34)cc21]

The title compound was obtained as the second eluting peak form the chiral separation described for Example 15 (25 mg, 21%) as white solid. $^1$H NMR (400 MHz, DMSO-d$_6$) δ [ppm] 11.71 (br s, 1H), 8.23 (d, J=5.02 Hz, 1H), 8.03 (s, 1H), 7.88-7.95 (m, 3H), 7.79-7.86 (m, 1H), 7.65 (s, 2H), 7.29 (dd, J=9.79, 2.26 Hz, 1H), 7.04 (td, J=9.22, 2.38 Hz, 1H), 5.19 (d, J=5.02 Hz, 1H); LC-MS: m/z 368 (M+Na)$^+$, $[\alpha]^{20}_D$ +33.66° (c=0.004 g/mL, DMSO).

Example 17: (−)-5-(6-fluoro-1H-indol-3-yl)-N-methyl-2,3-dihydrobenzo[d]isothiazole-3-carboxamide 1,1-dioxide

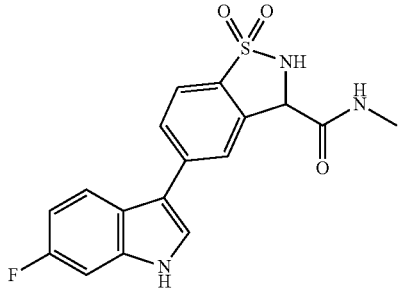 [SMILES: CNC(=O)C1NS(=O)(=O)c2ccc(-c3c[nH]c4cc(F)ccc34)cc21]

A solution of methyl 5-(1-(tert-butoxycarbonyl)-6-fluoro-1H-indol-3-yl)-2,3-dihydrobenzo[d]isothiazole-3-carboxylate 1,1-dioxide (120 mg, 0.261 mmol) in MeNH$_2$/EtOH (5 mL, 30%) was stirred at room temperature for 16 h. The reaction was concentrated to give the title compound as a racemic mixture. The enantiomers were separated by prep-chiral SFC to give 5-(6-fluoro-1H-indol-3-yl)-N-methyl-2,3-dihydrobenzo[d]isothiazole-3-carboxamide 1,1-dioxide as the first eluting peak (38 mg, 41%) as white solid. $^1$H NMR (400 MHz, DMSO-d$_6$) δ [ppm] 11.71 (br s, 1H), 8.37 (d, J=5.52 Hz, 1H), 8.16 (d, J=4.77 Hz, 1H), 8.00-8.08 (m, 1H), 7.80-7.96 (m, 4H), 7.29 (dd, J=9.79, 2.51 Hz, 1H), 7.06 (td, J=9.22, 2.38 Hz, 1H), 5.23 (d, J=5.02 Hz, 1H), 2.67 (d, J=4.52 Hz, 3H); LC-MS m/z S 381.9 (M+Na)$^+$, $[\alpha]^{20}_D$ −59.38° (c=0.0035 g/mL, DMSO).

Example 18: (+)-5-(6-fluoro-1H-indol-3-yl)-N-methyl-2,3-dihydrobenzo[d]isothiazole-3-carboxamide 1,1-dioxide

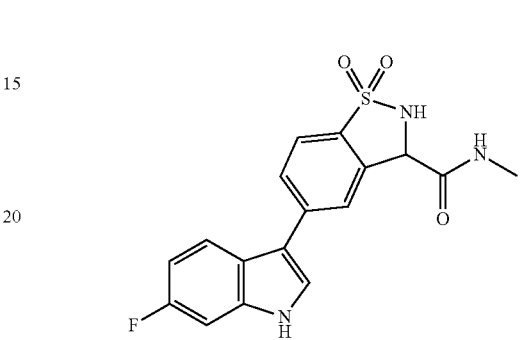

The title compound was obtained as the second eluting peak form the chiral separation described for Example 17 (35 mg, 37%) as white solid. $^1$H NMR (400 MHz, DMSO-d$_6$) δ [ppm] 11.71 (br s, 1H), 8.37 (d, J=5.52 Hz, 1H), 8.16 (d, J=4.77 Hz, 1H), 8.00-8.08 (m, 1H), 7.80-7.96 (m, 4H), 7.29 (dd, J=9.79, 2.51 Hz, 1H), 7.06 (td, J=9.22, 2.38 Hz, 1H), 5.23 (d, J=5.02 Hz, 1H), 2.67 (d, J=4.52 Hz, 3H); LC-MS: m/z 381.9 (M+Na)$^+$, $[\alpha]^{20}_D$ +76.85° (c=0.0036 g/mL, DMSO).

Example 19: (+)-3-(aminomethyl)-5-(6-fluoro-1H-indol-3-yl)-2,3-dihydrobenzo[d]isothiazole 1,1-dioxide

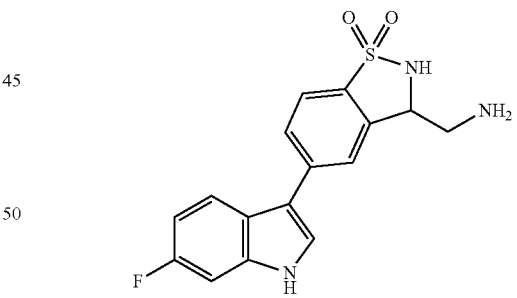

Step 1: N-(3-bromophenethyl)-2,2,2-trifluoroacetamide

To a cooled (ice bath) solution of 3-bromophenethylamine (21 g, 105 mmol) and TEA (12.7 g, 125 mmol) in DCM (150 mL) was added dropwise trifluoroacetic anhydride (24 g, 115 mmol). The reaction was stirred at room temperature for 18 h then poured into water (200 mL) and extracted with DCM (2×200 mL). The combined organic layers were concentrated then diluted with methyl tert-butyl ether (TBME) (250 mL) and H$_2$O (50 mL). The layers were separated and the organic phase was washed with brine (50 mL) then dried over Na$_2$SO$_4$, filtered and concentrated to give crude N-(3-bromophenethyl)-O-(2,2,2-trifluoro-acetyl)hydroxylamine (33 g, >100%) as a brown solid. $^1$H NMR (400 MHz, DMSO-d$_6$) δ [ppm] 9.49 (br s, 1H), 7.47-7.35 (m, 2H), 7.30-7.17 (m, 2H), 3.42 (d, J=4.0 Hz, 2H), 2.80 (t, J=7.0 Hz, 2H).

Step 2: 4-bromo-2-(2-(2,2,2-trifluoroacetamido)ethyl)benzene-1-sulfonyl chloride A solution of N-(3-bromophenethyl)-2,2,2-trifluoroacetamide (33 g, 110 mmol) in DCM(250 mL) was cooled in an ice bath then chlorosulfonic acid (121 g) was added dropwise. The reaction was stirred under a N$_2$ atmosphere at 5° C. for 4 h then at room temperature for 18 h. The reaction was carefully poured into ice water (500 mL) and extracted with TBME (2×200 mL). The combined organic layers were washed with brine (10 mL) and NaHCO$_3$ (sat) (50 mL) then dried over Na$_2$SO$_4$, filtered and concentrated to give crude 4-bromo-2-(2-(2,2,2-trifluoroacetamido)ethyl)benzene-1-sulfonyl chloride (35 g, 82%) as a brown solid. $^1$H NMR (400 MHz, DMSO-d$_6$) δ [ppm] 9.68 (br s, 1H), 7.67 (s, 1H), 7.52-7.25 (m, 2H), 3.62-3.40 (m, 2H), 3.27 (t, J=6.7 Hz, 2H).

Step 3: 5-bromo-2-(N-(tert-butyl)sulfamoyl)phenethyl acetate

To a cooled (ice bath) solution of 4-bromo-2-(2-(2,2,2-trifluoroacetamido)-ethyl)benzene-1-sulfonyl chloride (5 g, 13 mmol) in DCM (50 mL) was added dropwise tert-butylamine (4.0 mL, 38 mmol). The reaction was stirred in the ice bath for 10 min then concentrated and purified by column chromatography to give 5-bromo-2-(N-(tert-butyl)sulfamoyl)phenethyl acetate (5 g, 92%) as a light yellow oil. $^1$H NMR (400 MHz, DMSO-d$_6$) δ [ppm] 9.45 (t, J=5.4 Hz, 1H), 7.82 (d, J=8.5 Hz, 1H), 7.71-7.60 (m, 2H), 7.53 (d, J=2.0 Hz, 1H), 3.54 (q, J=6.3 Hz, 2H), 3.21 (t, J=6.7 Hz, 2H), 1.13 (s, 9H).

Step 4: N-(2-bromo-2-(5-bromo-2-(N-(tert-butyl)sulfamoyl)-phenyl)ethyl)-2,2,2-trifluoroacetamide A solution of N-(5-bromo-2-(N-(tert-butyl)sulfamoyl)phenethyl)-2,2,2-trifluoroacetamide (12 g, 28 mmol), NBS (7.4 g, 42 mmol) and AIBN (2.3 g, 14 mmol) in CCl$_4$ (350 mL) was stirred at 80° C. for 16 h then concentrated. The crude residue was purified by column chromatography to afford N-(2-bromo-2-(5-bromo-2-(N-(tert-butyl)sulfamoyl)phenyl)ethyl)-2,2,2-trifluoroacetamide (3.8 g, 27%) as yellow gum and 6.9 g of the starting material was recovered.

Step 5: N-((5-bromo-2-(tert-butyl)-1,1-dioxido-2,3-dihydrobenzo-[d]isothiazol-3-yl)methyl)-2,2,2-trifluoroacetamide A mixture of N-(2-bromo-2-(5-bromo-2-(N-(tert-butyl)sulfamoyl)-phenyl)ethyl)-2,2,2-trifluoroacetamide (3.8 g, 7.4 mmol) and K$_2$CO$_3$ (2.1 g, 15 mmol) in DMF (60 mL) was heated to 80° C. for 2 h then diluted with water (50 mL) and extracted with EtOAc (25 mL×2). The combined organic extracts were washed with brine (10 mL×3) then dried with Na$_2$SO$_4$, filtered and concentrated. The crude residue was purified by column chromatography to afford N-((5-bromo-2-(tert-butyl)-1,1-dioxido-2,3-dihydrobenzo[d]isothiazol-3-yl)methyl)-2,2,2-trifluoroacetamide (4.2 g, 100%) as yellow gum.

Step 6: tert-butyl 3-(2-(tert-butyl)-1,1-dioxido-3-((2,2,2-trifluoroacetamido)-methyl)-2,3-dihydrobenzo[d]isothiazol-5-yl)-6-fluoro-1H-indole-1-carboxylate To a suspension of N-((5-bromo-2-(tert-butyl)-1,1-dioxido-2,3-dihydrobenzo[d]isothiazol-3-yl)methyl)-2,2,2-trifluoroacetamide (4.2 g, 9.8 mmol), tert-butyl 6-fluoro-3-(4,4,5,5-tetramethyl-1,3,2-dioxaborolan-2-yl)-1H-indole-1-carboxylate (3.5 g, 9.8 mmol) and Cs$_2$CO$_3$ (6.4 mg, 20 mmol) in dioxane (60 mL) and H$_2$O (15 mL) was added PdCl$_2$(dppf) (0.72 g, 0.98 mmol). The reaction was stirred at 80° C. under a N$_2$ atmosphere for 1.5 h then concentrated. The crude residue was purified by column chromatography to give tert-butyl 3-(2-(tert-butyl)-1,1-dioxido-3-((2,2,2-trifluoroacetamido)-methyl)-2,3-dihydrobenzo[d]isothiazol-5-yl)-6-fluoro-1H-indole-1-carboxylate (2.9 g, 51%) as a yellow solid. $^1$H NMR (400 MHz, DMSO-d$_6$) δ [ppm] 9.37 (t, J=6.1 Hz, 1H), 8.07-7.98 (m, 2H), 7.94-7.88 (m, 2H), 7.86-7.80 (m, 2H), 7.25 (dt, J=2.5, 9.0 Hz, 1H), 5.15 (dd, J=2.4, 6.4 Hz, 1H), 3.88-3.79 (m, 1H), 3.56-3.49 (m, 1H), 1.66 (s, 9H), 1.51 (s, 9H).

Step 7: chiral 3-(aminomethyl)-2-(tert-butyl)-5-(6-fluoro-1H-indol-3-yl)-2,3-dihydrobenzo[d]isothiazole 1,1-dioxide To a solution of tert-butyl 3-(2-(tert-butyl)-1,1-dioxido-3-((2,2,2-trifluoro-acetamido)methyl)-2,3-dihydrobenzo[d]isothiazol-5-yl)-6-fluoro-1H-indole-1-carboxylate (500 mg, 0.857 mmol) in MeOH (6 mL) and H$_2$O (3 mL) was added NaOH (69 mg, 1.7 mmol). The reaction was stirred at 50° C. for 9 h then diluted with EtOAc/MeOH(10/1: 30 mL). The layers were separated and the organic phase was washed with brine (10 mL) then dried over anhydrous Na$_2$SO$_4$, filtered and concentrated. The residue was purified by column chromatography to give racemic 3-(aminomethyl)-2-(tert-butyl)-5-(6-fluoro-1H-indol-3-yl)-2,3-dihydrobenzo[d]isothiazole 1,1-dioxide (262 mg, 79%) as light yellow gum. The enantiomers were separated by prep-chiral SFC to give peak 1 (112 mg, 33.1%) and peak 2 (105 mg, 31.6%) each as a yellow gum.

Step 8: (+)-3-(aminomethyl)-5-(6-fluoro-1H-indol-3-yl)-2,3-dihydrobenzo[d]isothiazole 1,1-dioxide A solution of chiral 3-(aminomethyl)-2-(tert-butyl)-5-(6-fluoro-1H-indol-3-yl)-2,3-dihydrobenzo[d]isothiazole 1,1-dioxide (100 mg, 0.19 mmol) (step 7, peak 1) in HCl/MeOH (10 mL) was stirred at 30° C. for 16 h. The reaction was concentrated and purified by prep-HPLC to give (+)-3-(aminomethyl)-5-(6-fluoro-1H-indol-3-yl)-2,3-dihydrobenzo[d]isothiazole 1,1-dioxide (75 mg, 88%) as a white solid. $^1$H NMR (400 MHz, MeOD) δ [ppm] 7.98 (dd, J=1.0, 8.3 Hz, 1H), 7.95-7.89 (m, 2H), 7.84 (d, J=8.0 Hz, 1H), 7.73 (s, 1H), 7.18 (dd, J=2.3, 9.8 Hz, 1H), 6.96 (dt, J=2.5, 9.2 Hz, 1H), 5.03 (dd, J=3.5, 8.8 Hz, 1H), 3.56 (dd, J=3.6, 13.2 Hz, 1H), 3.28-3.21 (m, 1H), LC-MS: m/z 353.9 (M+Na)$^+$, [α]$^{20}_D$ +84.38° (c=0.0035 g/mL, MeOH).

Example 20: (−)-3-(aminomethyl)-5-(6-fluoro-1H-indol-3-yl)-2,3-dihydrobenzo[d]isothiazole 1,1-dioxide

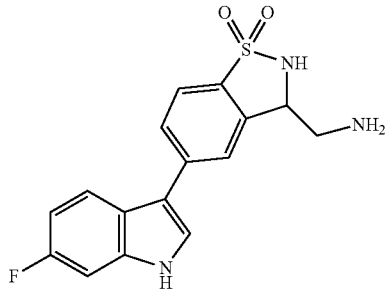 [SMILES: NCC1NS(=O)(=O)c2ccc(-c3c[nH]c4cc(F)ccc34)cc21]

A solution of chiral-3-(aminomethyl)-2-(tert-butyl)-5-(6-fluoro-1H-indol-3-yl)-2,3-dihydrobenzo[d]isothiazole 1,1-dioxide (100 mg, 0.19 mmol) (Example 19, step 7, peak 2) in HCl(g)/MeOH (10 mL) was stirred at 30° C. for 16 h. The reaction was concentrated and purified by prep HPLC to give (−)-3-(aminomethyl)-5-(6-fluoro-1H-indol-3-yl)-2,3-dihydrobenzo[d]isothiazole 1,1-dioxide (72 mg, 84%) as a white solid. $^1$H NMR (400 MHz, MeOD) δ [ppm] 8.01-7.96 (m, 1H), 7.95-7.89 (m, 2H), 7.84 (d, J=8.3 Hz, 1H), 7.73 (s, 1H), 7.18 (dd, J=2.3, 9.5 Hz, 1H), 6.96 (dt, J=2.4, 9.2 Hz, 1H), 5.03 (dd, J=3.5, 8.8 Hz, 1H), 3.56 (dd, J=3.5, 13.1 Hz, 1H), 3.24 (dd, J=8.8, 13.1 Hz, 1H), LC-MS: m/z 353.9 (M+H)$^+$, $[α]^{20}_D$ −65.21° (c=0.0035 g/mL, MeOH).

Example 21: (−)-methyl ((5-(6-fluoro-1H-indol-3-yl)-1,1-dioxido-2,3-dihydrobenzo[d]isothiazol-3-yl)methyl)carbamate

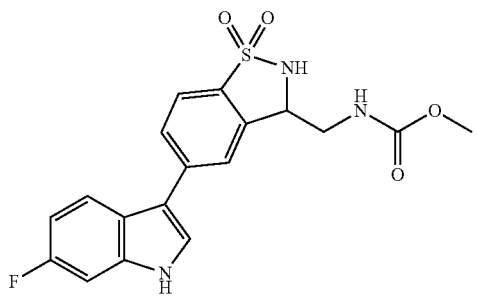 [SMILES: COC(=O)NCC1NS(=O)(=O)c2ccc(-c3c[nH]c4cc(F)ccc34)cc21]

Step 1: methyl ((2-(tert-butyl)-5-(6-fluoro-1H-indol-3-yl)-1,1-dioxido-2,3-dihydrobenzo[d]isothiazol-3-yl)methyl)carbamate To a solution of 3-(aminomethyl)-2-(tert-butyl)-5-(6-fluoro-1H-indol-3-yl)-2,3-dihydrobenzo[d]isothiazole 1,1-dioxide (300 mg, 0.774 mmol) and N,N-diisopropylethylamine (DIPEA) (200 mg, 1.55 mmol) in DCM (5 mL) was added methyl carbonochloridate (81 mg, 0.852 mmol) at 5° C. The reaction was stirred for 30 minutes then extracted with EtOAc (20 mL×2). The combined organic layers were washed with brine (15 mL) then dried over anhydrous Na$_2$SO$_4$, filtered and concentrated to give crude methyl ((2-(tert-butyl)-5-(6-fluoro-1H-indol-3-yl)-1,1-dioxido-2,3-dihydrobenzo[d]isothiazol-3-yl)methyl)carbamate (320 mg, 93% yield) as an off-white solid.

Step 2: (−)-methyl ((5-(6-fluoro-1H-indol-3-yl)-1,1-dioxido-2,3-dihydrobenzo[d]isothiazol-3-yl)methyl)carbamate A solution of methyl ((2-(tert-butyl)-5-(6-fluoro-1H-indol-3-yl)-1,1-dioxido-2,3-dihydrobenzo[d]isothiazol-3-yl)methyl)carbamate (320 mg, 0.718 mmol) and TFA (8 mL) in DCM (5 mL) was stirred at 50° C. for 3 h. The reaction was concentrated and neutralized with NaHCO$_3$ (sat) then extracted with EtOAc (20 mL×2). The combined organic layers were washed with brine (15 mL) then dried over anhydrous Na$_2$SO$_4$, filtered and concentrated. The crude residue was purified by prep-HPLC to give 100 mg of the racemic product. The enantiomers were separated by prep-chiral SFC to give (−)-methyl ((5-(6-fluoro-1H-indol-3-yl)-1,1-dioxido-2,3-dihydrobenzo[d]isothiazol-3-yl)methyl)carbamate as the first eluting peak (33 mg, 12%) as an off-white solid. $^1$H NMR (400 MHz, MeOD) δ [ppm] 7.97-7.88 (m, 2H), 7.86 (s, 1H), 7.77 (d, J=8.0 Hz, 1H), 7.68 (s, 1H), 7.16 (dd, J=2.4, 9.7 Hz, 1H), 6.95 (dt, J=2.4, 9.2 Hz, 1H), 4.87-4.82 (m, 1H), 3.71-3.58 (m, 4H), 3.50 (dd, J=7.0, 14.1 Hz, 1H), LC-MS: m/z, 411.9 (M+Na)$^+$, $[α]^{20}_D$ −85° (c=1 mg/mL, MeOH).

Example 22: (+)-methyl ((5-(6-fluoro-1H-indol-3-yl)-1,1-dioxido-2,3-dihydrobenzo[d]isothiazol-3-yl)methyl)carbamate

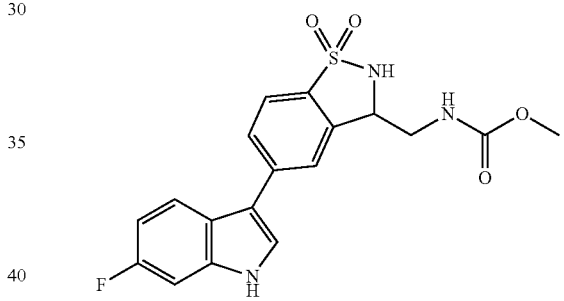

The title compound was obtained as the second eluting peak from the chiral separation described for Example 21 (37 mg, 13%) as an off-white solid. $^1$H NMR (400 MHz, MeOD) δ [ppm] 7.95-7.88 (m, 2H), 7.86 (s, 1H), 7.77 (d, J=8.3 Hz, 1H), 7.68 (s, 1H), 7.16 (dd, J=2.4, 9.7 Hz, 1H), 6.95 (dt, J=2.5, 9.2 Hz, 1H), 4.85 (d, J=5.8 Hz, 1H), 3.69-3.59 (m, 4H), 3.50 (dd, J=6.9, 14.2 Hz, 1H); LC-MS: m/z, 411.8 (M+Na)$^+$, $[α]^{20}_D$ +89° (c=1 mg/mL, MeOH).

Example 23: (−)-N-((5-(6-fluoro-1H-indol-3-yl)-1,1-dioxido-2,3-dihydrobenzo[d]isothiazol-3-yl)methyl)acetamide

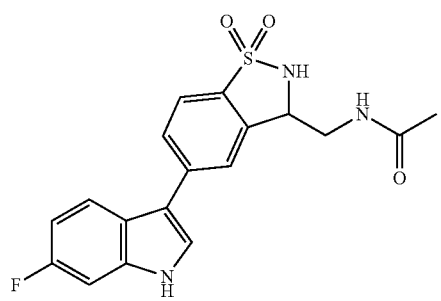 [SMILES: CC(=O)NCC1NS(=O)(=O)c2ccc(-c3c[nH]c4cc(F)ccc34)cc21]

Step 1: N-((2-(tert-butyl)-5-(6-fluoro-1H-indol-3-yl)-1,1-dioxido-2,3-dihydrobenzo[d]isothiazol-3-yl)methyl)acetamide To a cooled (ice bath) solution of 3-(aminomethyl)-2-(tert-butyl)-5-(6-fluoro-1H-indol-3-yl)-2,3-dihydrobenzo[d]isothiazole 1,1-dioxide (100 mg, 0.258 mmol) in DCM (5 mL) and DIPEA (0.09 mL, 0.52 mmol) was added dropwise a solution of acetyl chloride (22 mg, 0.28 mmol) in DCM (2 mL). The reaction was stirred at room temperature for 30 min then concentrated and purified by column chromatography to give the title compound as racemic mixture. The enantiomers were separated by prep-chiral SFC to give the first eluting peak of the tile compound (peak 1, 37 mg, 23%) and the second eluting peak (peak 2, 25 mg, yield: 23%) as white gum.

Step 2: (−)-N-((5-(6-fluoro-1H-indol-3-yl)-1,1-dioxido-2,3-dihydrobenzo[d]isothiazol-3-yl)methyl)acetamide A solution of chiral-N-((2-(tert-butyl)-5-(6-fluoro-1H-indol-3-yl)-1,1-dioxido-2,3-dihydrobenzo[d]isothiazol-3-yl)methyl)acetamide (step 1, peak 1, 25 mg, 0.07 mmol) in HCl(g)/MeOH (5 mL) was stirred at 30° C. for 18 h. The reaction was concentrated and purified by prep-TLC to give (−)-N-((5-(6-fluoro-1H-indol-3-yl)-1,1-dioxido-2,3-dihydrobenzo[d]isothiazol-3-yl)methyl)acetamide (11 mg, 44%) as a white solid. $^1$H NMR (400 MHz, MeOD) δ [ppm] 7.97-7.86 (m, 3H), 7.77 (d, J=8.0 Hz, 1H), 7.70-7.68 (m, 1H), 7.16 (dd, J=2.3, 9.5 Hz, 1H), 6.99-6.92 (m, 1H), 4.91-4.88 (m, 1H), 3.81 (dd, J=4.1, 13.9 Hz, 1H), 3.52 (dd, J=6.7, 13.9 Hz, 1H), 1.94 (s, 3H) LC-MS: m/z 373.9 (M+H)$^+$, $[α]^{20}_D$ −67.65° (c=0.00136 g/mL, MeOH).

Example 24: (+)-N-((5-(6-fluoro-1H-indol-3-yl)-1,1-dioxido-2,3-dihydrobenzo[d]isothiazol-3-yl)methyl)acetamide

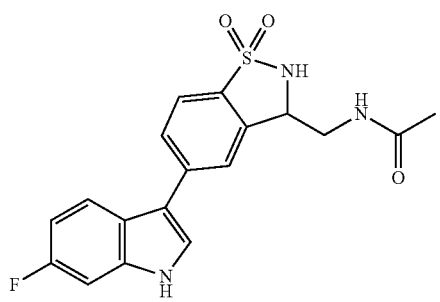 [SMILES: CC(=O)NCC1NS(=O)(=O)c2ccc(-c3c[nH]c4cc(F)ccc34)cc21]

A solution of chiral N-((2-(tert-butyl)-5-(6-fluoro-1H-indol-3-yl)-1,1-dioxido-2,3-dihydrobenzo[d]isothiazol-3-yl)methyl)acetamide (Example 23, step 1, peak 2, 37 mg, 0.09 mmol) in HCl/MeOH (5 mL) was stirred at 30° C. for 7 h. The reaction was concentrated and purified by Prep-TLC to give (+)-N-((5-(6-fluoro-1H-indol-3-yl)-1,1-dioxido-2,3-dihydrobenzo[d]isothiazol-3-yl) methyl)acetamide (27 mg, 83%) as a white solid. $^1$H NMR (400 MHz, MeOD) δ [ppm] 7.94-7.87 (m, 3H), 7.77 (d, J=8.0 Hz, 1H), 7.68 (s, 1H), 7.16 (dd, J=2.3, 9.8 Hz, 1H), 6.95 (dt, J=2.5, 9.2 Hz, 1H), 4.91-4.88 (m, 1H), 3.80 (dd, J=4.1, 13.9 Hz, 1H), 3.56-3.48 (m, 1H), 1.94 (s, 3H) LC-MS: m/z 395.9 (M+Na)$^+$, $[α]^{20}_D$ +81.67° (c=0.0024 g/mL, MeOH).

Example 25: (−)-3-((dimethylamino)methyl)-5-(6-fluoro-1H-indol-3-yl)-2,3-dihydrobenzo[d]isothiazole 1,1-dioxide

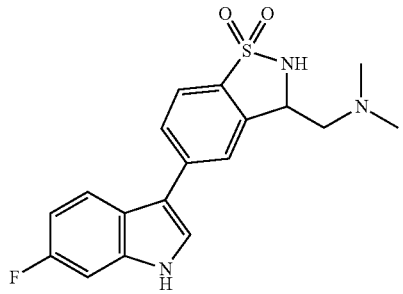

Step 1: 2-(tert-butyl)-3-((dimethylamino)methyl)-5-(6-fluoro-1H-indol-3-yl)-2,3-dihydrobenzo[d]isothiazole 1,1-dioxide To a solution of tert-butyl 3-(2-(tert-butyl)-1,1-dioxido-3-((2,2,2-trifluoroacetamido)methyl)-2,3-dihydrobenzo[d]isothiazol-5-yl)-6-fluoro-1H-indole-1-carboxylate (1.9 g, 3.3 mmol) in MeOH (20 mL) and H$_2$O (12 mL) was added NaOH (260 mg, 6.51 mmol). The reaction was stirred at 65° C. for 30 h then diluted with water (20 mL) and extracted with EtOAc (50 mL×2). The combined organic layers were washed with brine (50 mL) then dried over anhydrous Na$_2$SO$_4$, filtered and concentrated. The crude residue was purified by column chromatography to give 2-(tert-butyl)-3-((dimethylamino)methyl)-5-(6-fluoro-1H-indol-3-yl)-2,3-dihydrobenzo[d]isothiazole 1,1-dioxide (1.1 g, 87%) as an off-white solid.

Step 2: 2-(tert-butyl)-3-((dimethylamino)methyl)-5-(6-fluoro-1H-indol-3-yl)-2,3-dihydrobenzo[d]isothiazole 1,1-dioxide To a solution of 3-(aminomethyl)-2-(tert-butyl)-5-(6-fluoro-1H-indol-3-yl)-2,3-dihydrobenzo[d]isothiazole 1,1-dioxide (200 mg, 0.516 mmol) in MeOH (5 mL) was added formaldehyde (37% in water, 209 mg, 2.58 mmol) at room temperature. The reaction was stirred for 15 min then NaBH$_3$CN (49 mg, 0.77 mmol) was added followed by AcOH (31 mg, 0.52 mmol). The reaction was stirred at room temperature for 1 h then extracted with EtOAc (20 mL×2). The combined organic layers were washed with brine (15 mL) then dried over anhydrous Na$_2$SO$_4$, filtered and concentrated to give crude 2-(tert-butyl)-3-((dimethylamino)methyl)-5-(6-fluoro-1H-indol-3-yl)-2,3-dihydrobenzo[d]isothiazole 1,1-dioxide (200 mg, 93%) as yellow oil.

Step 3: (−)-3-((dimethylamino)methyl)-5-(6-fluoro-1H-indol-3-yl)-2,3-dihydrobenzo[d]isothiazole 1,1-dioxide A solution of 2-(tert-butyl)-3-((dimethylamino)methyl)-5-(6-fluoro-1H-indol-3-yl)-2,3-dihydrobenzo[d]isothiazole 1,1-dioxide (200 mg, 0.481 mmol) and TFA (5 mL) in DCM (5 mL) was stirred at 30° C. for 2 h then at 50° C. for 2 h. The reaction was concentrated then neutralized with NaHCO$_3$ (sat) and extracted with EtOAc (30 mL×2). The combined organic layers were washed with brine (15 mL) then dried over anhydrous Na$_2$SO$_4$, filtered and concentrated. The crude residue was purified by prep-HPLC to give the title compound as a racemic mixture. The enantiomers were separated by prep-chiral SFC to give (−)-3-((dimethylamino)methyl)-5-(6-fluoro-1H-indol-3-yl)-2,3-dihydrobenzo[d]isothiazole 1,1-dioxide as the first eluting peak (26 mg, 15%) as colorless oil. $^1$H NMR (400 MHz, MeOD) δ [ppm] 7.90-7.83 (m, 3H), 7.76 (d, J=8.0 Hz, 1H), 7.67 (s, 1H), 7.16 (dd, J=2.3, 9.5 Hz, 1H), 6.94 (dt, J=2.4, 9.2 Hz, 1H), 4.86 (dd, J=4.5, 9.3 Hz, 1H), 2.84 (dd, J=4.3, 12.8 Hz, 1H), 2.70 (dd, J=9.3, 12.8 Hz, 1H), 2.43 (s, 6H); LC-MS: m/z, 359.9 (M+H)$^+$, [α]$^{20}_D$ −270.66° (c=1 mg/mL, MeOH).

Example 26: (+)-3-((dimethylamino)methyl)-5-(6-fluoro-1H-indol-3-yl)-2,3-dihydrobenzo[d]isothiazole 1,1-dioxide

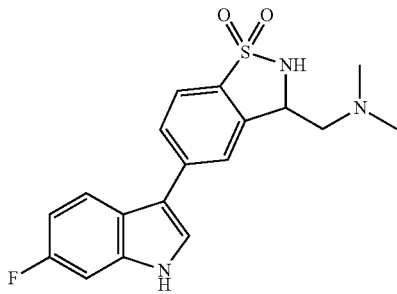 [SMILES: CN(C)CC1NS(=O)(=O)c2ccc(-c3c[nH]c4cc(F)ccc34)cc21]

The title compound was obtained as the second eluting peak from the chiral separation described for Example 25 (25 mg, 14%) as a white solid. $^1$H NMR (400 MHz, MeOD) δ [ppm] 7.92-7.81 (m, 3H), 7.75 (d, J=8.0 Hz, 1H), 7.65 (s, 1H), 7.15 (dd, J=2.3, 9.8 Hz, 1H), 6.94 (dt, J=2.3, 9.2 Hz, 1H), 4.83 (dd, J=4.5, 9.0 Hz, 1H), 2.84-2.75 (m, 1H), 2.66 (dd, J=9.0, 12.8 Hz, 1H), 2.40 (s, 6H); LC-MS: m/z, 359.7 (M+H)$^+$, [α]$^{20}_D$ +31° (c=1 mg/mL, MeOH).

Example 27: (+)-N-((5-(6-fluoro-1H-indol-3-yl)-1,1-dioxido-2,3-dihydrobenzo[d]isothiazol-3-yl)methyl)-N-methylacetamide

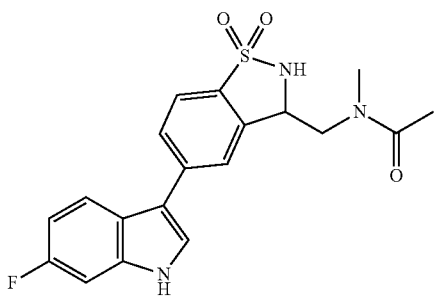 [SMILES: CC(=O)N(C)CC1NS(=O)(=O)c2ccc(-c3c[nH]c4cc(F)ccc34)cc21]

Step 1: tert-butyl 3-(2-(tert-butyl)-1,1-dioxido-3-((2,2,2-trifluoro-N-methylacetamido)methyl)-2,3-dihydrobenzo[d]isothiazol-5-yl)-6-fluoro-1H-indole-1-carboxylate To a solution of tert-butyl 3-(2-(tert-butyl)-1,1-dioxido-3-((2,2,2-trifluoroacetamido)methyl)-2,3-dihydrobenzo[d]isothiazol-5-yl)-6-fluoro-1H-indole-1-carboxylate (430 mg, 0.737 mmol) in DMF (5 mL) was added NaH (35 mg, 0.88 mmol, 60% dispersion in mineral oil). The suspension was stirred at 10° C. for 5 min then methyliodide (MeI) (523 mg, 3.68 mmol) was added and stirring was continued at 10° C. for 16 hrs. The reaction was quenched with NH$_4$Cl (sat) (15 mL) and extracted with EtOAc (30 mL×2). The combined organic layers were washed with brine (15 mL×3) then dried over anhydrous Na$_2$SO$_4$, filtered and concentrated to give crude tert-butyl 3-(2-(tert-butyl)-1,1-dioxido-3-((2,2,2-trifluoroacetamido)methyl)-2,3-dihydrobenzo[d]isothiazol-5-yl)-6-fluoro-1H-indole-1-carboxylate (500 mg>100%) as yellow oil.

Step 2: 2-(tert-butyl)-5-(6-fluoro-1H-indol-3-yl)-3-((methylamino)-methyl)-2,3-dihydrobenzo[d]isothiazole 1,1-dioxide To a solution of tert-butyl 3-(2-(tert-butyl)-1,1-dioxido-3-((2,2,2-trifluoro-acetamido)methyl)-2,3-dihydrobenzo[d]isothiazol-5-yl)-6-fluoro-1H-indole-1-carboxylate (500 mg, 0.837 mmol) in MeOH (10 mL) and H$_2$O (6 mL) was added NaOH (100 mg, 2.51 mmol). The reaction was stirred at 60° C. for 16 h then diluted with water (20 mL) and extracted with EtOAc (50 mL×3). The combined organic layers were washed with brine (50 mL) then dried over anhydrous Na$_2$SO$_4$, filtered and concentrated to give crude 2-(tert-butyl)-5-(6-fluoro-1H-indol-3-yl)-3-((methylamino)methyl)-2,3-dihydrobenz o[d]isothiazole 1,1-dioxide (330 mg, 98%) as an off-white solid.

Step 3: N-((2-(tert-butyl)-5-(6-fluoro-1H-indol-3-yl)-1,1-dioxido-2,3-dihydrobenzo[d]isothiazol-3-yl)methyl)-N-methylacetamide To a solution of 2-(tert-butyl)-5-(6-fluoro-1H-indol-3-yl)-3-((methylamino)methyl)-2,3-dihydrobenzo[d]isothiazole 1,1-dioxide (180 mg, 0.448 mmol) and DIPEA (0.148 mL, 0.897 mmol) in DCM (5 mL) was added dropwise a solution of acetyl chloride (38.7 mg/0.0351 mL, 0.493 mmol) in DCM (1 mL). The reaction was stirred at 10° C. for 1 h then concentrated, diluted with water (10 mL) and extracted with DCM (20 mL×3). The combined organic layers were washed with brine (10 mL) then dried over anhydrous Na$_2$SO$_4$, filtered and concentrated to give N-((2-(tert-butyl)-5-(6-fluoro-1H-indol-3-yl)-1,1-dioxido-2,3-dihydrobenzo[d]isothiazol-3-yl)methyl)-N-methylacetamide (220 mg, >100%) as an off-white solid.

Step 4: (+)-N-((5-(6-fluoro-1H-indol-3-yl)-1,1-dioxido-2,3-dihydrobenzo[d]isothiazol-3-yl)methyl)-N-methylacetamide A solution of N-((2-(tert-butyl)-5-(6-fluoro-1H-indol-3-yl)-1,1-dioxido-2,3-dihydrobenzo[d]isothiazol-3-yl)methyl)-N-methylacetamide (220 mg, 0.496 mmol) in TFA (10 mL) was stirred at 50° C. for 32 h. The reaction was concentrated then neutralized with NaHCO$_3$ (sat) (10 mL) and extracted with EtOAc (20 mL×3). The combined organic layers were washed with brine (20 mL) then dried over anhydrous Na$_2$SO$_4$, filtered and concentrated to give crude product (200 mg). The crude product was purified by prep-HPLC to give racemic N-((5-(6-fluoro-1H-indol-3-yl)-1,1-dioxido-2,3-dihydrobenzo[d]isothiazol-3-yl)methyl)-N-methylacetamide (54 mg, 28% yield) as colorless oil. The enantiomers were separated by prep-chiral SFC to give (+)-N-((5-(6-fluoro-1H-indol-3-yl)-1,1-dioxido-2,3-dihydrobenzo[d]isothiazol-3-yl) methyl)-N-methylacetamide as the first eluting peak (18 mg, 33%) as a white solid. $^1$H NMR (400 MHz, DMSO-$d_6$) δ [ppm] 11.68 (br s, 1H), 8.20-7.76 (m, 6H), 7.34-7.21 (m, 1H), 7.02 (t, J=9.3 Hz, 1H), 4.96 (br s, 1H), 4.04-3.48 (m, 2H), 3.09-2.89 (m, 3H), 2.02 (d, J=3.8 Hz, 3H); LC-MS: m/z, 388.1 (M+H)$^+$, [α]$^{20}_D$ +35° (c=2 mg/mL, DMSO).

Example 28: (−)-N-((5-(6-fluoro-1H-indol-3-yl)-1,1-dioxido-2,3-dihydrobenzo[d]isothiazol-3-yl)methyl)-N-methylacetamide

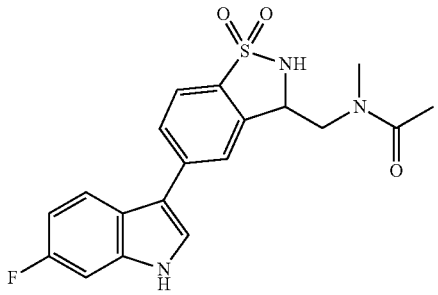 [SMILES: CC(=O)N(C)CC1NS(=O)(=O)c2ccc(-c3c[nH]c4cc(F)ccc34)cc21]

The title compound was obtained as the second eluting peak from the chiral separation described for Example 27 (18 mg, 33%) as a white solid. $^1$H NMR (400 MHz, DMSO-$d_6$) δ [ppm] 11.68 (br s, 1H), 8.18-7.78 (m, 6H), 7.27 (d, J=9.8 Hz, 1H), 7.02 (t, J=9.2 Hz, 1H), 4.97 (d, J=9.5 Hz, 1H), 4.05-3.48 (m, 2H), 3.08-2.91 (m, 3H), 2.02 (d, J=4.8 Hz, 3H); LC-MS: m/z, 387.9 (M+H)$^+$, [α]$^{20}_D$ −30.5° (c=2 mg/mL, DMSO).

Example 29: (−)-5-(6-fluoro-1H-indol-3-yl)-3-(2-hydroxyethyl)-2,3-dihydrobenzo[d]isothiazole 1,1-dioxide

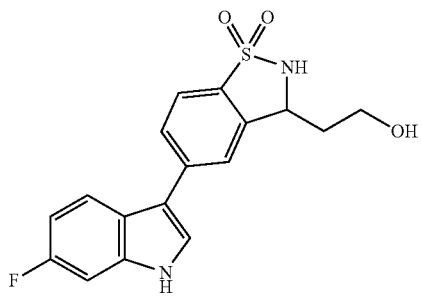 [SMILES: O=S1(=O)NC(CCO)c2cc(-c3c[nH]c4cc(F)ccc34)ccc21]

Step 1: 3-(3-bromophenyl)propan-1-ol

To a cooled (ice bath) solution of 3-(3-bromophenyl) propanoic acid (8.0 g, mmol) in anhydrous THF (100 mL) was added BH$_3$-THF (100 mL, 1.0 M) via addition funnel under a nitrogen atmosphere. The reaction was stirred at 0° C. for 1 h then at reflux for 16 h. The reaction was carefully quenched with HCl (37 mL, 2 M) then concentrated to remove THF. The suspension was diluted with DCM (300 mL) then filtered to remove the solids. The layers were separated and the organic phase was washed with water (50 mL) and brine (50 mL) then dried over anhydrous Na$_2$SO$_4$, filtered, and concentrated to give 3-(3-bromophenyl)propan-1-ol (9.8 g, >100%) as a yellow oil, which was used for next step without further purification.

Step 2: 3-(3-bromophenyl)propyl acetate

To a solution of 3-(3-bromophenyl)propan-1-ol (4.5 g, 16 mmol) in DCM (50 mL) was added Ac$_2$O (1.95 g, 19.1 mmol), Et$_3$N (4.83 g, 47.7 mmol) and DMAP (97 mg, 0.79 mmol). The reaction was stirred at 16° C. for 30 minutes then quenched with water (10 mL) and the layers were separated. The organic phase was washed with water (20 mL) and brine (20 mL) then dried over anhydrous Na$_2$SO$_4$, filtered, and concentrated. The crude oil was purified by column chromatography (silica gel, 0-50% EtOAc in Petroleum ether) to afford 3-(3-bromophenyl)propyl acetate (4.0 g, 98%) as a yellow oil. $^1$H NMR (400 MHz, DMSO-$d_6$) δ [ppm] 7.43 (s, 1H), 7.38 (td, J=1.9, 7.3 Hz, 1H), 7.27-7.21 (m, 2H), 3.98 (t, J=6.5 Hz, 2H), 2.65-2.61 (m, 2H), 1.99 (s, 3H), 1.90-1.80 (m, 2H).

Step 3: 3-(5-bromo-2-(chlorosulfonyl)phenyl)propyl acetate

To a cooled solution of 3-(3-bromophenyl)propyl acetate (3.8 g, 15 mmol) in CHCl$_3$ (50 mL) was added dropwise chlorosulfonic acid (17.2 g, 148 mmol) via addition funnel. The reaction was stirred at 14° C. for 3 h then poured into ice (200 g) and extracted with DCM (50 mL×3). The combined organic layers were washed with water (50 mL), NaHCO$_3$ (sat) (50 mL), water (50 mL) and brine (50 mL) then dried over anhydrous Na$_2$SO$_4$, filtered, and concentrated. The crude residue was purified by column chromatography to afford 3-(5-bromo-2-(chlorosulfonyl)phenyl) propylacetate (2.2 g, 42%) as a yellow oil.

Step 4: 3-(5-bromo-2-(N-(tert-butyl)sulfamoyl)phenyl)propyl acetate

To a solution of 3-(5-bromo-2-(chlorosulfonyl)phenyl) propyl acetate (1.7 g, 8.0 mmol) in DCM (30 mL) was added t-BuNH$_2$ (1.2 g, 16 mmol). The reaction was stirred at 14° C. for 30 min then quenched with water (15 mL) and concentrated to remove DCM. The residue was extracted with EtOAc (20 mL×3) and the combined organic layers were washed with water (20 mL) and brine (20 mL) then dried over anhydrous Na$_2$SO$_4$, filtered, and concentrated to afford 3-(5-bromo-2-(N-(tert-butyl)sulfamoyl)phenyl)propyl acetate (2.4 g, 81%) as a yellow oil, which was used for the next step without further purification.

Step 5: 3-bromo-3-(5-bromo-2-(N-(tert-butyl)sulfamoyl)phenyl)propyl acetate

To a solution of 3-(5-bromo-2-(N-(tert-butyl)sulfamoyl) phenyl)propyl acetate (2.4 g, 6.118 mmol) in CCl$_4$ (40 mL) was added NBS (1.2 g, 6.73 mmol) and AIBN (502 mg, 3.06 mmol). The reaction was stirred under a nitrogen atmosphere at 80° C. for 6 h then quenched with water (20 mL). The layers were separated and the organic phase was washed with water (20 mL×2) and brine (20 mL) then dried over anhydrous Na$_2$SO$_4$, filtered, and concentrated. The crude residue was purified by column chromatography to afford 3-bromo-3-(5-bromo-2-(N-(tert-butyl) sulfamoyl)phenyl) propyl acetate (3.0 g, >100%) as a brown oil.

Step 6: 2-(5-bromo-2-(tert-butyl)-1,1-dioxido-2,3-dihydrobenzo[d]isothiazol-3-yl)ethyl acetate To a solution of 3-bromo-3-(5-bromo-2-(N-(tert-butyl) sulfamoyl)-phenyl)propyl acetate (1.7 g, 3.5 mmol) in MeCN (20 mL) was added K₂CO₃ (968 mg, 7.00 mmol). The reaction was stirred at 40° C. for 16 h then quenched with water (15 mL) and extracted with EtOAc (20 mL×3). The combined organic layers were washed with water (20 mL) and brine (20 mL) then dried over anhydrous Na₂SO₄, filtered, and concentrated. The crude residue was purified by column chromatography to afford 2-(5-bromo-2-(tert-butyl)-1,1-dioxido-2,3-dihydrobenzo[d]isothiazol-3-yl)ethyl acetate (580 mg, 42%) as a yellow solid. $^1$H NMR (400 MHz, CDCl₃) δ [ppm] 7.66-7.59 (m, 2H), 7.56-7.54 (m, 1H), 4.82 (t, J=4.6 Hz, 1H), 4.28-4.23 (m, 1H), 4.06-3.99 (m, 1H), 2.34-2.30 (m, 2H), 1.88 (s, 3H), 1.55 (s, 9H).

Step 7: tert-butyl 3-(3-(2-acetoxyethyl)-2-(tert-butyl)-1,1-dioxido-2,3-dihydrobenzo[d]isothiazol-5-yl)-6-fluoro-1H-indole-1-carboxylate A solution of 2-(5-bromo-2-(tert-butyl)-1,1-dioxido-2,3-dihydrobenzo[d]isothiazol-3-yl)ethyl acetate (580 mg, 1.49 mmol), tert-butyl 6-fluoro-3-(4,4,5,5-tetramethyl-1,3,2-dioxaborolan-2-yl)-1H-indole-1-carboxylate (448 mg, 1.63 mmol), PdCl₂(dppf)CH₂Cl₂ (111 mg, 0.149 mmol), and K₃PO₄ (946 mg, 4.46 mmol) in 1,4-dioxane (10 mL) and water (2.5 mL) was sparged with nitrogen for 1 minute then stirred at 80° C. for 16 h. The crude reaction was extracted with EtOAc (15 mL×3) and the combined organic layers were washed with water (15 mL) and brine (15 mL) then dried over anhydrous Na₂SO₄, filtered, and concentrated. The crude product was purified by column chromatography (silica gel, 0-40% EtOAc in Petroleum ether) to afford tert-butyl 3-(3-(2-acetoxyethyl)-2-(tert-butyl)-1,1-dioxido-2,3-dihydrobenzo[d]isothiazol-5-yl)-6-fluoro-1H-indole-1-carboxylate (460 mg, 57%) as a yellow gum.

Step 8: 2-(5-(6-fluoro-1H-indol-3-yl)-1,1-dioxido-2,3-dihydrobenzo[d]isothiazol-3-yl)ethyl acetate A cooled (ice bath) solution of tert-butyl 3-(3-(2-acetoxyethyl)-2-(tert-butyl)-1,1-dioxido-2,3-dihydrobenzo[d]isothiazol-5-yl)-6-fluoro-1H-indole-1-carboxylate (660 mg, 1.21 mmol) in TFA (6 mL) was stirred at 6° C. for 3 h. The reaction was concentrated then diluted with DCM (60 mL) and neutralized with NaHCO₃ (sat) (20 mL). The layers were separated and the organic phase was washed with water (20 mL) and brine (20 mL) then dried over anhydrous Na₂SO₄, filtered, and concentrated to afford a crude 2-(5-(6-fluoro-1H-indol-3-yl)-1,1-dioxido-2,3-dihydrobenzo[d]isothiazol-3-yl)ethyl acetate (280 mg, 60%) as a white solid.

Step 9: (−)-5-(6-fluoro-1H-indol-3-yl)-3-(2-hydroxyethyl)-2,3-dihydrobenzo[d]isothiazole 1,1-dioxide To a solution of 2-(5-(6-fluoro-1H-indol-3-yl)-1,1-dioxido-2,3-dihydrobenzo[d]isothiazol-3-yl)ethyl acetate (280 mg, 0.721 mmol) in THF (20 mL) and water (10 mL) was added LiOH—H₂O (151 mg, 3.60 mmol). The reaction was stirred at 50° C. for 2 h then extracted with DCM (20 mL×3). The aqueous phase was lyophilized then dissolved in DCM/MeOH (40 mL/4 mL) and filtered. The filtrate was concentrated to afford racemic 5-(6-fluoro-1H-indol-3-yl)-3-(2-hydroxyethyl)-2,3-dihydrobenzo[d]isothiazole 1,1-dioxide (190 mg, 76%) as a white solid. The enantiomers were separated by prep-chiral SFC to give (−)-5-(6-fluoro-1H-indol-3-yl)-3-(2-hydroxyethyl)-2,3-dihydrobenzo[d]isothiazole 1,1-dioxide as the first eluting peak (54 mg, 28%) as a white solid. $^1$H NMR (400 MHz, DMSO-d₆) δ [ppm] 11.68 (br s, 1H), 7.95-7.90 (m, 2H), 7.88-7.77 (m, 4H), 7.26 (dd, J=2.4, 9.9 Hz, 1H), 7.01 (dt, J=2.4, 9.2 Hz, 1H), 4.81-4.74 (m, 1H), 4.70 (t, J=4.9 Hz, 1H), 3.67-3.57 (m, 2H), 2.22-2.13 (m, 1H), 1.83-1.74 (m, 1H); LC-MS: m/z 347.1 (M+H)⁺, [α]$^{20}_D$ −46.89° (c=1.045 mg/mL, MeOH).

Example 30: (+)-5-(6-fluoro-1H-indol-3-yl)-3-(2-hydroxyethyl)-2,3-dihydrobenzo[d]isothiazole 1,1-dioxide

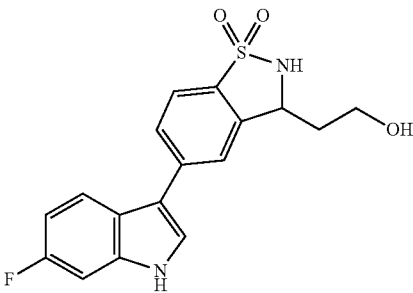 [SMILES: O=S1(=O)NC(CCO)c2cc(-c3c[nH]c4cc(F)ccc34)ccc21]

Step 1: (+)-5-(6-fluoro-1H-indol-3-yl)-3-(2-hydroxyethyl)-2,3-dihydrobenzo[d]isothiazole 1,1-dioxide The title compound was obtained as the second eluting peak form the chiral separation described for Example 29 (58 mg, 31%) as a white solid. $^1$H NMR (400 MHz, DMSO-d₆) δ [ppm] 11.68 (br s, 1H), 7.95-7.90 (m, 2H), 7.89-7.76 (m, 4H), 7.26 (dd, J=2.4, 9.9 Hz, 1H), 7.01 (dt, J=2.4, 9.2 Hz, 1H), 4.77 (dd, J=3.0, 9.5 Hz, 1H), 4.70 (br s, 1H), 3.65-3.57 (m, 2H), 2.22-2.14 (m, 1H), 1.77 (dt, J=5.0, 9.2 Hz, 1H), LC-MS: m/z 346.9 (M+H)⁺, [α]$^{20}_D$ +44.1° (c=1.155 mg/mL, MeOH).

Example 31: 2-(2-aminoethyl)-5-(6-fluoro-1H-indol-3-yl)-2,3-dihydrobenzo[d]isothiazole 1,1-dioxide

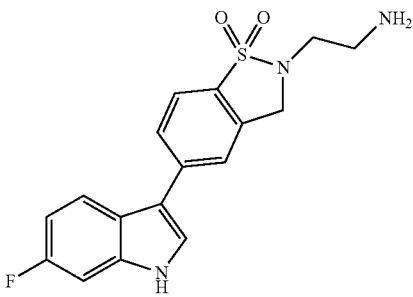 [SMILES: NCCN1Cc2cc(-c3c[nH]c4cc(F)ccc34)ccc2S1(=O)=O]

Step 1: 4-bromo-2-methylbenzene-1-sulfonyl chloride

To a colorless solution 1-bromo-3-methylbenzene (40 g, 230 mmol) in CHCl₃ (400 mL) was added chlorosulfonic acid (164 g, 1400 mmol) at 0° C. via addition funnel over 80 min. The resulting brown solution was stirred at 0° C. for 4 h then poured into ice (400 g) and extracted with dichloromethane (150 mL×3). The combined organic layers were washed with water (150 mL×2) and brine (150 mL) then dried over anhydrous $Na_2SO_4$, filtered and concentrated to afford 4-bromo-2-methylbenzene-1-sulfonyl chloride (45 g, 71%) as a white solid, which was used for next step without further purification. $^1$H NMR (400 MHz, CDCl$_3$) δ [ppm] 7.93 (dd, J=1.3, 8.5 Hz, 1H), 7.61 (s, 1H), 7.57 (d, J=8 Hz, 1H), 2.77 (s, 3H).

Step 2: 4-bromo-2-methylbenzenesulfonamide

To a yellow solution of 4-bromo-2-methylbenzene-1-sulfonyl chloride (45 g, 170 mmol) in 1,4-dioxane (350 mL) was added $NH_4OH$ (350 mL, 28% w/v) at 0° C. via addition funnel. The reaction was stirred at 24° C. for 10 h then concentrated. The resulting solid was washed with water (50 mL) then triturated with ether. The suspension was filtered and recrystallized with acetone/petroleum ether (100 mL/250 mL) to afford 4-bromo-2-methylbenzenesulfonamide (39 g, 94%) as a white crystalline solid. $^1$H NMR (400 MHz, CDCl$_3$) δ [ppm] 7.88 (d, J=8.5 Hz, 1H), 7.51 (s, 1H), 7.48-4.46 (m, 1H), 4.83 (br s, 2H), 2.67 (s, 3H).

Step 3: 5-bromobenzo[d]isothiazol-3(2H)-one 1,1-dioxide

A 500 mL three-necked round bottom flask equipped with magnetic stir bar and internal thermometer was charged with a solution of $H_5IO_6$ (46.3 g, 203 mmol) in MeCN (350 mL). The white suspension was stirred at 23° C. for 1 h then $CrO_3$ (254 mg, 2.54 mmol) was added followed by $Ac_2O$ (20.7 g, 203 mmol). The reaction was cooled to 0° C. and 4-bromo-2-methylbenzenesulfonamide (6.35 g, 25.4 mmol) was added with stirring at 0° C. for 15 min then room temperature for 16 h. The resulting yellow suspension was filtered and washed with water (300 mL). The white solid was dried to afford 5-bromobenzo[d]isothiazol-3(2H)-one 1,1-dioxide (5.6 g, 84%) as a white solid, which was used for next step without further purification. $^1$H NMR (400 MHz, DMSO-d$_6$) δ [ppm] 8.23-8.01 (m, 3H), 7.08 (br s, 1H).

Step 4: 5-bromo-2,3-dihydrobenzo[d]isothiazole 1,1-dioxide

To a cooled (ice bath) white suspension of 5-bromobenzo[d]isothiazol-3(2H)-one 1,1-dioxide (7.5 g, 29 mmol) in dry THF (160 mL) was slowly added $BH_3$.MeS (10 M, 14.3 mL, 143 mmol). The reaction was stirred at 75° C. for 2 h then slowly quenched with HCl (2 M, 150 mL) while remaining in the ice bath. The mixture was stirred for 1 h then concentrated and extracted with dichloromethane (100 mL×4). The combined organic layers were washed with brine, then dried over anhydrous $Na_2SO_4$, filtered, and concentrated to afford 5-bromo-2,3-dihydrobenzo[d]isothiazole 1,1-dioxide (6.6 g, 92%) as a white solid. $^1$H NMR (400 MHz, DMSO-d$_6$) δ [ppm] 7.91 (s, 1H), 7.84 (s, 1H), 7.80-7.72 (m, 2H), 4.39 (d, J=5.0 Hz, 2H). $^1$H NMR (400 MHz, CDCl$_3$) δ [ppm] 7.67 (d, J=1.0 Hz, 2H), 7.57 (s, 1H), 4.89 (br s, 1H), 4.52 (s, 2H).

Step 5: tert-butyl (2-hydroxyethyl)carbamate

To a colorless solution of $Boc_2O$ (21.8 g, 0.1 mol) in dichloromethane (20 mL) was added ethanolamine (6.71 g, 0.11 mol) in portions at 0° C. over 15 min. The reaction was stirred at 28° C. for 16 h then quenched with water (20 mL) and extracted with dichloromethane (30 mL×3). The combined organic layers were washed with water (20 mL) and brine (20 mL), then dried over anhydrous $Na_2SO_4$, filtered, and concentrated to afford tert-butyl (2-hydroxyethyl)carbamate (17 g, 100%) as a clear oil. $^1$H NMR (400 MHz, CDCl$_3$) δ [ppm] 5.23 (br s, 1H), 3.63-3.61 (m, 2H), 3.23 (br s, 2H), 1.41 (s, 9H).

Step 6: 2-((tert-butoxycarbonyl)amino)ethyl methanesulfonate

To an cooled (ice bath) solution of tert-butyl (2-hydroxyethyl)carbamate (10.0 g, 62.0 mmol) and $Et_3N$ (9.48 mL, 68.2 mmol) in dry dichloromethane (200 mL) was added a solution of MsCl (8.53 g, 74.4 mmol) in dichloromethane (100 mL) dropwise over 30 min. The reaction was stirred at 0° C. for 1 h then concentrated. The crude residue was diluted with ethyl acetate (100 mL) and water (60 mL). The organic layer was washed with aqueous 5% $NaHCO_3$ (50 mL) and brine (50 mL), then dried over $Na_2SO_4$, filtered and concentrated. The crude oil was purified by column chromatography (silica gel, 0-50% ethyl acetate/petroleum ether) to afford 2-((tert-butoxycarbonyl)amino)ethyl methanesulfonate (9.3 g, 62% yield) as colorless liquid. $^1$H NMR (400 MHz, CDCl$_3$) δ [ppm] 5.03 (br s, 1H), 4.26 (t, J=5.1 Hz, 2H), 3.44 (d, J=4.8 Hz, 2H), 3.01 (s, 3H), 1.42 (s, 9H).

Step 7: tert-butyl (2-(5-bromo-1,1-dioxidobenzo[d]isothiazol-2(3H)-yl)ethyl)carbamate An white suspension of 5-bromo-2,3-dihydrobenzo[d]isothiazole 1,1-dioxide (500 mg, 2.02 mmol) and $K_2CO_3$ (557 mg, 4.03 mmol) in DMF (8 mL) was stirred at 27° C. for 1 h then a solution of 2-((tert-butoxycarbonyl)amino)ethyl methanesulfonate (723 mg, 3.02 mmol) in DMF (2 mL) was added slowly. The reaction was sparged with $N_2$ for 1 min and stirred at 80° C. for 16 h. The reaction was cooled to ambient temperature, diluted with water (30 mL) and extracted with ethyl acetate (25 mL×3). The combined organic layers were washed with brine (20 mL×2), then dried over anhydrous $Na_2SO_4$, filtered, and concentrated. The crude yellow solid was purified by column chromatography (silica gel, 0-50% ethyl acetate/petroleum ether) to afford tert-butyl (2-(5-bromo-1,1-dioxidobenzo[d]isothiazol-2(3H)-yl)ethyl)carbamate (656 mg, 83%) as a pale-yellow solid. $^1$H NMR (400 MHz, CDCl$_3$) δ [ppm] 8.02 (s, 1H), 7.67 (s, 2H), 7.57 (s, 1H), 4.43 (s, 2H), 3.49-3.43 (m, 4H), 1.41 (s, 9H).

Step 8: tert-butyl 3-(2-(2-((tert-butoxycarbonyl)amino)ethyl)-1,1-dioxido-2,3-dihydrobenzo[d]isothiazol-5-yl)-6-fluoro-1H-indole-1-carboxylate A yellow solution of tert-butyl (2-(5-bromo-1,1-dioxidobenzo[d]isothiazol-2(3H)-yl)ethyl)carbamate (800 mg, 2.04 mmol), tert-butyl 6-fluoro-3-(4,4,5,5-tetramethyl-1,3,2-dioxaborolan-2-yl)-1H-indole-1-carboxylate (1.1 g, 2.5 mmol), $PdCl_2(dppf)CH_2Cl_2$ (153 mg, 0.204 mmol) and $K_3PO_4$ (1.3 g, 6.1 mmol) in 1,4-dioxane (16 mL) and water (4 mL) was sparged with $N_2$ for 1 min and stirred at 80° C. for 16 h. The crude reaction was concentrated then purified by column chromatography (silica gel, 0-50% ethyl acetate/petroleum ether) to afford tert-butyl 3-(2-(2-((tert-butoxycarbonyl)amino)ethyl)-1,1-dioxido-2,3-dihydrobenzo[d]isothiazol-5-yl)-6-fluoro-1H-indole-1-carboxylate (830 mg, 74%) as a yellow oil. LC-MS: m/z 568.1 (M+Na)$^+$.

Step 9: 2-(2-aminoethyl)-5-(6-fluoro-1H-indol-3-yl)-2,3-dihydrobenzo[d]isothiazole 1,1-dioxide To a cooled (ice bath) yellow solution of tert-butyl 3-(2-(2-((tert-butoxycarbonyl)amino)ethyl)-1,1-dioxido-2,3-dihydrobenzo[d]isothiazol-5-yl)-6-fluoro-1H-indole-1-carboxylate (330 mg, 0.61 mmol) in dichloromethane (4 mL) was added trifluoroacetic acid (2 mL) dropwise. The reaction was stirred at ambient temperature for 1 h then quenched with aqueous $NH_3/H_2O$ (5 mL) and extracted with dichloromethane (10 mL×3). The combined organic extracts were dried over anhydrous $Na_2SO_4$, then filtered and concentrated. The crude solid was purified by prep-HPLC to give 2-(2-aminoethyl)-5-(6-fluoro-1H-indol-3-yl)-2,3-dihydrobenzo[d]isothiazole 1,1-dioxide (24 mg, 20%) as a white solid. $^1$H NMR (400 MHz, DMSO-$d_6$) δ [ppm] 11.74 (br s, 1H), 8.33 (s, 1H), 7.97-7.86 (m, 5H), 7.27 (dd, J=2.3, 9.8 Hz, 1H), 7.01 (dt, J=2.4, 9.2 Hz, 1H), 4.56 (s, 2H), 3.33-3.31 (m, 2H), 2.98 (t, J=5.8 Hz, 2H); LC-MS: m/z 368.0 (M+Na)$^+$.

Example 32: 2-(2-(dimethylamino)ethyl)-5-(6-fluoro-1H-indol-3-yl)-2,3-dihydrobenzo[d]isothiazole 1,1-dioxide

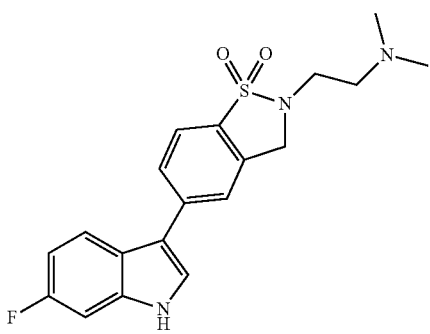 [SMILES: CN(C)CCN1Cc2cc(-c3c[nH]c4cc(F)ccc34)ccc2S1(=O)=O]

Step 1: 2-(2-(dimethylamino)ethyl)-5-(6-fluoro-1H-indol-3-yl)-2,3-dihydrobenzo[d]isothiazole 1,1-dioxide To a white solution of 2-(2-aminoethyl)-5-(6-fluoro-1H-indol-3-yl)-2,3-dihydrobenzo[d]isothiazole 1,1-dioxide (210 mg, 0.608 mmol) in methanol (10 mL) was added formaldehyde (247 mg, 1.22 mmol, 37% in water) at 27° C. The reaction was stirred at 27° C. for 30 min then cooled in an ice bath and $NaBH_4$ (46 mg, 1.22 mmol) was added. The reaction stirred for 16 h then diluted with water (10 mL) and extracted with dichloromethane (20 mL×3). The combined organic layers were washed with brine (10 mL), then dried over anhydrous $Na_2SO_4$, filtered, and concentrated. The crude residue was purified by prep-HPLC to obtained 2-(2-(dimethylamino)ethyl)-5-(6-fluoro-1H-indol-3-yl)-2,3-dihydrobenzo[d]isothiazole 1,1-dioxide (11 mg, 5%) as a white solid. $^1$H NMR (400 MHz, DMSO-$d_6$) δ [ppm] 11.67 (br s, 1H), 8.16 (s, 1H), 7.98-7.84 (m, 4H), 7.26 (dd, J=2.3, 9.8 Hz, 1H), 7.01 (dt, J=2.3, 9.3 Hz, 1H), 4.57 (s, 2H), 3.30 (t, J=6.5 Hz, 2H), 2.60 (t, J=6.5 Hz, 2H), 2.24 (s, 6H); LC-MS: m/z 374.1 (M+H)$^+$.

Example 33: 5-(6-fluoro-1H-indol-3-yl)-2-(2-hydroxyethyl)-2,3-dihydrobenzo[d]isothiazole 1,1-dioxide

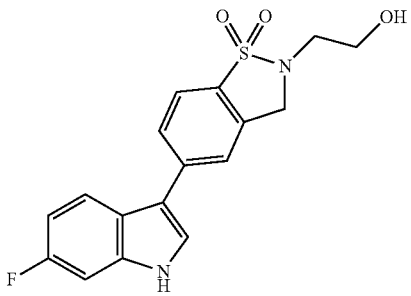 [SMILES: O=S1(=O)c2ccc(-c3c[nH]c4cc(F)ccc34)cc2CN1CCO]

Step 1: 5-bromo-2-(2-hydroxyethyl)-2,3-dihydrobenzo[d]isothiazole 1,1-dioxide A solution of 5-bromo-2,3-dihydrobenzo[d]isothiazole 1,1-dioxide (300 mg, 1.21 mmol), 2-bromoethanol (227 mg, 1.81 mmol) and $K_2CO_3$ (334 mg, 0.242 mmol) in DMF (5 mL) was stirred under a $N_2$ atmosphere at 80° C. for 16 h. The reaction was quenched with water (10 mL) and extracted with ethyl acetate (15 mL×3). The combined organic layers were washed with water (15 mL) and brine (15 mL) then dried over anhydrous $Na_2SO_4$, filtered, and concentrated. The crude yellow oil was purified by column chromatography (silica gel, 0-50% ethyl acetate/petroleum ether) to give 5-bromo-2-(2-hydroxyethyl)-2,3-dihydrobenzo-[d] isothiazole 1,1-dioxide (249 mg, 70%) as a white solid.

Step 2: tert-butyl 6-fluoro-3-(2-(2-hydroxyethyl)-1,1-dioxido-2,3-dihydrobenzo[d]isothiazol-5-yl)-1H-indole-1-carboxylate A solution of 5-bromo-2-(2-hydroxyethyl)-2,3-dihydrobenzo[d]isothiazole 1,1-dioxide (249 mg, 0.852 mmol), tert-butyl 6-fluoro-3-(4,4,5,5-tetramethyl-1,3,2-dioxaborolan-2-yl)-1H-indole-1-carboxylate (308 mg, 0.852 mmol), $PdCl_2(dppf)CH_2Cl_2$ (64 mg, 0.09 mmol), and $K_3PO_4$ (543 mg, 2.56 mmol) in 1,4-dioxane (8 mL) and water (2 mL) was sparged with $N_2$ for 1 min then stirred at 80° C. for 16 h. The crude reaction mixture was extracted with ethyl acetate (15 mL×3). The combined organic layers were washed with water (15 mL) and brine (15 mL) then dried over anhydrous $Na_2SO_4$, filtered, and concentrated. The crude product was purified by column chromatography (silica gel, 0-100% ethyl acetate/petroleum ether) to give tert-butyl 6-fluoro-3-(2-(2-hydroxyethyl)-1,1-dioxido-2,3-dihydrobenzo[d]isothiazol-5-yl)-1H-indole-1-carboxylate (290 mg, 76%) as a yellow solid. LC-MS: m/z 447.2 (M+H)$^+$.

Step 3: 2-(5-(6-fluoro-1H-indol-3-yl)-1,1-dioxidobenzo[d]isothiazol-2(3H)-yl)ethyl acetate To a cooled (ice bath) solution of tert-butyl 6-fluoro-3-(2-(2-hydroxyethyl)-1,1-dioxido-2,3-dihydrobenzo[d]isothiazol-5-yl)-1H-indole-1-carboxylate (290 mg, 0.55 mmol) in ethyl acetate (3 mL) was slowly added HCl (4M in ethyl acetate, 6 mL). The yellow solution was stirred at 17° C. for 12 h. The reaction was re-cooled in an ice bath then trifluoroacetic acid (3 mL) was added and the reaction was stirred at ambient temperature for 2 h. The reaction was quenched with water (5 mL), concentrated and the pH of the resulting solution was adjusted to 8 with NaHCO$_3$ (sat) (15 mL). The aqueous solution was extracted with dichloromethane (15 mL×3). The combined organic layers were washed with water (15 mL) and brine (15 mL) then dried over anhydrous Na$_2$SO$_4$, filtered, and concentrated. 2-(5-(6-fluoro-1H-indol-3-yl)-1,1-dioxidobenzo-[d]isothiazol-2 (3H)-yl)ethyl acetate (251 mg, >100%) was isolated as a brown solid. LC-MS: m/z 389.1 (M+H)$^+$.

Step 4: 5-(6-fluoro-1H-indol-3-yl)-2-(2-hydroxyethyl)-2,3-dihydrobenzo[d]isothiazole 1,1-dioxide To a cooled (ice bath) solution of 2-(5-(6-fluoro-1H-indol-3-yl)-1,1-dioxidobenzo[d]isothiazol-2(3H)-yl)ethyl acetate (251 mg, 0.52 mmol) in THF (4 mL) was slowly added a solution of LiOH.H$_2$O (54 mg, 1.3 mmol) in water (2 mL). The reaction was stirred at 50° C. for 3 h then concentrated and extracted with dichloromethane (15 mL). The organic phase was dried over anhydrous Na$_2$SO$_4$, filtered, concentrated. The crude residue was purified by prep-HPLC to give 5-(6-fluoro-1H-indol-3-yl)-2-(2-hydroxyethyl)-2,3-dihydrobenzo[d]isothiazole 1,1-dioxide (84 mg, 47%) as a white solid. $^1$H NMR (400 MHz, DMSO-d$_6$) δ [ppm] 11.66 (br s, 1H), 7.96 (dd, J=5.3, 8.8 Hz, 1H), 7.91-7.84 (m, 4H), 7.26 (dd, J=2.4, 9.9 Hz, 1H), 7.03-6.98 (m, 1H), 4.94 (t, J=5.1 Hz, 1H), 4.59 (s, 2H), 3.71 (q, J=5.7 Hz, 2H), 3.26 (t, J=5.8 Hz, 2H); LC-MS: m/z 347.1 (M+H)$^+$.

Example 34: (S)-2-(2,3-dihydroxypropyl)-5-(6-fluoro-1H-indol-3-yl)-2,3-dihydrobenzo[d]isothiazole 1,1-dioxide

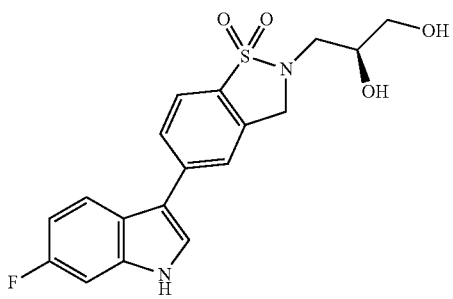

Step 1: (S)-5-bromo-2-((2,2-dimethyl-1,3-dioxolan-4-yl)methyl)-2,3-dihydrobenzo[d]isothiazole 1,1-dioxide A solution of 5-bromo-2,3-dihydrobenzo[d]isothiazole 1,1-dioxide (600 mg, 1.5 mmol), (R)-4-(chloromethyl)-2,2-dimethyl-1,3-dioxolane (328 mg, 2.2 mmol) and K$_2$CO$_3$ (501 mg, 3.63 mmol) in DMF (10 mL) was stirred under a N$_2$ atmosphere at 80° C. for 50 h. The reaction was quenched with water (10 mL) and extracted with ethyl acetate (15 mL×3). The combined organic layers were washed with water (10 mL) and brine (10 mL×3) then dried over anhydrous Na$_2$SO$_4$, filtered, and concentrated. The crude brown oil was purified by column chromatography (silica gel, 0-30% ethyl acetate/petroleum ether) to give (S)-5-bromo-2-((2,2-dimethyl-1,3-dioxolan-4-yl)methyl)-2,3-dihydrobenzo[d]isothiazole 1,1-dioxide (220 mg, 42%) as a yellow oil.

Step 2: (S)-tert-butyl 3-(2-((2,2-dimethyl-1,3-dioxolan-4-yl)methyl)-1,1-dioxido-2,3-dihydrobenzo[d]isothiazol-5-yl)-6-fluoro-1H-indole-1-carboxylate A solution of (S)-5-bromo-2-((2,2-dimethyl-1,3-dioxolan-4-yl)-methyl)-2,3-dihydrobenzo[d]isothiazole 1,1-dioxide (220 mg, 0.607 mmol), tert-butyl 6-fluoro-3-(4,4,5,5-tetramethyl-1,3,2-dioxaborolan-2-yl)-1H-indole-1-carboxylate (219 mg, 0.61 mmol), PdCl$_2$(dppf)CH$_2$Cl$_2$ (45 mg, 0.06 mmol), and K$_3$PO$_4$ (387 mg, 1.82 mmol) in 1,4-dioxane (8 mL) and water (2 mL) was sparged with N$_2$ for 1 minute. The reaction was stirred at 80° C. for 16 h then concentrated and purified by column chromatography (silica gel, 0-50% ethyl acetate/petroleum ether) to afford (S)-tert-butyl 3-(2-((2,2-dimethyl-1,3-dioxolan-4-yl)methyl)-1,1-dioxido-2,3-dihydrobenzo[d]isothiazol-5-yl)-6-fluoro-1Hindole-1-carboxylate (416 mg, >100%) as a brown oil, which was used for next step without further purification. LC-MS: m/z 539.1 (M+H)$^+$.

Step 3: (S)-2-(2,3-dihydroxypropyl)-5-(6-fluoro-1H-indol-3-yl)-2,3-dihydrobenzo[d]isothiazole 1,1-dioxide To a solution of (S)-tert-butyl 3-(2-((2,2-dimethyl-1,3-dioxolan-4-yl)methyl)-1,1-dioxido-2,3-dihydrobenzo[d]isothiazol-5-yl)-6-fluoro-1H-indole-1-carboxylate (416 mg, 0.81 mmol) in dichloromethane (4 mL) was added trifluoroacetic acid (2 mL). The reaction was stirred at 16° C. for 1 h then concentrated. The crude solid was neutralized to pH 7 by addition of NH$_3$—H$_2$O (0.5 mL), then purified by prep-HPLC to give (S)-2-(2,3-dihydroxypropyl)-5-(6-fluoro-1H-indol-3-yl)-2,3-dihydrobenzo[d]isothiazole 1,1-dioxide (45 mg, 27%) as a white solid. $^1$H NMR (400 MHz, DMSO-d$_6$) δ [ppm] 11.67 (br s, 1H), 7.97 (dd, J=5.3, 9.0 Hz, 1H), 7.92-7.85 (m, 4H), 7.26 (dd, J=2.3, 9.8 Hz, 1H), 7.01 (dt, J=2.4, 9.2 Hz, 1H), 5.05 (d, J=5.3 Hz, 1H), 4.73 (t, J=5.5 Hz, 1H), 4.68-4.53 (m, 2H), 3.79-3.76 (m, 1H), 3.45-3.36 (m, 3H), 3.04 (dd, J=7.5, 14.1 Hz, 1H), LC-MS: m/z 377.0 (M+H)$^+$, $[α]^{20}_D$ −4.91° (c=1.0189 mg/ml, methanol).

Example 35: (R)-2-(2,3-dihydroxypropyl)-5-(6-fluoro-1H-indol-3-yl)-2,3-dihydrobenzo[d]isothiazole 1,1-dioxide

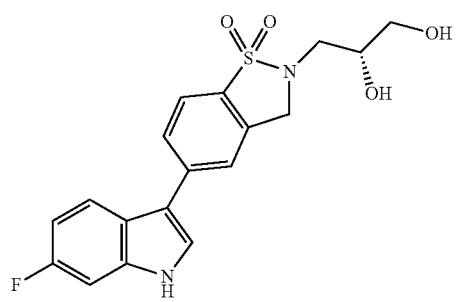 [SMILES: O=S1(=O)c2ccc(-c3c[nH]c4cc(F)ccc34)cc2CN1C[C@@H](O)CO]

Following the general methods as outlined in Example 34, using (S)-4-(chloromethyl)-2,2-dimethyl-1,3-dioxolane, the title compound was obtained as a as a white solid. $^1$H NMR (400 MHz, DMSO-d$_6$) δ [ppm] 11.68 (br s, 1H), 8.10-7.75 (m, 5H), 7.27 (dd, J=2.3, 9.8 Hz, 1H), 7.07-6.95 (m, 1H), 5.06 (d, J=5.3 Hz, 1H), 4.75 (t, J=5.5 Hz, 1H), 4.71-4.64 (m, 1H), 4.60-4.53 (m, 1H), 3.84-3.74 (m, 1H), 3.48-3.40 (m, 3H), 3.05 (dd, J=7.5, 14.1 Hz, 1H); LCMS: m/z 399.0 (M+Na)⁺, [α]²⁰_D +3.51° (c=1.14 mg/ml, methanol).

Example 36: 5-(6-fluoro-1H-indol-3-yl)-2-(piperidin-4-yl)-2,3-dihydrobenzo[d]isothiazole 1,1-dioxide

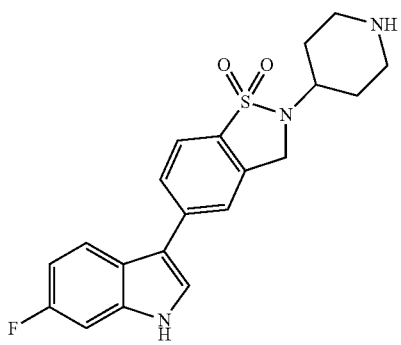 [SMILES: O=S1(=O)c2ccc(-c3c[nH]c4cc(F)ccc34)cc2CN1C1CCNCC1]

Step 1: tert-butyl 4-((methylsulfonyl)oxy)piperidine-1-carboxylate

To a cooled (ice bath) solution of tert-butyl 4-hydroxypiperidine-1-carboxylate (10 g, 50 mmol) in dichloromethane (100 mL) was added triethylamine (14 mL, 99 mmol) and methanesulfonyl chloride (6.8 g, 60 mmol). The reaction was warmed to ambient temperature and stirred for 1 h then quenched with water (50 mL) and extracted with dichloromethane (50 mL×2). The combined organic layers were washed with brine (50 mL), then dried over anhydrous sodium sulfate, filtered and concentrated to afford tert-butyl 4-((methylsulfonyl)oxy)piperidine-1-carboxylate (15 g, >100% yield) as a pale yellow solid, which was used in the next step without further purification. ¹H NMR (400 MHz, CDCl₃) δ [ppm] 4.90-4.86 (m, 1H), 3.73-3.67 (m, 2H), 3.33-3.27 (m, 2H), 3.04 (s, 3H), 1.99-1.94 (m, 2H), 1.85-1.79 (m, 2H), 1.46 (s, 9H).

Step 2: tert-butyl 4-(5-bromo-1,1-dioxidobenzo[d]isothiazol-2(3H)-yl)-piperidine-1-carboxylate A mixture of 5-bromo-2,3-dihydrobenzo[d]isothiazole 1,1-dioxide (1.0 g, 1.5 mmol) and K₂CO₃ (411 mg, 2.97 mmol) in DMF (20 mL) was stirred at 27° C. for 30 min then tert-butyl 4-((methylsulfonyl)oxy)piperidine-1-carboxylate (498 mg, 1.78 mmol) was added. The reaction was evacuated and back-filled with N₂ three times then stirred at 80° C. for 16 h. The reaction was quenched with water (30 mL) and extracted with ethyl acetate (30 mL×5). The combined organic layers were washed with brine (20 mL×3) then dried over anhydrous Na₂SO₄, filtered, and concentrated. The crude residue was purified by column chromatography (silica gel, 0-40% ethyl acetate/petroleum ether) to afford tert-butyl 4-(5-bromo-1,1-dioxidobenzo[d]isothiazol-2(3H)-yl)-piperidine-1-carboxylate (600 mg, 34.5% yield) as a white solid. LC-MS: m/z 454.8 (M+Na)⁺.

Step 3: tert-butyl 3-(2-(1-(tert-butoxycarbonyl)piperidin-4-yl)-1,1-dioxido-2,3-dihydrobenzo[d]isothiazol-5-yl)-6-fluoro-1H-indole-1-carboxylate A yellow solution of tert-butyl 4-(5-bromo-1,1-dioxidobenzo[d]isothiazol-2(3H)-yl)piperidine-1-carboxylate (405 mg, 1.25 mmol), tert-butyl 6-fluoro-3-(4,4,5,5-tetramethyl-1,3,2-dioxaborolan-2-yl)-1H-indole-1-carboxylate (497 mg, 1.38 mmol), PdCl₂(dppf)CH₂Cl₂ (93.5 mg, 0.125 mmol) and K₃PO₄ (797 mg, 3.76 mmol) in 1,4-dioxane (8.0 mL) and water (2.0 mL) was sparged with N₂ for 1 min then stirred at 80° C. for 4 h. The reaction was concentrated and purified by column chromatography (silica gel, 0-40% ethyl acetate/petroleum ether) to afford tert-butyl 3-(2-(1-(tert-butoxycarbonyl)piperidin-4-yl)-1,1-dioxido-2,3-dihydrobenzo[d]isothiazol-5-yl)-6-fluoro-1H-indole-1-carboxylate (498 mg, 68%) as a pale yellow solid. ¹H NMR (400 MHz, CDCl₃) δ [ppm] 7.96 (d, J=11.3 Hz, 1H), 7.88 (d, J=8.0 Hz, 1H), 7.78-7.78 (m, 2H), 7.67-7.62 (m, 1H), 7.11-7.06 (m, 1H), 4.46 (s, 2H), 4.24-4.18 (m, 2H), 3.89-3.83 (m, 1H), 2.94-2.88 (m, 2H), 2.08 (d, J=13.6 Hz, 2H), 1.87-1.77 (m, 2H), 1.71 (s, 9H), 1.48 (m, 9H); LC-MS: m/z 608.0 (M+Na)⁺.

Step 4: 5-(6-fluoro-1H-indol-3-yl)-2-(piperidin-4-yl)-2,3-dihydrobenzo[d]isothiazole 1,1-dioxide A pale yellow solution of tert-butyl 3-(2-(1-(tert-butoxycarbonyl)piperidin-4-yl)-1,1-dioxido-2,3-dihydrobenzo[d]isothiazol-5-yl)-6-fluoro-1H-indole-1-carboxylate (400 mg, 0.683 mmol) in ethyl acetate (6 mL) was added trifluoroacetic acid (3 mL). The reaction was stirred at 32° C. for 2 h then diluted with methanol (10 mL), cooled in an ice bath and treated with NH₃—H₂O (10 mL). The yellow solution was concentrated and purified by prep-HPLC to give 5-(6-fluoro-1H-indol-3-yl)-2-(piperidin-4-yl)-2,3-dihydrobenzo[d]isothiazole 1,1-dioxide (78 mg, 27%) as a white solid. ¹H NMR (400 MHz, DMSO-d₆) δ [ppm] 11.70 (br s, 1H), 8.32 (br s, 1H), 7.97-7.82 (m, 5H), 7.27 (dd, J=2.3, 9.8 Hz, 1H), 7.01 (dt, J=2.4, 9.2 Hz, 1H), 4.54 (s, 2H), 3.76-3.69 (m, 1H), 3.19 (d, J=11.5 Hz, 2H), 2.987-2.81 (m, 2H), 2.00-1.85 (m, 4H); LC-MS: m/z 385.9 (M+H)⁺.

Example 37: 5-(6-fluoro-1H-indol-3-yl)-2-(1-methylpiperidin-4-yl)-2,3-dihydrobenzo[d]isothiazole 1,1-dioxide

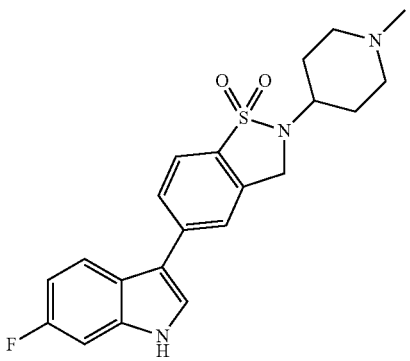 [SMILES: CN1CCC(N2Cc3cc(-c4c[nH]c5cc(F)ccc45)ccc3S2(=O)=O)CC1]

A yellow solution of 5-(6-fluoro-1H-indol-3-yl)-2-(piperidin-4-yl)-2,3-dihydrobenzo[d]isothiazole 1,1-dioxide (170 mg, 0.441 mmol), formaldehyde (40% in water) (46 mg, 0.57 mmol), and CH₃COOH (2 drops) in dichloromethane (3 mL) was stirred at 0° C. for 15 min then NaBH(OAc)₃ (100 mg, 0.472 mmol) was added as a suspension in dichloromethane (2 mL). The suspension was stirred at 0° C. for 1 h then quenched with water (5 mL) and extracted with dichloromethane (10 mL×3). The organic layers were washed with brine (5 mL) then dried over anhydrous Na₂SO₄, filtered and concentrated. The crude solid was purified by prep-HPLC to afford 5-(6-fluoro-1H-indol-3-yl)-2-(1-methylpiperidin-4-yl)-2,3-dihydrobenzo[d]isothiazole 1,1-dioxide (40 mg, 23%) as a white solid. ¹H NMR (400 MHz, DMSO-d₆) δ [ppm] 11.67 (br s, 1H), 7.97-7.81 (m, 5H), 7.26 (dd, J=2.3, 9.8 Hz, 1H), 7.01 (dt, J=2.4, 9.2 Hz, 1H), 4.53 (s, 2H), 2.85 (d, J=12.0 Hz, 1H), 2.20 (s, 3H), 1.99-1.88 (m, 4H), 1.23 (br s, 4H); LC-MS: m/z 399.9 (M+H)⁺.

Example 38: (R)-5-(6-fluoro-1H-indol-3-yl)-2-(tetrahydrofuran-3-yl)-2,3-dihydrobenzo[d]isothiazole 1,1-dioxide

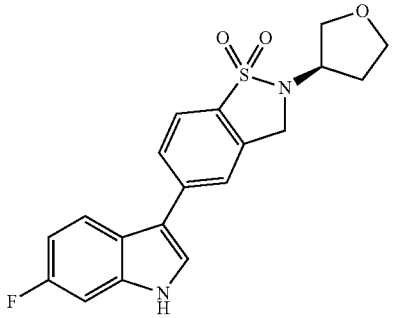 [SMILES: O=S1(=O)c2ccc(-c3c[nH]c4cc(F)ccc34)cc2CN1[C@@H]1CCOC1]

Following the general method as outlined in Example 36, starting with (S)-(+)-3-hydroxytetrahydrofuran, the title compound was obtained as a white solid. ¹H NMR (400 MHz, DMSO-d₆) δ [ppm] 11.80-11.56 (m, 1H), 8.00-7.83 (m, 5H), 7.27 (dd, J=2.3, 9.8 Hz, 1H), 7.06-6.97 (m, 1H), 4.60-4.51 (m, 2H), 4.32-4.23 (m, 1H), 3.98-3.90 (m, 2H), 3.87-3.79 (m, 1H), 3.75-3.66 (m, 1H), 2.34-2.24 (m, 1H), 2.23-2.13 (m, 1H); LC-MS: m/z 394.8 (M+Na)⁺, [α]²⁰_D +21.1° (c=0.95 mg/mL, DMSO).

Example 39: (S)-5-(6-fluoro-1H-indol-3-yl)-2-(tetrahydrofuran-3-yl)-2,3-dihydrobenzo[d]isothiazole 1,1-dioxide

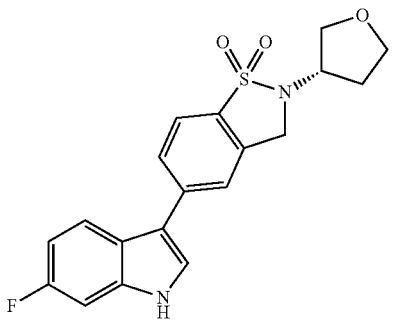 [SMILES: O=S1(=O)c2ccc(-c3c[nH]c4cc(F)ccc34)cc2CN1[C@H]1CCOC1]

Following the general method as outlined in Example 36, starting with (R)-(+)-3-hydroxytetrahydrofuran, the title compound was obtained as a white solid. ¹H NMR (400 MHz, DMSO-d₆) δ [ppm] 11.67 (br s, 1H), 7.99-7.82 (m, 5H), 7.26 (dd, J=2.5, 10.0 Hz, 1H), 7.01 (dt, J=2.3, 9.2 Hz, 1H), 4.60-4.51 (m, 2H), 4.31-4.23 (m, 1H), 3.98-3.91 (m, 2H), 3.82 (dd, J=6.0, 9.5 Hz, 1H), 3.74-3.66 (m, 1H), 2.33-2.23 (m, 1H), 2.22-2.13 (m, 1H); LC-MS: m/z 394.8 (M+Na)⁺, [α]²⁰_D −27.36° (c=0.95 mg/mL, DMSO).

Example 40: 2-(azetidin-3-yl)-5-(6-fluoro-1H-indol-3-yl)-2,3-dihydrobenzo[d]isothiazole 1,1-dioxide

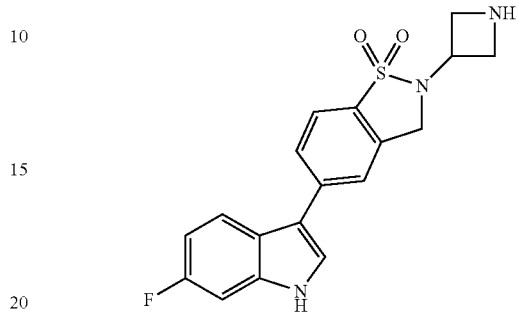

Following the general methods as outlined in Example 36, using N-Boc-3-OH-azetidine, the title compound was obtained as a as a white solid. ¹H NMR (400 MHz, DMSO-d₆) δ [ppm] 11.77 (br s, 1H), 8.35 (br s, 1H), 7.97-7.87 (m, 5H), 7.28 (dd, J=2.1, 9.9 Hz, 1H), 7.02 (dt, J=2.3, 9.3 Hz, 1H), 4.72 (s, 2H), 4.61 (d, J=8.0 Hz, 1H), 4.14 (br s, 4H); LC-MS: m/z 357.9 (M+H)⁺.

Example 41: 5-(6-fluoro-1H-indol-3-yl)-2-(1-methylazetidin-3-yl)-2,3-dihydrobenzo[d]isothiazole 1,1-dioxide

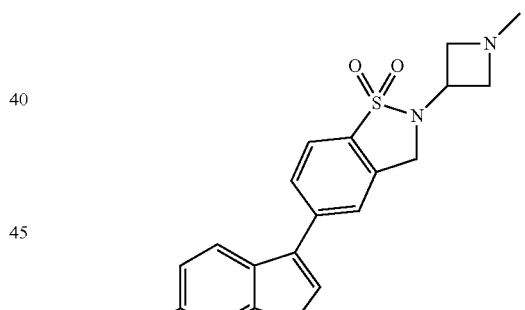

Step 1: 5-(6-fluoro-1-(hydroxymethyl)-1H-indol-3-yl)-2-(1-methylazetidin-3-yl)-2,3-dihydrobenzo[d]isothiazole 1,1-dioxide To a solution of 2-(azetidin-3-yl)-5-(6-fluoro-1H-indol-3-yl)-2,3-dihydrobenzo[d]isothiazole 1,1-dioxide (150 mg, 0.318 mmol) in methanol (5 mL) was added formaldehyde (37% in water, 129 mg, 1.59 mol) at ambient temperature. The reaction was stirred at 27° C. for 15 min then cooled in an ice bath and NaBH₃CN (30 mg, 0.477 mmol) was added. The reaction was slowly warmed to 27° C. and stirred for 12 h then diluted with water (4 mL) and extracted with dichloromethane (10 mL×3). The combined organic layers were washed with brine (10 mL) then dried over anhydrous Na₂SO₄, filtered, and concentrated to afford 5-(6-fluoro-1-

(hydroxymethyl)-1H-indol-3-yl)-2-(1-methylazetidin-3-yl)-2,3-dihydrobenzo[d]isothiazole 1,1-dioxide (134 mg, >100%) as a yellow solid.

Step 2: 5-(6-fluoro-1H-indol-3-yl)-2-(1-methylazetidin-3-yl)-2,3-dihydrobenzo[d]isothiazole 1,1-dioxide To a cooled (ice bath) yellow solution of 5-(6-fluoro-1-(hydroxymethyl)-1H-indol-3-yl)-2-(1-methylazetidin-3-yl)-2,3-dihydrobenzo[d]isothiazole 1,1-dioxide (124 mg, 0.309 mmol) in 1,4-dioxane (5 mL) was slowly added $NH_3/H_2O$ (2.5 mL). The reaction was stirred at 27° C. for 48 h then extracted with dichloromethane (15 mL×3). The combined organic layers were washed with water (10 mL) and brine (10 mL) then dried over anhydrous $Na_2SO_4$, filtered, and concentrated. The crude yellow oil was purified by prep-TLC (silica gel, 10% methanol in dichloromethane) to give 5-(6-fluoro-1H-indol-3-yl)-2-(1-methylazetidin-3-yl)-2,3-dihydrobenzo[d]isothiazole 1,1-dioxide (30 mg, 26%) as a white solid. $^1$H NMR (400 MHz, MeOD) δ [ppm] 7.91-7.87 (m, 2H), 7.84 (s, 1H), 7.77 (d, J=8.3 Hz, 1H), 7.68 (s, 1H), 7.16 (dd, J=2.3, 9.5 Hz, 1H), 6.95 (dt, J=2.4, 9.2 Hz, 1H), 4.56 (s, 2H), 4.27-4.22 (m, 1H), 3.73-3.69 (m, 2H), 3.55-3.51 (m, 2H), 2.44 (s, 3H); LC-MS: m/z 371.9 (M+H)$^+$.

Example 42: (+)-5-(6-fluoro-1H-indol-3-yl)-2-(2-(methylsulfinyl)ethyl)-2,3-dihydrobenzo[d]isothiazole 1,1-dioxide

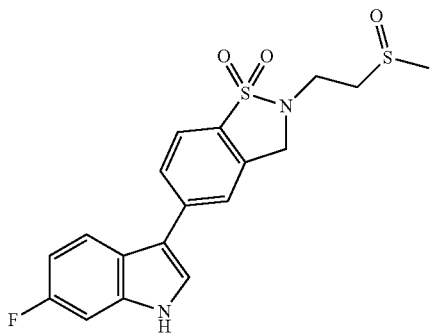 [SMILES: CS(=O)CCN1Cc2cc(-c3c[nH]c4cc(F)ccc34)ccc2S1(=O)=O]

Step 1: 5-bromo-2-(2-(methylthio)ethyl)-2,3-dihydrobenzo[d]isothiazole 1,1-dioxide A solution of 5-bromo-2,3-dihydrobenzo[d]isothiazole 1,1-dioxide (1000 mg, 4.03 mmol), (2-chloroethyl)(methyl)sulfane (892 mg, 8.06 mmol) and $K_2CO_3$ (1110 mg, 8.06 mmol) in DMF (10 mL) was evacuated and back-filled with $N_2$ three times then stirred at 85° C. for 7 h. The reaction was diluted with water (30 mL) and extracted with ethyl acetate (30 mL×3). The combined organic layers were washed with water (30 mL×2) and brine (30 mL×3) then dried over anhydrous $Na_2SO_4$, filtered, and concentrated. The crude residue was purified by column chromatography (silica gel, 0-50% ethyl acetate/petroleum ether) to give 5-bromo-2-(2-(methylthio)ethyl)-2,3-dihydrobenzo[d]isothiazole 1,1-dioxide (1.3 g, 43%) as a dark yellow oil. $^1$H NMR (400 MHz, DMSO-$d_6$) δ [ppm] 7.90 (d, J=0.8 Hz, 1H), 7.86-7.84 (m, 1H), 7.81-7.79 (m, 1H), 4.54 (s, 2H), 3.41 (t, J=8.0 Hz, 2H), 2.79 (t, J=8.0 Hz, 2H), 2.12 (s, 3H).

Step 2: 5-bromo-2-(2-(methylsulfinyl)ethyl)-2,3-dihydrobenzo[d]isothiazole 1,1-dioxide To a yellow solution of 5-bromo-2-(2-(methylthio)ethyl)-2,3-dihydrobenzo[d]isothiazole 1,1-dioxide (1000 mg, 3.103 mmol) in anhydrous dichloromethane (50 mL) was added meta-chloroperoxybenzoic acid (m-CPBA) (630 mg, 3.10 mmol) at −25° C. The yellow suspension was stirred for 30 min then washed with $H_2O$ (25 mL×3). The layers were separated and the organic phase was dried over $Na_2SO_4$, filtered, and concentrated. The crude product was purified by column chromatography (silica gel, 0-5% methanol/dichloromethane) to give 5-bromo-2-(2-(methylsulfinyl)ethyl)-2,3-dihydrobenzo[d]isothiazole 1,1-dioxide (652 mg, 62%) as a yellow solid. LC-MS: m/z 359.7 (M+Na)$^+$.

Step 3: tert-butyl 6-fluoro-3-(2-(2-(methylsulfinyl)ethyl)-1,1-dioxido-2,3-dihydrobenzo[d]isothiazol-5-yl)-1H-indole-1-carboxylate A yellow mixture of 5-bromo-2-(2-(methylsulfinyl)ethyl)-2,3-dihydrobenzo[d]isothiazole 1,1-dioxide (857 mg, 2.53 mmol), tert-butyl 6-fluoro-3-(4,4,5,5-tetramethyl-1,3,2-dioxaborolan-2-yl)-1H-indole-1-carboxylate (1100 mg, 3.04 mmol), $PdCl_2(dppf)CH_2Cl_2$ (189 mg, 0.025 mmol), and $K_3PO_4$ (1610 mg, 7.60 mmol) in 1,4-dioxane (10 mL) and water (3 mL) was sparged with $N_2$ for 1 minute. The reaction was stirred at 80° C. for 3 h then extracted with ethyl acetate (25 mL×3). The combined organic layers were washed with water (20 mL) and brine (25 mL) then dried over anhydrous $Na_2SO_4$, filtered, and concentrated. The crude material was purified by column chromatography (silica gel, 0-5% methanol/dichloromethane) to give tert-butyl-6-fluoro-3-(2-(2-(methylsulfinyl)ethyl)-1,1-dioxido-2,3-dihydrobenzo[d]isothiazol-5-yl)-1H-indole-1-carboxylate (1.33 g, 79%) as a black oil. LC-MS: m/z 493.0 (M+H)$^+$.

Step 4: (+)-5-(6-fluoro-1H-indol-3-yl)-2-(2-(methylsulfinyl)-ethyl)-2,3-dihydrobenzo[d]isothiazole 1,1-dioxide To a solution of tert-butyl 6-fluoro-3-(2-(2-(methylsulfinyl)ethyl)-1,1-dioxido-2,3-dihydrobenzo[d]isothiazol-5-yl)-1H-indole-1-carboxylate (1.3 g, 2.0 mmol) in dichloromethane (16 mL) was added trifluoroacetic acid (8 mL) at 0° C. The black solution was stirred at 26° C. for 16 h then concentrated and diluted with ethyl acetate (10 mL) and $NaHCO_3$ (sat) (20 mL). The layers were separated and the aqueous phase was back-extracted with ethyl acetate (20 mL×3). The combined organic layers were washed with water (20 mL) and brine (20 mL) then dried over anhydrous $Na_2SO_4$, filtered, and concentrated. The crude residue was purified by column chromatography (silica gel, 0-10% methanol/dichloromethane) to give racemic 5-(6-fluoro-1H-indol-3-yl)-2-(2-(methylsulfinyl)ethyl)-2,3-dihydrobenzo[d]isothiazole 1,1-dioxide (450 mg, 57%) as a yellow solid. LC-MS: m/z 392.9 (M+H)$^+$, 414.8 (M+Na)$^+$. The racemic product was separated by prep-chiral SFC to give (+)-5-(6-fluoro-1H-indol-3-yl)-2-(2-(methylsulfinyl)ethyl)-2,3-dihydrobenzo[d]isothiazole 1,1-dioxide as the first eluting peak (68 mg, 26%) as a white solid. $^1$H NMR (400 MHz, DMSO-$d_6$) δ [ppm] 11.69 (br s, 1H), 7.98-7.87 (m, 5H), 7.27 (d, J=10.0 Hz, 1H), 7.01 (t, J=9.2 Hz, 1H), 4.59 (s, 2H), 3.62 (t, J=6.7 Hz, 2H), 3.26-3.19 (m, 1H), 3.07-3.04 (m, 1H), 2.65 (s, 3H); LC-MS: m/z 393.1 (M+H)$^+$, $[α]^{20}_D$ +18.5° (c=1.515 mg/ml, DMSO).

Example 43: 3-(5-(6-fluoro-1H-indol-3-yl)-1,1-dioxidobenzo[d]isothiazol-2(3H)-yl)-N-methylpropanamide

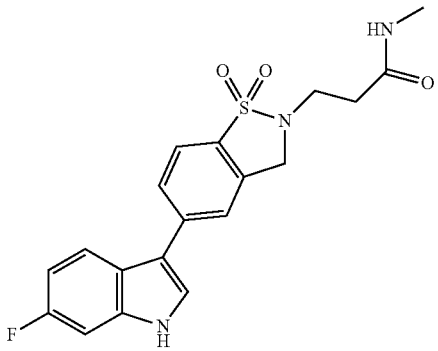 [SMILES: CNC(=O)CCN1Cc2cc(-c3c[nH]c4cc(F)ccc34)ccc2S1(=O)=O]

Step 1: ethyl 3-(5-bromo-1,1-dioxidobenzo[d]isothiazol-2(3H)-yl)propanoate

To a solution of 5-bromo-2,3-dihydrobenzo[d]isothiazole 1,1-dioxide (800 mg, 1.9 mmol) in DMF (20 mL) was added ethyl 3-bromopropanoate (420 mg, 2.32 mmol) and $K_2CO_3$ (535 mg, 3.87 mmol) then mixture was sparged with $N_2$ for 1 min and stirred at 80° C. for 16 h. The crude reaction was diluted with ethyl acetate (20 mL) and water (20 mL). The layers were separated and the aqueous layer was back-extracted with ethyl acetate (30 mL×2). The combined organic layers were washed with brine (10 mL×2) then dried over $Na_2SO_4$, filtered and concentrated. The crude material was purified by column chromatography (silica gel, 2-20% ethyl acetate/petroleum ether) to afford ethyl 3-(5-bromo-1,1-dioxidobenzo[d]isothiazol-2(3H)-yl)propanoate (530 mg, 79%) as a gray solid.

Step 2: tert-butyl 3-(2-(3-ethoxy-3-oxopropyl)-1,1-dioxido-2,3-dihydrobenzo[d]isothiazol-5-yl)-6-fluoro-1H-indole-1-carboxylate To a yellow solution of ethyl 3-(5-bromo-1,1-dioxidobenzo[d]isothiazol-2(3H)-yl)propanoate (530 mg, 1.52 mmol), tert-butyl 6-fluoro-3-(4,4,5,5-tetramethyl-1,3,2-dioxaborolan-2-yl)-1H-indole-1-carboxylate (605 mg, 1.67 mmol) and $K_3PO_4$ (646 mg, 3.04 mmol) in dioxane/$H_2O$ (12 ml/4 mL) was added Pd(dppf)Cl$_2$ (111 mg, 0.152 mmol) at 25° C. under $N_2$. The reaction was heated to 90° C. and stirred for 14 h then diluted with ethyl acetate (40 mL). The layers were separated and the organic phase was washed with $H_2O$ (10 mL) and brine (15 mL×2). The organic layer was dried over anhydrous $Na_2SO_4$, filtered and concentrated. The crude residue was purified by column chromatography (silica gel, 10-60% ethyl acetate/petroleum ether) to give tert-butyl 3-(2-(3-ethoxy-3-oxopropyl)-1,1-dioxido-2,3-dihydrobenzo[d]isothiazol-5-yl)-6-fluoro-1H-indole-1-carboxylate (220 mg, 29%) as a yellow gum and ethyl 3-(5-(6-fluoro-1H-indol-3-yl)-1,1-dioxidobenzo[d]isothiazol-2(3H)-yl)propanoate (360 mg, 60% yield) as a yellow gum.

Step 3: 3-(5-(6-fluoro-1H-indol-3-yl)-1,1-dioxidobenzo[d]isothiazol-2(3H)-yl)-N-methylpropanamide A yellow solution of tert-butyl 3-(2-(3-ethoxy-3-oxopropyl)-1,1-dioxido-2,3-dihydrobenzo[d]isothiazol-5-yl)-6-fluoro-1H-indole-1-carboxylate (220 mg, 0.438 mmol) in MeNH$_2$/EtOH (30% w/w, 10 mL) was stirred at 100° C. in a sealed tube for 14 h. The reaction was concentrated and purified by column chromatography (silica gel, 20-100% ethylacetate/petroleum ether) followed by prep-HPLC to give 3-(5-(6-fluoro-1H-indol-3-yl)-1,1-dioxidobenzo[d]isothiazol-2(3H)-yl)-N-methylpropanamide (58 mg, 34%) as a white solid. $^1$H NMR (400 MHz, DMSO-d$_6$) δ [ppm] 11.68 (br s, 1H), 8.01-7.81 (m, 6H), 7.26 (dd, J=2.5, 9.8 Hz, 1H), 7.06-6.96 (m, 1H), 4.50 (s, 2H), 3.45 (t, J=7.0 Hz, 2H), 2.60 (d, J=4.5 Hz, 3H), 2.56-2.51 (m, 2H); LC-MS: m/z 410.0 (M+Na)$^+$.

Example 44: 3-(5-(6-fluoro-1H-indol-3-yl)-1,1-dioxidobenzo[d]isothiazol-2(3H)-yl)propanamide

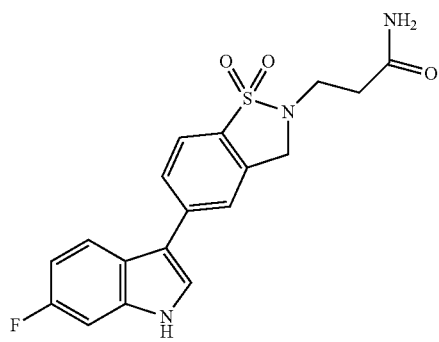 [SMILES: NC(=O)CCN1Cc2cc(-c3c[nH]c4cc(F)ccc34)ccc2S1(=O)=O]

Following the general method as outlined in Example 43, using 3-(5-bromo-1,1-dioxidobenzo[d]isothiazol-2(3H)-yl)propanamide, the title compound was obtained as a gray solid. $^1$H NMR (400 MHz, DMSO-d$_6$) δ [ppm] 11.68 (br s, 1H), 8.06-7.77 (m, 5H), 7.48 (br s, 1H), 7.26 (d, J=9.5 Hz, 1H), 7.10-6.88 (m, 2H), 4.51 (s, 2H), 3.44 (t, J=6.8 Hz, 2H), 2.58-2.52 (m, 2H); LC-MS: m/z for 396.0 (M+Na)$^+$.

Example 45: (+)-3-(5-(6-fluoro-1H-indol-3-yl)-3-methyl-1,1-dioxidobenzo[d]-isothiazol-2(3H)-yl)-N-methylpropanamide

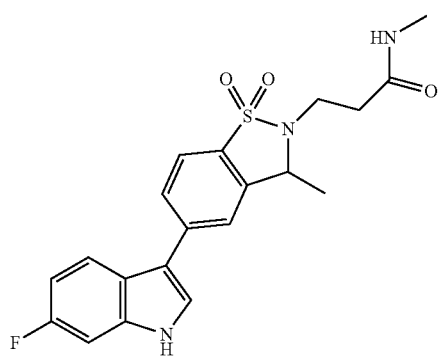 [SMILES: CNC(=O)CCN1C(C)c2cc(-c3c[nH]c4cc(F)ccc34)ccc2S1(=O)=O]

Step 1: Ethyl 3-(5-bromo-3-methyl-1,1-dioxido-benzo[d]isothiazol-2(3H)-yl)propanoate A yellow mixture of 5-bromo-3-methyl-2,3-dihydrobenzo[d]isothiazole 1,1-dioxide (1.5 g, 5.7 mmol), ethyl 3-bromopropanoate (1.24 g, 6.87 mmol) and $K_2CO_3$ (1.58 g, 11.4 mmol) in DMF (15 mL) was sparged with $N_2$ for 1 min and stirred at 80° C. for 16 h. The reaction mixture was diluted with ethyl acetate (50 mL) and water (10 mL). The layers were separated and the aqueous layer was back-extracted with ethyl acetate (20 mL×2). The combined organic layers were washed with brine (10 mL) then dried over $Na_2SO_4$, filtered and concentrated. The crude residue was purified by column chromatography (silica gel, 5-50% ethyl acetate/petroleum ether) to afford ethyl 3-(5-bromo-3-methyl-1,1-dioxidobenzo[d]isothiazol-2(3H)-yl)propanoate (1.6 g, 77%) as a black solid.

Step 2: tert-butyl 3-(4-(2-(3-ethoxy-3-oxopropyl)-3-methyl-1,1-dioxido-2,3-dihydrobenzo[d]isothiazol-5-yl)phenyl)-6-fluoro-1H-indole-1-carboxylate To a yellow solution of ethyl 3-(5-bromo-3-methyl-1,1-dioxidobenzo[d]-isothiazol-2(3H)-yl)propanoate (800 mg, 2.21 mmol), tert-butyl 6-fluoro-3-(4,4,5,5-tetramethyl-1,3,2-dioxaborolan-2-yl)-1H-indole-1-carboxylate (801 mg, 2.21 mmol) and $K_3PO_4$ (938 mg, 4.42 mmol) in Dioxane/$H_2O$ (12 mL/4 mL) was added Pd(dppf)$Cl_2$ (162 mg, 0.221 mmol) at 28° C. under $N_2$. The resulting red suspension was stirred at 80° C. for 16 h then diluted with water (8 mL) and extracted with ethyl acetate (15 mL×3). The combined organic layers were dried over anhydrous $Na_2SO_4$, filtered and concentrated. The crude material was purified by column chromatography (silica gel, 5-30% ethyl acetate/petroleum ether) to give tert-butyl 3-(4-(2-(3-ethoxy-3-oxopropyl)-3-methyl-1,1-dioxido-2,3-dihydrobenzo[d]isothiazol-5-yl)phenyl)-6-fluoro-1H-indole-1-carboxylate (500 mg, 38%) as a yellow gum.

Step 3: (+)-3-(5-(4-(6-fluoro-1H-indol-3-yl)phenyl)-3-methyl-1,1-dioxidobenzo[d]isothiazol-2(3H)-yl)-N-methylpropanamide A yellow solution of tert-butyl 3-(4-(2-(3-ethoxy-3-oxopropyl)-3-methyl-1,1-dioxido-2,3-dihydrobenzo[d]isothiazol-5-yl)phenyl)-6-fluoro-1H-indole-1-carboxylate (500 mg, 0.84 mmol) in MeNH$_2$/EtOH (30% w/w, 40 mL) was stirred at 50° C. in a sealed tube for 3 h. The crude reaction was concentrated and purified by column chromatography (SiO$_2$, petroleum ether/ethyl acetate=10/1-3/1) to give racemic 3-(5-(4-(6-fluoro-1H-indol-3-yl)phenyl)-3-methyl-1,1-dioxidobenzo[d]isothiazol-2(3H)-yl)-N-methylpropanamide (300 mg, 58%) as a red gum. The racemic material was separated by prep-chiral SFC to give (+)-3-(5-(6-fluoro-1H-indol-3-yl)-3-methyl-1,1-dioxidobenzo[d]isothiazol-2(3H)-yl)-N-methylpropanamide as the first eluting peak (90 mg, 27%) as a pale yellow solid. $^1$H NMR (400 MHz, CDCl$_3$) δ [ppm] 8.63 (br s, 1H), 7.86-7.71 (m, 3H), 7.57 (s, 1H), 7.42 (d, J=2.3 Hz, 1H), 7.16 (dd, J=2.3, 9.3 Hz, 1H), 7.01 (dt, J=2.3, 9.2 Hz, 1H), 6.07 (br s, 1H), 4.50 (q, J=6.1 Hz, 1H), 3.80-3.61 (m, 2H), 2.84-2.61 (m, 5H), 1.59 (d, J=6.5 Hz, 3H); LC-MS: m/z 401.9 (M+H)$^+$, [α]$^{20}_D$ +6.7° (c=0.0015 g/mL, methanol).

Example 46: (−)-3-(5-(6-fluoro-1H-indol-3-yl)-3-methyl-1,1-dioxidobenzo[d]isothiazol-2(3H)-yl)-N-methylpropanamide

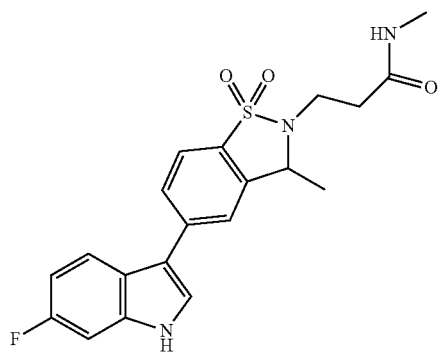 [SMILES: CNC(=O)CCN1C(C)c2cc(-c3c[nH]c4cc(F)ccc34)ccc2S1(=O)=O]

The title compound was isolated as the second eluting peak from the chiral separation described for Example 45 (100 mg, 30%) as a pale yellow solid. $^1$H NMR (400 MHz, CDCl$_3$) δ [ppm] 8.61 (br s, 1H), 7.89-7.70 (m, 3H), 7.57 (s, 1H), 7.42 (d, J=2.5 Hz, 1H), 7.16 (dd, J=2.3, 9.0 Hz, 1H), 7.01 (dt, J=2.4, 9.1 Hz, 1H), 6.07 (d, J=4.3 Hz, 1H), 4.50 (d, J=6.5 Hz, 1H), 3.84-3.59 (m, 2H), 2.91-2.59 (m, 5H), 1.59 (d, J=6.5 Hz, 3H); LC-MS: m/z 401.9 (M+H)$^+$, [α]$^{20}_D$ −10.9° (c=0.0011 g/mL, methanol).

Example 47: (+)-3-(5-(6-fluoro-1H-indol-3-yl)-3-methyl-1,1-dioxidobenzo[d]isothiazol-2(3H)-yl) propanamide

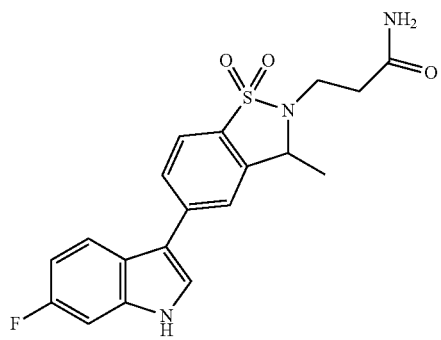 [SMILES: CC1c2cc(-c3c[nH]c4cc(F)ccc34)ccc2S(=O)(=O)N1CCC(N)=O]

Step 1: 1-tert-butyl 2-methyl 4-((4-bromophenyl)sulfonyl)piperazine-1,2-dicarboxylate To a stirred solution of piperazine-1, 2-dicarboxylic acid 1-tert-butyl ester 2-methyl ester (977 mg, 4.0 mmol) in DCM (20 mL) at 0° C. was added 4-bromo-benzenesulfonyl chloride (1.02 mg, 4.0 mmol). Then TEA (404 mg, 4.0 mmol) was added dropwise and the mixture was stirred at room temperature for 1 hr. The mixture was concentrated and purified by silica gel chromatography (petroleum ether/EtOAc=20/1 to 5/1) to afford 1.66 g (90%) of the title compound as a white solid. $^1$H NMR (400 MHz, CDCl$_3$) δ [ppm] 7.69 (d, J=8.8 Hz, 2H), 7.61 (d, J=8.8 Hz, 2H), 4.89-4.60 (m, 1H), 4.27-4.20 (m, 1H), 4.04-3.82 (m, 1H), 3.77 (s, 3H), 3.76-3.61 (m, 1H), 3.35-3.11 (m, 1H), 2.51 (dd, J=11.6, 4.0 Hz, 1H), 2.33 (td, J=11.6, 4.0 Hz, 1H), 1.44 (s, 9H).

Step 2: tert-butyl 4-((4-bromophenyl)sulfonyl)-2-(hydroxymethyl)-piperazine-1-carboxylate To a stirred solution of 4-(4-bromo-benzenesulfonyl)-piperazine-1, 2-dicarboxylic acid 1-tert-butyl ester 2-methyl ester (1.66 g, 3.59 mmol) in anhydrous THF (20 mL) at 0° C. was added LiAlH$_4$ (137 mg, 3.59 mmol). The mixture was stirred at room temperature for 1 hr before it was diluted with EtOAc (100 mL) and water (0.5 mL). The organic mixture was dried over anhydrous Na$_2$SO$_4$ and filtered. The filtrate was concentrated and purified by silica gel chromatography (petroleum ether/EtOAc=5/1 to 3/1) to afford 910 mg (58%) of the title compound as a white solid. $^1$H NMR (300 MHz, CDCl$_3$) δ [ppm] 7.69 (d, J=8.8 Hz, 2H), 7.61 (d, J=8.8 Hz, 2H), 4.28-4.20 (m, 1H), 4.04-3.93 (m, 1H), 3.91-3.71 (m, 3H), 3.70-3.64 (m, 1H), 3.19-3.09 (m, 1H), 2.44-2.27 (m, 2H), 1.99 (t, J=5.7 Hz, 1H), 1.42 (s, 9H).

Step 3: tert-butyl 3-(4-((4-(tert-butoxycarbonyl)-3-(hydroxymethyl)-piperazin-1-yl)sulfonyl)phenyl)-6-fluoro-1H-indole-1-carboxylate A mixture of 4-(4-bromo-benzenesulfonyl)-2-hydroxymethyl-piperazine-1-carboxylic acid tert-butyl ester (120 mg, 0.277 mmol), 6-fluoro-3-(4,4,5,5-tetramethyl-[1,3,2]dioxaborolan-2-yl)-indole-1-carboxylic acid tert-butyl ester (Intermediate 1, 100 mg, 0.277 mmol), K$_2$CO$_3$ (114 mg, 0.831 mmol) and Pd(dppf)Cl$_2$ (20 mg, 0.028 mmol) in dioxane/water (10 mL/2 mL) was stirred at 90° C. under N$_2$ for 4 hours. The mixture was cooled and diluted with EtOAc (60 mL). The organic layer was dried with anhydrous Na$_2$SO$_4$ and filtered. The filtrate was concentrated and purified by silica gel chromatography (petroleum ether/EtOAc=5/1 to 3/1) to afford 120 mg (74%) of the title compound as a white solid. $^1$H NMR (400 MHz, CDCl$_3$) δ [ppm] 7.97 (d, J=9.2 Hz, 1H), 7.83 (d, J=8.8 Hz, 2H), 7.81-7.74 (m, 3H), 7.74-7.68 (m, 1H), 7.08 (td, J=8.8, 2.4 Hz, 1H), 4.29-4.21 (m, 1H), 4.02-3.95 (m, 1H), 3.95-3.79 (m, 2H), 3.79-3.71 (m, 2H), 3.17 (t, J=12.8 Hz, 1H), 2.49 (dd, J=12.0, 4.0 Hz, 1H), 2.41 (td, J=12.0, 4.0 Hz, 1H), 2.02 (brs, 1H), 1.70 (s, 9H), 1.42 (s, 9H).

Step 4: (4-((4-(6-fluoro-1H-indol-3-yl)phenyl)sulfonyl)piperazin-2-yl)methanol To a stirred solution of 3-[4-(4-tert-butoxycarbonyl-3-hydroxymethyl-piperazine-1-sulfonyl)-phenyl]-6-fluoro-indole-1-carboxylic acid tert-butyl ester (120 mg, 0.204 mmol) in anhydrous DCM (5 mL) was added TFA (3 mL) dropwise at 0° C. The mixture was stirred at room temperature for 3 hours before EtOAc (60 mL) and TEA (5 mL) was added. The mixture was washed with water (20 mL) and brine (20 mL×2). The organic layer was dried over anhydrous Na$_2$SO$_4$ and filtered. The filtrate was concentrated and purified by preparative HPLC (NH$_3$H$_2$O as additive) to afford 36 mg (46%) of the title compound as a white solid. LC-MS for O$_{19}$H$_{20}$FN$_3$O$_3$S+H$^+$[M+H]$^+$: calcd: 390.1. found: 390.1. $^1$H NMR (400 MHz, DMSO-d$_6$) δ [ppm] 11.67 (brs, 1H), 7.99-7.91 (m, 4H), 7.72 (d, J=8.4 Hz, 2H), 7.26 (dd, J=10.0, 2.0 Hz, 1H), 7.01 (td, J=8.8, 2.4 Hz, 1H), 4.67 (t, J=5.2 Hz, 1H), 3.58 (d, J=10.0 Hz, 1H), 3.45 (t, J=11.2 Hz, 1H), 3.27-3.16 (m, 1H), 2.91 (d, J=12.0 Hz, 1H), 2.70-2.60 (m, 2H), 2.21-2.13 (m, 1H), 1.89 (t, J=10.8 Hz, 1H).

Step 5: tert-butyl 3-(4-(2-(3-ethoxy-3-oxopropyl)-3-methyl-1,1-dioxido-2,3-dihydrobenzo[d]isothiazol-5-yl)phenyl)-6-fluoro-1H-indole-1-carboxylate Following the general method described in steps 1-4 above, starting from 1-tert-butyl 3-methyl piperazine-1,3-dicarboxylate, the title compound was obtained as a white solid. LC-MS for C$_{19}$H$_{20}$FN$_3$O$_3$S—H$^-$[M−H]$^-$: calcd: 388.1. found: 388.1. $^1$H NMR (400 MHz, DMSO-d$_6$) δ [ppm] 11.66 (br s, 1H), 7.95-7.91 (m, 4H), 7.83 (d, J=8.4 Hz, 2H), 7.26 (dd, J=10.0, 2.4 Hz, 1H), 7.01 (td, J=8.8, 2.4 Hz, 1H), 4.76 (br s, 1H), 3.77-3.72 (m, 1H), 3.68-3.64 (m, 1H), 3.51-3.48 (m, 1H), 3.37-3.29 (m, 2H), 3.04-2.92 (m, 2H), 2.71-2.68 (m, 1H), 2.49-2.40 (m, 2H).

Step 6

A yellow solution of tert-butyl 3-(4-(2-(3-ethoxy-3-oxopropyl)-3-methyl-1,1-dioxido-2,3-dihydrobenzo[d]isothiazol-5-yl)phenyl)-6-fluoro-1H-indole-1-carboxylate (Step 5, 500 mg, 1.2 mmol) in NH$_3$/EtOH (30% w/w, 30 mL) was stirred at 80° C. in a sealed tube for 14 h. The reaction was concentrated and purified by column chromatography (SiO$_2$, petroleum ether/ethyl acetate=2/1-1/4) to give racemic 3-(5-(6-fluoro-1H-indol-3-yl)-3-methyl-1,1-dioxidobenzo[d]isothiazol-2(3H)-yl)propanamide (170 mg, 52%) as a red solid. The racemic material was separated by prep-chiral SFC to give (+)-3-(5-(6-fluoro-1H-indol-3-yl)-3-methyl-1,1-dioxidobenzo[d]isothiazol-2(3H)-yl) propanamide as the first eluting peak (90 mg, 27%) as a pale yellow solid. $^1$H NMR (400 MHz, DMSO-d$_6$) δ [ppm] 11.70 (br s, 1H), 8.11-7.80 (m, 5H), 7.48 (br s, 1H), 7.31-7.24 (m, 1H), 7.02 (d, J=2.0 Hz, 1H), 6.95 (br s, 1H), 4.67 (d, J=6.5 Hz, 1H), 3.60-3.43 (m, 2H), 2.64-2.53 (m, 2H), 1.56 (d, J=6.5 Hz, 3H); LC-MS: m/z 409.9 (M+Na)$^+$, [α]$^{20}_D$ +2° (c=0.002 g/mL, DMSO).

Example 48: (−)-3-(5-(6-fluoro-1H-indol-3-yl)-3-methyl-1,1-dioxidobenzo[d]isothiazol-2(3H)-yl) propanamide

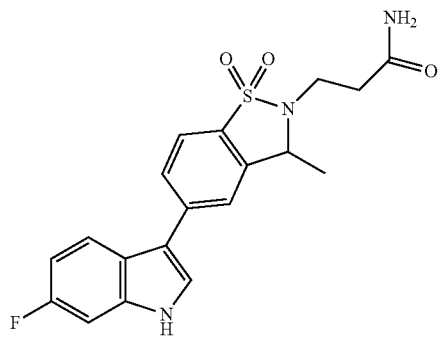 [SMILES: CC1c2cc(-c3c[nH]c4cc(F)ccc34)ccc2S(=O)(=O)N1CCC(N)=O]

The title compound was obtained as the second eluting peak from the chiral separation described for Example 47 (80 mg, 24%) as a pale yellow solid. $^1$H NMR (400 MHz, DMSO-d$_6$) δ [ppm] 11.70 (br s, 1H), 7.98-7.82 (m, 5H), 7.48 (br s, 1H), 7.28 (dd, J=2.4, 9.9 Hz, 1H), 7.02 (dt, J=2.4, 9.2 Hz, 1H), 6.95 (br s, 1H), 4.67 (q, J=6.7 Hz, 1H), 3.57-3.46

(m, 2H), 2.64-2.54 (m, 2H), 1.56 (d, J=6.3 Hz, 3H); LC-MS: m/z 409.9 (M+Na)$^+$, $[\alpha]^{20}_D$ −2.14° (c=0.0014 g/mL, DMSO).

Example 49: (+)-3-(5-(6-fluoro-1H-indol-3-yl)-3-methyl-1,1-dioxido-benzo [d]isothiazol-2(3H)-yl)-1-(piperazin-1-yl)propan-1-one

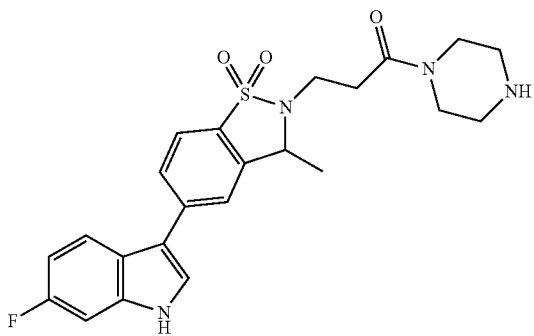 [SMILES: CC1c2cc(-c3c[nH]c4cc(F)ccc34)ccc2S(=O)(=O)N1CCC(=O)N1CCNCC1]

Step 1: 3-(5-(6-fluoro-1H-indol-3-yl)-3-methyl-1,1-dioxidobenzo[d]isothiazol-2(3H)-yl)propanoic acid To a yellow solution of tert-butyl 3-(2-(3-ethoxy-3-oxopropyl)-3-methyl-1,1-dioxido-2,3-dihydrobenzo[d]isothiazol-5-yl)-6-fluoro-1H-indole-1-carboxylate (210 mg, 0.354 mmol) in THF (5 mL) and H$_2$O (5 mL) was added LiOH—H$_2$O (47 mg, 1.1 mmol). The reaction was stirred at 28° C. for 18 h then concentrated and diluted with H$_2$O (5 mL). The resulting solution was adjusted to pH 6 with 1N HCl then extracted with 5% methanol in ethyl acetate (10 mL×3). The combined organic layers were dried over Na$_2$SO$_4$, filtered and concentrated to give crude 3-(5-(6-fluoro-1H-indol-3-yl)-3-methyl-1,1-dioxidobenzo[d]isothiazol-2(3H)-yl)propanoic acid (202 mg, >100%) as a yellow gum which was used directly for the next step.

Step 2: tert-butyl 4-(3-(5-(6-fluoro-1H-indol-3-yl)-3-methyl-1,1-dioxidobenzo[d]isothiazol-2(3H)-yl)propanoyl)piperazine-1-carboxylate A yellow suspension of 3-(5-(6-fluoro-1H-indol-3-yl)-3-methyl-1,1-dioxidobenzo[d]isothiazol-2(3H)-yl)propanoic acid (200 mg, 0.354 mmol), tert-butyl piperazine-1-carboxylate (132 mg, 0.708 mmol) and DIPEA (0.123 mL, 0.708 mmol) in dry DMF (5 mL) was stirred at 28° C. for 10 min then HATU (202 mg, 0.531 mmol) was added. The reaction was stirred at 28° C. for 6 h, concentrated then diluted with H$_2$O (10 mL) and extracted with ethyl acetate (10 mL×3). The combined organic layers were washed with brine (5 mL) then dried over anhydrous Na$_2$SO$_4$, filtered and concentrated. The crude product was purified by column chromatography (silica gel, 10-60% ethyl acetate/petroleum ether) to give 110 mg as a racemic mixture. The racemic product was purified by chiral SFC to give (+)tert-butyl 4-(3-(5-(6-fluoro-1H-indol-3-yl)-3-methyl-1,1-dioxidobenzo[d]isothiazol-2(3H)-yl) propanoyl)piperazine-1-carboxylate (total 46 mg, 17%) as a yellow oil and (−)tert-butyl 4-(3-(5-(6-fluoro-1H-indol-3-yl)-3-methyl-1,1-dioxidobenzo[d]isothiazol-2(3H)-yl)propanoyl)piperazine-1-carboxylate (31 mg, 17% yield) as a yellow oil.

Step 3: (+)-3-(5-(6-fluoro-1H-indol-3-yl)-3-methyl-1,1-dioxidobenzo[d]isothiazol-2(3H)-yl)-1-(piperazin-1-yl)propan-1-one To a solution of (+)-tert-butyl 4-(3-(5-(6-fluoro-1H-indol-3-yl)-3-methyl-1,1-dioxidobenzo[d]isothiazol-2(3H)-yl) propanoyl) piperazine-1-carboxylate (46 mg, 0.08 mmol) in dichloromethane (5 mL) was added HCl(g)/ethyl acetate (4N) (5 mL). The reaction was stirred at 28° C. for 5 h then concentrated to give a solid which was washed with ethyl acetate (10 mL). The solid was dried to give (+)-3-(5-(6-fluoro-1H-indol-3-yl)-3-methyl-1,1-dioxidobenzo[d]isothiazol-2(3H)-yl)-1-(piperazin-1-yl)propan-1-one (42 mg, 100%) as a white solid. $^1$H NMR (400 MHz, DMSO-d$_6$) δ [ppm] 11.75 (br s, 1H), 9.25 (br s, 1H), 7.97-7.87 (m, 4H), 7.86-7.82 (m, 1H), 7.27 (dd, J=2.4, 9.9 Hz, 1H), 7.06-6.96 (m, 1H), 4.76-4.68 (m, 1H), 3.69 (br s, 4H), 3.59-3.49 (m, 2H), 3.13-3.02 (m, 4H), 2.90-2.76 (m, 2H), 1.55 (d, J=6.3 Hz, 3H); LCMS: m/z 479.0 (M+Na)$^+$, $[\alpha]^{20}_D$ +2.67° (c=1.5 mg/ml, methanol).

Example 50: (−)3-(5-(6-fluoro-1H-indol-3-yl)-3-methyl-1,1-dioxidobenzo[d]isothiazol-2(3H)-yl)-1-(piperazin-1-yl)propan-1-one

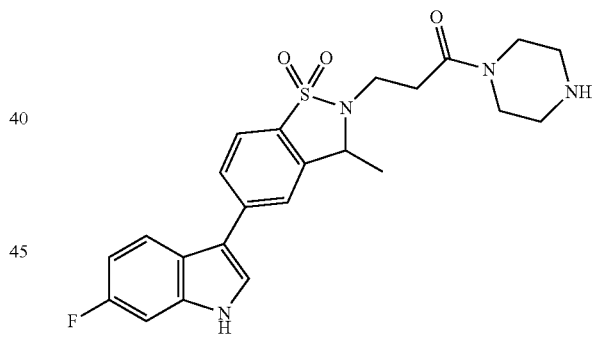

To a solution of (−)-tert-butyl 4-(3-(5-(6-fluoro-1H-indol-3-yl)-3-methyl-1,1-dioxidobenzo[d]isothiazol-2(3H)-yl) propanoyl) piperazine-1-carboxylate (45 mg, 0.08 mmol) in dichloromethane (5 mL) was added HCl (g)/ethyl acetate (4N) (5 mL). The reaction was stirred at 28° C. for 5 h then concentrated to give a solid which was washed with ethyl acetate (10 mL). The solid was dried to give (−)-3-(5-(6-fluoro-1H-indol-3-yl)-3-methyl-1,1-dioxidobenzo[d]isothiazol-2(3H)-yl)-1-(piperazin-1-yl)propan-1-one (40 mg, 100%) as a white solid. $^1$H NMR (400 MHz, DMSO-d$_6$) δ [ppm] 11.76 (br s, 1H), 9.30 (br s, 1H), 7.98-7.88 (m, 4H), 7.87-7.81 (m, 1H), 7.27 (dd, J=2.4, 9.9 Hz, 1H), 7.01 (dt, J=2.4, 9.2 Hz, 1H), 4.72 (q, J=6.3 Hz, 1H), 3.70 (br s, 4H), 3.62-3.49 (m, 2H), 3.16-3.00 (m, 4H), 2.93-2.73 (m, 2H), 1.56 (d, J=6.5 Hz, 3H); LC-MS: m/z 479.1 (M+Na)$^+$, $[\alpha]^{20}_D$ −2.67° (c=1.3 mg/ml, methanol).

Example 51: (−)-5-(6-fluoro-1H-indol-3-yl)-3-methyl-2-(piperidin-4-yl)-2,3-dihydrobenzo[d]isothiazole 1,1-dioxide

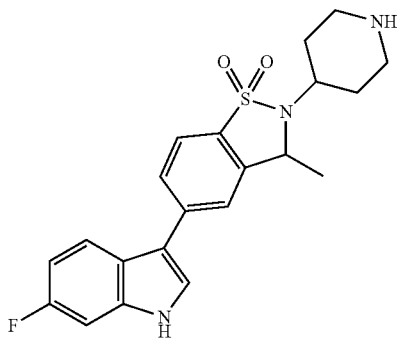 [SMILES: CC1c2cc(-c3c[nH]c4cc(F)ccc34)ccc2S(=O)(=O)N1C1CCNCC1]

Step 1: tert-butyl 4-(5-bromo-3-methyl-1,1-dioxidobenzo[d]isothiazol-2(3H)-yl)piperidine-1-carboxylate A brown suspension of 5-bromo-3-methyl-2,3-dihydrobenzo[d]isothiazole 1,1-dioxide (400 mg, 1.53 mmol), tert-butyl 4-((methylsulfonyl)oxy)piperidine-1-carboxylate (853 mg, 3.05 mmol) and $K_2CO_3$ (211 mg, 1.53 mmol) in DMF (5 mL) was stirred at 80° C. for 18 h. The reaction was cooled to ambient temperature then poured into water (100 mL) and extracted with ethyl acetate (3×20 mL). The combined organic layers were washed with brine (2×10 mL) then dried over $Na_2SO_4$, filtered and concentrated. The crude residue was purified by column chromatography (silica gel, 0-20% ethyl acetate/petroleum ether) to give tert-butyl 4-(5-bromo-3-methyl-1,1-dioxidobenzo[d]isothiazol-2(3H)-yl)piperidine-1-carboxylate (250 mg, 37%) as light yellow solid.

Step 2: tert-butyl 4-(5-bromo-3-methyl-1,1-dioxidobenzo[d]isothiazol-2(3H)-yl)piperidine-1-carboxylate A solution of the tert-butyl 4-(5-bromo-3-methyl-1,1-dioxidobenzo[d]-isothiazol-2(3H)-yl)piperidine-1-carboxylate (200 mg, 0.449 mmol) and tert-butyl 6-fluoro-3-(4,4,5,5-tetramethyl-1,3,2-dioxaborolan-2-yl)-1H-indole-1-carboxylate (211 mg, 0.584 mmol) in dioxane (5 mL) was added $K_3PO_4$ aq (2 M in water, 191 mg, 0.898 mmol) and $Pd(dppf)_2Cl_2$ (33 mg, 0.045 mmol). The reaction solution was sparged with $N_2$ for 2 min, sealed and stirred at 80° C. for 3 h. The crude reaction was cooled to ambient temperature and concentrated then purified by column chromatography (silica gel, 0-20% ethyl acetate/petroleum ether) to give tert-butyl 3-(2-(1-(tert-butoxycarbonyl)piperidin-4-yl)-3-methyl-1,1-dioxido-2,3-dihydrobenzo[d]sothiazol-5-yl)-6-fluoro-1H-indole-1-carboxylate (210 mg, 82%) as light yellow gum. LCMS (M+Na, 622).

Step 3: (−)-5-(6-fluoro-1H-indol-3-yl)-3-methyl-2-(piperidin-4-yl)-2,3-dihydrobenzo[d]isothiazole 1,1-dioxide Racemic tert-butyl 3-(2-(1-(tert-butoxycarbonyl)piperidin-4-yl)-3-methyl-1,1-dioxido-2,3-dihydrobenzo[d]sothiazol-5-yl)-6-fluoro-1H-indole-1-carboxylate (150 mg, 0.25 mmol was separated by chiral SFC to give two peaks. The first peak (65 mg, 0.11 mmol) was dissolved in dichloromethane (5 mL) and HCl/ethyl acetate (4 M, 10 mL) then stirred at ambient temperature for 4 h. The reaction was concentrated and purified by prep-HPLC to give (−)-5-(6-fluoro-1H-indol-3-yl)-3-methyl-2-(piperidin-4-yl)-2,3-dihydrobenzo[d]isothiazole 1,1-dioxide (10 mg, 21%). $^1$H NMR (400 MHz, DMSO-$d_6$) δ [ppm] 11.66-11.87 (m, 1H), 8.63-9.08 (m, 1H), 7.88-8.02 (m, 4H), 7.75-7.86 (m, 1H), 7.29 (dd, J=9.79, 2.26 Hz, 1H), 6.98-7.07 (m, 1H), 4.90 (q, J=6.53 Hz, 1H), 3.91 (t, J=11.17 Hz, 1H), 3.29 (br s, 2H), 3.05 (br s, 2H), 2.06-2.33 (m, 4H), 1.61 (d, J=6.53 Hz, 3H); LC-MS: m/z 399.9 (M+1)$^+$, $[\alpha]^{20}_D$ −8.79° (c=1.1 mg/ml, DMSO).

Example 52: (+)-5-(6-fluoro-1H-indol-3-yl)-3-methyl-2-(piperidin-4-yl)-2,3-dihydrobenzo[d]isothiazole 1,1-dioxide

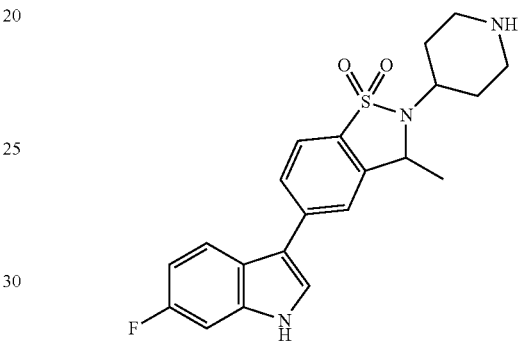

The second peak from chiral separation described in Example 51 (70 mg, 0.12 mmol) was dissolved in dichloromethane (5 mL) then cooled to 0° C. and HCl/ethyl acetate (10 mL, 4M) was added dropwise. The reaction was stirred at ambient temperature for 4 h, concentrated and purified by prep-HPLC to give (+)-5-(6-fluoro-1H-indol-3-yl)-3-methyl-2-(piperidin-4-yl)-2,3-dihydrobenzo[d]isothiazole 1,1-dioxide (10 mg, 24%) as a white solid. $^1$H NMR (400 MHz, DMSO-$d_6$) δ [ppm] 11.79 (br s, 1H), 8.79-9.21 (m, 1H), 7.87-7.98 (m, 4H), 7.78-7.86 (m, 1H), 7.29 (dd, J=9.79, 2.26 Hz, 1H), 7.02 (m, 1H), 4.90 (q, J=6.53 Hz, 1H), 3.91 (t, J=11.17 Hz, 1H), 3.33 (br s, 2H), 3.05 (br s, 2H), 2.00-2.40 (m, 4H), 1.62 (d, J=6.53 Hz, 3H); LC-MS: m/z 399.9 (M+1)$^+$, $[\alpha]^{20}_D$ +8.1° (c=0.9 mg/ml, DMSO).

Example 53: (+)-5-(6-fluoro-1H-indol-3-yl)-3-methyl-2-(2-(methylsulfonyl)ethyl)-2,3-dihydrobenzo[d]isothiazole 1,1-dioxide

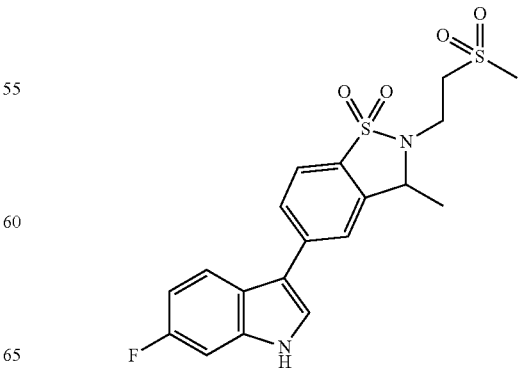

Step 1: 5-bromo-3-methyl-2-(2-(methylthio)ethyl)-2,3-dihydrobenzo[d]isothiazole 1,1-dioxide A red solution of 5-bromo-3-methyl-2,3-dihydrobenzo[d]isothiazole 1,1-dioxide (400 mg, 1.53 mmol), (2-chloroethyl)(methyl)sulfane (169 mg, 1.534 mmol) and K₂CO₃ (422 mg, 3.05 mmol) in DMF (5 mL) was evacuated and back-filled with N₂ three times then stirred at 85° C. for 14 h. The reaction was diluted with ethyl acetate (50 mL), and washed with H₂O (10 mL×3). The organic phase was dried over Na₂SO₄, filtered and concentrated to give crude 5-bromo-3-methyl-2-(2-(methylthio)ethyl)-2,3-dihydrobenzo[d]isothiazole 1,1-dioxide (513 mg, 100%) as a red gum.

Step 2: 5-bromo-3-methyl-2-(2-(methylsulfonyl)ethyl)-2,3-dihydrobenzo[d]isothiazole 1,1-dioxide A red solution of 5-bromo-3-methyl-2-(2-(methylthio)ethyl)-2,3-dihydrobenzo[d]isothiazole 1,1-dioxide (513 mg, 1.53 mmol) and Oxone (938 mg, 1.53 mmol) in THF/H₂O (10 mL/2) was stirred at 25° C. for 1 h. The reaction was diluted with ethyl acetate (50 mL) and washed with H₂O (10 mL×3). The combined organic extracts were dried over Na₂SO₄, filtered and concentrated. The crude reside was purified by column chromatography (SiO₂, /ethyl acetate/petroleum ether=1/5-1/1) to give 5-bromo-3-methyl-2-(2-(methylsulfonyl)ethyl)-2,3-dihydrobenzo[d]isothiazole 1,1-dioxide (400 mg, 71%) as a red solid.

Step 3: tert-butyl 6-fluoro-3-(3-methyl-2-(2-(methylsulfonyl)ethyl)-1,1-dioxido-2,3-dihydrobenzo[d]isothiazol-5-yl)-1H-indole-1-carboxylate A yellow solution of 5-bromo-3-methyl-2-(2-(methylsulfonyl)ethyl)-2,3-dihydrobenzo[d]isothiazole 1,1-dioxide (394 mg, 1.09 mmol), tert-butyl 6-fluoro-3-(4,4,5,5-tetramethyl-1,3,2-dioxaborolan-2-yl)-1H-indole-1-carboxylate (400 mg, 1.09 mmol), PdCl₂(dppf) (80 mg, 0.11 mmol) and Cs₂CO₃ (710 mg, 2.18 mmol) in dioxane (8 mL) and H₂O (2 mL) was stirred at 85° C. under a N₂ atmosphere for 14 h. The resulting black solution was diluted with ethyl acetate (50 mL) and washed with brine (20 mL). The organic phase was dried over anhydrous Na₂SO₄, filtered and concentrated to give crude tert-butyl 6-fluoro-3-(3-methyl-2-(2-(methylsulfonyl)ethyl)-1,1-dioxido-2,3-dihydrobenzo[d]isothiazol-5-yl)-1H-indole-1-carboxylate as a red gum.

Step 4: (+)-5-(6-fluoro-1H-indol-3-yl)-3-methyl-2-(2-(methylsulfonyl)ethyl)-2,3-dihydrobenzo[d]isothiazole 1,1-dioxide A red solution of crude tert-butyl 6-fluoro-3-(3-methyl-2-(2-(methylsulfonyl)ethyl)-1,1-dioxido-2,3-dihydrobenzo[d]isothiazol-5-yl)-1H-indole-1-carboxylate (570 mg, 1.09 mmol) in trifluoroacetic acid/dichloromethane (5 mL/5 mL) was stirred at 20° C. under a N₂ atmosphere for 2 h. The resulting yellow suspension was concentrated and neutralized with NaHCO₃ (sat) (10 mL) then extracted dichloromethane (20 mL×3). The combined organic layers were dried over Na₂SO₄, filtered and concentrated. The crude residue was purified by column chromatography (SiO₂, petroleum ether/ethyl acetate=1/1-1/4) to give the racemic product (150 mg) as a red solid. The racemic mixture was separated by prep-chiral SFC to give (+)-5-(6-fluoro-1H-indol-3-yl)-3-methyl-2-(2-(methylsulfonyl)ethyl)-2,3-dihydrobenzo[d]isothiazole 1,1-dioxide as the first eluting peak (65 mg, 14%) as a pale yellow solid. ¹H NMR (400 MHz, DMSO-d₆) δ [ppm] 11.72 (br s, 1H), 8.11-7.75 (m, 5H), 7.28 (dd, J=2.3, 9.8 Hz, 1H), 7.03 (dt, J=2.5, 9.3 Hz, 1H), 4.80 (q, J=6.5 Hz, 1H), 3.85-3.52 (m, 4H), 3.11 (s, 3H), 1.60 (d, J=6.5 Hz, 3H); LC-MS: m/z 444.8 (M+Na)⁺; [α]²⁰_D +0.67° (c=0.0035 g/mL, DMSO).

Example 54: (−)-5-(6-fluoro-1H-indol-3-yl)-3-methyl-2-(2-(methylsulfonyl)ethyl)-2,3-dihydrobenzo[d]isothiazole 1,1-dioxide

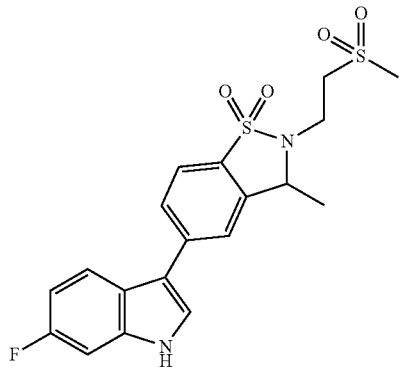 [SMILES: CC1c2cc(-c3c[nH]c4cc(F)ccc34)ccc2S(=O)(=O)N1CCS(C)(=O)=O]

The title compound was isolated as the second eluting peak from the chiral separation described in Example 53 (30 mg, 7%) as a pale yellow solid. ¹H NMR (400 MHz, DMSO-d₆) δ [ppm] 11.72 (br s, 1H), 8.09-7.83 (m, 5H), 7.28 (dd, J=2.3, 9.8 Hz, 1H), 7.03 (dt, J=2.4, 9.2 Hz, 1H), 4.80 (q, J=6.4 Hz, 1H), 3.84-3.50 (m, 4H), 3.16-3.05 (m, 3H), 1.60 (d, J=6.5 Hz, 3H); LC-MS: m/z 444.8 (M+Na)⁺, [α]²⁰_D=−1.62° (c=0.0036 g/mL, DMSO).

Example 55: (+)-5-(6-fluoro-1H-indol-3-yl)-3-methyl-2-(2-(methylsulfinyl)ethyl)-2,3-dihydrobenzo[d]isothiazole 1,1-dioxide

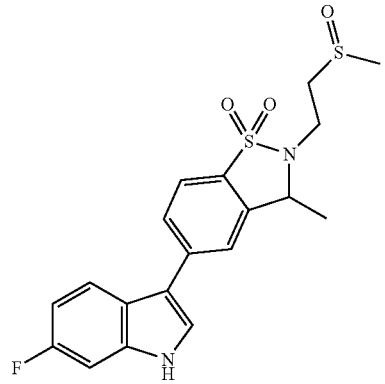 [SMILES: CC1c2cc(-c3c[nH]c4cc(F)ccc34)ccc2S(=O)(=O)N1CCS(C)=O]

Step 1: 5-bromo-3-methyl-2-(2-(methylsulfinyl)ethyl)-2,3-dihydrobenzo[d]isothiazole 1,1-dioxide To a yellow solution of 5-bromo-3-methyl-2-(2-(methylthio)ethyl)-2,3-dihydrobenzo[d]isothiazole 1,1-dioxide (1.05 g, 3.12 mmol) in anhydrous dichloromethane (50 mL) was added m-CPBA (634 mg, 3.12 mmol) at −25° C. The yellow suspension was stirred at −25° C. for 1 h then washed with H₂O (10 mL×2). The layers were separated and the organic phase was dried over Na₂SO₄, filtered concentrated. The crude material was purified by column chromatography (SiO₂, petroleum ether/ethyl acetate=6/1-3/1) to give 5-bromo-3-methyl-2-(2-(methylsulfinyl)ethyl)-2,3-dihydrobenzo[d]isothiazole 1,1-dioxide (1.0 g, 91%) as a yellow gum.

Step 2: tert-butyl 6-fluoro-3-(3-methyl-2-(2-(methylsulfinyl)ethyl)-1,1-dioxido-2,3-dihydrobenzo[d]isothiazol-5-yl)-1H-indole-1-carboxylate A yellow solution of tert-butyl 6-fluoro-3-(4,4,5,5-tetramethyl-1,3,2-dioxaborolan-2-yl)-1H-indole-1-carboxylate (513 mg, 1.42 mmol), 5-bromo-3-methyl-2-(2-(methylsulfinyl)ethyl)-2,3-dihydrobenzo[d]isothiazole 1,1-dioxide (500 mg, 1.42 mmol), PdCl₂(dppf) (104 mg, 0.142 mmol) and Cs₂CO₃ (925 mg, 2.84 mmol) in dioxane (8 mL) and H₂O (2 mL) was stirred at 85° C. under a N₂ atmosphere for 14 h. The resulting black solution was diluted with ethyl acetate (50 mL) and washed with brine (20 mL). The organic layer was dried over anhydrous Na₂SO₄, filtered and concentrated to give crude tert-butyl 6-fluoro-3-(3-methyl-2-(2-(methylsulfinyl)ethyl)-1,1-dioxido-2,3-dihydrobenzo[d]isothiazol-5-yl)-1H-indole-1-carboxylate as a red gum, which was used in the next step without purification.

Step 3: (+)-5-(6-fluoro-1H-indol-3-yl)-3-methyl-2-(2-(methylsulfinyl)ethyl)-2,3-dihydrobenzo[d]isothiazole 1,1-dioxide A red solution of tert-butyl 3-(4-(N-(3-amino-3-oxopropyl)sulfamoyl)-3-isobutylphenyl)-6-fluoro-1H-indole-1-carboxylate (719 mg, 1.42 mmol) in trifluoroacetic acid/dichloromethane (5 mL/5 mL) was stirred at 20° C. under a N₂ atmosphere for 1 h. The yellow suspension was concentrated, neutralized with NaHCO₃ (sat) (10 mL) and extracted ethyl acetate (20 mL×3). The combined organic layers were dried over Na₂SO₄, filtered and concentrated. The crude residue was purified by column chromatography (SiO₂, petroleum ether/ethyl acetate=1/1 to ethyl acetate/methanol=10/1) followed by prep-HPLC to give the racemic 5-(6-fluoro-1H-indol-3-yl)-3-methyl-2-(2-(methylsulfinyl)ethyl)-2,3-dihydrobenzo[d]isothiazole 1,1-dioxide as a red solid. The mixture of diastereomers were separated by prep-chiral SFC to give (+)-5-(6-fluoro-1H-indol-3-yl)-3-methyl-2-(2-(methylsulfinyl)ethyl)-2,3-dihydrobenz o[d]isothiazole 1,1-dioxide as the first eluting peak (40 mg, 24%) as a pale yellow solid. ¹H NMR (400 MHz, CDCl₃) δ [ppm] 8.63 (br s, 1H), 7.87-7.81 (m, 1H), 7.79-7.71 (m, 2H), 7.57 (s, 1H), 7.42 (d, J=2.8 Hz, 1H), 7.16 (dd, J=2.3, 9.0 Hz, 1H), 7.01 (dt, J=2.3, 9.2 Hz, 1H), 4.68 (q, J=6.5 Hz, 1H), 4.01-3.90 (m, 1H), 3.87-3.74 (m, 1H), 3.44-3.32 (m, 1H), 3.09 (td, J=5.8, 13.2 Hz, 1H), 2.76-2.66 (m, 3H), 1.65 (d, J=6.5 Hz, 3H); LC-MS: m/z 428.8 (M+Na)⁺, [α]²⁰_D +25.1° (c=0.0016 g/mL, methanol).

Example 56: (−)-5-(6-fluoro-1H-indol-3-yl)-3-methyl-2-(2-(methylsulfinyl)ethyl)-2,3-dihydrobenzo[d]isothiazole 1,1-dioxide

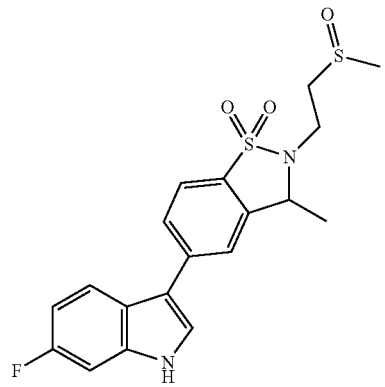 [SMILES: CC1c2cc(-c3c[nH]c4cc(F)ccc34)ccc2S(=O)(=O)N1CCS(C)=O]

The title compound was obtained as the second eluting peak from the chiral separation described in Example 55 (40 mg, 24%) as a pale yellow solid. ¹H NMR (400 MHz, CDCl₃) δ [ppm] 8.56 (br s, 1H), 7.87-7.73 (m, 3H), 7.59 (s, 1H), 7.43 (d, J=2.5 Hz, 1H), 7.16 (dd, J=2.3, 9.3 Hz, 1H), 7.02 (dt, J=2.4, 9.1 Hz, 1H), 4.70 (q, J=6.7 Hz, 1H), 4.02-3.90 (m, 1H), 3.82 (d, J=7.0 Hz, 1H), 3.43-3.32 (m, 1H), 3.14-3.05 (m, 1H), 2.71 (s, 3H), 1.66 (d, J=6.5 Hz, 3H); LC-MS: m/z 428.8 (M+Na)⁺, [α]²⁰_D −20° (c=0.0016 g/mL, methanol).

Example 57: (−)-5-(6-fluoro-1H-indol-3-yl)-3-methyl-2-(2-(methylsulfinyl)ethyl)-2,3-dihydrobenzo[d]isothiazole 1,1-dioxide

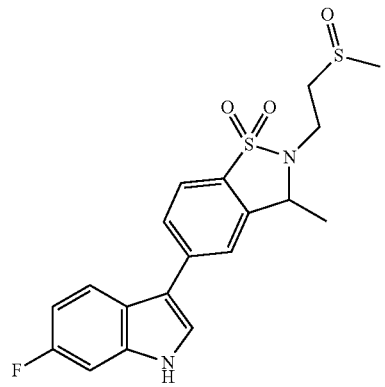 [SMILES: CC1c2cc(-c3c[nH]c4cc(F)ccc34)ccc2S(=O)(=O)N1CCS(C)=O]

The title compound was obtained as the third eluting peak from the chiral separation described in Example 55 (40 mg, 24%) as a pale yellow solid. ¹H NMR (400 MHz, CDCl₃) δ [ppm] 8.56 (br s, 1H), 7.88-7.72 (m, 3H), 7.60 (s, 1H), 7.44 (d, J=2.8 Hz, 1H), 7.16 (dd, J=2.3, 9.3 Hz, 1H), 7.01 (dt, J=2.3, 9.2 Hz, 1H), 4.52 (q, J=6.4 Hz, 1H), 3.96-3.88 (m, 1H), 3.85-3.75 (m, 1H), 3.38 (ddd, J=6.0, 10.3, 13.3 Hz, 1H), 3.05-2.94 (m, 1H), 2.69 (s, 3H), 1.71 (d, J=6.5 Hz, 3H); LC-MS: m/z 428.8 (M+Na)⁺, [α]²⁰_D −10° (c=0.0019 g/mL, methanol).

Example 58: (+)-5-(6-fluoro-1H-indol-3-yl)-3-methyl-2-(2-(methylsulfinyl)ethyl)-2,3-dihydrobenzo[d]isothiazole 1,1-dioxide

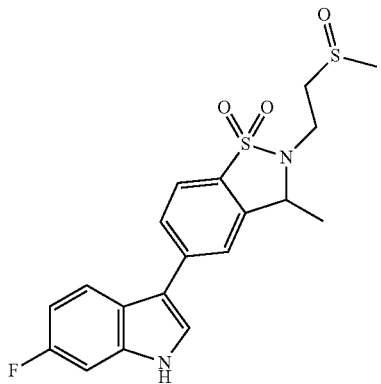 [SMILES: CC1c2cc(-c3c[nH]c4cc(F)ccc34)ccc2S(=O)(=O)N1CCS(C)=O]

The title compound was obtained as the forth eluting peak from the chiral separation described in Example 55 (40 mg, 24%) as a pale yellow solid. $^1$H NMR (400 MHz, CDCl$_3$) δ [ppm] 8.61-8.49 (m, 1H), 7.89-7.72 (m, 3H), 7.60 (s, 1H), 7.44 (d, J=2.5 Hz, 1H), 7.16 (dd, J=2.3, 9.3 Hz, 1H), 7.02 (dt, J=2.3, 9.2 Hz, 1H), 4.52 (q, J=6.3 Hz, 1H), 3.97-3.88 (m, 1H), 3.86-3.75 (m, 1H), 3.38 (ddd, J=6.0, 10.3, 13.6 Hz, 1H), 3.02-2.95 (m, 1H), 2.72-2.65 (m, 3H), 1.71 (d, J=6.5 Hz, 3H); LC-MS: m/z 428.8 (M+Na)$^+$, [α]$^{20}_D$ +0.67° (c=0.0015 g/mL, methanol).

Example 59: (−)-2-(5-(6-fluoro-1H-indol-3-yl)-3-methyl-1,1-dioxidobenzo[d]isothiazol-2(3H)-yl)-N-methylethane-1-sulfonamide

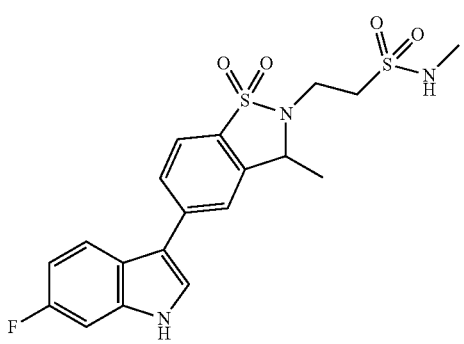 [SMILES: CNS(=O)(=O)CCN1C(C)c2cc(-c3c[nH]c4cc(F)ccc34)ccc2S1(=O)=O]

Step 1: 2-(5-bromo-3-methyl-1,1-dioxidobenzo[d]-isothiazol-2(3H)-yl)ethanesulfonyl chloride A red solution of 5-bromo-3-methyl-2,3-dihydrobenzo[d] isothiazole 1,1-dioxide (500 mg, 1.9 mmol), 2-chloroethanesulfonyl chloride (933 mg, 5.72 mmol) and K$_2$CO$_3$ (1050 mg, 7.63 mmol) in MeCN (15 mL) was evacuated and back-filled with N$_2$ three times then stirred at 85° C. for 48 h. The yellow suspension of 2-(5-bromo-3-methyl-1,1-dioxidobenzo[d]-isothiazol-2(3H)-yl)ethanesulfonyl chloride was used in the next step directly.

Step 2: 2-(5-bromo-3-methyl-1,1-dioxidobenzo[d]isothiazol-2(3H)-yl)-N-methylethanesulfonamide The suspension of 2-(5-bromo-3-methyl-1,1-dioxido-benzo[d]isothiazol-2(3H)-yl)ethanesulfonyl chloride (Step 1) was cooled to 25° C. and MeNH$_2$ in H$_2$O (10 mL) was added. The reaction was stirred at 25° C. for 4 h then diluted with ethyl acetate (50 mL) and washed with H$_2$O (10 mL×3). The organic layer was dried over Na$_2$SO$_4$, filtered and concentrated then purified by column chromatography (SiO$_2$, petroleum ether/ethyl acetate=3/1-1/1) to give crude 2-(5-bromo-3-methyl-1,1-dioxidobenzo[d]isothiazol-2 (3H)-yl)-N-methylethanesulfonamide (270 mg, 37%) as a red gum.

Step 3: tert-butyl 6-fluoro-3-(3-methyl-2-(2-(N-methylsulfamoyl)ethyl)-1,1-dioxido-2,3-dihydrobenzo[d]isothiazol-5-yl)-1H-indole-1-carboxylate A yellow solution of tert-butyl 6-fluoro-3-(4,4,5,5-tetramethyl-1,3,2-dioxaborolan-2-yl)-1H-indole-1-carboxylate (254 mg, 0.704 mmol), 2-(5-bromo-3-methyl-1,1-dioxido-benzo[d]isothiazol-2(3H)-yl)-N-methylethanesulfonamide (270 mg, 0.704 mmol), PdCl2(dppf) (51.5 mg, 0.0704 mmol) and Cs$_2$CO$_3$ (459 mg, 1.41 mmol) in dioxane (8 mL) and H$_2$O (2 mL) was stirred at 85° C. under a N$_2$ atmosphere for 14 h. The resulting black solution was diluted with ethyl acetate (50 mL) and washed with brine (20 mL). The organic phase was dried over anhydrous Na$_2$SO$_4$, filtered and concentrated to give crude tert-butyl 6-fluoro-3-(3-methyl-2-(2-(N-methylsulfamoyl)ethyl)-1,1-dioxido-2,3-dihydrobenz o[d]isothiazol-5-yl)-1H-indole-1-carboxylate as a red gum, which was used in the next step without purification.

Step 4: (−)-2-(5-(6-fluoro-1H-indol-3-yl)-3-methyl-1,1-dioxidobenzo[d]isothiazol-2(3H)-yl)-N-methyl-ethane-1-sulfonamide A red solution of tert-butyl 6-fluoro-3-(3-methyl-2-(2-(N-methylsulfamoyl)ethyl)-1,1-dioxido-2,3-dihydrobenzo[d] isothiazol-5-yl)-1H-indole-1-carboxylate (378 mg, 0.703 mmol) in trifluoroacetic acid/dichloromethane (5 mL/5 mL) was stirred at 20° C. under a N$_2$ atmosphere for 1 h. The yellow suspension was concentrated and neutralized with NaHCO$_3$ (sat) (10 mL) then extracted ethyl acetate (20 mL×3). The combined organic layers were dried over Na$_2$SO$_4$, filtered and concentrated. The crude residue was purified by column chromatography (SiO$_2$, petroleum ether/ethyl acetate=1/1-1/4) to give a mixture of enantiomers. The racemic mixture was separated by prep-chiral SFC to give (−)-2-(5-(6-fluoro-1H-indol-3-yl)-3-methyl-1,1-dioxido-benzo[d]isothiazol-2(3H)-yl)-N-methylethane-1-sulfonamide as the first eluting peak (20 mg, 7%) as a pale yellow solid. $^1$H NMR (400 MHz, MeOD) δ [ppm] 7.96-7.86 (m, 2H), 7.85-7.79 (m, 2H), 7.71 (s, 1H), 7.18 (dd, J=2.4, 9.7 Hz, 1H), 6.97 (dt, J=2.4, 9.2 Hz, 1H), 4.77 (d, J=6.5 Hz, 1H), 3.89-3.71 (m, 2H), 3.63-3.47 (m, 2H), 2.78 (s, 3H), 1.66 (d, J=6.5 Hz, 3H); LC-MS: m/z 459.9 (M+Na)$^+$, [α]$^{20}_D$ −1.33° (c=0.003 g/mL, methanol)

Example 60: (+)-2-(5-(6-fluoro-1H-indol-3-yl)-3-methyl-1,1-dioxidobenzo[d]isothiazol-2(3H)-yl)-N-methylethane-1-sulfonamide

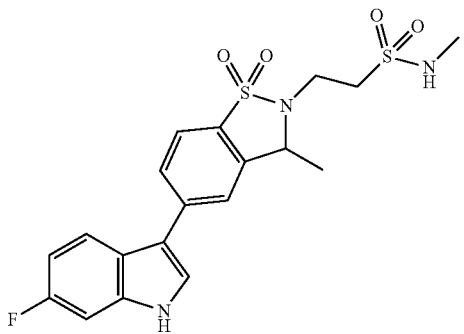 [SMILES: CNS(=O)(=O)CCN1C(C)c2cc(-c3c[nH]c4cc(F)ccc34)ccc2S1(=O)=O]

The title compound was obtained as the second eluting peak from the chiral separation described in Example 59 (20 mg, 7%) as a pale yellow solid. $^1$H NMR (400 MHz, MeOD) δ [ppm] 7.95-7.86 (m, 2H), 7.85-7.80 (m, 2H), 7.71 (s, 1H), 7.18 (dd, J=2.4, 9.7 Hz, 1H), 6.97 (dt, J=2.4, 9.2 Hz, 1H), 4.78 (d, J=6.5 Hz, 1H), 3.90-3.71 (m, 2H), 3.65-3.48 (m, 2H), 2.78 (s, 3H), 1.67 (d, J=6.5 Hz, 3H); LC-MS: m/z 459.9 (M+Na)$^+$, $[\alpha]^{20}_D$ +0.42° (c=0.004 g/mL, methanol).

Example 61: (+)-2-(5-(6-fluoro-1H-indol-3-yl)-3-methyl-1,1-dioxidobenzo[d]isothiazol-2(3H)-yl)ethane-1-sulfonamide

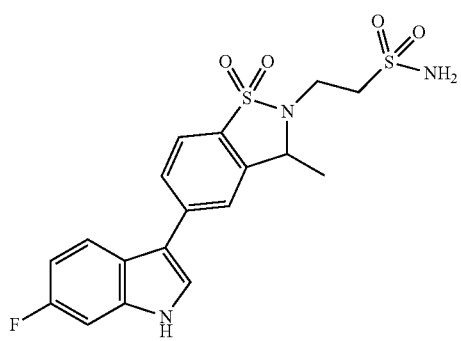 [SMILES: CC1c2cc(-c3c[nH]c4cc(F)ccc34)ccc2S(=O)(=O)N1CCS(N)(=O)=O]

Step 1: 2-(5-bromo-3-methyl-1,1-dioxidobenzo[d]isothiazol-2(3H)-yl)ethanesulfonamide A suspension of 2-(5-bromo-3-methyl-1,1-dioxidobenzo[d]isothiazol-2(3H)-yl)ethanesulfonyl chloride (737 mg, 1.9 mmol) in MeCN (15 mL) was cooled to 25° C. and NH$_4$OH (5 mL) was added. Stirring was continued at 25° C. for 4 h then the reaction was diluted with ethyl acetate (50 mL) and washed with H$_2$O (10 mL×3). The organic phase was dried over Na$_2$SO$_4$, filtered and concentrated, then purified by column chromatography (SiO$_2$, petroleum ether/ethyl acetate=3/1-1/1) to give 2-(5-bromo-3-methyl-1,1-dioxidobenzo[d]isothiazol-2(3H)-yl)ethanesulfonamide (280 mg, 40%) as a red gum.

Step 2: tert-butyl 6-fluoro-3-(3-methyl-1,1-dioxido-2-(2-sulfamoylethyl)-2,3-dihydrobenzo[d]isothiazol-5-yl)-1H-indole-1-carboxylate A yellow solution of tert-butyl 6-fluoro-3-(4,4,5,5-tetramethyl-1,3,2-dioxaborolan-2-yl)-1H-indole-1-carboxylate (275 mg, 0.760 mmol), 2-(5-bromo-3-methyl-1,1-dioxidobenzo[d]isothiazol-2(3H)-yl)ethanesulfonamide (280 mg, 0.758 mmol), PdCl$_2$(dppf) (56 mg, 0.08 mmol) and Cs$_2$CO$_3$ (495 mg, 1.52 mmol) in dioxane (8 mL) and H$_2$O (2 mL) was stirred at 85° C. under a N$_2$ atmosphere for 14 h. The resulting black solution was diluted with ethyl acetate (50 mL) and the layers were separated. The organic layer was washed with brine (20 mL) then dried over anhydrous Na$_2$SO$_4$, filtered and concentrated to give crude tert-butyl 6-fluoro-3-(3-methyl-1,1-dioxido-2-(2-sulfamoylethyl)-2,3-dihydrobenzo[d]isothiazol-5-yl)-1H-indole-1-carboxylate as a red gum, which was used in the next step without purification.

Step 3: (+)-2-(5-(6-fluoro-1H-indol-3-yl)-3-methyl-1,1-dioxidobenzo[d]isothiazol-2(3H)-yl)ethane-1-sulfonamide A red solution of tert-butyl 6-fluoro-3-(3-methyl-1,1-dioxido-2-(2-sulfamoylethyl)-2,3-dihydrobenzo[d]isothiazol-5-yl)-1H-indole-1-carboxylate (398 mg, 0.76 mmol) in trifluoroacetic acid/dichloromethane (5 mL/5 mL) was stirred at 20° C. under a N$_2$ atmosphere for 1 h. The reaction was concentrated then neutralized with NaHCO$_3$(sat) (10 mL) and extracted with ethyl acetate (20 mL×3). The combined organic layers were dried over Na$_2$SO$_4$, filtered and concentrated then purified by column chromatography (SiO$_2$, petroleum ether/ethyl acetate=1/1-1/4) to give the racemic material (100 mg) as a red solid.

The enantiomers were separated by prep-chiral SFC to give (+)-2-(5-(6-fluoro-1H-indol-3-yl)-3-methyl-1,1-dioxidobenzo[d]isothiazol-2(3H)-yl)ethane-1-sulfonamide as the first eluting peak (30 mg, 9%) as a pale yellow solid. $^1$H NMR (400 MHz, MeOD) δ [ppm] 7.96-7.86 (m, 2H), 7.85-7.80 (m, 2H), 7.71 (s, 1H), 7.18 (dd, J=2.3, 9.5 Hz, 1H), 7.01-6.94 (m, 1H), 4.81-4.75 (m, 1H), 3.94-3.78 (m, 2H), 3.68-3.51 (m, 2H), 1.67 (d, J=6.5 Hz, 3H); LC-MS: m/z for 445.9 (M+Na)$^+$; $[\alpha]^{20}_D$ +6° (c=0.002 g/mL, methanol).

Example 62: (−)-2-(5-(6-fluoro-1H-indol-3-yl)-3-methyl-1,1-dioxidobenzo[d]-isothiazol-2(3H)-yl)ethane-1-sulfonamide

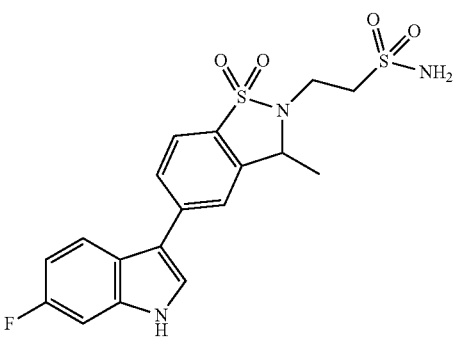 [SMILES: CC1c2cc(-c3c[nH]c4cc(F)ccc34)ccc2S(=O)(=O)N1CCS(N)(=O)=O]

The title compound was obtained as the second eluting peak from the chiral separation described in Example 61 (30 mg, 9%) as a pale yellow solid. $^1$H NMR (400 MHz, MeOD) δ [ppm] 7.97-7.86 (m, 2H), 7.86-7.80 (m, 2H), 7.71 (s, 1H), 7.19 (dd, J=2.4, 9.7 Hz, 1H), 6.97 (dt, J=2.4, 9.2 Hz, 1H), 4.78 (q, J=6.4 Hz, 1H), 3.95-3.78 (m, 2H), 3.68-3.51 (m, 2H), 1.67 (d, J=6.3 Hz, 3H); LC-MS: m/z 445.9 (M+Na)$^+$, $[\alpha]^{20}_D$=−1.33° (c=0.003 g/mL, methanol).

Example 63: (+)-5-(6-fluoro-1H-indol-3-yl)-2-(2-hydroxyethyl)-3-methyl-2,3-dihydrobenzo[d]isothiazole 1,1-dioxide

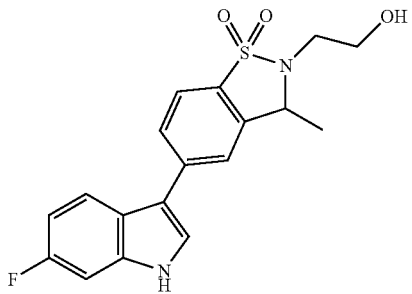 [SMILES: CC1c2cc(-c3c[nH]c4cc(F)ccc34)ccc2S(=O)(=O)N1CCO]

Step 1: 5-bromo-2-(2-hydroxyethyl)-3-methyl-2,3-dihydrobenzo[d]isothiazole 1,1-dioxide A red solution of 5-bromo-3-methyl-2,3-dihydrobenzo[d]isothiazole 1,1-dioxide (500 mg, 1.91 mmol), 2-bromoethanol (477 mg, 3.81 mmol) and K$_2$CO$_3$ (1050 mg, 7.63 mmol) in MeCN (5 mL) was evaluated and back-filled with N$_2$ three times, then stirred at 85° C. for 48 h. The crude reaction was diluted with ethyl acetate (50 mL), and washed with H$_2$O (10 mL×3). The organic phase was dried over Na$_2$SO$_4$, filtered and concentrated to give 5-bromo-2-(2-hydroxyethyl)-3-methyl-2,3-dihydrobenzo[d]isothiazole 1,1-dioxide (500 mg, 86%) as a red gum.

Step 2: tert-butyl 6-fluoro-3-(2-(2-hydroxyethyl)-3-methyl-1,1-dioxido-2,3-dihydrobenzo[d]isothiazol-5-yl)-1H-indole-1-carboxylate A yellow solution of tert-butyl 6-fluoro-3-(4,4,5,5-tetramethyl-1,3,2-dioxaborolan-2-yl)-1H-indole-1-carboxylate (500 mg, 1.38 mmol), 5-bromo-2-(2-hydroxyethyl)-3-methyl-2,3-dihydrobenzo[d]isothiazole 1,1-dioxide (500 mg, 1.63 mmol), PdCl$_2$(dppf) (101 mg, 0.138 mmol) and Cs$_2$CO$_3$ (902 mg, 2.77 mmol) in dioxane (8 mL) and H$_2$O (2 mL) was stirred at 85° C. under a N$_2$ atmosphere for 14 h. The resulting black solution was diluted with ethyl acetate (50 mL) and the layers were separated. The organic layer was washed with brine (20 mL) then dried over anhydrous Na$_2$SO$_4$, filtered and concentrated to give crude tert-butyl 6-fluoro-3-(2-(2-hydroxyethyl)-3-methyl-1,1-dioxido-2,3-dihydrobenzo[d]isothiazol-5-yl)-1H-indole-1-carboxylate as a red gum, which was used in the next step without purification.

Step 3: (+)-5-(6-fluoro-1H-indol-3-yl)-2-(2-hydroxyethyl)-3-methyl-2,3-dihydrobenzo[d]isothiazole 1,1-dioxide A red solution of tert-butyl 6-fluoro-3-(2-(2-hydroxyethyl)-3-methyl-1,1-dioxido-2,3-dihydrobenzo[d]isothiazol-5-yl)-1H-indole-1-carboxylate (637 mg, 1.38 mmol) in trifluoroacetic acid/dichloromethane (5 mL/5 mL) was stirred at 20° C. under a N$_2$ atmosphere for 1 h. The yellow suspension was concentrated then neutralized with NaHCO$_3$ (sat) (10 mL) and extracted ethyl acetate (20 mL×3). The combined organic layers were dried over Na$_2$SO$_4$, filtered and concentrated. The crude residue was purified by column chromatography (SiO$_2$, petroleum ether/ethyl acetate=1/1-1/4) to give the racemic product (150 mg) as a red solid. The enantiomers were separated by prep-chiral SFC to give (+)-5-(6-fluoro-1H-indol-3-yl)-2-(2-hydroxyethyl)-3-methyl-2,3-dihydrobenzo[d]isothiazole 1,1-dioxide as the first eluting peak (35 mg, 7%) as a pale yellow solid. $^1$H NMR (400 MHz, MeOD) δ [ppm] 7.95-7.86 (m, 2H), 7.85-7.77 (m, 2H), 7.70 (s, 1H), 7.18 (dd, J=2.3, 9.5 Hz, 1H), 6.97 (dt, J=2.1, 9.2 Hz, 1H), 4.80 (q, J=6.6 Hz, 1H), 3.94-3.83 (m, 2H), 3.58-3.42 (m, 2H), 1.66 (d, J=6.5 Hz, 3H); LC-MS: m/z 360.9 (M+H)$^+$, $[\alpha]^{20}_D$ +15.7° (c=0.0021 g/mL, methanol).

Example 64: (−)-5-(6-fluoro-1H-indol-3-yl)-2-(2-hydroxyethyl)-3-methyl-2,3-dihydrobenzo[d]isothiazole 1,1-dioxide

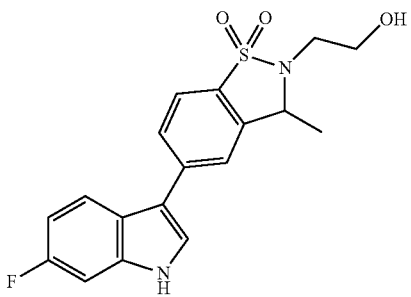 [SMILES: CC1c2cc(-c3c[nH]c4cc(F)ccc34)ccc2S(=O)(=O)N1CCO]

The title compound was obtained as the second eluting peak from the chiral separation described in Example 63 (40 mg, 8%) as a pale yellow solid. $^1$H NMR (400 MHz, MeOD) δ [ppm] 7.96-7.86 (m, 2H), 7.84-7.78 (m, 2H), 7.70 (s, 1H), 7.18 (dd, J=2.5, 9.5 Hz, 1H), 6.97 (dt, J=2.3, 9.2 Hz, 1H), 4.84-4.77 (m, 1H), 3.93-3.84 (m, 2H), 3.59-3.42 (m, 2H), 1.66 (d, J=6.5 Hz, 3H); LC-MS: m/z 360.9 (M+H)$^+$, $[\alpha]^{20}_D$ −17° (c=0.002 g/mL, methanol).

Example 65: (−)1-(2-(5-(6-fluoro-1H-indol-3-yl)-3-methyl-1,1-dioxidobenzo[d]isothiazol-2(3H)-yl)ethyl)piperazin-2-one

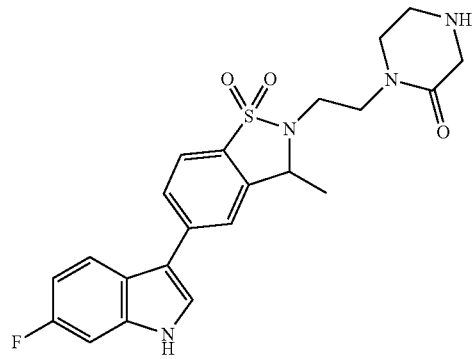 [SMILES: CC1c2cc(-c3c[nH]c4cc(F)ccc34)ccc2S(=O)(=O)N1CCN1CCNCC1=O]

Step 1: 2-(5-bromo-3-methyl-1,1-dioxidobenzo[d]isothiazol-2(3H)-yl)ethyl methanesulfonate To a solution of 5-bromo-2-(2-hydroxyethyl)-3-methyl-2,3-dihydrobenzo[d]isothiazole 1,1-dioxide (900 mg, 2.94 mmol) (Example 173, step 1) and TEA (892 mg, 8.82 mmol) in DCM (10 ml) was added methansulfonylchloride (MsCl (673 mg, 5.88 mmol). The reaction was stirred at 20° C. for 16 h then poured into water (100 ml) and extracted with DCM (100 ml×2). The combined organic layers were washed with brine (100 ml) then dried over anhydrous $Na_2SO_4$, filtered and concentrated to give crude 2-(5-bromo-3-methyl-1,1-dioxidobenzo[d]isothiazol-2(3H)-yl)ethyl methanesulfonate (1.1 g) as yellow oil, which was used directly for the next step without further purification.

Step 2: tert-butyl 4-(2-(5-bromo-3-methyl-1,1-dioxidobenzo[d]isothiazol-2(3H)-yl)ethyl)-3-oxopiperazine-1-carboxylate To a suspension of 2-(5-bromo-3-methyl-1,1-dioxidobenzo[d]isothiazol-2(3H)-yl)ethyl methanesulfonate (1.5 g, 3.9 mmol) and t-BuOK (876 mg, 7.81 mmol) in DMF (30 ml) was added tert-butyl 3-oxopiperazine-1-carboxylate (938 mg, 4.68 mmol). The reaction was stirred at 80° C. for 16 h then poured into water (100 ml), extracted with EtOAc (100 ml×2). The combined organic layers were washed with brine (100 ml×3) then dried over anhydrous $Na_2SO_4$, filtered and concentrated to give tert-butyl 4-(2-(5-bromo-3-methyl-1,1-dioxidobenzo[d]isothiazol-2(3H)-yl)ethyl)-3-oxopiperazine-1-carboxylate (1800 mg, crude) as yellow oil, which was used for next step without further purification.

Step 3: tert-butyl 3-(2-(2-(4-(tert-butoxycarbonyl)-2-oxopiperazin-1-yl)ethyl)-3-methyl-1,1-dioxido-2,3-dihydrobenzo[d]isothiazol-5-yl)-6-fluoro-1H-indole-1-carboxylate To a suspension of tert-butyl (3-(5-bromo-3-methyl-1,1-dioxidobenzo[d]isothiazol-2(3H)-yl)-1-(methylamino)-1-oxopropan-2-yl)carbamate (1.8 g, 3.7 mmol) and tert-butyl 6-fluoro-3-(4,4,5,5-tetramethyl-1,3,2-dioxaborolan-2-yl)-1H-indole-1-carboxylate (1.5 g, 4.1 mmol) in dioxane/water (20 ml/6 ml) was added Pd(dppf)Cl$_2$ (270 mg, 0.369 mmol) and K$_3$PO$_4$ (1.6 g, 7.4 mmol). The reaction was stirred at 80° C. for 16 h then concentrated and purified by column chromatography (silica gel, petroleum ether/ethyl acetate (PE/EA)=4/1) followed by prep-HPLC to give the title compound as a racemic mixture (400 mg). The enantiomers were separated by prep-chiral SFC to give chiral tert-butyl 3-(2-(2-(4-(tert-butoxycarbonyl)-2-oxopiperazin-1-yl)ethyl)-3-methyl-1,1-dioxido-2,3-dihydrobenzo[d]isothiazol-5-yl)-6-fluoro-1H-indole-1-carboxylate as the first eluting peak (200 mg) as a white solid and chiral tert-butyl 3-(2-(2-(4-(tert-butoxycarbonyl)-2-oxopiperazin-1-yl)-ethyl)-3-methyl-1,1-dioxido-2,3-dihydrobenzo[d]isothiazol-5-yl)-6-fluoro-1H-indole-1-carboxylate as the second eluting peak (200 mg) as a white solid.

Step 4: (−)1-(2-(5-(6-fluoro-1H-indol-3-yl)-3-methyl-1,1-dioxidobenzo[d]isothiazol-2(3H)-yl)ethyl)piperazin-2-one A solution of tert-butyl 3-(2-(2-(4-(tert-butoxycarbonyl)-2-oxopiperazin-1-yl)ethyl)-3-methyl-1,1-dioxido-2,3-dihydrobenzo[d]isothiazol-5-yl)-6-fluoro-1H-indole-1-carboxylate (300 mg, 0.467 mmol) (step 3, peak 1) in HCl/EA (10 ml) was stirred at 20° C. for 36 h. The reaction was concentrated and dried to give (−)1-(2-(5-(6-fluoro-1H-indol-3-yl)-3-methyl-1,1-dioxidobenzo[d]isothiazol-2(3H)-yl)ethyl)piperazin-2-one (154 mg, 75%) as a yellow solid. $^1$H NMR (400 MHz, DMSO-d$_6$) δ [ppm] 12.00 (br s, 1H), 10.84-10.05 (m, 1H), 8.43-7.80 (m, 5H), 7.29 (br s, 1H), 7.23-6.94 (m, 1H), 4.81 (br s, 1H), 3.83-3.46 (m, 10H), 1.86-1.51 (m, 3H); LC-MS: m/z 443.1 (M+H)$^+$, [α]$^{20}_D$ −15° (c=0.001 g/mL, DMSO).

Example 66: (+)1-(2-(5-(6-fluoro-1H-indol-3-yl)-3-methyl-1,1-dioxidobenzo[d]isothiazol-2(3H)-yl)ethyl)piperazin-2-one

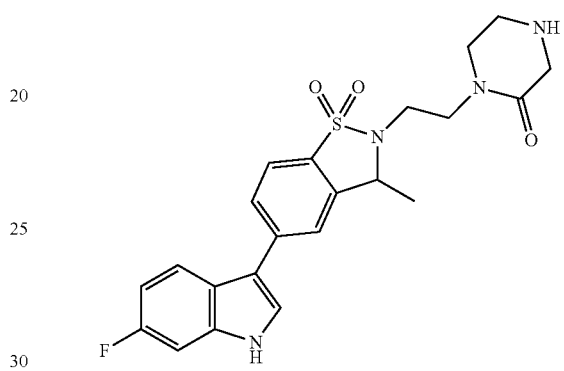

A solution of tert-butyl 3-(2-(2-(4-(tert-butoxycarbonyl)-2-oxopiperazin-1-yl)ethyl)-3-methyl-1,1-dioxido-2,3-dihydrobenzo[d]isothiazol-5-yl)-6-fluoro-1H-indole-1-carboxylate (300 mg, 0.467 mmol) (Example 176, step 3, peak 2) in HCl/EA (10 ml) was stirred at 20° C. for 36 h. The reaction was concentrated and dried to give (+) 1-(2-(5-(6-fluoro-1H-indol-3-yl)-3-methyl-1,1-dioxidobenzo[d]isothiazol-2(3H)-yl)ethyl)piperazin-2-one (149 mg, 72%) as a yellow solid. $^1$H NMR (400 MHz, DMSO-d$_6$) δ [ppm] 11.80 (br s, 1H), 9.87 (br s, 1H), 7.98-7.89 (m, 5H), 7.28 (dd, J=2.3, 9.8 Hz, 1H), 7.01 (d, J=2.0 Hz, 1H), 4.80 (d, J=6.3 Hz, 1H), 3.70-3.37 (m, 10H), 1.58 (d, J=6.5 Hz, 3H); LC-MS: m/z 443.0 (M+H)$^+$, [α]$^{20}_D$ 13° (c=0.001 g/mL, DMSO).

Example 67: (+)-5-(6-fluoro-1H-indol-3-yl)-2-(2-(5-hydroxy-3-methyl-1H-pyrazol-1-yl)ethyl)-3-methyl-2,3-dihydrobenzo[d]isothiazole 1,1-dioxide

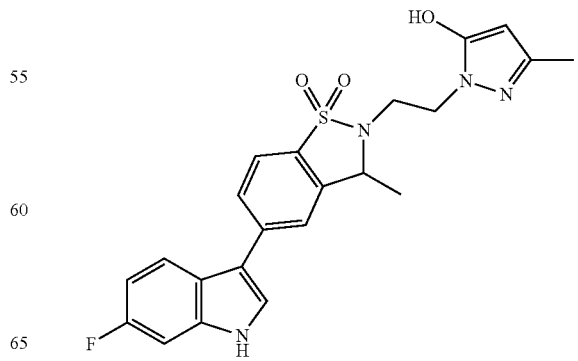

Step 1: chiral tert-butyl 6-fluoro-3-(3-methyl-2-(2-((methylsulfonyl)-oxy)ethyl)-1,1-dioxido-2,3-dihydrobenzo[d]isothiazol-5-yl)-1H-indole-1-carboxylate To a yellow solution of chiral tert-butyl 6-fluoro-3-(2-(2-hydroxyethyl)-3-methyl-1,1-dioxido-2,3-dihydrobenzo[d]isothiazol-5-yl)-1H-indole-1-carboxylate (200 mg, 0.434 mmol) and DIPEA (112 mg, 0.869 mmol) in dichloromethane (20 mL) was added MsCl (74.6 mg, 0.651 mmol) at 0° C. The reaction was stirred at 25° C. for 2 h then concentrated to afford chiral tert-butyl 6-fluoro-3-(2-(2-((methylsulfonyl)oxy)ethyl)-1,1-dioxido-2,3-dihydrobenzo[d]isothiazol-5-yl)-1H-indole-1-carboxylate (0.23 g, 100%) as a yellow gum, which was used directly in the next step.

Step 2: chiral 5-(6-fluoro-1H-indol-3-yl)-2-(2-hydrazinylethyl)-3-methyl-2,3-dihydrobenzo[d]isothiazole 1,1-dioxide A yellow solution of chiral tert-butyl 6-fluoro-3-(3-methyl-2-(2-((methylsulfonyl)oxy)ethyl)-1,1-dioxido-2,3-dihydrobenzo[d]isothiazol-5-yl)-1H-indole-1-carboxylate (234 mg, 0.434 mmol) in EtOH/NH$_2$NH$_2$H$_2$O (10 mL/2 mL) was stirred at 25° C. for 18 h. The reaction was concentrated to afford chiral 5-(6-fluoro-1H-indol-3-yl)-2-(2-hydrazinylethyl)-3-methyl-2,3-dihydrobenzo[d]isothiazole 1,1-dioxide (163 mg, 100%) as yellow gum, which was used directly in the next step.

Step 3: (+)-5-(6-fluoro-1H-indol-3-yl)-2-(2-(5-hydroxy-3-methyl-1H-pyrazol-1-yl)ethyl)-3-methyl-2,3-dihydrobenzo[d]isothiazole 1,1-dioxide A yellow solution of chiral 5-(6-fluoro-1H-indol-3-yl)-2-(2-hydrazinylethyl)-3-methyl-2,3-dihydrobenzo[d]isothiazole 1,1-dioxide (163 mg, 0.435 mmol) and ethyl acetoacetate (57 mg, 0.44 mmol) in EtOH (10 mL) was stirred at 25° C. for 14 h. The reaction was concentrated and purified by prep-HPLC to give (+)-5-(6-fluoro-1H-indol-3-yl)-2-(2-(5-hydroxy-3-methyl-1H-pyrazol-1-yl)ethyl)-3-methyl-2,3-dihydrobenzo[d]isothiazole 1,1-dioxide (75 mg, 39%) as a yellow solid. $^1$H NMR (400 MHz, DMSO-d$_6$) δ [ppm] 11.70 (br s, 1H), 10.86 (br s, 1H), 8.06-7.79 (m, 5H), 7.27 (dd, J=2.3, 9.8 Hz, 1H), 7.02 (dt, J=2.4, 9.2 Hz, 1H), 5.18 (s, 1H), 4.88-4.58 (m, 1H), 4.21-3.74 (m, 2H), 3.70-3.45 (m, 2H), 2.15-1.94 (m, 3H), 1.68-1.36 (m, 3H); LC-MS: m/z 440.9 (M+H)$^+$, [α]$^{20}_D$ +2.2° (c=0.005 g/mL, DMSO).

Example 68: (−)-5-(6-fluoro-1H-indol-3-yl)-2-(2-(5-hydroxy-3-methyl-1H-pyrazol-1-yl)ethyl)-3-methyl-2,3-dihydrobenzo[d]isothiazole 1,1-dioxide

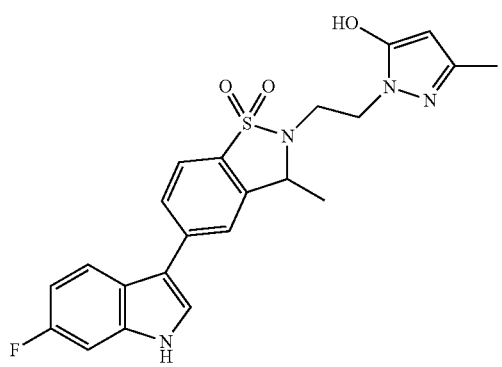 [SMILES: Cc1cc(O)n(CCN2C(C)c3cc(-c4c[nH]c5cc(F)ccc45)ccc3S2(=O)=O)n1]

Following the general method as outlined in Example 67, starting with chiral tert-butyl 6-fluoro-3-(3-methyl-2-(2-((methylsulfonyl)oxy)-ethyl)-1,1-dioxido-2,3-dihydrobenzo[d]isothiazol-5-yl)-1H-indole-1-carboxylate, the title compound was obtained as a yellow solid. $^1$H NMR (400 MHz, DMSO-d$_6$) δ [ppm] 11.70 (br s, 1H), 10.86 (br s, 1H), 8.06-7.79 (m, 5H), 7.27 (dd, J=2.3, 9.8 Hz, 1H), 7.02 (dt, J=2.4, 9.2 Hz, 1H), 5.18 (s, 1H), 4.88-4.58 (m, 1H), 4.21-3.74 (m, 2H), 3.70-3.45 (m, 2H), 2.15-1.94 (m, 3H), 1.68-1.36 (m, 3H); LC-MS: m/z 440.9 (M+H)$^+$, [α]$^{20}_D$ −2° (c=0.003 g/mL, DMSO).

Example 69: (+)-3-(2-(5-(6-fluoro-1H-indol-3-yl)-3-methyl-1,1-dioxidobenzo[d]isothiazol-2(3H)-yl)ethyl)oxazolidin-2-one

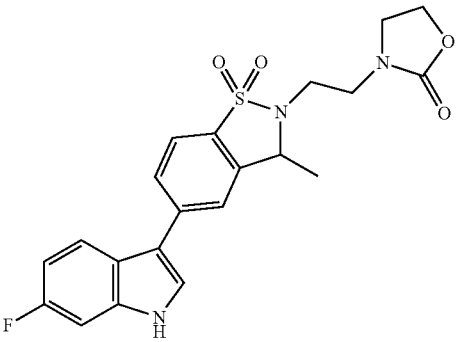 [SMILES: CC1c2cc(-c3c[nH]c4cc(F)ccc34)ccc2S(=O)(=O)N1CCN1CCOC1=O]

Step 1: 2-(2-oxooxazolidin-3-yl)ethyl methanesulfonate

To a cooled (ice bath) solution of 3-(2-hydroxyethyl)oxazolidin-2-one (3.0 g, 23 mmol) and Et$_3$N (2.55 g, 25.2 mmol) in dry dichloromethane (50 mL) was added dropwise a solution of MsCl (3.14 g, 27.5 mmol) in dichloromethane (10 mL) over 15 min. The reaction was stirred at 0° C. for 2 h then diluted with water (25 mL). The layers were separated and the organic layer was washed with aqueous NaHCO$_3$ (15 mL×3), water (15 mL) and brine (15 mL). The organic layer was dried over anhydrous Na$_2$SO$_4$, filtered, and concentrate to provide 2-(2-oxooxazolidin-3-yl)ethyl-methanesulfonate (3.0 g, 63%) as a yellow oil. $^1$H NMR (400 MHz, CDCl$_3$) δ [ppm] 4.41-4.35 (m, 4H), 3.74-3.61 (m, 4H), 3.06 (s, 3H).

Step 2: 3-(2-(5-bromo-3-methyl-1,1-dioxidobenzo[d]isothiazol-2(3H)-yl)ethyl)oxazolidin-2-one To a solution of 5-bromo-3-methyl-2,3-dihydrobenzo[d]isothiazole 1,1-dioxide (500 mg, 1.91 mmol) in DMF (10 mL) was added K$_2$CO$_3$ (527 mg, 3.81 mmol). The reaction was stirred at ambient temperature for 30 min then, 2-(2-oxooxazolidin-3-yl)ethyl methanesulfonate (649 mg, 2.48 mmol) was added and stirring was continued at 80° C. for 16 h. The black mixture was diluted with water (30 mL) and extracted with ethyl acetate (25 mL×3). The combined organic layers were washed with water (20 mL×2) and brine (20 mL×2) then dried over anhydrous Na$_2$SO$_4$, filtered, and concentrated. The crude oil was purified by column chromatography (silica gel, 50-100% ethyl acetate/petroleum ether) to afford 3-(2-(5-bromo-3-methyl-1,1-dioxidobenzo[d] isothiazol-2(3H)-yl)ethyl)oxazolidin-2-one (418 mg, 58%) as a brown solid. ¹H NMR (400 MHz, CDCl₃) δ [ppm] 7.69-7.63 (m, 2H), 7.57 (s, 1H), 4.72-4.69 (m, 1H), 4.36-4.31 (m, 2H), 3.83-3.73 (m, 2H), 3.68-3.64 (m, 2H), 3.48-3.41 (m, 2H), 1.57 (d, J=6.5 Hz, 3H); LC-MS: m/z 398.7 (M+Na)⁺.

Step 3: tert-butyl 6-fluoro-3-(3-methyl-1,1-dioxido-2-(2-(2-oxooxazolidin-3-yl)ethyl)-2,3-dihydrobenzo[d]isothiazol-5-yl)-1H-indole-1-carboxylate A yellow mixture of 3-(2-(5-bromo-3-methyl-1,1-dioxidobenzo[d]isothiazol-2(3H)-yl)ethyl)oxazolidin-2-one (400 mg, 0.85 mmol), tert-butyl 6-fluoro-3-(4,4,5,5-tetramethyl-1,3,2-dioxaborolan-2-yl)-1H-indole-1-carboxylate (484 mg, 0.938 mmol), PdCl₂(dppf)CH₂Cl₂ (63.7 mg, 0.0853 mmol) and K₃PO₄ (543 mg, 2.56 mmol) in 1,4-dioxane (8 mL) and water (2 mL) was sparged with N₂ for 1 minute then stirred at 80° C. for 16 h. The reaction was concentrated and purified by column chromatography (silica gel, 0-80% ethyl acetate/petroleum ether) to afford tert-butyl 6-fluoro-3-(3-methyl-1,1-dioxido-2-(2-(2-oxooxazolidin-3-yl)ethyl)-2,3-dihydrobenzo[d]isothiazol-5-yl)-1H-indole-1-carboxylate 280 mg, 62%) as a yellow solid. ¹H NMR (400 MHz, CDCl₃) δ [ppm] 7.98-7.96 (m, 1H), 7.88-7.86 (m, 1H), 7.79-7.77 (m, 2H), 7.66 (dd, J=5.4, 8.7 Hz, 1H), 7.61 (s, 1H), 7.09 (dt, J=2.4, 9.0 Hz, 1H), 4.83-4.78 (m, 1H), 4.39-4.33 (m, 2H), 3.90-3.78 (m, 2H), 3.74-3.68 (m, 2H), 3.54-3.47 (m, 2H), 1.72 (s, 9H), 1.64 (d, J=6.5 Hz, 3H). LC-MS: m/z 530.0 (M+H)⁺, 552.0 (M+Na)⁺.

Step 4: (+)-3-(2-(5-(6-fluoro-1H-indol-3-yl)-3-methyl-1,1-dioxidobenzo[d]isothiazol-2(3H)-yl)ethyl)oxazolidin-2-one To a cooled (ice bath) yellow solution of tert-butyl 6-fluoro-3-(3-methyl-1,1-dioxido-2-(2-(2-oxooxazolidin-3-yl)ethyl)-2,3-dihydrobenzo[d]isothiazol-5-yl)-1H-indole-1-carboxylate (280 mg, 0.529 mmol) in dichloromethane (5 mL) was slowly added trifluoroacetic acid (2 mL). The reaction was stirred at 27° C. for 1 h then concentrated and neutralized (pH=7-8) with NH₃/H₂O (5 mL). The mixture was extracted with dichloromethane (15 mL×3) and the combined organic layers were washed with brine (15 mL) then dried over anhydrous Na₂SO₄, filtered, and concentrated. The crude yellow solid was purified by column chromatography (silica gel, 0-5% methanol/dichloromethane) to afford racemic 3-(2-(5-(6-fluoro-1H-indol-3-yl)-3-methyl-1,1-dioxidobenzo[d]isothiazol-2(3H)-yl)ethyl)oxazolidin-2-one (220 mg, 97%) as a yellow solid. The enantiomers were separated by prep-chiral SFC to give (+)-3-(2-(5-(6-fluoro-1H-indol-3-yl)-3-methyl-1,1-dioxidobenzo[d]isothiazol-2(3H)-yl)ethyl)oxazolidin-2-one as the first eluting peak (36 mg, 22%) as a white solid. ¹H NMR (400 MHz, DMSO-d₆) δ [ppm] 11.69 (br s, 1H), 7.96-7.84 (m, 5H), 7.27 (dd, J=2.3, 9.8 Hz, 1H), 7.04-6.99 (m, 1H), 4.78 (q, J=6.4 Hz, 1H), 4.26-4.21 (m, 2H), 3.69-3.62 (m, 2H), 3.53-3.50 (m, 2H), 3.43-3.40 (m, 2H), 1.57 (d, J=6.5 Hz, 3H); LC-MS: m/z 430.0 (M+H)⁺, [α]²⁰_D +16.0° (c=1 mg/ml, methanol).

Example 70: (−)-3-(2-(5-(6-fluoro-1H-indol-3-yl)-3-methyl-1,1-dioxidobenzo[d]isothiazol-2(3H)-yl)ethyl)oxazolidin-2-one

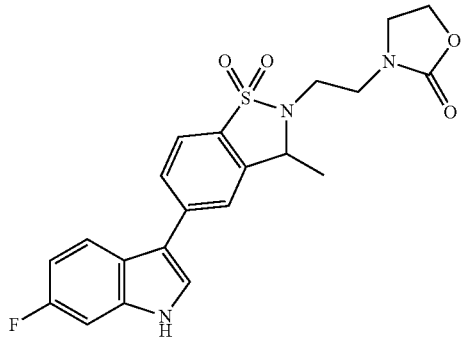 [SMILES: CC1c2cc(-c3c[nH]c4cc(F)ccc34)ccc2S(=O)(=O)N1CCN1CCOC1=O]

The title compound was obtained as the second eluting peak from the chiral separation described in Example 69 (33 mg, 20%) as a white solid. ¹H NMR (400 MHz, DMSO-d₆) δ [ppm] 11.69 (br s, 1H), 7.84-7.96 (m, 5H), 7.27 (dd, J=2.3, 9.8 Hz, 1H), 7.04-6.99 (m, 1H), 4.78 (q, J=6.4 Hz, 1H), 4.26-4.21 (m, 2H), 3.72-3.60 (m, 2H), 3.53-3.50 (m, 2H), 3.43-3.38 (m, 2H), 1.57 (d, J=6.5 Hz, 3H); LC-MS: m/z 429.9 (M+H)⁺, [α]²⁰_D −46.0° (c=1 mg/ml, methanol).

Example 71: (+)-1-(4-(5-(6-fluoro-1H-indol-3-yl)-3-methyl-1,1-dioxidobenzo[d]isothiazol-2(3H)-yl)piperidin-1-yl)ethanone

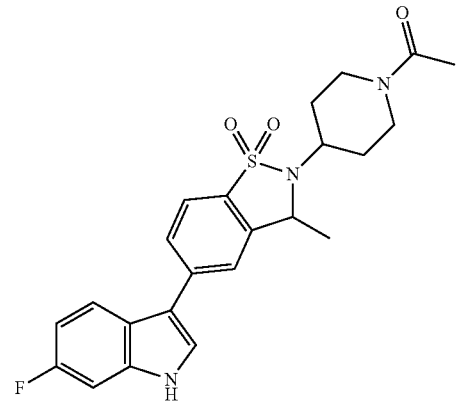 [SMILES: CC(=O)N1CCC(N2C(C)c3cc(-c4c[nH]c5cc(F)ccc45)ccc3S2(=O)=O)CC1]

Step 1: tert-butyl 4-((methylsulfonyl)oxy)piperidine-1-carboxylate

To a clear solution of tert-butyl 4-hydroxypiperidine-1-carboxylate (10 g, 50 mmol) and triethylamine (14 mL, 99 mmol) in dichloromethane (100 mL) at 0° C. was added dropwise methanesulfonyl chloride (6.8 g, 60 mmol). The reaction was warmed to ambient temperature and stirred for 2 h then quenched with NaHCO₃ (sat) (50 mL). The layers were separated and the aqueous phase was extracted with dichloromethane (50 mL×2). The combined organic layers were washed with water (50 mL) and brine (50 mL) then dried over anhydrous sodium sulfate, filtered and concentrated to afford tert-butyl 4-((methylsulfonyl)oxy)piperidine-1-carboxylate (14 g, >100%) as a pale yellow solid, which was used for next step without further purification. ¹H NMR (400 MHz, CDCl₃) δ [ppm] 4.91-4.85 (m, 1H), 3.73-3.67 (m, 2H), 3.33-3.27 (m, 2H), 3.04 (s, 3H), 1.99-1.94 (m, 2H), 1.83-1.79 (m, 2H), 1.46 (s, 9H).

Step 2: tert-butyl 4-(5-bromo-3-methyl-1,1-dioxidobenzo[d]isothiazol-2(3H)-yl)piperidine-1-carboxylate A solution of 5-bromo-3-methyl-2,3-dihydrobenzo[d]isothiazole 1,1-dioxide (500 mg, 1.91 mmol), tert-butyl 4-((methylsulfonyl)oxy)piperidine-1-carboxylate (799 mg, 2.86 mmol) and K₂CO₃ (527 mg, 3.81 mmol) in DMF (10 mL) was stirred under a N₂ atmosphere at 80° C. for 19 h. The reaction was cooled to ambient temperature and quenched with water (30 mL) and extracted with ethyl acetate (30 mL×3). The combined organic layers were washed with water (30 mL×2) and brine (30 mL×2) then dried over anhydrous Na₂SO₄, filtered, and concentrated. The crude residue was purified by column chromatography (silica gel, 0-20% ethyl acetate/petroleum ether) to give tert-butyl 4-(5-bromo-3-methyl-1,1-dioxidobenzo[d]isothiazol-2(3H)-yl)piperidine-1-carboxylate (400 mg, 47%) as a black oil. LC-MS: m/z 467.0 (M+Na)⁺.

Step 3: 5-bromo-3-methyl-2-(piperidin-4-yl)-2,3-dihydrobenzo[d]isothiazole 1,1-dioxide To a cooled (ice bath) solution of tert-butyl 4-(5-bromo-3-methyl-1,1-dioxidobenzo[d]isothiazol-2(3H)-yl)piperidine-1-carboxylate (800 mg, 1.1 mmol) in ethyl acetate (5 mL) was slowly added HCl (4 M in ethyl acetate, 10 mL). The reaction was stirred at 21° C. for 16 h then concentrated and diluted with water (8 mL) and ethyl acetate (8 mL). The layers were separated and the aqueous phase was washed with ethyl acetate (8 mL×3) then lyophilized to give 5-bromo-3-methyl-2-(piperidin-4-yl)-2,3-dihydrobenzo[d]isothiazole 1,1-dioxide (230 mg, 56%) as a yellow solid. LC-MS: m/z 364.9 (M+H)⁺.

Step 4: 1-(4-(5-bromo-3-methyl-1,1-dioxidobenzo[d]isothiazol-2(3H)-yl)piperidin-1-yl)ethanone To a yellow solution of 5-bromo-3-methyl-2-(piperidin-4-yl)-2,3-dihydrobenzo[d]isothiazole 1,1-dioxide (230 mg, 0.54 mmol) in dichloromethane (5 mL) was added triethylamine (163 mg, 0.224 mL, 1.61 mmol). The reaction was stirred at 21° C. for 15 min then acetic anhydride (66 mg, 0.06 mL, 0.64 mmol) was added dropwise. The reaction was stirred at 21° C. for 2 h then quenched with NaHCO₃ (sat) (10 mL) and extracted with dichloromethane (10 mL×3). The combined organic layers were washed with water (10 mL) and brine (10 mL) then dried over anhydrous Na₂SO₄, filtered, and concentrated to afford racemic 1-(4-(5-bromo-3-methyl-1,1-dioxidobenzo[d]isothiazol-2(3H)-yl)piperidin-1-yl)ethanone (480 mg, >100% yield) as a brown solid, which was used for next step without further purification. LC-MS: m/z 408.9 (M+Na)⁺.

Step 5: tert-butyl 3-(2-(1-acetylpiperidin-4-yl)-3-methyl-1,1-dioxido-2,3-dihydrobenzo[d]isothiazol-5-yl)-6-fluoro-1H-indole-1-carboxylate A solution of 1-(4-(5-bromo-3-methyl-1,1-dioxidobenzo[d]isothiazol-2(3H)-yl)piperidin-1-yl)ethanone (280 mg, 0.723 mmol), tert-butyl 6-fluoro-3-(4,4,5,5-tetramethyl-1,3,2-dioxaborolan-2-yl)-1H-indole-1-carboxylate (261 mg, 0.723 mmol), PdCl₂(dppf)CH₂Cl₂ (54 mg, 0.07 mmol) and K₃PO₄ (460 mg, 2.17 mmol) in 1,4-dioxane (6 mL) and water (1.5 mL) was sparged with N₂ for 1 minute. The reaction was stirred at 80° C. for 16 h then extracted with ethyl acetate (20 mL×3). The combined organic layers were washed with water (20 mL) and brine (20 mL) then dried over anhydrous Na₂SO₄, filtered, and concentrated to give a crude tert-butyl 3-(2-(1-acetylpiperidin-4-yl)-3-methyl-1,1-dioxido-2,3-dihydrobenzo[d]isothiazol-5-yl)-6-fluoro-1H-indole-1-carboxylate which was used for next step without further purification. LC-MS: m/z 542.2 (M+H)⁺.

Step 6: (+)-1-(4-(5-(6-fluoro-1H-indol-3-yl)-3-methyl-1,1-dioxidobenzo[d]isothiazol-2(3H)-yl)piperidin-1-yl)ethanone To a cooled (ice bath) solution of tert-butyl 3-(2-(1-acetylpiperidin-4-yl)-3-methyl-1,1-dioxido-2,3-dihydrobenzo[d]isothiazol-5-yl)-6-fluoro-1H-indole-1-carboxylate (410 mg, 0.53 mmol) in ethyl acetate (8 mL) was slowly added HCl (4 M in ethyl acetate, 8 mL). The reaction was stirred at 21° C. for 16 h then neutralized (pH=7-8) with NaHCO₃ (sat) (6 mL) and extracted with ethyl acetate (10 mL×3). The combined organic layers were washed with water (10 mL) and brine (10 mL) then dried over anhydrous Na₂SO₄, filtered, and concentrated. The crude oil was purified by column chromatography (silica gel, 0-5% methanol/dichloromethane) to give racemic 1-(4-(5-(6-fluoro-1H-indol-3-yl)-3-methyl-1,1-dioxidobenzo[d]isothiazol-2(3H)-yl)piperidin-1-yl)ethanone (220 mg, 94%) as a brown solid. LC-MS: m/z 442.2 (M+H)⁺, 464.2 (M+Na)⁺. The enantiomers were separated by prep-chiral SFC to give (+)-1-(4-(5-(6-fluoro-1H-indol-3-yl)-3-methyl-1,1-dioxidobenzo[d]isothiazol-2(3H)-yl)piperidin-1-yl)ethanone as the first eluting peak (35 mg, 20%) as a pale-yellow solid. ¹H NMR (400 MHz, DMSO-d₆) δ [ppm] 11.68 (br s, 1H), 7.95-7.79 (m, 5H), 7.28-7.26 (m, 1H), 7.04-6.99 (m, 1H), 4.93-4.90 (m, 1H), 4.47 (t, J=11.9 Hz, 1H), 3.93-3.87 (m, 1H), 3.82-3.79 (m, 1H), 3.17-3.13 (m, 1H), 2.67-2.58 (m, 1H), 2.02 (s, 3H), 1.98-1.68 (m, 4H), 1.56 (d, J=4.5 Hz, 3H); LC-MS: m/z 442.1 (M+H)⁺, [α]²⁰_D +60.9° (c=1.05 mg/ml, methanol).

Example 72: (−)-1-(4-(5-(6-fluoro-1H-indol-3-yl)-3-methyl-1,1-dioxidobenzo[d]isothiazol-2(3H)-yl)piperidin-1-yl)ethanone

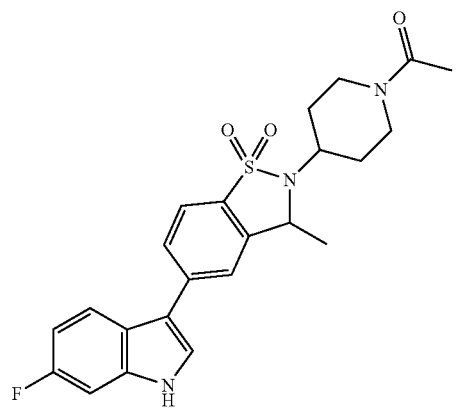 [SMILES: CC(=O)N1CCC(N2C(C)c3cc(-c4c[nH]c5cc(F)ccc45)ccc3S2(=O)=O)CC1]

The title compound was obtained as the second eluting peak from the chiral separation described in Example 71 as a pale-yellow solid (50 mg, 28%). $^1$H NMR (400 MHz, DMSO-$d_6$) δ [ppm] 11.68 (br s, 1H), 7.95-7.79 (m, 5H), 7.27 (dd, J=2.3, 9.8 Hz, 1H), 7.04-6.99 (m, 1H), 4.91 (q, J=6.1 Hz, 1H), 4.47 (t, J=13.1 Hz, 1H), 3.90-3.88 (m, 1H), 3.80-3.76 (m, 1H), 3.18-3.10 (m, 1H), 2.67-2.59 (m, 1H), 2.02 (d, J=2.5 Hz, 3H), 1.99-1.68 (m, 4H), 1.56 (dd, J=2.4, 6.4 Hz, 3H); LC-MS: m/z 442.1 (M+H)$^+$, $[α]^{20}_D$ −43.7° (c=1.03 mg/ml, methanol).

Example 73: (+)-1-(3-(5-(6-fluoro-1H-indol-3-yl)-3-methyl-1,1-dioxidobenzo[d]isothiazol-2(3H)-yl) pyrrolidin-1-yl)ethanone (Peak 1)

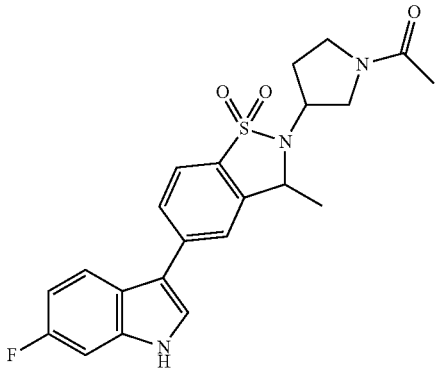 [SMILES: CC(=O)N1CCC(N2C(C)c3cc(-c4c[nH]c5cc(F)ccc45)ccc3S2(=O)=O)C1]

Following the general method as outlined in Example 71, starting with tert-butyl 3-hydroxypyrrolidine-1-carboxylate, the title compound was obtained as the first eluting peak as a white solid. $^1$H NMR (400 MHz, DMSO-$d_6$) δ [ppm] 11.70 (s., 1H), 7.96-7.89 (m, 4H), 7.85-7.82 (m, 1H), 7.29-7.25 (m, 1H), 7.01 (dt, J=2.1, 9.1 Hz, 1H), 4.92-4.84 (m, 1H), 4.23-4.05 (m, 1H), 3.92-3.78 (m, 1H), 3.71-3.25 (m, 3H), 2.47-2.27 (m, 2H), 1.97 (d, J=7.3 Hz, 3H), 1.57 (dd, J=6.5, 9.8 Hz, 3H); LC-MS: m/z 428.1 (M+H)$^+$, $[α]^{20}_D$ +1.9° (c=1.04 mg/ml, DMSO).

Example 74: (+)-1-(3-(5-(6-fluoro-1H-indol-3-yl)-3-methyl-1,1-dioxidobenzo[d]isothiazol-2(3H)-yl) pyrrolidin-1-yl)ethanone

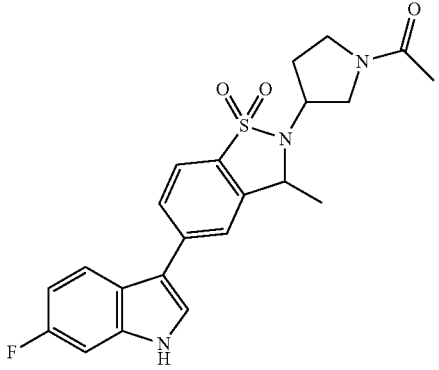 [SMILES: CC(=O)N1CCC(N2C(C)c3cc(-c4c[nH]c5cc(F)ccc45)ccc3S2(=O)=O)C1]

The title compound was obtained as the second eluting peak from the chiral separation in Example 73 (48 mg, 6%) as a white solid. $^1$H NMR (400 MHz, DMSO-$d_6$) δ [ppm] 11.69 (br s, 1H), 7.96-7.89 (m, 4H), 7.84-7.83 (m, 1H), 7.27 (dd, J=2.3, 9.8 Hz, 1H), 7.02 (dt, J=2.3, 9.3 Hz, 1H), 4.93-4.81 (m, 1H), 4.22-4.06 (m, 1H), 3.83-3.23 (m, 4H), 2.39-2.17 (m, 2H), 1.96 (d, J=1.3 Hz, 3H), 1.61-1.50 (m, 3H); LC-MS: m/z 428.1 (M+H)$^+$, $[α]^{20}_D$ +5.88° (c=1.02 mg/ml, DMSO).

Example 75: (−)-1-(3-(5-(6-fluoro-1H-indol-3-yl)-3-methyl-1,1-dioxidobenzo[d]isothiazol-2(3H)-yl) pyrrolidin-1-yl)ethanone

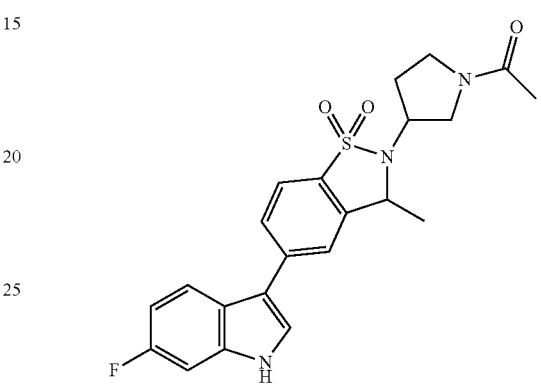

The title compound was obtained as the third eluting peak from the chiral separation in Example 73 (52 mg, 6%) as a white solid. $^1$H NMR (400 MHz, DMSO-$d_6$) δ [ppm] 11.69 (br s, 1H), 7.96-7.89 (m, 4H), 7.85-7.82 (m, 1H), 7.28-7.26 (m, 1H), 7.01 (dt, J=2.3, 9.2 Hz, 1H), 4.92-4.84 (m, 1H), 4.23-4.05 (m, 1H), 3.92-3.78 (m, 1H), 3.72-3.25 (m, 3H), 2.39-2.22 (m, 2H), 1.97 (d, J=7.3 Hz, 3H), 1.57 (dd, J=6.5, 9.5 Hz, 3H); LC-MS: m/z 428.1 (M+H)$^+$, $[α]^{20}_D$ −1.90° (c=1.05 mg/ml, DMSO).

Example 76: (−)-1-(3-(5-(6-fluoro-1H-indol-3-yl)-3-methyl-1,1-dioxidobenzo[d]isothiazol-2(3H)-yl) pyrrolidin-1-yl)ethanone

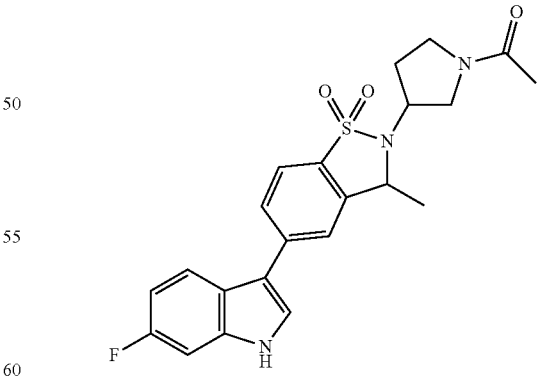

The title compound was obtained as the fourth eluting peak from the chiral separation in Example 73 (100 mg, 12%) as a white solid. $^1$H NMR (400 MHz, DMSO-$d_6$) δ [ppm] 11.70 (br s, 1H), 7.96-7.88 (m, 4H), 7.85-7.83 (m, 1H), 7.27 (dd, J=2.3, 9.8 Hz, 1H), 7.02 (dt, J=2.3, 9.3 Hz, 1H), 4.95-4.87 (m, 1H), 4.22-4.04 (m, 1H), 3.85-3.73 (m, 1H), 3.67-3.45 (m, 2H), 3.30-3.23 (m, 1H), 2.44-2.17 (m, 2H), 1.96 (d, J=1.3 Hz, 3H), 1.56 (dd, J=6.7, 7.9 Hz, 3H); LC-MS: m/z 428.1 (M+H)$^+$, $[\alpha]^{20}_D$ −4.0° (c=1.00 mg/ml, DMSO).

Example 77: (−) 5-(6-fluoro-1H-indol-3-yl)-3-methyl-2-(piperidin-4-ylmethyl)-2,3-dihydrobenzo[d]isothiazole 1,1-dioxide

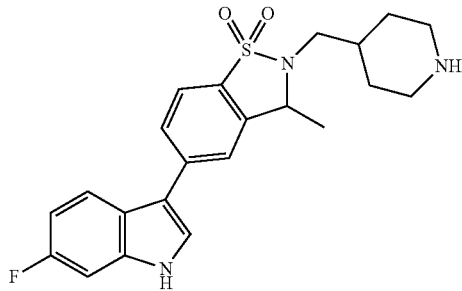 [SMILES: CC1c2cc(-c3c[nH]c4cc(F)ccc34)ccc2S(=O)(=O)N1CC1CCNCC1]

Following the general method as outlined in Example 69, starting with N-BOC-4-piperidinemethanol, the title compound was obtained as a white solid. $^1$H NMR (400 MHz, DMSO-d$_6$) δ [ppm] 11.77 (br s, 1H), 8.95 (d, J=10.0 Hz, 1H), 8.70 (d, J=9.0 Hz, 1H), 8.00-7.79 (m, 4H), 7.28 (d, J=9.8 Hz, 1H), 7.01 (t, J=9.2 Hz, 1H), 4.65 (q, J=6.3 Hz, 1H), 3.34-3.19 (m, 3H), 3.08 (dd, J=8.8, 14.3 Hz, 1H), 2.96-2.78 (m, 2H), 2.09-1.89 (m, 3H), 1.56 (d, J=6.5 Hz, 3H), 1.48-1.30 (m, 2H); LCMS: m/z 414.0 (M+H)$^+$, $[\alpha]^{20}_D$ −9.2° (c=0.4 mg/ml, DMSO).

Example 78: (+)-5-(6-fluoro-1H-indol-3-yl)-3-methyl-2-(piperidin-4-ylmethyl)-2,3-dihydrobenzo[d]isothiazole 1,1-dioxide

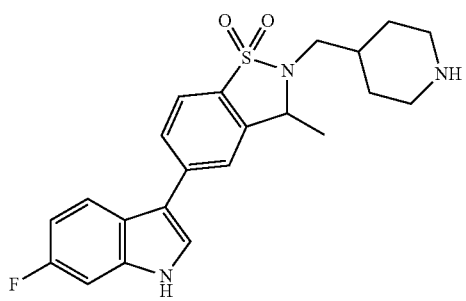 [SMILES: CC1c2cc(-c3c[nH]c4cc(F)ccc34)ccc2S(=O)(=O)N1CC1CCNCC1]

The title compound was obtained as the second eluting peak from the chiral separation in Example 78. $^1$H NMR (400 MHz, DMSO-d$_6$) δ [ppm] 11.76 (br s, 1H), 8.89 (d, J=9.8 Hz, 1H), 8.64 (d, J=8.5 Hz, 1H), 7.97-7.88 (m, 4H), 7.27 (dd, J=2.4, 9.9 Hz, 1H), 7.01 (dt, J=2.3, 9.3 Hz, 1H), 4.65 (q, J=6.1 Hz, 1H), 3.34-3.19 (m, 3H), 3.11-3.05 (m, 1H), 2.95-2.79 (m, 2H), 2.11-1.86 (m, 3H), 1.56 (d, J=6.5 Hz, 3H), 1.46-1.31 (m, 2H); LCMS: m/z 414.0 (M+H)$^+$, $[\alpha]^{20}_D$ +33.3° (c=0.4 mg/ml, DMSO).

Example 79: (−)-5-(6-fluoro-1H-indol-3-yl)-3-methyl-2-((1-methylpiperidin-4-yl)methyl)-2,3-dihydrobenzo[d]isothiazole 1,1-dioxide

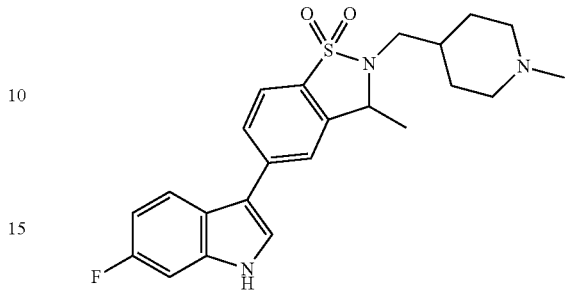

To a white solution of 5-(6-fluoro-1H-indol-3-yl)-3-methyl-2-(piperidin-4-ylmethyl)-2,3-dihydrobenzo[d]isothiazole 1,1-dioxide (100 mg, 0.242 mmol) in methanol (5 ml) was added formaldehyde (37% in water, 98.1 mg, 1.21 mmol) at 25° C. The reaction was stirred at 25° C. for 15 min then cooled in an ice bath and NaBH$_3$CN (23 mg, 0.36 mmol) was added. The reaction was warmed to 25° C. and stirred for 1 h then concentrated to give racemic 5-(6-fluoro-1H-indol-3-yl)-3-methyl-2-((1-methylpiperidin-4-yl)methyl)-2,3-dihydro benzo[d]isothiazole 1,1-dioxide. The enantiomers were separated by prep-chiral SFC to give the title compound as the first eluting peak (46 mg, 44%) as a white solid. $^1$H NMR (400 MHz, DMSO-d$_6$) δ [ppm] 11.70 (br s, 1H), 7.96-7.81 (m, 5H), 7.27 (dd, J=2.5, 9.8 Hz, 1H), 7.01 (dt, J=2.5, 9.3 Hz, 1H), 4.62 (q, J=6.4 Hz, 1H), 3.20 (dd, J=5.9, 14.2 Hz, 1H), 3.03 (dd, J=8.9, 13.9 Hz, 1H), 2.86 (br s, 2H), 2.24 (s, 3H), 2.07-1.95 (m, 2H), 1.86-1.69 (m, 3H), 1.54 (d, J=6.5 Hz, 3H), 1.32-1.17 (m, 2H); LCMS: m/z 428.1 (M+H)$^+$, $[\alpha]^{20}_D$ −8.3° (c=1.8 mg/ml, DMSO).

Example 80: (+)-5-(6-fluoro-1H-indol-3-yl)-3-methyl-2-((1-methylpiperidin-4-yl)methyl)-2,3-dihydrobenzo[d]isothiazole 1,1-dioxide

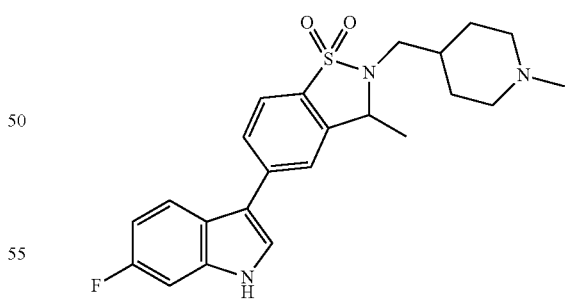

The title compound was obtained as the second eluting peak from the separation described in Example 79 (42 mg, 41%) as a white solid. $^1$H NMR (400 MHz, DMSO-d$_6$) δ [ppm] 11.70 (br s, 1H), 7.98-7.79 (m, 5H), 7.26 (d, J=9.5 Hz, 1H), 7.01 (t, J=9.4 Hz, 1H), 4.66-4.56 (m, 1H), 3.20 (dd, J=5.4, 14.4 Hz, 1H), 3.09-2.98 (m, 1H), 2.84 (br s, 2H), 2.23 (s, 3H), 1.99 (q, J=11.5 Hz, 2H), 1.86-1.66 (m, 3H), 1.54 (d, J=6.5 Hz, 3H), 1.31-1.16 (m, 2H); LCMS: m/z 428.1 (M+H)$^+$, $[\alpha]^{20}_D$ +7.1° (c=0.7 mg/ml, DMSO).

Example 81: (+)-(5S)-5-((5-(6-fluoro-1H-indol-3-yl)-3-methyl-1,1-dioxidobenzo[d]isothiazol-2(3H)-yl)methyl)-5-methylpyrrolidin-2-one

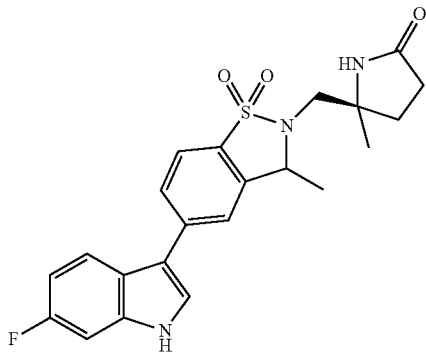 [SMILES: CC1c2cc(-c3c[nH]c4cc(F)ccc34)ccc2S(=O)(=O)N1C[C@]1(C)CCC(=O)N1]

Following the general method as outlined in Example 69, starting with (S)-5-(hydroxymethyl)-5-methylpyrrolidin-2-one, the title compound was obtained as a white solid. $^1$H NMR (400 MHz, DMSO-d$_6$) δ [ppm] 11.70 (br s, 1H), 7.99-7.86 (m, 5H), 7.76 (s, 1H), 7.27 (dd, J=2.5, 9.8 Hz, 1H), 7.01 (dt, J=2.1, 9.2 Hz, 1H), 4.79 (q, J=6.4 Hz, 1H), 3.29 (s, 1H), 3.24-3.17 (m, 1H), 2.30-2.14 (m, 3H), 1.82-1.72 (m, 1H), 1.56 (d, J=6.5 Hz, 3H), 1.28 (s, 3H); LCMS: m/z 427.9 [M+H]$^+$, LCMS: m/z 428.1 (M+H)$^+$, [α]$^{20}$$_D$ +1.6° (c=4.2 mg/ml, DMSO).

Example 82: (+)-(5S)-5-((5-(6-fluoro-1H-indol-3-yl)-3-methyl-1,1-dioxidobenzo[d]isothiazol-2(3H)-yl)methyl)-5-methylpyrrolidin-2-one

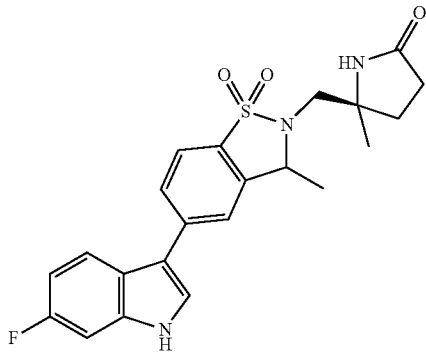 [SMILES: CC1c2cc(-c3c[nH]c4cc(F)ccc34)ccc2S(=O)(=O)N1C[C@]1(C)CCC(=O)N1]

The title compound was obtained as the second eluting peak from the chiral separation in Example 81. $^1$H NMR (400 MHz, DMSO-d$_6$) δ [ppm] 11.70 (br s, 1H), 7.97-7.85 (m, 5H), 7.69 (s, 1H), 7.27 (dd, J=2.3, 9.8 Hz, 1H), 7.01 (dt, J=2.3, 9.3 Hz, 1H), 4.83 (q, J=6.2 Hz, 1H), 3.44 (d, J=15.3 Hz, 1H), 3.15 (d, J=15.3 Hz, 1H), 2.41-2.30 (m, 1H), 2.23-2.11 (m, 2H), 1.87-1.77 (m, 1H), 1.55 (d, J=6.5 Hz, 3H), 1.26 (s, 3H); LCMS: m/z 427.9 (M+H)$^+$, [α]$^{20}$$_D$ +24.7° (c=3.0 mg/ml, DMSO).

Example 83: (−)-(5R)-5-((5-(6-fluoro-1H-indol-3-yl)-3-methyl-1,1-dioxidobenzo[d]isothiazol-2(3H)-yl)methyl)-5-methylpyrrolidin-2-one

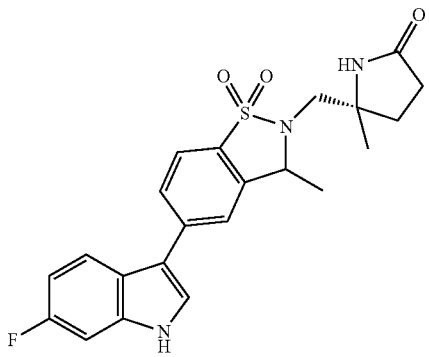 [SMILES: CC1c2cc(-c3c[nH]c4cc(F)ccc34)ccc2S(=O)(=O)N1C[C@@]1(C)CCC(=O)N1]

Following the general method as outlined in Example 69, starting with (R)-5-(hydroxymethyl)-5-methylpyrrolidin-2-one, the title compound was obtained as a white solid. $^1$H NMR (400 MHz, DMSO-d$_6$) δ [ppm] 1.24-1.34 (s, 3H), 1.57 (d, J=6.53 Hz, 3H), 1.71-1.83 (m, 1H), 2.14-2.31 (m, 3H), 3.16-3.32 (m, 2H), 4.79 (q, J=6.44 Hz, 1H), 7.02 (td, J=9.29, 2.51 Hz, 1H), 7.27 (dd, J=9.79, 2.26 Hz, 1H), 7.72-7.78 (m, 1H), 7.84-8.03 (m, 5H), 11.70 (br s, 1H); LC-MS: m/z 427.9 (M+H)$^+$, [α]$^{20}$$_D$ −7.52° (c=0.62 mg/ml, DMSO).

Example 84: (−)-(5R)-5-((5-(6-fluoro-1H-indol-3-yl)-3-methyl-1,1-dioxidobenzo[d]isothiazol-2(3H)-yl)methyl)-5-methylpyrrolidin-2-one

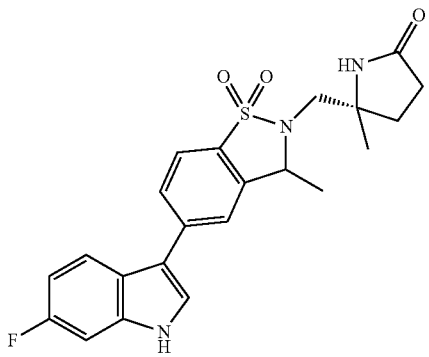 [SMILES: CC1c2cc(-c3c[nH]c4cc(F)ccc34)ccc2S(=O)(=O)N1C[C@@]1(C)CCC(=O)N1]

The title compound was obtained as the second eluting peak from the chiral separation for Example 83. $^1$H NMR (400 MHz, DMSO-d$_6$) δ [ppm] 1.24-1.34 (s, 3H), 1.57 (d, J=6.53 Hz, 3H), 1.71-1.83 (m, 1H), 2.14-2.31 (m, 3H), 3.16-3.32 (m, 2H), 4.79 (q, J=6.44 Hz, 1H), 7.02 (td, J=9.29, 2.51 Hz, 1H), 7.27 (dd, J=9.79, 2.26 Hz, 1H), 7.72-7.78 (m, 1H), 7.84-8.03 (m, 5H), 11.70 (br s, 1H); LCMS m/z 427.9 (M+1)$^+$; [α]$^{20}$$_D$ −97.3° (c=0.5 mg/ml, DMSO).

Example 85: (−)-5-(6-fluoro-1H-indol-3-yl)-3-methyl-2-((1-methyl-1H-1,2,4-triazol-3-yl)methyl)-2,3-dihydrobenzo[d]isothiazole 1,1-dioxide

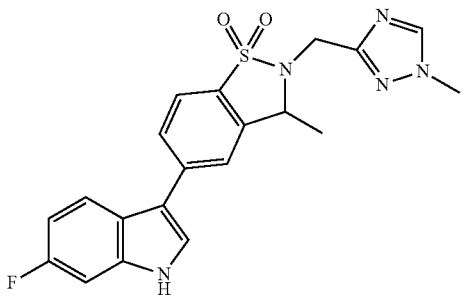 [SMILES: CC1c2cc(-c3c[nH]c4cc(F)ccc34)ccc2S(=O)(=O)N1Cc1ncn(C)n1]

Following the general method as outlined in Example 69, starting with (1-methyl-1H-1,2,4-triazol-3-yl)methanol, the title compound was obtained as a white solid. $^1$H NMR (400 MHz, DMSO-$d_6$) δ [ppm] 11.69 (br s, 1H), 8.46 (s, 1H), 7.98-7.83 (m, 5H), 7.26 (dd, J=2.3, 9.8 Hz, 1H), 7.00 (dt, J=2.5, 9.3 Hz, 1H), 4.86 (q, J=6.4 Hz, 1H), 4.51-4.39 (m, 2H), 3.86 (s, 3H), 1.54 (d, J=6.5 Hz, 3H); LC-MS: m/z 411.8 (M+H)$^+$, [α]$^{20}_D$ −15° (c=1.3 mg/mL, methanol).

Example 86: (+)-5-(6-fluoro-1H-indol-3-yl)-3-methyl-2-((1-methyl-1H-1,2,4-triazol-3-yl)methyl)-2,3-dihydrobenzo[d]isothiazole 1,1-dioxide

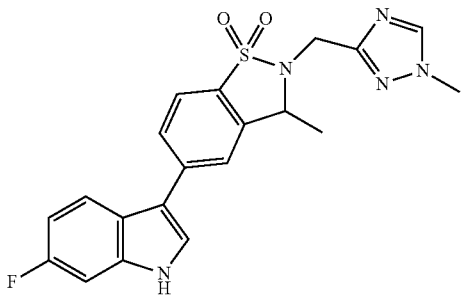 [SMILES: CC1c2cc(-c3c[nH]c4cc(F)ccc34)ccc2S(=O)(=O)N1Cc1ncn(C)n1]

The title compound was obtained as the second eluting peak from the chiral separation described for Example 85. $^1$H NMR (400 MHz, DMSO-$d_6$) δ [ppm] 11.69 (br s, 1H), 8.46 (s, 1H), 7.98-7.84 (m, 5H), 7.27 (dd, J=2.3, 9.8 Hz, 1H), 7.00 (dt, J=2.5, 9.3 Hz, 1H), 4.86 (q, J=6.5 Hz, 1H), 4.51-4.40 (m, 2H), 3.86 (s, 3H), 1.55 (d, J=6.5 Hz, 3H); LC-MS: m/z 412.0 (M+H)$^+$, [α]$^{20}_D$ +9° (c=1.3 mg/mL, methanol).

Example 87: (+4-((5-(6-fluoro-1H-indol-3-yl)-3-methyl-1,1-dioxidobenzo[d]isothiazol-2(3H)-yl)methyl)-4-methyloxazolidin-2-one

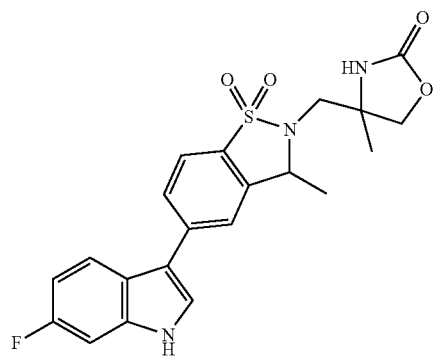 [SMILES: CC1c2cc(-c3c[nH]c4cc(F)ccc34)ccc2S(=O)(=O)N1CC1(C)COC(=O)N1]

Following the general method as outlined in Example 69, starting with 4-(hydroxymethyl)-4-methyloxazolidin-2-one, the title compound was obtained the first eluting peak as a white solid. $^1$H NMR (400 MHz, DMSO-$d_6$) δ [ppm] 11.70 (br s, 1H), 7.97-7.85 (m, 5H), 7.79 (s, 1H), 7.27 (d, J=12.0 Hz, 1H), 7.02 (t, J=9.5 Hz, 1H), 4.89 (d, J=6.5 Hz, 1H), 4.34 (d, J=9.0 Hz, 1H), 4.05 (d, J=9.0 Hz, 1H), 3.41 (s, 1H), 3.28 (s, 1H), 1.56 (d, J=6.5 Hz, 3H), 1.33 (s, 3H); LC-MS: m/z 429.9 (M+H)$^+$, [α]$^{20}_D$ −45° (c=1.3 mg/mL, methanol).

Example 88: (−)-4-((5-(6-fluoro-1H-indol-3-yl)-3-methyl-1,1-dioxidobenzo[d]isothiazol-2(3H)-yl)methyl)-4-methyloxazolidin-2-one

The title compound was obtained as the second eluting peak from the chiral separation in Example 87 (50 mg, 25%) as a white solid. $^1$H NMR (400 MHz, DMSO-$d_6$) δ [ppm] 11.71 (br s, 1H), 7.99-7.85 (m, 6H), 7.26 (d, J=10.0 Hz, 1H), 7.01 (t, J=9.3 Hz, 1H), 4.87-4.79 (m, 1H), 4.40 (d, J=8.5 Hz, 1H), 4.02 (d, J=8.5 Hz, 1H), 3.39 (s, 1H), 3.29 (s, 1H), 1.57 (d, J=6.5 Hz, 3H), 1.35 (s, 3H); LC-MS: m/z 429.9 (M+H)$^+$, [α]$^{20}_D$ −2.38° (c=1.4 mg/mL, methanol).

Example 89: (+)-4-((5-(6-fluoro-1H-indol-3-yl)-3-methyl-1,1-dioxidobenzo[d]isothiazol-2(3H)-yl)methyl)-4-methyloxazolidin-2-one

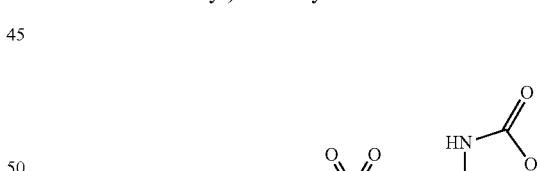

The title compound was obtained as the third eluting peak from the chiral separation in Example 87 (23 mg, 12%) as a white solid. $^1$H NMR (400 MHz, DMSO-$d_6$) δ [ppm] 11.70 (br s, 1H), 7.97-7.86 (m, 5H), 7.80 (s, 1H), 7.27 (dd, J=2.4, 9.7 Hz, 1H), 7.06-6.98 (m, 1H), 4.93-4.85 (m, 1H), 4.34 (d, J=8.8 Hz, 1H), 4.05 (d, J=8.8 Hz, 1H), 3.48-3.37 (m, 2H), 1.56 (d, J=6.3 Hz, 3H), 1.33 (s, 3H); LC-MS: m/z 430.0 (M+H)+, [α]$^{20}_D$ +50° (c=1.2 mg/mL, methanol).

Example 90: (+)-4-((5-(6-fluoro-1H-indol-3-yl)-3-methyl-1,1-dioxidobenzo[d]isothiazol-2(3H)-yl)methyl)-4-methyloxazolidin-2-one

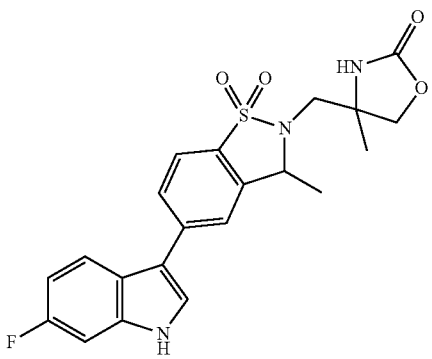 [SMILES: CC1c2cc(-c3c[nH]c4cc(F)ccc34)ccc2S(=O)(=O)N1CC1(C)COC(=O)N1]

The title compound was obtained as the fourth eluting peak from the chiral separation in Example 87 (23 mg, 12% yield) as a white solid. $^1$H NMR (400 MHz, DMSO-d$_6$) δ [ppm] 11.70 (br s, 1H), 8.01-7.85 (m, 6H), 7.27 (dd, J=2.3, 9.8 Hz, 1H), 7.01 (dt, J=2.3, 9.2 Hz, 1H), 4.83 (q, J=6.0 Hz, 1H), 4.40 (d, J=9.0 Hz, 1H), 4.02 (d, J=9.0 Hz, 1H), 3.41-3.38 (m, 1H), 3.30-3.24 (m, 1H), 1.57 (d, J=6.5 Hz, 3H), 1.36 (s, 3H); LC-MS: m/z 430.0 (M+H)+, [α]$^{20}_D$ +2.86° (c=1.4 mg/mL, methanol).

Example 91: (−)-2-(azetidin-3-yl)-5-(6-fluoro-1H-indol-3-yl)-3-methyl-2,3-dihydrobenzo[d]isothiazole 1,1-dioxide

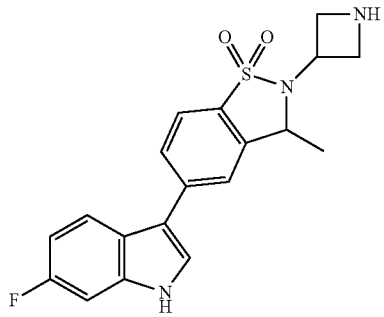

Following the general method as outlined in Example 69, starting with N-Boc-3-OH-azetidine, the title compound was obtained as the first eluting peak in the chiral separation as a white solid. $^1$H NMR (400 MHz, DMSO-d$_6$) δ [ppm] 11.71 (br s, 1H), 7.99-7.87 (m, 4H), 7.86-7.80 (m, 1H), 7.28 (dd, J=2.0, 10.0 Hz, 1H), 7.07-6.98 (m, 1H), 4.78 (d, J=6.5 Hz, 1H), 4.32 (br s, 1H), 4.22-3.69 (m, 3H), 3.61 (br s, 2H), 1.54 (d, J=6.5 Hz, 3H); LC-MS: m/z 393.9 (M+Na)+, [α]$^{20}_D$ −35.3° (c=1.1 mg/mL, methanol).

Example 92: (+)-2-(azetidin-3-yl)-5-(6-fluoro-1H-indol-3-yl)-3-methyl-2,3-dihydrobenzo[d]isothiazole 1,1-dioxide

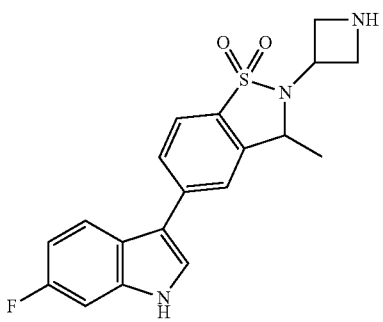 [SMILES: CC1c2cc(-c3c[nH]c4cc(F)ccc34)ccc2S(=O)(=O)N1C1CNC1]

The title compound was obtained as the second eluting peak from the chiral separation in Example 91 as a white solid. $^1$H NMR (400 MHz, MeOD) δ [ppm] 7.94 (d, J=9.0 Hz, 1H), 7.87 (dd, J=5.3, 8.8 Hz, 1H), 7.83-7.78 (m, 2H), 7.71 (s, 1H), 7.17 (dd, J=2.3, 9.8 Hz, 1H), 6.96 (dt, J=2.5, 9.3 Hz, 1H), 4.80-4.74 (m, 1H), 4.74-4.69 (m, 1H), 4.68-4.62 (m, 2H), 4.42-4.32 (m, 2H), 1.62 (d, J=6.5 Hz, 3H); LC-MS: m/z 394.0 (M+Na)+, [α]$^{20}_D$ +7.5° (c=1.07 mg/mL, methanol).

Example 93: (+2-((R)-2,3-dihydroxypropyl)-5-(6-fluoro-1H-indol-3-yl)-3-methyl-2,3-dihydrobenzo[d]isothiazole 1,1-dioxide

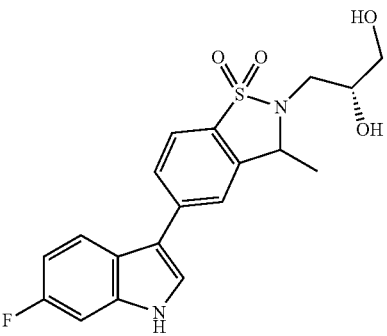 [SMILES: CC1c2cc(-c3c[nH]c4cc(F)ccc34)ccc2S(=O)(=O)N1C[C@@H](O)CO]

Step 1: 5-bromo-2-(((R)-2,2-dimethyl-1,3-dioxolan-4-yl)methyl)-3-methyl-2,3-dihydrobenzo[d]isothiazole 1,1-dioxide A suspension of 5-bromo-3-methyl-2,3-dihydrobenzo[d]isothiazole 1,1-dioxide (500 mg, 1.91 mmol), (S)-4-(chloromethyl)-2,2-dimethyl-1,3-dioxolane (287 mg, 1.91 mmol) and K$_2$CO$_3$ (527 mg, 3.81 mmol) in DMF (6 ml) was stirred at 90° C. for 48 h. The reaction was cooled to 25° C. and poured into water (100 ml) then extracted with ethyl acetate (25 ml×3). The combined organic layers were washed with brine (15 ml×2) then dried over anhydrous Na$_2$SO$_4$, filtered and concentrated. The crude residue was purified by column chromatography (silica gel, 30% petroleum ether/ethyl acetate) to afford the title compound (234 mg, 54%).

Step 2: tert-butyl 3-(2-((2,2-dimethyl-1,3-dioxolan-4-yl)methyl)-3-methyl-1,1-dioxido-2,3-dihydrobenzo[d]isothiazol-5-yl)-6-fluoro-1H-indole-1-carboxylate To a suspension of 5-bromo-2-((2,2-dimethyl-1,3-dioxolan-4-yl)methyl)-3-methyl-2,3-dihydrobenzo[d]isothiazole 1,1-dioxide (234 mg, 0.622 mmol), tert-butyl 6-fluoro-3-(4,4,5,5-tetramethyl-1,3,2-dioxaborolan-2-yl)-1H-indole-1-carboxylate (385 mg, 0.746 mmol) and $Cs_2CO_3$ (405 mg, 1.24 mmol) in dioxane (9 ml) and $H_2O$ (3 ml) was added $PdCl_2$(dppf) (46 mg, 0.06 mmol). The reaction was stirred at 80° C. under a $N_2$ atmosphere for 6 h then the solids were filtered off. The filtrate was concentrated to give crude tert-butyl 3-(2-((2,2-dimethyl-1,3-dioxolan-4-yl)methyl)-3-methyl-1,1-dioxido-2,3-dihydrobenzo[d]isothiazol-5-yl)-6-fluoro-1H-indole-1-carboxylate, which was used in the next step without further purification.

Step 3: (+2-((R)-2,3-dihydroxypropyl)-5-(6-fluoro-1H-indol-3-yl)-3-methyl-2,3-dihydrobenzo[d]isothiazole 1,1-dioxide To a solution of tert-butyl 3-(2-((2,2-dimethyl-1,3-dioxolan-4-yl)methyl)-3-methyl-1,1-dioxido-2,3-dihydrobenzo[d]isothiazol-5-yl)-6-fluoro-1H-indole-1-carboxylate (320 mg, 0.602 mmol) in dichloromethane (10 ml) was added trifluoroacetic acid (5 ml). The reaction was stirred at 30° C. for 2 h then concentrated. The residue was diluted with ethyl acetate (20 ml) and $H_2O$ (15 ml). The mixture was neutralized with $NaHCO_3$ (sat) to pH 7. The layers were separated and the organic layer was dried over anhydrous $Na_2SO_4$, filtered and concentrated. The crude residue was purified by column chromatography (silica gel, dichloromethane/methanol=1/0-5/1) and prep-HPLC to give racemic 2-((R)-2,3-dihydroxypropyl)-5-(6-fluoro-1H-indol-3-yl)-3-methyl-2,3-dihydrobenzo[d]isothiazole 1,1-dioxide. The enantiomers were separated by prep-chiral SFC to give the title compound as the first eluting peak (20 mg, 9%) as a white solid. $^1$H NMR (400 MHz, MeOD) δ [ppm] 7.92-7.85 (m, 2H), 7.83-7.78 (m, 2H), 7.69 (s, 1H), 7.16 (dd, J=2.4, 9.7 Hz, 1H), 6.95 (dt, J=2.5, 9.2 Hz, 1H), 4.77-4.73 (m, 1H), 4.60 (br s, 1H), 4.04-3.97 (m, 1H), 3.71-3.53 (m, 3H), 1.65 (d, J=6.3 Hz, 3H); LC-MS: m/z 390.9 (M+H)$^+$, [α]$^{20}_D$ −26.4° (c=0.43 mg/ml, DMSO).

Example 94: (+)-2-((R)-2,3-dihydroxypropyl)-5-(6-fluoro-1H-indol-3-yl)-3-methyl-2,3-dihydrobenzo[d]isothiazole 1,1-dioxide

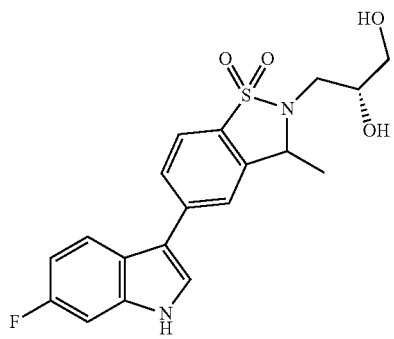 [SMILES: CC1c2cc(-c3c[nH]c4cc(F)ccc34)ccc2S(=O)(=O)N1C[C@@H](O)CO]

The title compound was obtained as the second eluting peak from the chiral separation in Example 93 (40 mg, 18%) as a white solid. $^1$H NMR (400 MHz, MeOD) δ [ppm] 7.92-7.84 (m, 2H), 7.82-7.78 (m, 2H), 7.68 (s, 1H), 7.16 (dd, J=2.4, 9.7 Hz, 1H), 6.95 (dt, J=2.4, 9.2 Hz, 1H), 4.60 (br s, 1H), 4.08-4.01 (m, 1H), 3.68-3.59 (m, 2H), 3.52 (dd, J=5.4, 14.7 Hz, 1H), 3.39-3.33 (m, 1H), 1.65 (d, J=6.5 Hz, 3H); LC-MS: m/z 390.9 (M+H)$^+$, [α]$^{20}_D$=+36.1° (c=0.61 mg/ml, DMSO).

Example 95: (+2-((S)-2,3-dihydroxypropyl)-5-(6-fluoro-1H-indol-3-yl)-3-methyl-2,3-dihydrobenzo[d]isothiazole 1,1-dioxide

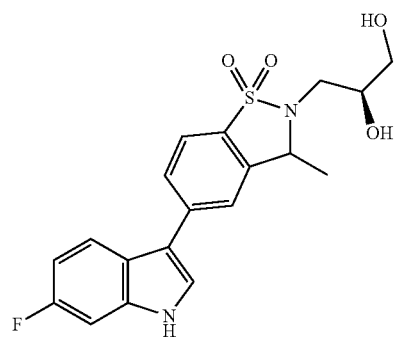 [SMILES: CC1c2cc(-c3c[nH]c4cc(F)ccc34)ccc2S(=O)(=O)N1C[C@H](O)CO]

Following the general method as outlined in Example 93, starting with (R)-(+)-4-(chloromethyl)-2,2-dimethyl-1,3-dioxolane, the title compound was obtained as the first eluting peak in the chiral separation as a white solid. $^1$H NMR (400 MHz, DMSO-d$_6$) δ [ppm] 11.69 (br s, 1H), 7.99-7.82 (m, 5H), 7.27 (dd, J=2.3, 9.8 Hz, 1H), 7.01 (dt, J=2.3, 9.2 Hz, 1H), 5.02 (d, J=5.0 Hz, 1H), 4.93 (q, J=6.2 Hz, 1H), 4.73 (t, J=5.5 Hz, 1H), 3.88-3.78 (m, 1H), 3.50-3.41 (m, 3H), 3.19-3.06 (m, 1H), 1.56 (d, J=6.5 Hz, 3H); LC-MS: m/z 390.9 (M+H)$^+$, [α]$^{20}_D$ −16° (c=1.0 mg/mL, DMSO).

Example 96: (+)-2-((S)-2,3-dihydroxypropyl)-5-(6-fluoro-1H-indol-3-yl)-3-methyl-2,3-dihydrobenzo[d]isothiazole 1,1-dioxide

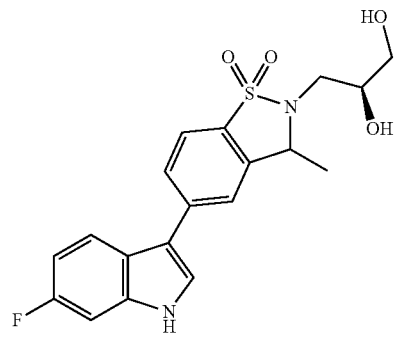 [SMILES: CC1c2cc(-c3c[nH]c4cc(F)ccc34)ccc2S(=O)(=O)N1C[C@H](O)CO]

The title compound was obtained as the second eluting peak from the chiral separation in Example 95 (65 mg, 32%) as a yellow solid. $^1$H NMR (400 MHz, DMSO-d$_6$) δ [ppm] 11.69 (br s, 1H), 7.99-7.81 (m, 5H), 7.27 (dd, J=2.3, 9.8 Hz, 1H), 7.01 (dt, J=2.5, 9.3 Hz, 1H), 4.93 (d, J=5.0 Hz, 1H), 4.75 (q, J=6.5 Hz, 1H), 4.69 (t, J=5.5 Hz, 1H), 3.83-3.74 (m, 1H), 3.45-3.40 (m, 3H), 3.19-3.06 (m, 1H), 1.56 (d, J=6.5 Hz, 3H); LC-MS: m/z 390.9; (M+H)+, [α]$^{20}_D$ +9.5° (c=1.05 mg/mL, DMSO).

Example 97: (+)-3-(5-(6-fluoro-1H-indol-3-yl)-3-methyl-1,1-dioxidobenzo[d]isothiazol-2(3H)-yl)-2-hydroxy-N-methylpropanamide

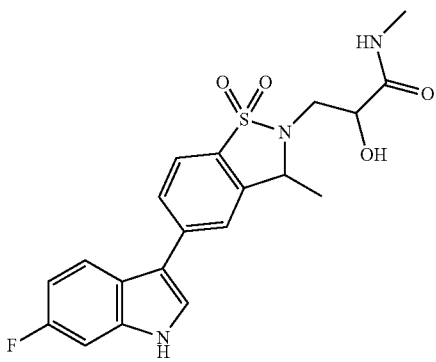 [SMILES: CNC(=O)C(O)CN1C(C)c2cc(-c3c[nH]c4cc(F)ccc34)ccc2S1(=O)=O]

Step 1: methyl oxirane-2-carboxylate

Methyl acrylate (19 g, 220 mmol) was added to an 8% aqueous solution of NaOCl (300 mL) at 0° C. The biphasic mixture was stirred vigorously at 0° C. for 30 min then warmed to 40° C. for 2 h. The reaction was cooled to 25° C. then extracted with dichloromethane (200 mL×2). The combined organic layers were dried over Na$_2$SO$_4$, filtered and concentrated to give crude methyl oxirane-2-carboxylate (9 g, 39%) as clear oil. $^1$H NMR (400 MHz, CDCl$_3$) δ [ppm] 3.79 (s, 3H), 3.46 (dd, J=2.6, 4.1 Hz, 1H), 3.02-2.90 (m, 2H).

Step 2: methyl 3-(5-bromo-3-methyl-1,1-dioxidobenzo[d]isothiazol-2(3H)-yl)-2-hydroxypropanoate A suspension of 5-bromo-3-methyl-2,3-dihydrobenzo[d]isothiazole 1,1-dioxide (3 g, 11 mmol), methyl oxirane-2-carboxylate (8.2 g, 80 mmol) and Cs$_2$CO$_3$ (11 g, 34 mmol) in DMF (30 mL) was stirred at 80° C. for 16 h. The reaction was cooled and diluted with water (100 mL) and extracted with ethyl acetate (150 mL×3). The combined organic layers were washed with brine (200 mL×3) then dried over anhydrous Na$_2$SO$_4$, filtered and concentrated. The crude residue was purified by column chromatography (silica gel, 30% ethyl acetate/petroleum ether) to give methyl 3-(5-bromo-3-methyl-1,1-dioxidobenzo[d]isothiazol-2(3H)-yl)-2-hydroxypropanoate (1.5 g, 36%) as black oil.

Step 3: 3-(5-bromo-3-methyl-1,1-dioxidobenzo[d]isothiazol-2(3H)-yl)-2-hydroxy-N-methylpropanamide A yellow solution of methyl 3-(5-bromo-3-methyl-1,1-dioxidobenzo[d]isothiazol-2(3H)-yl)-2-hydroxypropanoate (1.5 g, 4.1 mmol) in MeNH$_2$ (30% in EtOH, 30 mL) was stirred at 50° C. for 3 h. The reaction was concentrated to give crude 3-(5-bromo-3-methyl-1,1-dioxidobenzo[d]isothiazol-2(3H)-yl)-2-hydroxy-N-methylpropanamide (1.8 g, >100%) as black oil, which was used directly for the next step.

Step 4: tert-butyl 6-fluoro-3-(2-(2-hydroxy-3-(methylamino)-3-oxopropyl)-3-methyl-1,1-dioxido-2,3-dihydrobenzo[d]isothiazol-5-yl)-1H-indole-1-carboxylate A suspension of 3-(5-bromo-3-methyl-1,1-dioxidobenzo[d]isothiazol-2(3H)-yl)-2-hydroxy-N-methylpropanamide (600 mg, 1.65 mmol), tert-butyl 6-fluoro-3-(4,4,5,5-tetramethyl-1,3,2-dioxaborolan-2-yl)-1H-indole-1-carboxylate (895 mg, 2.48 mmol), PdCl$_2$(dppf) (121 mg, 0.165 mmol) and K$_3$PO$_4$ (701 mg, 3.30 mmol) in dioxane (12 mL) and H$_2$O (4 mL) was stirred at 80° C. under a N$_2$ atmosphere for 2 h. The reaction was diluted with water (10 mL) and extracted with ethyl acetate (20 mL×2). The combined organic layers were washed with brine (20 mL) then dried over anhydrous Na$_2$SO$_4$, filtered and concentrated. The crude residue was purified by column chromatography (silica gel, ethyl acetate) to give tert-butyl 6-fluoro-3-(2-(2-hydroxy-3-(methylamino)-3-oxopropyl)-3-methyl-1,1-dioxido-2,3-dihydrobenzo[d]isothiazol-5-yl)-1H-indole-1-carboxylate (390 mg, 46%) as a yellow solid.

Step 5: (+)-3-(5-(6-fluoro-1H-indol-3-yl)-3-methyl-1,1-dioxidobenzo[d]isothiazol-2(3H)-yl)-2-hydroxy-N-methylpropanamide A solution of tert-butyl 6-fluoro-3-(2-(2-hydroxy-3-(methylamino)-3-oxopropyl)-3-methyl-1,1-dioxido-2,3-dihydrobenzo[d]isothiazol-5-yl)-1H-indole-1-carboxylate (390 mg, 0.754 mmol) and trifluoroacetic acid (2 mL) in dichloromethane (10 mL) was stirred at 20° C. under a N$_2$ atmosphere for 2 h. The reaction was concentrated then purified by column chromatography (silica gel, ethyl acetate) to give a mixture of diastereomers. The diastereomers were separated by prep-chiral SFC to give (+)-3-(5-(6-fluoro-1H-indol-3-yl)-3-methyl-1,1-dioxidobenzo[d]isothiazol-2(3H)-yl)-2-hydroxy-N-methylpropanamide as the first eluting peak (30 mg, 10%) as a white solid. $^1$H NMR (400 MHz, DMSO-d$_6$) δ [ppm] 11.68 (br s, 1H), 8.02-7.82 (m, 6H), 7.27 (dd, J=2.5, 9.8 Hz, 1H), 7.01 (dt, J=2.4, 9.2 Hz, 1H), 6.04 (d, J=6.0 Hz, 1H), 4.97 (q, J=6.4 Hz, 1H), 4.30-4.17 (m, 1H), 3.68 (dd, J=2.6, 15.4 Hz, 1H), 3.28 (d, J=6.5 Hz, 1H), 2.64 (d, J=4.5 Hz, 3H), 1.53 (d, J=6.5 Hz, 3H); LC-MS: m/z 440.0 (M+Na)+, [α]$^{20}_D$ +20.3° (c=4 mg/mL, DMSO).

Example 98: (−)-3-(5-(6-fluoro-1H-indol-3-yl)-3-methyl-1,1-dioxidobenzo[d]isothiazol-2(3H)-yl)-2-hydroxy-N-methylpropanamide

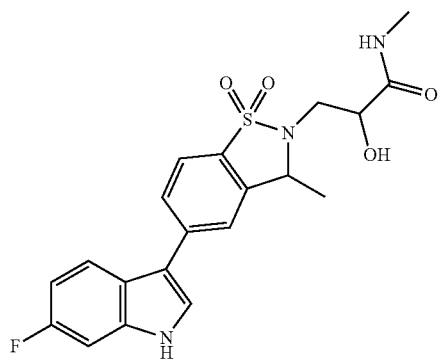 [SMILES: CNC(=O)C(O)CN1C(C)c2cc(-c3c[nH]c4cc(F)ccc34)ccc2S1(=O)=O]

The title compound was obtained as the second eluting peak from the chiral separation described in Example 97 (30 mg, 10%) as a white solid. $^1$H NMR (400 MHz, DMSO-d$_6$) δ [ppm] 11.69 (br s, 1H), 8.03-7.79 (m, 6H), 7.27 (dd, J=2.3, 9.8 Hz, 1H), 7.01 (dt, J=2.5, 9.3 Hz, 1H), 6.05 (d, J=6.0 Hz, 1H), 4.98 (q, J=6.4 Hz, 1H), 4.29-4.18 (m, 1H), 3.69 (dd, J=2.9, 15.2 Hz, 1H), 3.28 (dd, J=8.5, 15.1 Hz, 1H), 2.64 (d, J=4.8 Hz, 3H), 1.53 (d, J=6.5 Hz, 3H); LC-MS: m/z 440.2 (M+Na)$^+$, [α]$^{20}_D$ -8° (c=1 mg/ml, DMSO).

Example 99: (+)-3-(5-(6-fluoro-1H-indol-3-yl)-3-methyl-1,1-dioxidobenzo[d]isothiazol-2(3H)-yl)-2-hydroxy-N-methylpropanamide

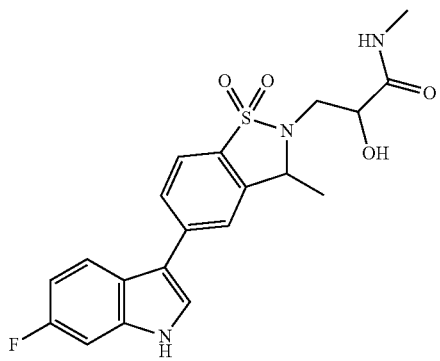 [SMILES: CNC(=O)C(O)CN1C(C)c2cc(-c3c[nH]c4cc(F)ccc34)ccc2S1(=O)=O]

The title compound was obtained as the third eluting peak from the chiral separation described in Example 97 (33 mg, 10%) as a white solid. $^1$H NMR (400 MHz, DMSO-d$_6$) δ [ppm] 11.69 (br s, 1H), 8.04-7.80 (m, 6H), 7.27 (dd, J=2.5, 9.8 Hz, 1H), 7.01 (dt, J=2.4, 9.2 Hz, 1H), 5.94 (d, J=5.5 Hz, 1H), 4.74 (q, J=6.3 Hz, 1H), 4.18 (t, J=8.0 Hz, 1H), 3.66 (dd, J=3.3, 14.6 Hz, 1H), 3.27 (dd, J=7.5, 14.6 Hz, 1H), 2.63 (d, J=4.5 Hz, 3H), 1.56 (d, J=6.5 Hz, 3H); LC-MS: m/z 440.0 (M+Na)$^+$, [α]$^{20}_D$ +19.25° (c=4 mg/ml, DMSO).

Example 100: (-)-3-(5-(6-fluoro-1H-indol-3-yl)-3-methyl-1,1-dioxidobenzo[d]isothiazol-2(3H)-yl)-2-hydroxy-N-methylpropanamide

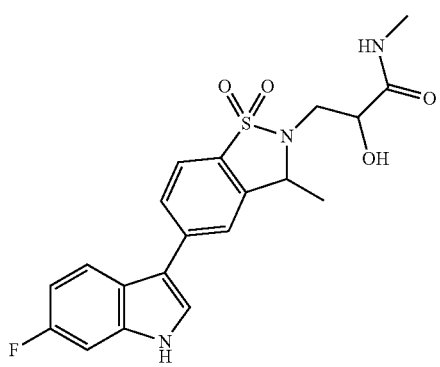 [SMILES: CNC(=O)C(O)CN1C(C)c2cc(-c3c[nH]c4cc(F)ccc34)ccc2S1(=O)=O]

The title compound was obtained as the fourth eluting peak from the chiral separation described in Example 97 (33 mg, 10%) as a white solid. $^1$H NMR (400 MHz, DMSO-d$_6$) δ [ppm] 11.68 (br s, 1H), 8.00-7.78 (m, 6H), 7.27 (dd, J=2.4, 9.9 Hz, 1H), 7.01 (dt, J=2.4, 9.3 Hz, 1H), 5.95 (d, J=5.5 Hz, 1H), 4.74 (q, J=6.7 Hz, 1H), 4.17 (t, J=8.3 Hz, 1H), 3.64 (dd, J=3.4, 14.7 Hz, 1H), 3.29-3.22 (m, 1H), 2.62 (d, J=4.8 Hz, 3H), 1.55 (d, J=6.5 Hz, 3H); LC-MS: m/z 440.0 (M+Na)$^+$, [α]$^{20}_D$ -7° (c=4 mg/ml, DMSO).

Example 101: (+2-amino-3-(5-(6-fluoro-1H-indol-3-yl)-3-methyl-1,1-dioxidobenzo[d]isothiazol-2(3H)-yl)-N-methylpropanamide

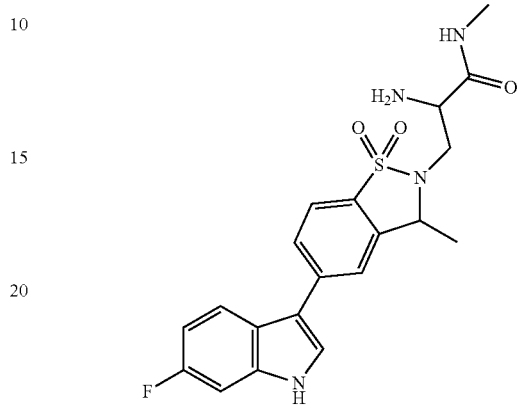

Step 1: 5-bromo-2-(2-hydroxyethyl)-3-methyl-2,3-dihydrobenzo[d]isothiazole 1,1-dioxide To a solution of methyl 3-(5-bromo-3-methyl-1,1dioxidobenzo[d]isothiazol-2(3H)-yl)-2-hydroxypropanoate (Example 207, 500 mg, 1.38 mmol) and TEA (418 mg, 4.13 mmol) in DCM (10 ml) was added MsCl (315 mg, 2.75 mmol). The reaction was stirred at 20° C. for 16 h then poured into water (10 ml) and extracted with DCM (10×2). The combined organic layers were washed with brine (10 ml) then dried over anhydrous Na$_2$SO$_4$, filtered and concentrated to crude give 5-bromo-2-(2-hydroxyethyl)-3-methyl-2,3-dihydrobenzo[d]isothiazole 1,1-dioxide as yellow oil, which was used directly for next step without further purification.

Step 2: 2-azido-3-(5-bromo-3-methyl-1,1-dioxido-benzo[d]isothiazol-2(3H)-yl)-N-methylpropanamide To a solution of methyl 3-(5-bromo-3-methyl-1,1dioxidobenzo[d]isothiazol-2(3H)-yl)-2-hydroxypropanoate (600 mg, 1.36 mmol) in DMF (10 ml) was added NaN$_3$ (106 mg, 1.20 mmol). The reaction was stirred at 80° C. for 16 h then poured into water (20 ml) and extracted with DCM (20 mL×2). The combined organic layers were washed with brine (20 mL) then dried over anhydrous Na$_2$SO$_4$, filtered and concentrated to give crude 2-azido-3-(5-bromo-3-methyl-1,1-dioxidobenzo[d]isothiazol-2(3H)-yl)-N-methylpropanamide (450 mg) as yellow oil, which was used directly for next step without further purification.

Step 3: tert-butyl (3-(5-bromo-3-methyl-1,1-dioxidobenzo[d]isothiazol-2(3H)-yl)-1-(methylamino)-1-oxopropan-2-yl)carbamate A solution of methyl 2-azido-3-(5-bromo-3-methyl-1,1-dioxidobenzo[d]isothiazol-2(3H)-yl)propanoate (450 mg, 1.16 mmol) and PPh$_3$ (1210 mg, 4.62 mmol) in THF (20 ml) and water (0.5 ml) was stirred at 60° C. for 16 h. To the resulting yellow solution was added TEA (468 mg, 4.63 mmol) and (Boc)$_2$O (757 mg, 3.47 mmol). The reaction was stirred at 20° C. for 16 h then poured into water (50 ml) and extracted with EtOAc (50 ml×2). The combined organic layers were washed with brine (50 ml) then dried over anhydrous Na$_2$SO$_4$, filtered and concentrated. The crude residue was purified by column chromatography to give tert-butyl (3-(5-bromo-3-methyl-1,1-dioxidobenzo[d]isothiazol-2(3H)-yl)-1-(methylamino)-1-oxopropanyl)carbamate (250 mg, 47%) as a yellow solid.

Step 4: chiral tert-butyl 3-(2-(2-((tert-butoxycarbonyl)amino)-3-(methylamino)-3-oxopropyl)-3-methyl-1,1-dioxido-2,3-dihydrobenzo[d]isothiazol-5-yl)-6-fluoro-1H-indole-1-carboxylate To a suspension of tert-butyl (3-(5-bromo-3-methyl-1,1-dioxidobenzo[d]isothiazol-2(3H)-yl)-1-(methylamino)-1-oxopropan-2-yl)carbamate (200 mg, 0.433 mmol) and tert-butyl 6-fluoro-3-(4,4,5,5-tetramethyl-1,3,2-dioxaborolan-2-yl)-1H-indole-1-carboxylate (172 mg, 0.476 mmol) in dioxane/water (8 ml/3 ml) was added Pd(dppf)Cl$_2$ (32 mg, 0.04 mmol) and K$_3$PO$_4$ (184 mg, 0.865 mmol). The reaction was stirred at 80° C. for 2 h then concentrated and purified by column chromatography to give tert-butyl 3-(2-(2-((tert-butoxycarbonyl)amino)-3-(methylamino)-3-oxopropyl)-3-methyl-1,1-dioxido-2,3-dihydrobenzo[d]isothiazol-5-yl)-6-fluoro-1H-indole-1-carboxylate (270 mg) as a mixture of diastereomers. The mixture was purified by prep-chiral SFC to give four products; (peak 1 (60 mg), peak 2 (60 mg), peak 3 (30 mg) and peak 4 (40 mg) each as a yellow solid.

Step 5: (−)-2-amino-3-(5-(6-fluoro-1H-indol-3-yl)-3-methyl-1,1-dioxidobenzo[d]isothiazol-2(3H)-yl)-N-methylpropanamide A solution of tert-butyl 3-(2-(2-((tert-butoxycarbonyl)amino)-3-(methylamino)-3-oxopropyl)-3-methyl-1,1-dioxido-2,3-dihydrobenzo[d]isothiazol-5-yl)-6-fluoro-1H-indole-1-carboxylate (peak 1, 60 mg, 0.097 mmol) in HCl/EtOAc (3 ml) was stirred at 20° C. for 20 h. The reaction was concentrated then purified by prep-HPLC to give (−)-2-amino-3-(5-(6-fluoro-1H-indol-3-yl)-3-methyl-1,1-dioxidobenzo[d]isothiazol-2(3H)-yl)-N-methylpropanamide (14 mg, 34%) as a yellow solid. $^1$H NMR (400 MHz, DMSO-d$_6$) δ [ppm] 11.77 (br s, 1H), 8.69 (br s, 1H), 8.42 (br s, 2H), 7.99-7.88 (m, 4H), 7.33-7.26 (m, 1H), 7.06-6.99 (m, 1H), 4.76-4.68 (m, 1H), 4.06-3.98 (m, 1H), 3.70-3.62 (m, 1H), 3.60-3.53 (m, 1H), 2.69 (d, J=4.5 Hz, 3H), 2.54 (s, 1H), 1.61 (d, J=6.3 Hz, 3H); LC-MS: m/z 439.1 (M+Na)$^+$, [α]$^{20}_D$ −4.09° (c=0.001 g/mL, DMSO).

Example 102: (+)-2-amino-3-(5-(6-fluoro-1H-indol-3-yl)-3-methyl-1,1-dioxidobenzo[d]isothiazol-2(3H)-yl)-N-methylpropanamide

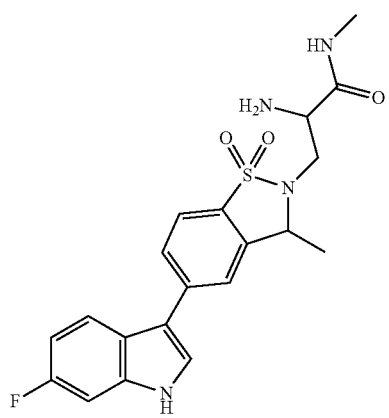

A solution of tert-butyl 3-(2-(2-((tert-butoxycarbonyl)amino)-3-(methylamino)-3-oxopropyl)-3-methyl-1,1-dioxido-2,3-dihydrobenzo[d]isothiazol-5-yl)-6-fluoro-1H-indole-1-carboxylate (60 mg, 0.097 mmol) (Example 211, step 4, peak 2) in HCl/EA (3 ml) was stirred at 20° C. for 20 h. The reaction was concentrated then purified by prep-HPLC to give (+)-2-amino-3-(5-(6-fluoro-1H-indol-3-yl)-3-methyl-1,1-dioxidobenzo[d]isothiazol-2(3H)-yl)-N-methylpropanamide (9 mg, 23%) as a yellow solid. $^1$H NMR (400 MHz, DMSO-d$_6$) δ [ppm] 11.77 (br s, 1H), 8.69 (br s, 1H), 8.42 (br s, 2H), 7.99-7.88 (m, 4H), 7.33-7.26 (m, 1H), 7.06-6.99 (m, 1H), 4.76-4.68 (m, 1H), 4.06-3.98 (m, 1H), 3.70-3.62 (m, 1H), 3.60-3.53 (m, 1H), 2.69 (d, J=4.5 Hz, 3H), 2.54 (s, 1H), 1.61 (d, J=6.3 Hz, 3H); LC-MS: m/z 439.0 (M+Na)$^+$, [α]$^{20}_D$ 0.8° (c=0.0075 g/mL, DMSO).

Example 103: (−)-2-amino-3-(5-(6-fluoro-1H-indol-3-yl)-3-methyl-1,1-dioxidobenzo[d]isothiazol-2(3H)-yl)-N-methylpropanamide

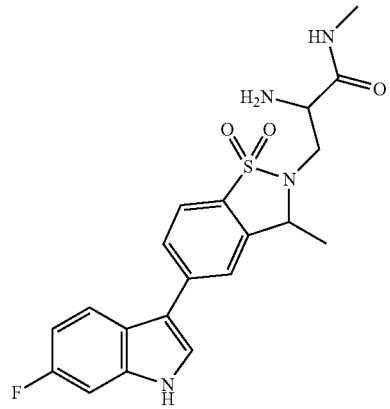 [SMILES: CNC(=O)C(N)CN1C(C)c2cc(-c3c[nH]c4cc(F)ccc34)ccc2S1(=O)=O]

A solution of tert-butyl 3-(2-(2-((tert-butoxycarbonyl)amino)-3-(methylamino)-3-oxopropyl)-3-methyl-1,1-dioxido-2,3-dihydrobenzo[d]isothiazol-5-yl)-6-fluoro-1H-indole-1-carboxylate (30 mg, 0.05 mmol) (Example 101, step 4, peak 3) in HCl/EA (3 ml) was stirred at 20° C. for 20 h. The reaction was stirred for another 16 h then concentrated and purified by prep-HPLC to give (−)-2-amino-3-(5-(6-fluoro-1H-indol-3-yl)-3-methyl-1,1-dioxidobenzo[d]isothiazol-2 (3H)-yl)-N-methylpropanamide (7 mg, 36%) as a pale yellow solid. $^1$H NMR (400 MHz, DMSO-d$_6$) δ [ppm] 11.81 (br s, 1H), 8.69 (d, J=4.5 Hz, 1H), 8.61-8.45 (m, 2H), 8.00-7.86 (m, 5H), 7.27 (s, 1H), 7.06-6.98 (m, 1H), 4.94-4.86 (m, 1H), 4.07-3.97 (m, 1H), 3.73-3.57 (m, 2H), 2.66 (d, J=4.5 Hz, 3H), 1.54 (d, J=6.5 Hz, 3H); LC-MS: m/z 438.9 (M+Na)$^+$, [α]$^{20}_D$ −21° (c=0.001 g/mL, DMSO).

Example 104: (+) 2-amino-3-(5-(6-fluoro-1H-indol-3-yl)-3-methyl-1,1-dioxidobenzo[d]isothiazol-2(3H)-yl)-N-methylpropanamide

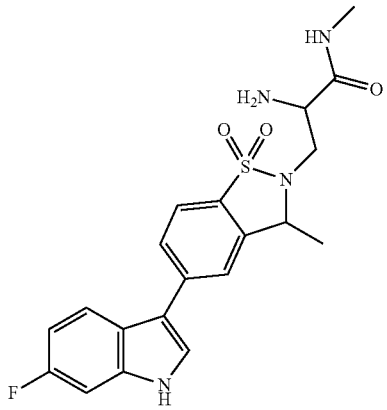

A solution of tert-butyl 3-(2-(2-((tert-butoxycarbonyl)amino)-3-(methylamino)-3-oxopropyl)-3-methyl-1,1-dioxido-2,3-dihydrobenzo[d]isothiazol-5-yl)-6-fluoro-1H-indole-carboxylate (40 mg, 0.07 mmol) (Example 101, step 4, peak 4) in HCl/EA (3 ml) was stirred at 20° C. for 20 h. The reaction was stirred for another 16 h then concentrated and purified by prep-HPLC to give (+)-2-amino-3-(5-(6-fluoro-1H-indol-3-yl)-3-methyl-1,1-dioxidobenzo[d]isothiazol-2(3H)-yl)-N-methylpropanamide (12 mg, 43%) as a yellow solid. $^1$H NMR (400 MHz, DMSO-$d_6$) δ [ppm] 11.80 (s, 1H), 8.72-8.63 (m, 1H), 8.50 (br s, 2H), 7.99-7.87 (m, 5H), 7.32-7.26 (m, 1H), 7.06-6.99 (m, 1H), 4.93-4.84 (m, 1H), 4.06-3.97 (m, 1H), 3.73-3.58 (m, 2H), 2.67 (d, J=4.5 Hz, 3H), 1.54 (d, J=6.5 Hz, 3H); LC-MS: m/z 438.9 (M+Na)$^+$, $[α]^{20}_D$ +10.67° (c=0.001 g/mL, DMSO).

Example 105: (+)-3-(5-(6-fluoro-1H-indol-3-yl)-3-methyl-1,1-dioxidobenzo[d]isothiazol-2(3H)-yl)-2-methoxy-N-methylpropanamide

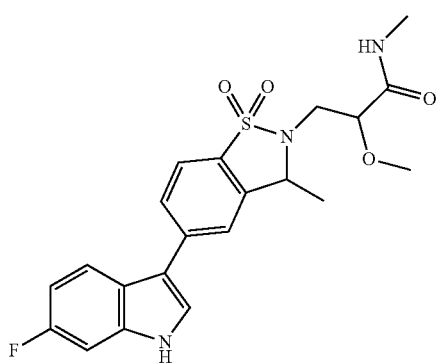 [SMILES: CNC(=O)C(CN1C(C)c2cc(-c3c[nH]c4cc(F)ccc34)ccc2S1(=O)=O)OC]

Step 1: N-2,2-trimethyl-1,3-dioxolane-4-carboxamide

To a solution of methyl 2,2-dimethyl-1,3-dioxolane-4-carboxylate (5.0 g, 31 mmol) in EtOH (50 mL) was added MeNH$_2$ (30% in EtOH, 9.7 g, 94 mmol). The reaction was stirred at 25° C. for 16 h then concentrated. The residue was dissolved in MeNH$_2$ (30% in EtOH, 30 mL) then transferred to a sealed tube and stirred at 50° C. for 3 h. The crude reaction was diluted with water (20 mL) and extracted with ethyl acetate (40 mL×2). The combined organic layers were washed with brine (20 mL) then dried over anhydrous Na$_2$SO$_4$, filtered and concentrated to give N, 2,2-trimethyl-1,3-dioxolane-4-carboxamide (2.5 g, 50%) as a yellow oil. $^1$H NMR (400 MHz, CDCl$_3$) δ [ppm] 6.60 (br s, 1H), 4.49 (dd, J=5.5, 7.5 Hz, 1H), 4.29 (t, J=8.3 Hz, 1H), 4.09 (dd, J=5.3, 8.8 Hz, 1H), 2.86 (d, J=5.0 Hz, 1H), 1.49 (s, 3H), 1.39 (s, 3H).

Step 2: 2,3-dihydroxy-N-methylpropanamide

To a solution of N, 2,2-trimethyl-1,3-dioxolane-4-carboxamide (2.5 g, 16 mmol) in dichloromethane (40 mL) was added trifluoroacetic acid (20 mL). The reaction was stirred at 25° C. for 2 h then concentrated to give 2,3-dihydroxy-N-methylpropanamide (2 g, >100%) as a black oil, which was used directly for the next step. $^1$H NMR (400 MHz, CDCl$_3$) δ [ppm] 4.13-4.01 (m, 1H), 3.82-3.63 (m, 2H), 2.78 (s, 3H).

Step 3: 3-((tert-butyldiphenylsilyl)oxy)-2-hydroxy-N-methylpropanamide

To a solution of 2,3-dihydroxy-N-methylpropanamide (2.0 g, 17 mmol) in DMF (20 mL) was added imidazole (3.5 g, 52 mmol) and tert-butyldiphenylsilyl chloride(TBDPSCl) (7.1 g, 26 mmol). The reaction was stirred at 25° C. for 16 h then diluted with water (60 mL) and extracted with ethyl acetate (100 mL×2). The combined organic layers were washed with brine (150 mL×3) then dried over anhydrous Na$_2$SO$_4$, filtered and concentrated. The crude residue was purified by column chromatography (silica gel, 40% ethyl acetate/petroleum ether) to give 3-((tert-butyldiphenylsilyl)oxy)-2-hydroxy-N-methylpropanamide (2.2 g, 36% yield) as a yellow solid. $^1$H NMR (400 MHz, CDCl$_3$) δ [ppm] 7.64 (dd, J=1.4, 7.9 Hz, 4H), 7.49-7.36 (m, 6H), 6.77 (br s, 1H), 4.22-4.14 (m, 1H), 3.90 (dd, J=2.8, 5.8 Hz, 2H), 3.25 (d, J=4.3 Hz, 1H), 2.87 (d, J=5.0 Hz, 3H), 1.08 (s, 9H).

Step 4: 3-((tert-butyldiphenylsilyl)oxy)-2-methoxy-N-methylpropanamide

To a yellow solution of 3-((tert-butyldiphenylsilyl)oxy)-2-hydroxy-N-methylpropanamide (2.2 g, 6.2 mmol) in anhydrous THF (20 mL) was added MeI (4.4 g, 31 mmol) and Ag$_2$O (11.4 g, 49.2 mmol). The reaction was stirred at 25° C. for 16 h then transferred to a sealed tube and MeI (20 g, 141 mmol) was added. The reaction was sealed stirred at 40° C. for 16 h. The resulting yellow suspension was filtered and the filtrate was concentrated then purified by column chromatography (silica gel, 40-50% ethyl acetate/petroleum ether) to give 3-((tert-butyldiphenylsilyl)oxy)-2-methoxy-N-methylpropanamide (1.5 g, 66%% yield) as a yellow oil.

Step 5: 3-hydroxy-2-methoxy-N-methylpropanamide

To a yellow solution of 3-((tert-butyldiphenylsilyl)oxy)-2-methoxy-N-methylpropanamide (2.2 g, 5.92 mmol) in anhydrous THF (10 mL) was added tetra-n-butylammonium fluoride (TBAF) (1 M in THF, 23.7 mL g, 23.7 mmol). The reaction was stirred at 25° C. for 16 h then diluted with water (20 mL) and extracted with ethyl acetate (40 mL×3). The combined organic layers were washed with brine (30 mL) then dried over anhydrous $Na_2SO_4$, filtered and concentrated. The crude residue was purified by column chromatography (silica gel, 40-80% ethyl acetate/petroleum ether) to give 3-hydroxy-2-methoxy-N-methylpropanamide (300 mg, 38%) as yellow oil. $^1$H NMR (400 MHz, CDCl$_3$) δ [ppm] 6.71 (br s, 1H), 3.87-3.82 (m, 2H), 3.80-3.71 (m, 1H), 3.33-3.20 (m, 1H), 2.86 (d, J=5.0 Hz, 3H).

Step 6: 2-methoxy-3-(methylamino)-3-oxopropyl methanesulfonate

To a yellow solution of 3-hydroxy-2-methoxy-N-methylpropanamide (370 mg, 2.78 mmol) in anhydrous dichloromethane (10 mL) was added DIPEA (718 mg, 5.56 mmol) and MsCl (477 mg, 4.17 mmol). The reaction was stirred at 25° C. for 1 h then concentrated, diluted with water (10 mL) and extracted with ethyl acetate (10 mL×3). The combined organic layers were washed with water (10 mL) then dried over anhydrous $Na_2SO_4$, filtered and concentrated to crude give 2-methoxy-3-(methylamino)-3-oxopropyl methanesulfonate (350 mg, 60%) as a yellow oil. $^1$H NMR (400 MHz, CDCl$_3$) δ [ppm] 6.73 (br s, 1H), 4.60 (d, J=11.2 Hz, 1H), 4.47 (dd, J=4.4, 11.2 Hz, 1H), 3.94 (s, 1H), 3.54 (s, 3H), 3.04 (s, 3H), 2.88 (d, J=5.2 Hz, 3H).

Step 7: 3-(5-bromo-3-methyl-1,1-dioxidobenzo[d]isothiazol-2(3H)-yl)-2-methoxy-N-methylpropanamide A solution of 5-bromo-3-methyl-2,3-dihydrobenzo[d]isothiazole 1,1-dioxide (434 mg, 1.7 mmol), 2-methoxy-3-(methylamino)-3-oxopropyl methanesulfonate (350 mg, 1.66 mmol) and $K_2CO_3$ (458 mg, 3.31 mmol) in DMSO (10 mL) was stirred at 80° C. for 2 h. The crude reaction was diluted with brine (20 mL) and extracted with ethyl acetate (30 mL×2). The combined organic layers were washed with brine (20 mL×3) then dried over anhydrous $Na_2SO_4$, filtered and concentrated. The crude residue was purified by column chromatography (silica) gel, ethyl acetate) to give 3-(5-bromo-3-methyl-1,1-dioxidobenzo[d]isothiazol-2(3H)-yl)-2-methoxy-N-methylpropanamide (130 mg, 21% yield) as a black oil.

Step 8: tert-butyl 6-fluoro-3-(2-(2-methoxy-3-(methylamino)-3-oxopropyl)-3-methyl-1,1-dioxido-2,3-dihydrobenzo[d]isothiazol-5-yl)-1H-indole-1-carboxylate A red suspension of 3-(5-bromo-3-methyl-1,1-dioxidobenzo[d]isothiazol-2(3H)-yl)-2-methoxy-N-methylpropanamide (200 mg, 0.530 mmol), tert-butyl 6-fluoro-3-(4,4,5,5-tetramethyl-1,3,2-dioxaborolan-2-yl)-1H-indole-1-carboxylate (249 mg, 0.689 mmol), PdCl$_2$(dppf) (39 mg, 0.05 mmol) and $K_3PO_4$ (225 mg, 1.06 mmol) in dioxane (8 mL) and $H_2O$ (2 mL) was stirred at 80° C. under a $N_2$ atmosphere for 2 h. The mixture was diluted with water (15 mL) and extracted with ethyl acetate (20 mL×3). The combined organic layers were washed with brine (15 mL) then dried over anhydrous $Na_2SO_4$, filtered and concentrated. The crude residue was purified by column chromatography (silica gel, 80-100% ethyl acetate/petroleum ether) to give tert-butyl 6-fluoro-3-(2-(2-methoxy-3-(methyl-amino)-3-oxopropyl)-3-methyl-1,1-dioxido-2,3-dihydrobenzo[d]isothiazol-5-yl)-1H-indole-1-carboxylate (220 mg, 78% yield) as a black oil.

Step 9: (+)-3-(5-(6-fluoro-1H-indol-3-yl)-3-methyl-1,1-dioxidobenzo[d]isothiazol-2(3H)-yl)-2-methoxy-N-methylpropanamide To a solution of tert-butyl 6-fluoro-3-(2-(2-methoxy-3-(methylamino)-3-oxopropyl)-3-methyl-1,1-dioxido-2,3-dihydrobenzo[d]isothiazol-5-yl)-1H-indole-1-carboxylate (220 mg, 0.414 mmol) in dichloromethane (10 mL) was added trifluoroacetic acid (2 mL). The reaction was stirred at 20° C. for 16 h then concentrated and neutralized pH 7 with NaHCO$_3$ (sat). The mixture was extracted with ethyl acetate (40 mL×3) and the combined organic layers were washed with brine (15 mL), dried over anhydrous $Na_2SO_4$, filtered and concentrated. The crude residue was purified by column chromatography (silica gel, 80%-100% ethyl acetate/petroleum ether) to give a mixture of diastereomers (150 mg). The diastereomers were separated by prep-chiral SFC to give (+)-3-(5-(6-fluoro-1H-indol-3-yl)-3-methyl-1,1-dioxidobenzo[d]isothiazol-2(3H)-yl)-2-methoxy-N-methylpropanamide as the first eluting peak (28 mg, 16%) as an off-white solid. $^1$H NMR (400 MHz, DMSO-d$_6$) δ [ppm] 11.68 (br s, 1H), 8.10 (d, J=4.8 Hz, 1H), 8.00-7.82 (m, 5H), 7.27 (dd, J=2.4, 9.9 Hz, 1H), 7.01 (dt, J=2.4, 9.1 Hz, 1H), 4.81 (q, J=6.2 Hz, 1H), 3.93 (dd, J=3.8, 7.8 Hz, 1H), 3.59-3.51 (m, 1H), 3.44 (d, J=5.5 Hz, 1H), 3.33 (s, 3H), 2.65 (d, J=4.5 Hz, 3H), 1.54 (d, J=6.5 Hz, 3H); LC-MS: m/z 432.1 (M+H)$^+$, $[α]^{20}_D$ +6.75° (c=4 mg/mL, DMSO).

Example 106: (−)-3-(5-(6-fluoro-1H-indol-3-yl)-3-methyl-1,1-dioxidobenzo[d]isothiazol-2(3H)-yl)-2-methoxy-N-methylpropanamide

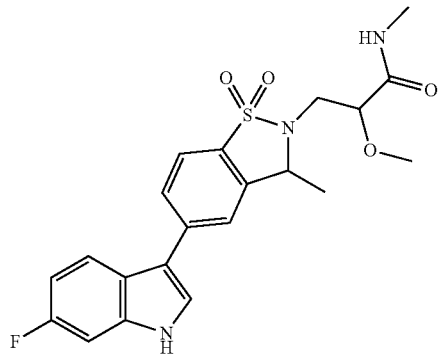

The title compound was obtained as the second eluting peak from the chiral separation described in Example 105 (21 mg, 12%) as an off-white solid. $^1$H NMR (400 MHz, DMSO-d$_6$) δ [ppm] 11.69 (br s, 1H), 8.10 (d, J=4.8 Hz, 1H), 8.05-7.76 (m, 5H), 7.27 (dd, J=2.4, 9.9 Hz, 1H), 7.01 (dt, J=2.4, 9.2 Hz, 1H), 4.81 (q, J=6.5 Hz, 1H), 3.94 (dd, J=3.5, 7.8 Hz, 1H), 3.61-3.50 (m, 1H), 3.43 (d, J=7.8 Hz, 1H), 3.33 (s, 3H), 2.65 (d, J=4.8 Hz, 3H), 1.54 (d, J=6.5 Hz, 3H); LC-MS: m/z 432.1 (M+H)$^+$, $[α]^{20}_D$ −7° (c=4 mg/ml, DMSO).

Example 107: (+)-3-(5-(6-fluoro-1H-indol-3-yl)-3-methyl-1,1-dioxidobenzo[d]isothiazol-2(3H)-yl)-2-methoxy-N-methylpropanamide

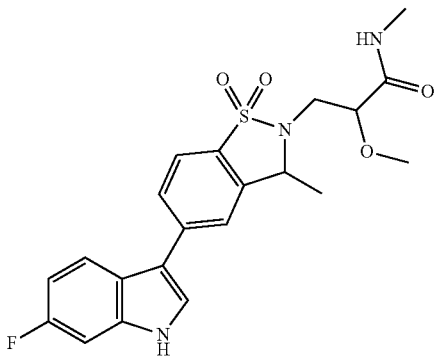

The title compound was obtained as the third eluting peak from the chiral separation described in Example 105 (21 mg, 12%) as an off-white solid. $^1$H NMR (400 MHz, DMSO-d$_6$) δ [ppm] 11.68 (br s, 1H), 8.06 (d, J=4.5 Hz, 1H), 7.99-7.81 (m, 5H), 7.27 (dd, J=2.3, 9.8 Hz, 1H), 7.01 (dt, J=2.5, 9.3 Hz, 1H), 4.71 (q, J=6.3 Hz, 1H), 3.90 (dd, J=3.5, 7.3 Hz, 1H), 3.62 (dd, J=3.5, 15.1 Hz, 1H), 3.43 (d, J=2.5 Hz, 1H), 3.36 (s, 3H), 2.64 (d, J=4.8 Hz, 3H), 1.54 (d, J=6.5 Hz, 3H); LC-MS: m/z 432.2 (M+H)$^+$, [α]$^{20}_D$ +3.25° (c=4 mg/ml, DMSO).

Example 108: (−)-3-(5-(6-fluoro-1H-indol-3-yl)-3-methyl-1,1-dioxidobenzo[d]isothiazol-2(3H)-yl)-2-methoxy-N-methylpropanamide

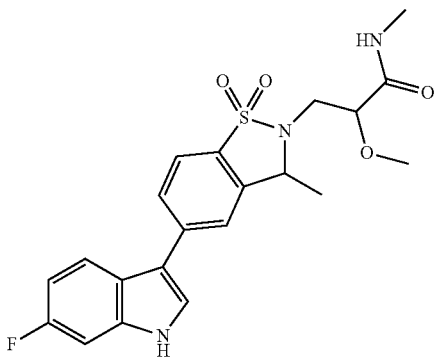 [SMILES: CNC(=O)C(CN1C(C)c2cc(-c3c[nH]c4cc(F)ccc34)ccc2S1(=O)=O)OC]

The title compound was obtained as the fourth eluting peak from the chiral separation described in Example 105 (11 mg, 6%) as an off-white solid. $^1$H NMR (400 MHz, DMSO-d$_6$) δ [ppm] 11.68 (br s, 1H), 8.06 (d, J=4.8 Hz, 1H), 7.98-7.81 (m, 5H), 7.27 (dd, J=2.3, 9.8 Hz, 1H), 7.01 (dt, J=2.4, 9.2 Hz, 1H), 4.71 (q, J=6.3 Hz, 1H), 3.90 (dd, J=3.4, 7.4 Hz, 1H), 3.62 (dd, J=3.6, 14.9 Hz, 1H), 3.48-3.47 (m, 1H), 3.35 (s, 3H), 2.64 (d, J=4.8 Hz, 3H), 1.54 (d, J=6.5 Hz, 3H); LC-MS: m/z, 432.1 (M+H)$^+$, [α]$^{20}_D$ −4.75° (c=4 mg/ml, DMSO).

Example 109: (−)-ethyl (2-(5-(6-fluoro-1H-indol-3-yl)-3-methyl-1,1-dioxidobenzo[d]isothiazol-2(3H)-yl)ethyl)carbamate

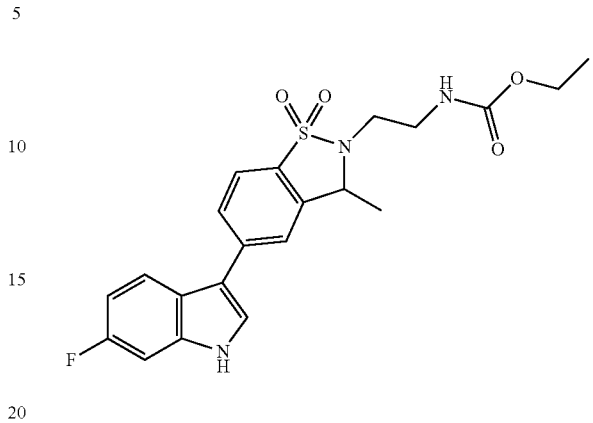

Step 1: tert-butyl (2-(5-bromo-3-methyl-1,1-dioxidobenzo-[d]isothiazol-2(3H)-yl) ethyl)carbamate A mixture of 5-bromo-3-methyl-2,3-dihydro-1,2-benzothiazole 1,1-dioxide (300 mg, 1.14 mmol), tert-butyl n-(2-bromoethyl)carbamate (282 mg, 1.26 mmol) and K$_2$CO$_3$ (316 mg, 2.29 mmol) in DMF (5.7 mL) was sparged with N$_2$ for 1 min then stirred at 80° C. for 16 h. The reaction mixture was diluted with ethyl acetate (10 mL) and water (10 mL). The layers were separated and the aqueous layer was extracted with ethyl acetate (10 mL×2). The combined organic layers were washed with NaHCO$_3$ (sat) (10 mL) and brine (10 mL) then dried (Na$_2$SO$_4$), filtered and concentrated. The crude residue was purified by column chromatography (silica gel, 4-60% ethyl acetate/Petroleum ether) to afford tert-butyl (2-(5-bromo-3-methyl-1,1-dioxidobenzo[d]isothiazol-2(3H)-yl)ethyl)-carbamate (410 mg, 88%) as a yellow gum. LC-MS: m/z 428.8 (M+Na)$^+$.

Step 2: tert-butyl 3-(2-(2-((tert-butoxycarbonyl)amino)ethyl)-3-methyl-1,1-dioxido-2,3-dihydrobenzo[d]isothiazol-5-yl)-6-fluoro-1H-indole-1-carboxylate A brown mixture of tert-butyl (2-(5-bromo-3-methyl-1,1-dioxidobenzo[d]isothiazol-2(3H)-yl)ethyl)carbamate (300 mg, 0.74 mmol), tert-butyl 6-fluoro-3-(4,4,5,5-tetramethyl-1,3,2-dioxaborolan-2-yl)-1H-indole-1-carboxylate (382 mg, 0.74 mmol), PdCl$_2$(dppf)-CH$_2$Cl$_2$ (55.3 mg, 0.074 mmol) and K$_3$PO$_4$ (471 mg, 2.22 mmol) in 1,4-dioxane (7.4 mL) was sparged with N$_2$ for 1 min then stirred at 80° C. for 5 h. The reaction mixture was concentrated and purified by column chromatography (silica gel, 4-60% ethyl acetate/petroleum ether) to give tert-butyl 3-(2-(2-((tert-butoxycarbonyl)amino)ethyl)-3-methyl-1,1-dioxido-2,3-dihydrobenzo[d]isothiazol-5-yl)-6-fluoro-1H-indole-1-carboxylate (367 mg, 87%) as a yellow gum. LC-MS: m/z 582.0 (M+Na)$^+$.

Step 3: 2-(2-aminoethyl)-5-(6-fluoro-1H-indol-3-yl)-3-methyl-2,3-dihydrobenzo[d]isothiazole 1,1-dioxide To a yellow solution of tert-butyl 3-(2-(2-((tert-butoxycarbonyl)-amino)ethyl)-3-methyl-1,1-dioxido-2,3-dihydrobenzo[d]isothiazol-5-yl)-6-fluoro-1H-indole-1-carboxylate (245 mg, 0.44 mmol) in CH$_2$Cl$_2$ (5 mL) was added trifluoroacetic acid (3 mL) at 0° C. The reaction solution was stirred at 25° C. for 3 h, diluted with methanol and concentrated to give crude 2-(2-aminoethyl)-5-(6-fluoro-1H-indol-3-yl)-3-methyl-2,3-dihydrobenzo[d]isothiazole 1,1-dioxide (288 mg, 100%) as a yellow solid, which was used directly in the next step.

Step 4: ethyl 3-(2-(2-((ethoxycarbonyl)amino)ethyl)-3-methyl-1,1-dioxido-2,3-dihydrobenzo[d]isothiazol-5-yl)-6-fluoro-1H-indole-1-carboxylate To a cooled (ice bath) solution of 2-(2-aminoethyl)-5-(6-fluoro-1H-indol-3-yl)-3-methyl-2,3-dihydrobenzo[d]isothiazole 1,1-dioxide (157 mg, 0.44 mmol) in CH$_2$Cl$_2$ (8 mL) was added Et$_3$N (0.183 mL, 1.31 mmol) following by ethyl chloroformate (110 mg, 1.01 mmol). The reaction was warmed to 25° C. and stirred for 3 h. The reaction solution was quenched with water (10 mL) and extracted with ethyl acetate (10 mL×2). The combined organic layers were concentrated and purified by column chromatography (silica gel, 4-100% ethyl acetate/petroleum ether) to give ethyl 3-(2-(2-((ethoxycarbonyl)amino)-ethyl)-3-methyl-1,1-dioxido-2,3-dihydrobenzo[d]isothiazol-5-yl)-6-fluoro-1H-indole-1-carboxylate (174 mg, 79%) as a yellow solid. LC-MS: m/z 526.0 (M+Na)$^+$.

Step 5: (−)-ethyl (2-(5-(6-fluoro-1H-indol-3-yl)-3-methyl-1,1-dioxidobenzo[d]isothiazol-2(3H)-yl)ethyl)carbamate To a yellow mixture of ethyl 3-(2-(2-((ethoxycarbonyl)amino)ethyl)-3-methyl-1,1-dioxido-2,3-dihydrobenzo[d]isothiazol-5-yl)-6-fluoro-1H-indole-1-carboxylate (174 mg, 0.35 mmol) in EtOH (8 mL) was added K$_2$CO$_3$ (95.5 mg, 0.69 mmol). The reaction mixture was stirred at 25° C. for 3 h. The crude reaction was filtered and washed with methanol then concentrated. The crude residue was purified by column (silica gel, 5-100% ethyl acetate/petroleum ether) to give racemic ethyl (2-(5-(6-fluoro-1H-indol-3-yl)-3-methyl-1,1-dioxidobenzo[d]isothiazol-2(3H)-yl)ethyl)carbamate (74 mg, 50%) as a yellow solid. The enantiomers were separated by prep-chiral SFC to give (−)-ethyl (2-(5-(6-fluoro-1H-indol-3-yl)-3-methyl-1,1-dioxidobenzo[d] isothiazol-2(3H)-yl)ethyl) carbamate as the first eluting peak (15 mg, 15%) as a white solid. $^1$H NMR (400 MHz, MeOD) δ [ppm] 7.93-7.84 (m, 2H), 7.83-7.77 (m, 2H), 7.68 (s, 1H), 7.16 (dd, J=2.0, 9.5 Hz, 1H), 6.99-6.91 (m, 1H), 4.73 (d, J=6.5 Hz, 1H), 4.59 (s, 1H), 4.08 (q, J=7.2 Hz, 2H), 3.50-3.41 (m, 4H), 1.62 (d, J=6.5 Hz, 3H), 1.22 (t, J=7.0 Hz, 3H); LC-MS: m/z 432.0 (M+H)$^+$, [α]$^{20}_D$ −5° (c=1.2 mg/mL, methanol).

Example 110: (+)-ethyl (2-(5-(6-fluoro-1H-indol-3-yl)-3-methyl-1,1-dioxidobenzo[d]isothiazol-2(3H)-yl)ethyl)carbamate

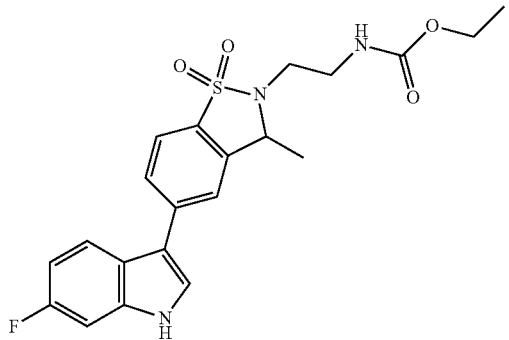 [SMILES: CCOC(=O)NCCN1C(C)c2cc(-c3c[nH]c4cc(F)ccc34)ccc2S1(=O)=O]

The title compound was obtained as the second eluting peak from the chiral separation described in Example 109 (25 mg, 24%) as a white solid. $^1$H NMR (400 MHz, MeOD) δ [ppm] 7.92-7.82 (m, 2H), 7.81-7.75 (m, 2H), 7.67 (s, 1H), 7.16 (dd, J=2.0, 10.0 Hz, 1H), 6.94 (dt, J=2.0, 9.3 Hz, 1H), 4.71 (d, J=6.5 Hz, 1H), 4.60 (s, 1H), 4.08 (q, J=7.0 Hz, 2H), 3.48-3.41 (m, 4H), 1.61 (d, J=6.5 Hz, 3H), 1.22 (t, J=7.0 Hz, 3H); LC-MS: m/z 432.0 (M+H)$^+$, [α]$^{20}_D$ +5.56° (c=3.6 mg/mL, methanol).

Example 111: (−)-2-(5-(6-fluoro-1H-indol-3-yl)-3-methyl-1,1-dioxidobenzo[d]isothiazol-2(3H)-yl)-N-methylacetamide

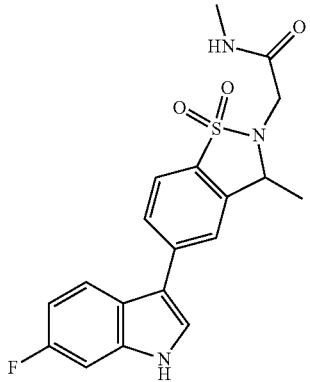

Step 1: tert-butyl 2-(5-bromo-3-methyl-1,1-dioxidobenzo[d]isothiazol-2(3H)-yl)acetate To a brown solution of 5-bromo-3-methyl-2,3-dihydrobenzo[d]isothiazole-1,1-dioxide (1.2 g, 4.6 mmol) in DMF (20 mL) was added tert-butyl 2-bromoacetate (1.1 g, 5.5 mmol) and K$_2$CO$_3$ (1.27 g, 9.16 mmol) then the reaction was sparged with N$_2$ for 1 min and stirred at 80° C. for 16 h. The reaction was diluted with ethyl acetate (20 mL) and water (20 mL). The layers were separated and the aqueous layer was back-extracted with ethyl acetate (30 mL×2). The combined organic layers were washed with brine (10 mL×2) then dried over Na$_2$SO$_4$, filtered and concentrated. The crude residue was purified by column chromatography (silica gel, 2-20% ethyl acetate/petroleum ether) to afford tert-butyl 2-(5-bromo-3-methyl-1,1-dioxidobenzo[d]isothiazol-2(3H)-yl)acetate (1.38 g, 80%) as a black solid.

Step 2: tert-butyl 2-(5-(6-fluoro-1H-indol-3-yl)-3-methyl-1,1-dioxidobenzo[d]isothiazol-2(3H)-yl)acetate To a black solution of tert-butyl 2-(5-bromo-3-methyl-1,1-dioxidobenzo[d]isothiazol-2(3H)-yl)acetate (1.38 g, 3.67 mmol), tert-butyl 6-fluoro-3-(4,4,5,5-tetramethyl-1,3,2-dioxaborolan-2-yl)-1H-indole-1-carboxylate (1.57 g, 3.70 mmol) and K$_3$PO$_4$ (1.43 g, 6.72 mmol) in Dioxane/H$_2$O(30 ml/10 mL) was added Pd (dppf)Cl$_2$ (246 mg, 0.336 mmol) at 28° C. under N$_2$. The reaction was stirred at 90° C. for about 6 h then diluted with ethyl acetate (40 mL). The layers were separated and the organic layer was washed with H$_2$O (10 mL) and brine (15 mL×2) then dried over anhydrous Na$_2$SO$_4$, filtered and concentrated. The crude residue was purified by column chromatography (silica gel, 10-40% ethyl acetate/petroleum ether) to give tert-butyl 2-(5-(6- fluoro-1H-indol-3-yl)-3-methyl-1,1-dioxidobenzo[d]isothiazol-2(3H)-yl)acetate (597 mg, 38% yield) as a yellow gum.

Step 3: 2-(5-(6-fluoro-1H-indol-3-yl)-3-methyl-1,1-dioxidobenzo[d]isothiazol-2(3H)-yl)acetic acid A yellow solution of tert-butyl 2-(5-(6-fluoro-1H-indol-3-yl)-3-methyl-1,1-dioxidobenzo[d]isothiazol-2(3H)-yl)acetate (597 mg, 1.39 mmol) in trifluoroacetic acid (12 mL) was stirred at 25° C. for 71 h. The reaction was concentrated to give crude 2-(5-(6-fluoro-1H-indol-3-yl)-3-methyl-1,1-dioxidobenzo[d]isothiazol-2(3H)-yl)acetic acid (560 mg, >100%) as a green solid which was directly used for the next step.

Step 4: (−)-2-(5-(6-fluoro-1H-indol-3-yl)-3-methyl-1,1-dioxidobenzo[d]isothiazol-2(3H)-yl)-N-methylacetamide A solution of 2-(5-(6-fluoro-1H-indol-3-yl)-3-methyl-1,1-dioxidobenzo[d]isothiazol-2(3H)-yl)acetic acid (175 mg, 0.467 mmol), methanamine HCl salt (97 mg, 0.94 mmol) and DIPEA (0.326 mL, 1.87 mmol) in dry DMF (5 mL) was stirred at 25° C. for 5 min then HATU (267 mg, 0.701 mmol) was added. The reaction was stirred at 25° C. for 3 h then diluted with ethyl acetate (30 mL) and washed with water (10 mL) and brine (10 mL). The organic layer was dried over $Na_2SO_4$, filtered and concentrated then purified by column chromatography (silica gel, 30-100% ethyl acetate/petroleum ether) to give the racemic product (135 mg). The enantiomers were separated by prep-chiral SFC to give (−)-2-(5-(6-fluoro-1H-indol-3-yl)-3-methyl-1,1-dioxidobenzo[d]isothiazol-2(3H)-yl)-N-methylacetamide as the first eluting peak (29 mg, 16% yield) as a white solid. $^1$H NMR (400 MHz, DMSO-$d_6$) δ [ppm] 11.70 (br s, 1H), 8.04-7.82 (m, 6H), 7.27 (dd, J=2.3, 9.8 Hz, 1H), 7.01 (dt, J=2.4, 9.2 Hz, 1H), 4.92 (d, J=6.5 Hz, 1H), 3.96-3.80 (m, 2H), 2.63 (d, J=4.5 Hz, 3H), 1.54 (d, J=6.5 Hz, 3H); LC-MS: m/z 409.9 (M+Na)$^+$, $[α]^{20}_D$ −7.11° (c=1.97 mg/ml, DMSO).

Example 112: (+)-2-(5-(6-fluoro-1H-indol-3-yl)-3-methyl-1,1-dioxidobenzo[d]isothiazol-2(3H)-yl)-Nmethylacetamide

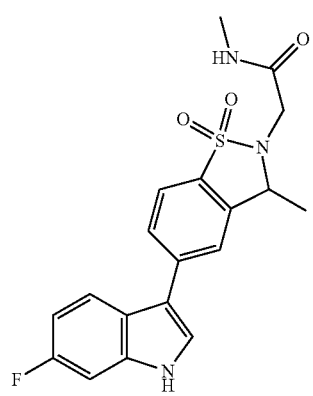 [SMILES: CNC(=O)CN1C(C)c2cc(-c3c[nH]c4cc(F)ccc34)ccc2S1(=O)=O]

The title compound was obtained as the second eluting peak from the chiral separation described in Example 111 (16 mg, 9%) as a white solid. $^1$H NMR (400 MHz, DMSO-$d_6$) δ [ppm] 11.70 (br s, 1H), 8.09-7.80 (m, 6H), 7.27 (dd, J=2.4, 9.9 Hz, 1H), 7.01 (dt, J=2.5, 9.2 Hz, 1H), 4.92 (d, J=6.5 Hz, 1H), 3.89 (d, J=3.3 Hz, 2H), 2.63 (d, J=4.8 Hz, 3H), 1.54 (d, J=6.5 Hz, 3H); LCMS: m/z 409.8 (M+Na)$^+$, $[α]^{20}_D$ +9.32° (c=2.11 mg/ml, DMSO).

Example 113: (−)-2-(5-(6-fluoro-1H-indol-3-yl)-3-methyl-1,1-dioxidobenzo[d]isothiazol-2(3H)-yl)-N,N-dimethylacetamide

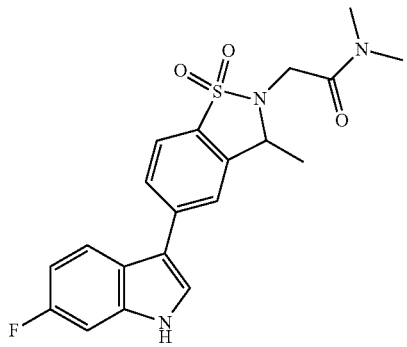 [SMILES: CC1c2cc(-c3c[nH]c4cc(F)ccc34)ccc2S(=O)(=O)N1CC(=O)N(C)C]

A cooled (ice bath) solution of 2-(5-(6-fluoro-1H-indol-3-yl)-3-methyl-1,1-dioxidobenzo[d]isothiazol-2(3H)-yl) acetic acid (260 mg, 0.260 mmol) and dimethylamine HCl salt (42 mg, 0.51 mmol) in dry DMF (5 mL) was added DIPEA (133 mg, 1.03 mmol). The reaction was stirred in the ice bath for 5 min then HATU (147 mg, 0.385 mmol) was added and stirring was continued at 25° C. for 2 h. The reaction was diluted with ethyl acetate (10 mL) and $H_2O$ (20 mL) then the layers were separated. The aqueous phase was back-extracted with ethyl acetate (10 mL×3) and combined organic layers were dried over $Na_2SO_4$, filtered and concentrated. The crude residue was purified by column chromatography (silica gel, 1-5% methanol/dichloromethane) and further purified by prep-TLC (ethyl acetate) to give racemic 2-(5-(6-fluoro-1H-indol-3-yl)-3-methyl-1,1-dioxidobenzo[d]isothiazol-2(3H)-yl)-N,N-dimethylacetamide (76 mg, 74%) as yellow gum. The enantiomers were separated by SFC to give (−)2-(5-(6-fluoro-1H-indol-3-yl)-3-methyl-1,1-dioxidobenzo[d]isothiazol-2(3H)-yl)-N,N-dimethylacetamide as the first eluting peak (19 mg, 28%) as a white solid. $^1$H NMR (400 MHz, DMSO-$d_6$) δ [ppm] 11.69 (br s, 1H), 8.03-7.78 (m, 5H), 7.27 (dd, J=2.0, 9.8 Hz, 1H), 7.01 (dt, J=2.3, 9.3 Hz, 1H), 4.98 (q, J=6.4 Hz, 1H), 4.31-4.06 (m, 2H), 3.08-2.99 (m, 3H), 2.84 (s, 3H), 1.50 (d, J=6.8 Hz, 3H); LC-MS: m/z 424.1 (M+Na)$^+$; $[α]^{20}_D$ −30.7° (c=2.9 mg/ml, DMSO).

Example 114: (+) 2-(5-(6-fluoro-1H-indol-3-yl)-3-methyl-1,1-dioxidobenzo[d]isothiazol-2(3H)-yl)-N,N-dimethylacetamide

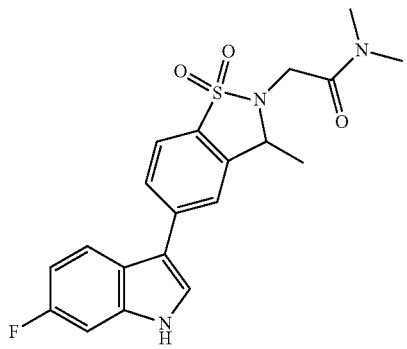 [SMILES: CC1c2cc(-c3c[nH]c4cc(F)ccc34)ccc2S(=O)(=O)N1CC(=O)N(C)C]

The title compound was obtained as the second eluting peak from the chiral separation described in Example 113 (10 mg, 15%) as a white solid. $^1$H NMR (400 MHz, DMSO-$d_6$) δ [ppm] 11.69 (br s, 1H), 8.00-7.82 (m, 5H), 7.27 (dd, J=2.0, 9.8 Hz, 1H), 7.01 (dt, J=2.3, 9.3 Hz, 1H), 4.96 (q, J=6.4 Hz, 1H), 4.31-4.06 (m, 2H), 3.08-2.99 (m, 3H), 2.84 (s, 3H), 1.54 (d, J=6.8 Hz, 3H); LCMS: m/z 424.0 (M+Na)$^+$; $[α]^{20}_D$ +21.9° (c=2.55 mg/ml, DMSO).

Example 115: (+) 2-(5-(6-fluoroindolin-3-yl)-3-methyl-1,1-dioxidobenzo[d]isothiazol-2(3H)-yl) acetamide

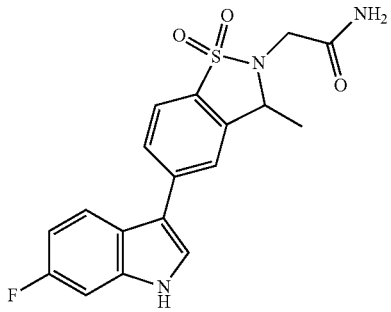 [SMILES: CC1c2cc(-c3c[nH]c4cc(F)ccc34)ccc2S(=O)(=O)N1CC(N)=O]

A light green solution of 2-(5-(6-fluoro-1H-indol-3-yl)-3-methyl-1,1-dioxidobenzo[d]isothiazol-2(3H)-yl)acetic acid (300 mg, 0.30 mmol), NH$_4$Cl solid (32 mg, 0.59 mmol) and DIPEA (153 mg, 1.19 mmol) in dry DMF (5 mL) was stirred at 25° C. for 3 min then HATU (169 mg, 0.445 mmol) was added. The reaction was stirred at 25° C. for 3 h then diluted with ethyl acetate (10 mL) and H$_2$O (20 mL). The layers were separated and the aqueous phase was back-extracted with ethyl acetate (10 mL×3). The combined organic layers were dried over Na$_2$SO$_4$, filtered and concentrated. The crude residue was purified by column chromatography (silica gel, 50-100% petroleum ether/ethyl acetate) to give the racemic product. The enantiomers were separated by prep-chiral SFC to give 2-(5-(6-fluoro-1H-indol-3-yl)-3-methyl-1,1-dioxidobenzo[d]isothiazol-2(3H)-yl)acetamide as the first eluting peak (17 mg, 28%) as a white solid. $^1$H NMR (400 MHz, DMSO-$d_6$) δ [ppm] 11.70 (br s, 1H), 7.99-7.83 (m, 5H), 7.45 (br s, 1H), 7.33-7.21 (m, 2H), 7.07-6.96 (m, 1H), 4.96 (q, J=6.3 Hz, 1H), 3.94-3.81 (m, 2H), 1.54 (d, J=6.3 Hz, 3H); LCMS: m/z 396.1 (M+Na)$^+$, $[α]^{20}_D$ +12.2° (c=2.45 mg/ml, DMSO).

Example 116: (−)-2-(5-(6-fluoroindolin-3-yl)-3-methyl-1,1-dioxidobenzo[d]isothiazol-2(3H)-yl) acetamide

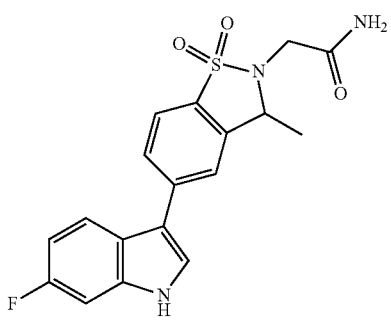 [SMILES: CC1c2cc(-c3c[nH]c4cc(F)ccc34)ccc2S(=O)(=O)N1CC(N)=O]

The title compound was obtained as the second eluting peak from the chiral separation described in Example 115 (18 mg, 30%) as a white solid. $^1$H NMR (400 MHz, DMSO-$d_6$) δ [ppm] 11.69 (br s, 1H), 8.00-7.82 (m, 5H), 7.44 (br s, 1H), 7.34-7.19 (m, 2H), 7.01 (t, J=8.9 Hz, 1H), 4.96 (q, J=6.0 Hz, 1H), 3.95-3.80 (m, 2H), 1.54 (d, J=6.3 Hz, 3H); LCMS: m/z 396.1 (M+Na)$^+$, $[α]^{20}_D$ −13.6° (c=2.55 mg/ml, DMSO).

Example 117: (−)-5-(6-fluoro-1H-indol-3-yl)-3-methyl-2-(2-morpholinoethyl)-2,3-dihydrobenzo[d] isothiazole 1,1-dioxide

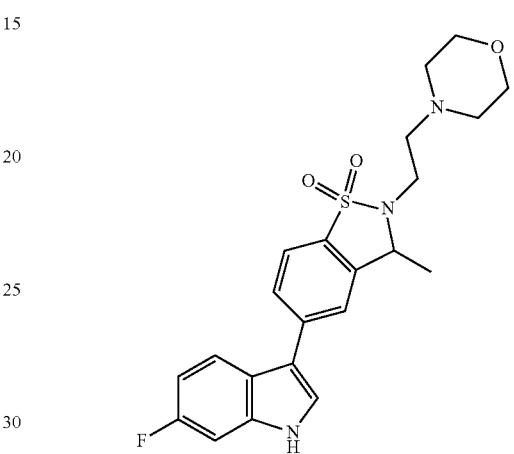

Step 1: 2-chloro-1-morpholinoethanone

To a solution of 2-chloroacetyl chloride (1.0 g, 8.8 mmol) and morpholine (771 mg, 8.85 mmol) in anhydrous dichloromethane (10 mL) was added triethylamine (1.34 g, 13.3 mmol). The reaction was stirred at 25° C. for 1 h then concentrated and purified by column chromatography (silica gel, 30% ethyl acetate/petroleum ether) to give 2-chloro-1-morpholinoethanone (1.1 g, 96%) as yellow oil. $^1$H NMR (400 MHz, CDCl$_3$) δ [ppm] 4.07 (s, 2H), 3.72 (td, J=4.9, 10.0 Hz, 4H), 3.67-3.60 (m, 2H), 3.59-3.48 (m, 2H).

Step 2: 2-(5-bromo-3-methyl-1,1-dioxidobenzo[d] isothiazol-2(3H)-yl)-1-morpholinoethanone A solution of 5-bromo-3-methyl-2,3-dihydrobenzo[d]isothiazole 1,1-dioxide (300 mg, 1.14 mmol), 2-chloro-1-morpholinoethanone (225 mg, 1.37 mmol) and K$_2$CO$_3$ (316 mg, 2.29 mmol) in DMSO (5 mL) was stirred at 80° C. for 18 h. The resulting suspension was diluted with brine (20 mL) and extracted with ethyl acetate (20 mL×2). The combined organic layers were dried over anhydrous Na$_2$SO$_4$, filtered and concentrated. The crude residue was purified by column chromatography (silica gel, 50-100% ethyl acetate/petroleum ether) to give 2-(5-bromo-3-methyl-1,1-dioxidobenzo [d]isothiazol-2(3H)-yl)-1-morpholinoethanone (270 mg, 61% yield) as yellow oil.

Step 3: 5-bromo-3-methyl-2-(2-morpholinoethyl)-2,3-dihydrobenzo-[d]isothiazole 1,1-dioxide To a solution of 2-(5-bromo-3-methyl-1,1-dioxidobenzo [d]isothiazol-2(3H)-yl)-1-morpholinoethanone (270 mg, 0.694 mmol) in anhydrous THF (10 mL) was added BH$_3$-

THF (2.77 mL, 2.77 mmol). The reaction was stirred at 30° C. for 48 h then additional BH₃-THF (2.77 mL, 2.77 mmol) was added and stirring was continued at 70° C. for 16 h. The reaction was quenched with 2 N HCl and stirred at 40° C. for 1 hr then diluted with water (10 mL) and neutralized to pH 7 with solid NaHCO₃. The mixture was extracted with ethyl acetate (20 mL×2) and the combined organic layers were washed with brine (20 mL), dried over anhydrous Na₂SO₄, filtered and concentrated. The crude residue was purified by column chromatography (silica gel, ethyl acetate) to give 5-bromo-3-methyl-2-(2-morpholinoethyl)-2,3-dihydrobenzo[d]isothiazole 1,1-dioxide (250 mg, 96%) as yellow oil.

Step 4: tert-butyl 6-fluoro-3-(3-methyl-2-(2-morpholinoethyl)-1,1-dioxido-2,3-dihydrobenzo[d]isothiazol-5-yl)-1H-indole-1-carboxylate A red suspension of 5-bromo-3-methyl-2-(2-morpholinoethyl)-2,3-dihydrobenzo[d]isothiazole 1,1-dioxide (250 mg, 0.666 mmol), tert-butyl 6-fluoro-3-(4,4,5,5-tetramethyl-1,3,2-dioxaborolan-2-yl)-1H-indole-1-carboxylate (361 mg, 0.799 mmol), PdCl₂(dppf) (39 mg, 0.05 mmol) and K₃PO₄ (226 mg, 1.07 mmol) in dioxane (8 mL) and H₂O (2 mL) was stirred at 80° C. under a N₂ atmosphere for 2 h. The resulting mixture was diluted with water (15 mL) and extracted with ethyl acetate (20 mL×3). The combined organic layers were washed with brine (15 mL) then dried over anhydrous Na₂SO₄, filtered and concentrated. The crude residue was purified by column chromatography (silica gel, 80% ethyl acetate/petroleum ether) to give tert-butyl 6-fluoro-3-(3-methyl-2-(2-morpholinoethyl)-1,1-dioxido-2,3-dihydrobenzo[d]isothiazol-5-yl)-1H-indole-1-carboxylate (180 mg, 64%) as yellow oil.

Step 5: (−)-5-(6-fluoro-1H-indol-3-yl)-3-methyl-2-(2-morpholinoethyl)-2,3-dihydrobenzo[d]isothiazole 1,1-dioxide To a yellow solution of tert-butyl 6-fluoro-3-(3-methyl-2-(2-morpholinoethyl)-1,1-dioxido-2,3-dihydrobenzo[d]isothiazol-5-yl)-1H-indole-1-carboxylate (180 mg, 0.340 mmol) in dichloromethane (8 mL) was added trifluoroacetic acid (2 mL). The reaction was stirred at 25° C. for 1 h then concentrated and neutralized to pH 7 with NaHCO₃ (sat). The mixture was extracted with ethyl acetate (30 mL×2) and the combined organic layers were washed with brine (20 mL), dried over anhydrous Na₂SO₄, filtered and concentrated. The crude residue was purified by column chromatography (silica gel, 3% methanol/dichloromethane) to give the racemic product (130 mg) as yellow oil. The enantiomers were separated by prep-chiral SFC to give (−)-5-(6-fluoro-1H-indol-3-yl)-3-methyl-2-(2-morpholinoethyl)-2,3-dihydrobenzo[d]isothiazole 1,1-dioxide as the first eluting peak (40 mg, 27%) as an off-white solid. ¹H NMR (400 MHz, DMSO-d₆) δ [ppm] 11.68 (br s, 1H), 7.99-7.79 (m, 5H), 7.27 (dd, J=2.5, 9.8 Hz, 1H), 7.01 (dt, J=2.4, 9.2 Hz, 1H), 4.78 (q, J=6.4 Hz, 1H), 3.58 (t, J=4.6 Hz, 4H), 3.38-3.31 (m, 2H), 2.73-2.55 (m, 2H), 2.46 (d, J=5.8 Hz, 4H), 1.55 (d, J=6.5 Hz, 3H); LC-MS: m/z, 430.1 (M+H)⁺, [α]²⁰_D −3.6° (c=1.1 mg/mL, methanol).

Example 118: (+)-5-(6-fluoro-1H-indol-3-yl)-3-methyl-2-(2-morpholinoethyl)-2,3-dihydrobenzo[d]isothiazole 1,1-dioxide

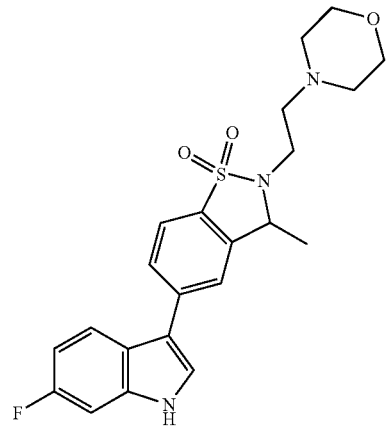 [SMILES: CC1c2cc(-c3c[nH]c4cc(F)ccc34)ccc2S(=O)(=O)N1CCN1CCOCC1]

The title compound was obtained as the second eluting peak from the chiral separation described in Example 117 (45 mg, 31%) as an off-white solid. ¹H NMR (400 MHz, DMSO-d₆) δ [ppm] 11.69 (br s, 1H), 8.02-7.79 (m, 5H), 7.27 (d, J=9.8 Hz, 1H), 7.01 (t, J=9.0 Hz, 1H), 4.78 (d, J=6.3 Hz, 1H), 3.58 (br s, 4H), 3.35-3.26 (m, 2H), 2.70-2.55 (m, 2H), 2.49-2.37 (m, 4H), 1.55 (d, J=6.0 Hz, 3H); LC-MS: m/z 430.0 (M+H)⁺, [α]²⁰_D +4.6° (c=1.3 mg/mL, methanol).

Example 119: (−)-4-(-5-(6-fluoro-1H-indol-3-yl)-3-methyl-1,1-dioxidobenzo[d]isothiazol-2(3H)-yl) piperidin-2-one

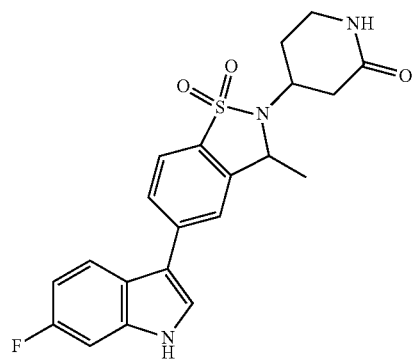

Step 1: 4-(5-bromo-3-methyl-1,1-dioxidobenzo[d]isothiazol-2(3H)-yl) piperidin-2-one To a solution of 5,6-dihydropyridin-2(1H)-one (500 mg, 5.15 mmol) in methanol (15 ml) was added 5-bromo-3-methyl-2,3-dihydrobenzo[d]isothiazole 1,1-dioxide (2.7 g, 10 mmol) and Cs₂CO₃ (1.68 g, 5.15 mmol). The reaction was stirred at 55° C. for 2 days then concentrated. The crude product was purified by column chromatography (silica gel, ethyl acetate/methanol=1/0-20/1) to give the title compound (475 mg, 13%) as yellow oil.

Step 2: tert-butyl 6-fluoro-3-(3-methyl-1,1-dioxido-2-(2-oxopiperidin-4-yl)-2,3-dihydrobenzo[d]isothiazol-5-yl)-1H-indole-1-carboxylate To a suspension of 4-(5-bromo-3-methyl-1,1-dioxido-benzo[d]isothiazol-2(3H)-yl)piperidin-2-one (475 mg, 1.32 mmol), tert-butyl 6-fluoro-3-(4,4,5,5-tetramethyl-1,3,2-dioxaborolan-2-yl)-1H-indole-1-carboxylate (637 mg, 1.59 mmol) and $Cs_2CO_3$ (862 mg, 0.334 mmol) in dioxane (10 ml) and $H_2O$ (3 ml) was added $PdCl_2$(dppf) (96.7 mg, 0.132 mmol). The reaction was stirred at 85° C. under a $N_2$ atmosphere for 1.5 h then concentrated and purified by column chromatography (silica gel, ethyl acetate/methanol=1/0-10/1) to give the title compound (338 mg, 14%) as brown oil.

Step 3: (−)-4-(-5-(6-fluoro-1H-indol-3-yl)-3-methyl-1,1-dioxidobenzo[d]isothiazol-2(3H)-yl)piperidin-2-one A solution of tert-butyl 6-fluoro-3-(3-methyl-1,1-dioxido-2-(2-oxopiperidin-4-yl)-2,3-dihydrobenzo[d]isothiazol-5-yl)-1H-indole-1-carboxylate (235 mg, 0458 mmol) in HCl/methanol (20 ml, 4M) was stirred 20° C. for 6 h. The reaction was concentrated and the mixture of diastereomers was separated by prep-chiral SFC. The title compound was obtained as the first eluting peak (25 mg, 13.2%) as a white solid. $^1$H NMR (400 MHz, MeOD) δ [ppm] 7.91-7.85 (m, 2H), 7.80 (s, 1H), 7.75 (d, J=8.3 Hz, 1H), 7.68 (s, 1H), 7.16 (dd, J=2.3, 9.5 Hz, 1H), 6.95 (dt, J=2.4, 9.2 Hz, 1H), 4.96-4.91 (m, 1H), 4.17-4.05 (m, 1H), 3.48-3.33 (m, 2H), 2.98-2.87 (m, 1H), 2.83-2.70 (m, 1H), 2.33-2.18 (m, 2H), 1.65 (d, J=6.5 Hz, 3H); LC-MS: m/z 435.9 (M+Na)$^+$, $[α]^{20}_D$ −5.6° (c=3.3 mg/ml, methanol).

Example 120: (+)-4-((S)-5-(6-fluoro-1H-indol-3-yl)-3-methyl-1,1-dioxidobenzo[d]isothiazol-2(3H)-yl)piperidin-2-one

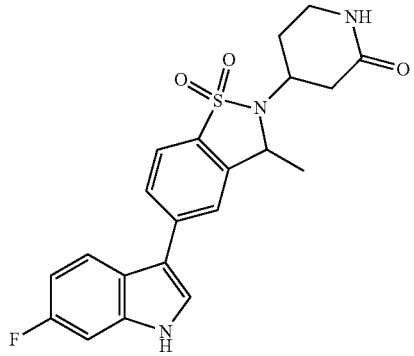 [SMILES: CC1c2cc(-c3c[nH]c4cc(F)ccc34)ccc2S(=O)(=O)N1C1CCNC(=O)C1]

The title compound was obtained as the second eluting peak from the chiral separation described in Example 119 (15 mg, 8%) as a white solid. $^1$H NMR (400 MHz, MeOD) δ [ppm] 7.92-7.85 (m, 2H), 7.81 (s, 1H), 7.76 (d, J=8.3 Hz, 1H), 7.69 (s, 1H), 7.17 (dd, J=2.3, 9.8 Hz, 1H), 6.95 (dt, J=2.3, 9.2 Hz, 1H), 4.94-4.90 (m, 1H), 4.15-4.04 (m, 1H), 3.46-3.34 (m, 2H), 2.93-2.77 (m, 2H), 2.38-2.30 (m, 2H), 1.65 (d, J=6.5 Hz, 3H); LC-MS: m/z 436.0 (M+Na)$^+$, $[α]^{20}_D$ +4.8° (c=4.2 mg/ml, methanol).

Example 121: (+)-4-(-5-(6-fluoro-1H-indol-3-yl)-3-methyl-1,1-dioxidobenzo[d]isothiazol-2(3H)-yl)piperidin-2-one

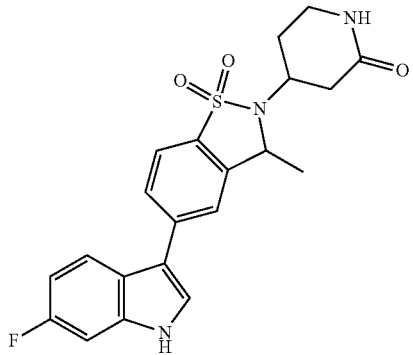 [SMILES: CC1c2cc(-c3c[nH]c4cc(F)ccc34)ccc2S(=O)(=O)N1C1CCNC(=O)C1]

The title compound was obtained as the third eluting peak from the chiral separation described in Example 119 (6 mg, 7%) as a white solid. $^1$H NMR (400 MHz, MeOD) δ [ppm] 7.92-7.85 (m, 2H), 7.81 (s, 1H), 7.76 (d, J=8.0 Hz, 1H), 7.69 (s, 1H), 7.17 (dd, J=2.1, 9.7 Hz, 1H), 6.95 (dt, J=2.4, 9.2 Hz, 1H), 4.91 (d, J=6.3 Hz, 1H), 4.15-4.03 (m, 1H), 3.48-3.34 (m, 2H), 2.92-2.77 (m, 2H), 2.39-2.27 (m, 2H), 1.65 (d, J=6.5 Hz, 3H); LC-MS: m/z 435.9 (M+Na)$^+$, $[α]^{20}_D$ +3.7° (c=3.9 mg/ml, methanol).

Example 122: (−)-4-(-5-(6-fluoro-1H-indol-3-yl)-3-methyl-1,1-dioxidobenzo[d]isothiazol-2(3H)-yl)piperidin-2-one

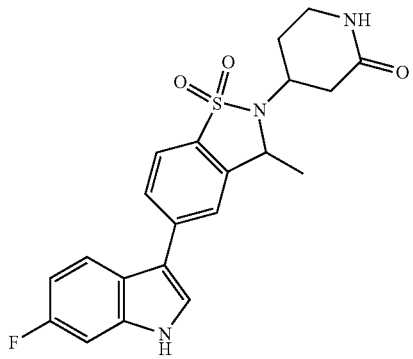 [SMILES: CC1c2cc(-c3c[nH]c4cc(F)ccc34)ccc2S(=O)(=O)N1C1CCNC(=O)C1]

The title compound was obtained as the forth eluting peak from the chiral separation described in Example 119 (36 mg, 45%) as an off-white solid. $^1$H NMR (400 MHz, MeOD) δ [ppm] 7.92-7.85 (m, 2H), 7.81 (s, 1H), 7.76 (d, J=8.0 Hz, 1H), 7.68 (s, 1H), 7.16 (dd, J=2.1, 9.7 Hz, 1H), 6.95 (dt, J=2.4, 9.2 Hz, 1H), 4.96-4.91 (m, 1H), 4.16-4.07 (m, 1H), 3.46-3.34 (m, 2H), 2.96-2.88 (m, 1H), 2.81-2.72 (m, 1H), 2.30-2.23 (m, 2H), 1.65 (d, J=6.5 Hz, 3H), LC-MS: m/z 435.9 (M+23)$^+$, $[α]^{20}_D$ −3.4° (c=3.6 mg/ml, methanol).

Example 123: (+)4-(5-(6-fluoro-1H-indol-3-yl)-3-methyl-1,1-dioxidobenzo[d]isothiazol-2(3H)-yl)pyrrolidin-2-one

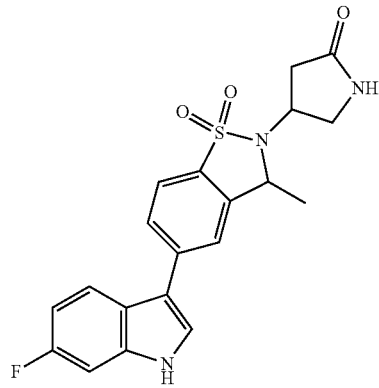 [SMILES: CC1c2cc(-c3c[nH]c4cc(F)ccc34)ccc2S(=O)(=O)N1C1CNC(=O)C1]

Step 1: 5-oxopyrrolidin-3-yl methanesulfonate

To a cooled (ice bath) suspension of 4-hydroxy-2-pyrrolidone (1.0 g, 9.9 mmol) in $CH_2Cl_2$ (33.0 mL) was added $Et_3N$ (1.52 mL, 10.9 mmol) followed by slow addition of MsCl (0.84 mL, 10.9 mmol). The ice bath was removed and the reaction was stirred for 1 h. The crude reaction was concentrated to afford 5-oxopyrrolidin-3-yl methanesulfonate (1.8 g, 100%) as a yellow solid which was used directly in the next step without further purification.

Step 2: 4-azidopyrrolidin-2-one

To a solution of 5-oxopyrrolidin-3-yl methanesulfonate (6.0 g, 33 mmol) in DMF (111 mL) was added $NaN_3$ (6.5 g, 100 mmol). The reaction was heated at 60° C. for 18 h then cooled and diluted with EtOAc (400 mL). The solution was washed $NaHCO_3$ (sat) and further extracted with EtOAc (200 mL×2). The combined organic layers were washed with brine (200 mL×2) then dried over anhydrous $Na_2SO_4$, filtered and concentrated with some EtOAc remaining. The mixture was diluted with THF (150 mL) and $PPh_3$ (13.1 g, 50.1 mmol, 1.5 eq.) and water (50 mL) were added at 25° C. The reaction was heated at 65° C. for 18 h then concentrated and acidified to pH 1 with 2M HCl. The aqueous phase was washed with $CH_2Cl_2$ (150 mL×3) then concentrated to afford 4-aminopyrrolidin-2-one (959 mg, 21%) as brown gum. $^1$H NMR (400 MHz, DMSO-$d_6$) δ [ppm] 8.43 (br s, 2H), 7.90-7.80 (m, 1H), 3.55 (dd, J=7.0, 11.0 Hz, 1H), 3.47-3.40 (m, 1H), 3.25 (dd, J=3.3, 10.8 Hz, 1H), 2.56 (dd, J=8.3, 17.3 Hz, 1H), 2.21 (dd, J=4.0, 17.1 Hz, 1H).

Step 3: 4-bromo-2-ethyl-N-(5-oxopyrrolidin-3-yl)benzenesulfonamide

To a yellow solution of 4-aminopyrrolidin-2-one (959 mg, 7.02 mmol) in water (1.0 mL) was added THF (34 mL), DIPEA (4.3 mL, 25 mmol) and 4-bromo-2-ethylbenzene-1-sulfonyl chloride (3.9 g, 14 mmol) at 15° C. The reaction was stirred at 15° C. for 4.5 h then diluted with EtOAc (20 mL) and water (10 mL). The layers were separated and the aqueous layer was back-extracted with EtOAc (40 mL×2). The combined organic layers were washed with brine (20 mL×2) and $NaHCO_3$ (sat) (20 mL×1) then dried over $Na_2SO_4$, filtered and concentrated. The crude residue was purified by column chromatography to afford 4-bromo-2-ethyl-N-(5-oxopyrrolidin-3-yl)benzene-sulfonamide (685 mg, 28%) as a yellow solid.

Step 4: 4-bromo-2-(1-bromoethyl)-N-(5-oxopyrrolidin-3-yl)benzenesulfonamide

A yellow suspension of 4-bromo-2-ethyl-N-(5-oxopyrrolidin-3-yl)benzene-sulfonamide (841 mg, 2.42 mmol), NBS (560 mg, 3.15 mmol, 1.3 eq.) and AIBN (199 mg, 1.21 mmol, 0.5 eq.) in $CCl_4$ (48.4 mL) was heated at 70° C. for 3 h. The reaction was concentrated and diluted with EtOAc (20 mL) and water (15 mL). The layers were separated and the aqueous layer was back-extracted with EtOAc (15 mL×2). The combined organic layers were dried over $Na_2SO_4$, filtered and concentrated. The crude residue was purified by column chromatography to afford 4-bromo-2-(1-bromoethyl)-N-(5-oxopyrrolidin-3-yl)benzenesulfonamide (814 mg, 79%) as yellow solid.

Step 5: 4-(5-bromo-3-methyl-1,1-dioxidobenzo[d]isothiazol-2(3H)-yl)pyrrolidin-2-one To a mixture of 4-bromo-2-(1-bromoethyl)-N-(5-oxopyrrolidin-3-yl)benzene-sulfonamide (814 mg, 1.91 mmol) in acetone (35 mL) was added $K_2CO_3$ (528 mg, 3.82 mmol) and water (3.4 mL). The reaction was heated to 50° C. for 15 h then concentrated and purified by column chromatography to afford 4-(5-bromo-3-methyl-1,1-dioxidobenzo[d]isothiazol-2(3H)-yl)pyrrolidin-2-one (470 mg, 71%) as a yellow solid.

Step 6: tert-butyl 6-fluoro-3-(3-methyl-1,1-dioxido-2-(5-oxopyrrolidin-3-yl)-2,3-dihydrobenzo[d]isothiazol-5-yl)-1H-indole-1-carboxylate A mixture of 4-(5-bromo-3-methyl-1,1-dioxidobenzo[d]isothiazol-2(3H)-yl)pyrrolidin-2-one (457 mg, 1.32 mmol), tert-butyl 6-fluoro-3-(4,4,5,5-tetramethyl-1,3,2-dioxaborolan-2-yl)-1H-indole-1-carboxylate (478 mg, 1.32 mmol), $PdCl_2(dppf)$ (99 mg, 0.13 mmol) and $K_3PO_4$ (562 mg, 2.65 mmol) in 1,4-dioxane (13 mL) and water (0.5 mL) was sparged with nitrogen for 60 seconds then stirred at 85° C. for 2 h. The reaction was concentrated and purified by column chromatography to afford tert-butyl 6-fluoro-3-(3-methyl-1,1-dioxido-2-(5-oxopyrrolidin-3-yl)-2,3-dihydrobenzo[d]-isothiazol-5-yl)-1H-indole-1-carboxylate (476 mg, 72%) as yellow gum. $^1$H NMR (400 MHz, DMSO-$d_6$) δ [ppm] 8.13 (s, 1H), 8.02-7.80 (m, 6H), 7.25 (d, J=9.5 Hz, 1H), 4.88 (br s, 1H), 4.47 (br s, 1H), 3.17 (d, J=5.0 Hz, 2H), 2.71-2.56 (m, 2H), 1.66 (s, 9H), 1.58 (br s, 3H); LC-MS: m/z 522.0 (M+Na)$^+$.

Step 7: (+)-4-(5-(6-fluoro-1H-indol-3-yl)-3-methyl-1,1-dioxidobenzo-[d]isothiazol-2(3H)-yl)pyrrolidin-2-one To a cooled (ice bath) solution of tert-butyl 6-fluoro-3-(3-methyl-1,1-dioxido-2-(5-oxopyrrolidin-3-yl)-2,3-dihydrobenzo[d]isothiazol-5-yl)-1H-indole-1-carboxylate (330 mg, 0.66 mmol) in $CH_2Cl_2$ (10.0 mL) was added TFA (4.0 mL). The reaction was stirred at 5° C. for 4 h then concentrated. The crude residue was neutralized with $NaHCO_3$ (sat) and diluted with DCM. The layers were separated and the aqueous layer was back-extracted with $CH_2Cl_2$ (20 mL×2). The combined organic layers were concentrated and purified by column chromatography to afford 4-(5-(6-fluoro-1H-indol-3-yl)-3-methyl-1,1-dioxidobenzo[d]isothiazol-2(3H)-yl)pyrrolidin-2-one (183 mg, 69%) as a mixture of diastereomers. The mixture was separated by prep-chiral SFC to give (+)-4-(5-(6-fluoro-1H-indol-3-yl)-3-methyl-1,1-dioxido-benzo[d]isothiazol-2(3H)-yl)pyrrolidin-2-one as the first eluting peak (30 mg, 16.0%) as a yellow solid. $^1$H NMR (400 MHz, DMSO-d$_6$) δ [ppm] 11.72 (br s, 1H), 7.97-7.89 (m, 4H), 7.86-7.80 (m, 2H), 7.27 (dd, J=2.5, 9.5 Hz, 1H), 7.01 (dt, J=2.5, 9.3 Hz, 1H), 4.86 (q, J=6.2 Hz, 1H), 4.46 (td, J=6.9, 14.3 Hz, 1H), 3.66-3.54 (m, 2H), 2.71-2.62 (m, 1H), 2.55 (d, J=6.5 Hz, 1H), 1.57 (d, J=6.5 Hz, 3H); LC-MS: m/z 421.9 (M+Na)$^+$, [α]$^{20}_D$ +4.62° (c=0.00087 g/mL, MeOH).

Example 124: (−)-4-(5-(6-fluoro-1H-indol-3-yl)-3-methyl-1,1-dioxido-benzo[d]isothiazol-2(3H)-yl)pyrrolidin-2-one

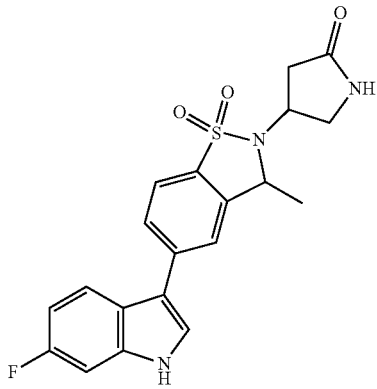 [SMILES: CC1c2cc(-c3c[nH]c4cc(F)ccc34)ccc2S(=O)(=O)N1C1CNC(=O)C1]

The title compound was obtained as the second eluting peak from the chiral separation described for Example 123 (25 mg, 14%) as a yellow solid. $^1$H NMR (400 MHz, DMSO-d$_6$) δ [ppm] 11.70 (br s, 1H), 7.99-7.88 (m, 4H), 7.88-7.80 (m, 2H), 7.27 (dd, J=2.3, 9.8 Hz, 1H), 7.01 (dt, J=2.5, 9.3 Hz, 1H), 4.86 (q, J=6.4 Hz, 1H), 4.46 (td, J=7.1, 14.4 Hz, 1H), 3.66-3.54 (m, 2H), 2.70-2.63 (m, 1H), 2.55 (d, J=6.5 Hz, 1H), 1.57 (d, J=6.5 Hz, 3H); LC-MS: m/z 421.9 (M+Na); [α]$^{20}_D$ −30.00° (c=0.00067 g/mL, MeOH).

Example 125: (−)-4-(5-(6-fluoro-1H-indol-3-yl)-3-methyl-1,1-dioxido-benzo[d]isothiazol-2(3H)-yl)pyrrolidin-2-one

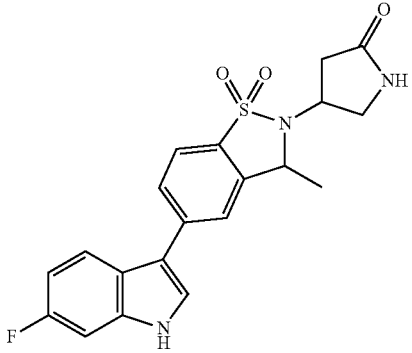 [SMILES: CC1c2cc(-c3c[nH]c4cc(F)ccc34)ccc2S(=O)(=O)N1C1CNC(=O)C1]

The title compound was obtained as the third eluting peak from the chiral separation described for Example 123 (25 mg, 14%) as a yellow solid. $^1$H NMR (400 MHz, DMSO-d$_6$) δ [ppm] 11.72 (br s, 1H), 8.00-7.81 (m, 6H), 7.28 (d, J=8.0 Hz, 1H), 7.02 (dt, J=2.5, 9.3 Hz, 1H), 4.86 (q, J=6.5 Hz, 1H), 4.46 (td, J=7.1, 14.4 Hz, 1H), 3.72-3.65 (m, 1H), 3.48 (dd, J=5.5, 10.0 Hz, 1H), 2.65-2.53 (m, 2H), 1.59 (d, J=6.5 Hz, 3H); LC-MS: m/z 421.9 (M+Na)$^+$, [α]$^{20}_D$ −10.00° (c=0.001 g/mL, MeOH).

Example 126: (+)-4-(5-(6-fluoro-1H-indol-3-yl)-3-methyl-1,1-dioxidobenzo[d]isothiazol-2(3H)-yl)pyrrolidin-2-one

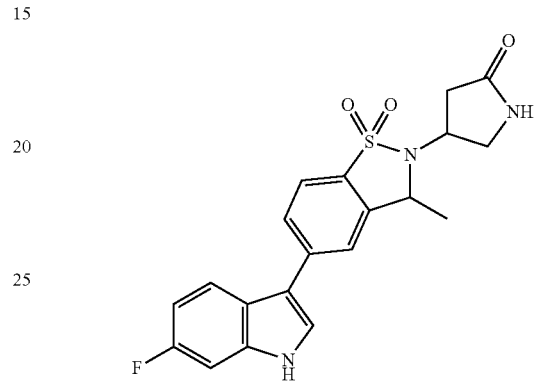

The title compound was obtained as the forth eluting peak from the chiral separation described for Example 123 (35 mg, 19%) as a yellow solid. $^1$H NMR (400 MHz, DMSO-d$_6$) δ [ppm] 11.70 (br s, 1H), 8.00-7.80 (m, 6H), 7.27 (d, J=10.0 Hz, 1H), 7.01 (t, J=9.0 Hz, 1H), 4.93-4.81 (m, 1H), 4.53-4.38 (m, 1H), 3.67-3.53 (m, 2H), 2.70-2.62 (m, 1H), 2.55 (d, J=7.0 Hz, 1H), 1.57 (d, J=6.5 Hz, 3H); LC-MS: m/z 421.9 (M+Na)$^+$, [α]$^{20}_D$ +12.50° (c=0.00080 g/mL, MeOH).

Example 127: (−)-2-(5-(6-fluoro-1H-indol-3-yl)-3-(hydroxymethyl)-1,1-dioxidobenzo[d]isothiazol-2(3H)-yl)-N-methylacetamide

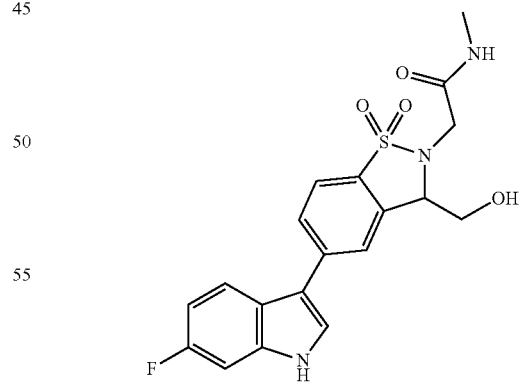

Step 1: tert-butyl 3-(2-(2-ethoxy-2-oxoethyl)-3-(hydroxymethyl)-1,1-dioxido-2,3-dihydrobenzo[d]isothiazol-5-yl)-6-fluoro-1H-indole-1-carboxylate To a suspension of tert-butyl 6-fluoro-3-(3-(hydroxymethyl)-1,1-dioxido-2,3-dihydrobenzo[d]isothiazol-5-yl)-1H- indole-1-carboxylate (Example 112, 500 mg, 0.462 mmol) and K$_2$CO$_3$ (192 mg, 1.39 mmol) in DMF (5 mL) was added dropwise ethyl 2-bromoacetate (232 mg, 1.39 mmol). The reaction was stirred at room temperature for 15 h then poured into water (50 mL) and extracted with EtOAc (3×10 mL). The combined organic layers were dried over Na$_2$SO$_4$, filtered and concentrated. The crude residue was purified by column chromatography to give tert-butyl 3-(2-(2-ethoxy-2-oxoethyl)-3-(hydroxymethyl)-1,1-dioxido-2,3-dihydrobenzo[d]isothiazol-5-yl)-6-fluoro-1H-indole-1-carboxylate (450 mg, 78%) as yellow gum.

Step 2

A solution of tert-butyl 3-(2-(2-ethoxy-2-oxoethyl)-3-(hydroxymethyl)-1,1-dioxido-2,3-dihydrobenzo[d]isothiazol-5-yl)-6-fluoro-1H-indole-1-carboxylate (100 mg, 0.193 mmol) (Step 1) in MeNH$_2$/EtOH (30%, 5 mL) was stirred at room temperature for 16 h. The reaction was concentrated and purified by column chromatography to give the title compound as a racemic mixture. The enantiomers were separated by prep-chiral SFC to give (−)2-(5-(6-fluoro-1H-indol-3-yl)-3-(hydroxymethyl)-1,1-dioxidobenzo[d]isothiazol-2 (3H)-yl)-N-methylacetamide as the first eluting peak (28 mg, 18%) as white solid. $^1$H NMR (400 MHz, DMSO-d$_6$) δ [ppm] 11.70 (br s, 1H), 7.85-80.6 (m, 6H), 7.28 (dd, J=9.91, 2.38 Hz, 1H), 7.02 (td, J=9.22, 2.38 Hz, 1H), 5.25-5.40 (m, 1H), 4.85 (t, J=4.14 Hz, 1H), 3.77-4.14 (m, 4H), 2.59-2.74 (m, 3H); LCMS: m/z 404.0 (M+H)$^+$, [α]$^{20}_D$ −4.54° (c=0.0022 g/mL, DMSO).

Example 128: (+)-2-(5-(6-fluoro-1H-indol-3-yl)-3-(hydroxymethyl)-1,1-dioxidobenzo[d]isothiazol-2 (3H)-yl)-N-methylacetamide

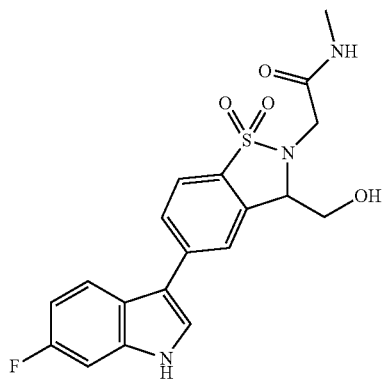 [SMILES: CNC(=O)CN1C(CO)c2cc(-c3c[nH]c4cc(F)ccc34)ccc2S1(=O)=O]

The title compound was obtained as the second eluting peak from the chiral separation described in Example 127 (33 mg, 21%) as white solid. $^1$H NMR (400 MHz, DMSO-d$_6$) δ [ppm] 11.70 (br s, 1H), 7.85-80.6 (m, 6H), 7.28 (dd, J=9.91, 2.38 Hz, 1H), 7.02 (td, J=9.22, 2.38 Hz, 1H), 5.25-5.40 (m, 1H), 4.85 (t, J=4.14 Hz, 1H), 3.77-4.14 (m, 4H), 2.59-2.74 (m, 3H); LCMS: m/z 404.1 (M+H)$^+$, [α]$^{20}_D$ +7.42° (c=0.0035 g/mL, DMSO).

Example 129: (−)-5-(6-fluoro-1H-indol-3-yl)-3-(hydroxymethyl)-2-((1-methyl-1H-1,2,4-triazol-3-yl)methyl)-2,3-dihydrobenzo[d]isothiazole 1,1-dioxide

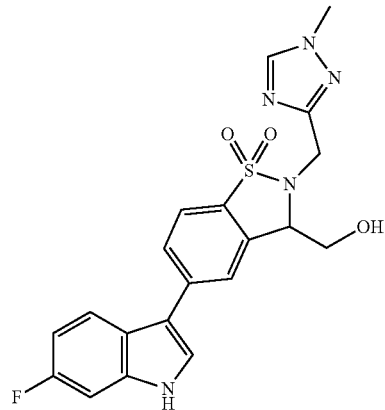 [SMILES: Cn1cnc(CN2C(CO)c3cc(-c4c[nH]c5cc(F)ccc45)ccc3S2(=O)=O)n1]

Step 1: (1-methyl-1H-1,2,4-triazol-3-yl)methyl methanesulfonate

To a cooled (ice bath) solution of (1-methyl-1H-1,2,4-triazol-3-yl)methanol (400 mg, 3.54 mmol) and DIEA (0.98 mL, 7.1 mmol) in CH$_2$Cl$_2$ (35 mL) was added MsCl (0.41 mL, 5.3 mmol). The reaction was stirred at room temperature for 3 h then quenched with NaHCO$_3$ (sat) (20 mL). The layers were separated and the aqueous layer was back-extracted with CH$_2$Cl$_2$ (15 mL×2). The combined organic layers were washed with brine (20 mL×2) then dried over anhydrous Na$_2$SO$_4$, filtered and concentrated to give (1-methyl-1H-1,2,4-triazol-3-yl)methyl methanesulfonate (650 mg, 96%) as yellow oil. $^1$H NMR (400 MHz, CDCl$_3$) δ [ppm] 8.05 (s, 1H), 5.29 (s, 2H), 3.93 (s, 3H), 3.09 (s, 3H).

Step 2: tert-butyl 6-fluoro-3-(3-(hydroxymethyl)-2-((1-methyl-1H-1,2,4-triazol-3-yl)methyl)-1,1-dioxido-2,3-dihydrobenzo[d]isothiazol-5-yl)-1H-indole-1-carboxylate A mixture of tert-butyl 6-fluoro-3-(3-(hydroxymethyl)-1,1-dioxido-2,3-dihydrobenzo[d]isothiazol-5-yl)-1H-indole-1-carboxylate (200 mg, 0.46 mmol), (1-methyl-1H-1,2,4-triazol-3-yl)methyl methanesulfonate (133 mg, 0.69 mmol) and K$_2$CO$_3$ (128 mg, 0.92 mmol) in DMF (2.3 mL) was sparged with nitrogen for seconds then heated at 70° C. for 12 h. The reaction was diluted with EtOAc (10 mL) and water (10 mL) and the layers were separated. The aqueous layer was back-extracted with EtOAc (10 mL×2) and the combined organic layers were washed with brine (10 mL×2) then dried over anhydrous Na$_2$SO$_4$, filtered and concentrated. The crude residue was purified by column chromatography to afford tert-butyl 6-fluoro-3-(3-(hydroxymethyl)-2-((1-methyl-1H-1,2,4-triazol-3-yl)methyl)-1,1-dioxido-2,3-dihydrobenzo[d]isothiazol-5-yl)-1H-indole-1-carboxylate (196 mg, 80%) as yellow gum.

Step 3: (−)-5-(6-fluoro-1H-indol-3-yl)-3-(hydroxymethyl)-2-((1-methyl-1H-1,2,4-triazol-3-yl)methyl)-2,3-dihydrobenzo[d]isothiazole 1,1-dioxide To a solution of tert-butyl 6-fluoro-3-(3-(hydroxymethyl)-2-((1-methyl-1H-1,2,4-triazol-3-yl)methyl)-1,1-dioxido-2, 3-dihydrobenzo[d]isothiazol-5-yl)-1H-indole-1-carboxylate (196 mg, 0.37 mmol) in EtOH (5 mL) and CH$_2$Cl$_2$ (2 mL) was added MeNH$_2$/EtOH (25%, 5.0 mL, 32 mmol). The reaction was stirred at 15° C. for 15 h then concentrated and purified by column chromatography to afford 5-(6-fluoro-1H-indol-3-yl)-3-(hydroxymethyl)-2-((1-methyl-1H-1,2,4-triazol-3-yl)methyl)-2,3-dihydrobenzo[d]isothiazole 1,1-dioxide (75 mg, 47%) as racemic mixture. The enantiomers were separated by prep-chiral SFC to give (−)-5-(6-fluoro-1H-indol-3-yl)-3-(hydroxymethyl)-2-((1-methyl-1H-1,2,4-triazol-3-yl) methyl)-2,3-dihydrobenzo[d]isothiazole 1,1-dioxide as the first eluting peak (15 mg, 20%) as a white solid. $^1$H NMR (400 MHz, DMSO-d$_6$) δ [ppm] 11.72-11.65 (m, 1H), 8.47 (s, 1H), 7.99-7.82 (m, 5H), 7.27 (dd, J=2.3, 9.8 Hz, 1H), 7.01 (dt, J=2.5, 9.3 Hz, 1H), 5.35 (t, J=6.0 Hz, 1H), 4.85 (t, J=4.0 Hz, 1H), 4.57 (q, J=16.2 Hz, 2H), 4.00-3.86 (m, 2H), 3.85 (s, 3H); LC-MS: m/z 427.9 (M+H)$^+$, [α]$^{20}_D$ −100.91° (c=0.00073 g/mL, MeOH).

Example 130: (+)-5-(6-fluoro-1H-indol-3-yl)-3-(hydroxymethyl)-2-((1-methyl-1H-1,2,4-triazol-3-yl)methyl)-2,3-dihydrobenzo[d]isothiazole 1,1-dioxide

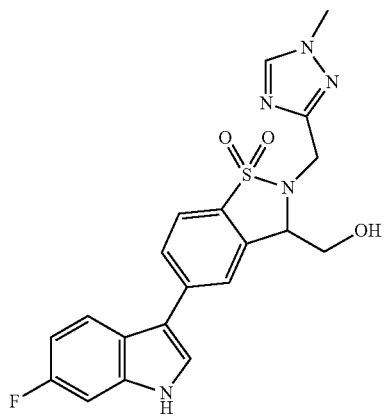 [SMILES: Cn1cnc(CN2C(CO)c3cc(-c4c[nH]c5cc(F)ccc45)ccc3S2(=O)=O)n1]

The title compound was obtained as the second eluting peak from the chiral separation described for Example 129 (20 mg, 27%) as a white solid. $^1$H NMR (400 MHz, DMSO-d$_6$) δ [ppm] 11.68 (br s, 1H), 8.47 (s, 1H), 8.00-7.81 (m, 5H), 7.27 (d, J=9.5 Hz, 1H), 7.01 (dt, J=2.5, 9.3 Hz, 1H), 5.36 (br s, 1H), 4.85 (t, J=4.0 Hz, 1H), 4.56 (q, J=16.6 Hz, 2H), 4.01-3.86 (m, 2H), 3.86-3.83 (m, 3H); LC-MS: m/z 449.9 (M+Na)$^+$, [α]$^{20}_D$ +27.27° (c=0.00073 g/mL, MeOH).

Example 131: (+)-5-(6-fluoro-1H-indol-3-yl)-2-(2-hydroxyethyl)-3-(hydroxymethyl)-2,3-dihydrobenzo[d]isothiazole 1,1-dioxide

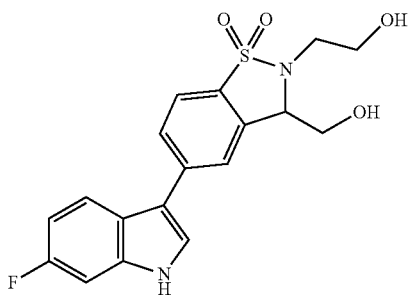 [SMILES: O=S1(=O)c2ccc(-c3c[nH]c4cc(F)ccc34)cc2C(CO)N1CCO]

Step 1: tert-butyl 3-(2-(2-(tert-butoxy)-2-oxoethyl)-3-(hydroxymethyl)-1,1-dioxido-2,3-dihydrobenzo[d]isothiazol-5-yl)-6-fluoro-1H-indole-1-carboxylate To a yellow suspension of tert-butyl 6-fluoro-3-(3-(hydroxymethyl)-1,1-dioxido-2,3-dihydrobenzo[d]isothiazol-5-yl)-1H-indole-1-carboxylate (500 mg, 1.16 mmol) (Example 122) and K$_2$CO$_3$ (192 mg, 1.39 mmol) in DMF (10 mL) was added tert-butyl bromoacetate (271 mg, 1.39 mmol) at 20° C. The reaction was stirred at 25° C. for 2 h then poured into water (20 mL) and extracted with EtOAc (3×10 mL). The combined organic layers were dried over Na$_2$SO$_4$, filtered and concentrated then purified by column chromatography to give tert-butyl 3-(2-(2-(tert-butoxy)-2-oxoethyl)-3-(hydroxymethyl)-1,1-dioxido-2,3-dihydrobenzo [d]isothiazol-5-yl)-6-fluoro-1H-indole-1-carboxylate (540 mg, 85% yield) as yellow gum.

Step 2: 2-(5-(6-fluoro-1H-indol-3-yl)-3-(hydroxymethyl)-1,1-dioxidobenzo[d]isothiazol-2(3H)-yl)acetic acid A solution of tert-butyl 3-(2-(2-(tert-butoxy)-2-oxoethyl)-3-(hydroxymethyl)-1,1-dioxido-2,3-dihydrobenzo[d]isothiazol-5-yl)-6-fluoro-1H-indole-1-carboxylate (540 mg, 0.84 mmol) in TFA (20 mL) was stirred at 30° C. for 18 h then concentrated to give crude 2-(5-(6-fluoro-1H-indol-3-yl)-3-(hydroxymethyl)-1,1-dioxidobenzo[d]isothiazol-2(3H)-yl) acetic acid (360 mg) which was directly used for the next step.

Step 3: (+)-5-(2-((3-fluorophenyl)amino)vinyl)-2-(2-hydroxyethyl)-3-(hydroxymethyl)-2,3-dihydrobenzo [d]isothiazole 1,1-dioxide A solution of crude 2-(5-(6-fluoro-1H-indol-3-yl)-3-(hydroxymethyl)-1,1-dioxidobenzo[d]isothiazol-2(3H)-yl)acetic acid (310 mg, 0.794 mmol) in THF (3 mL) was stirred in an ice bath for 5 min then BH$_3$-DMS (0.5 mL, 10 M, 5 mmol) was slowly added. The reaction was warmed to room temperature and stirred for 4 h. Additional BH$_3$-DMS (1.0 mL, 1.0 mmol) was slowly added and the reaction was stirred at room temperature for 14 hrs. The crude reaction was cooled in an ice bath then slowly quenched with NH$_4$Cl (sat) until gas evolution stopped. The mixture was diluted with EtOAc (20 mL) and NH$_4$Cl (sat) (10 mL) then the layers were separated. The aqueous layer was back-extracted with EtOAc(10 mL×3) then the combined organic layers were dried over Na$_2$SO$_4$, filtered and concentrated. The crude product was purified by prep HPLC to give racemic 5-(6-fluoro-1H-indol-3-yl)-2-(2-hydroxyethyl)-3-(hydroxymethyl)-2,3-dihydrobenzo[d]isothiazole 1,1-dioxide as a white solid. The enantiomers were separated by prep-chiral SFC to give (+)5-(2-((3-fluorophenyl)amino)vinyl)-2-(2-hydroxyethyl)-3-(hydroxymethyl)-2,3-dihydrobenzo [d]isothiazole 1,1-dioxide as the first eluting peak (41 mg, 14%) as a light yellow solid. $^1$H NMR (400 MHz, DMSO-d$_6$) δ [ppm] 11.73-11.63 (m, 1H), 7.91 (s, 5H), 7.31-7.24 (m, 1H), 7.06-6.97 (m, 1H), 5.20-5.13 (m, 1H), 5.03-4.96 (m, 1H), 4.76-4.69 (m, 1H), 3.96-3.81 (m, 2H), 3.70 (d, J=5.8 Hz, 2H), 3.49 (s, 1H), 3.35-3.29 (m, 1H), LCMS: m/z 399.0 (M+Na)$^+$, [α]$^{20}_D$ +2.33° (c=0.0018 g/mL, MeOH).

Example 132: (−)-5-(6-fluoro-1H-indol-3-yl)-2-(2-hydroxyethyl)-3-(hydroxymethyl)-2,3-dihydrobenzo[d]isothiazole 1,1-dioxide

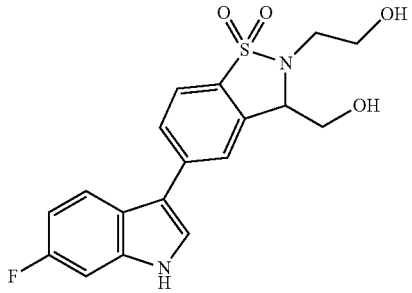

The title compound was obtained as the second eluting peak from the chiral separation described for Example 131 (45 mg, 15%) as a white solid. $^1$H NMR (400 MHz, DMSO-$d_6$) δ [ppm] 11.68 (br s, 1H), 8.02-7.87 (m, 4H), 7.87-7.79 (m, 1H), 7.27 (dd, J=2.1, 9.9 Hz, 1H), 7.01 (dt, J=2.3, 9.2 Hz, 1H), 5.16 (s, 1H), 4.99 (t, J=5.3 Hz, 1H), 4.72 (s, 1H), 3.97-3.81 (m, 2H), 3.75-3.64 (m, 2H), 3.56-3.46 (m, 1H), 3.35-3.28 (m, 1H); LC-MS: m/z for 399.0 (M+Na)$^+$, $[α]^{20}_D$ −1.72° (c=0.0018 g/mL, MeOH).

Example 133: (−)-5-(2-(5-(6-fluoro-1H-indol-3-yl)-3-methyl-1,1-dioxidobenzo[d]isothiazol-2(3H)-yl)ethyl)-1,3,4-oxadiazol-2(3H)-one

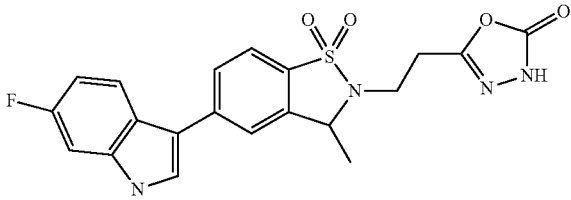 [SMILES: CC1c2cc(-c3c[nH]c4cc(F)ccc34)ccc2S(=O)(=O)N1CCc1n[nH]c(=O)o1]

Step 1: 3-(5-bromo-3-methyl-1,1-dioxidobenzo[d]isothiazol-2(3H)-yl)propanehydrazide A yellow solution of ethyl 3-(5-bromo-3-methyl-1,1-dioxidobenzo[d]-isothiazol-2(3H)-yl)propanoate (600 mg, 1.66 mmol) in EtOH/NH$_2$NH$_2$H$_2$O (10 mL/2 mL) was stirred at 25° C. for 14 h then concentrated to afford 3-(5-bromo-3-methyl-1,1-dioxidobenzo[d]isothiazol-2(3H)-yl)propane hydrazide (570 mg, 99%) as yellow gum.

Step 2: 5-(2-(5-bromo-3-methyl-1,1-dioxidobenzo[d]isothiazol-2(3H)-yl)ethyl)-1,3,4-oxadiazol-2(3H)-one To a solution of 3-(5-bromo-3-methyl-1,1-dioxidobenzo[d]isothiazol-2(3H)-yl)propanehydrazide (500 mg, 1.44 mmol) in DCE (30 mL) was added triphosgene (213 mg, 0.718 mmol) at 0° C. The reaction was heated to 80° C. and stirred for 2 h then diluted with dichloromethane (50 mL) and washed with NaHCO$_3$ (sat) (10 mL). The organic phase was dried over Na$_2$SO$_4$, filtered and concentrated. The crude residue was purified by column chromatography (DCM/methanol=120/1-10/1) to give 5-(2-(5-bromo-3-methyl-1,1-dioxidobenzo[d]isothiazol-2(3H)-yl)ethyl)-1,3,4-oxadiazol-2(3H)-one (484 mg, 90%) as yellow solid.

Step 3: (−)-5-(2-(5-(6-fluoro-1H-indol-3-yl)-3-methyl-1,1-dioxidobenzo[d]isothiazol-2 (3H)-yl) ethyl)-1,3,4-oxadiazol-2(3H)-one To a solution of 5-(2-(5-bromo-3-methyl-1,1-dioxidobenzo[d]isothiazol-2(3H)-yl)ethyl)-1,3,4-oxadiazol-2(3H)-one (552 mg, 1.48 mmol), tert-butyl 6-fluoro-3-(4,4,5,5-tetramethyl-1,3,2-dioxaborolan-2-yl)-1H-indole-1-carboxylate (533 mg, 1.48 mmol) and K$_3$PO$_4$ (626 mg, 2.95 mmol) in dioxane/H$_2$O (12 mL/4 mL) was added Pd(dppf)Cl$_2$ (108 mg, 0.148 mmol) at 28° C. The reaction was stirred at 80° C. for 16 h then diluted with water (8 mL) and extracted with ethyl acetate (15 mL×3). The combined organic layers were dried over anhydrous Na$_2$SO$_4$, filtered and concentrated. The crude residue was purified by column chromatography (silica gel, 50-100% ethyl acetate/petroleum ether) to give racemic 5-(2-(5-(6-fluoro-1H-indol-3-yl)-3-methyl-1,1-dioxidobenzo[d]isothiazol-2(3H)-yl)ethyl)-1,3,4-oxadiazol-2(3H)-one (150 mg, 24%) as a yellow solid. The enantiomers were separated by prep-chiral SFC to give (−)-5-(2-(5-(6-fluoro-1H-indol-3-yl)-3-methyl-1,1-dioxidobenzo[d]isothiazol-2(3H)-yl)ethyl)-1,3,4-oxadiazol-2(3H)-one as the first eluting peak (45 mg. 7%) as a pale yellow solid. $^1$H NMR (400 MHz, MeOD) δ [ppm] 7.90 (d, J=1.3 Hz, 2H), 7.84-7.77 (m, 2H), 7.70 (s, 1H), 7.18 (dd, J=2.4, 9.7 Hz, 1H), 6.97 (dt, J=2.4, 9.2 Hz, 1H), 4.75 (d, J=6.3 Hz, 1H), 3.75 (d, J=2.5 Hz, 2H), 3.08 (t, J=6.9 Hz, 2H), 1.64 (d, J=6.5 Hz, 3H); LC-MS: m/z 428.9 (M+H)$^+$, $[α]^{20}_D$ −4.67° (c=0.0015 g/mL, methanol).

Example 134: (+)-5-(2-(5-(6-fluoro-1H-indol-3-yl)-3-methyl-1,1-dioxidobenzo[d]isothiazol-2 (3H)-yl) ethyl)-1,3,4-oxadiazol-2(3H)-one

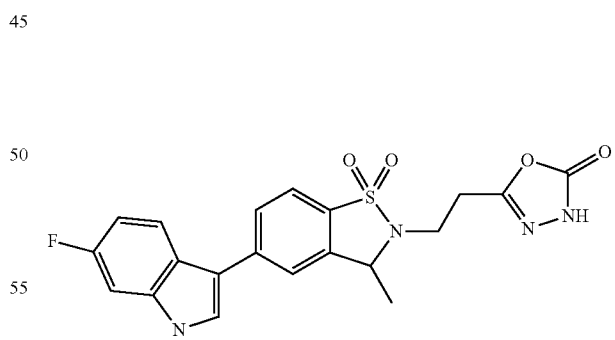

The title compound was obtained as the second eluting peak from the chiral separation described for Example 133 (45 mg, 7%) as a pale yellow solid. $^1$H NMR (400 MHz, MeOD) δ [ppm] 7.94-7.85 (m, 2H), 7.84-7.77 (m, 2H), 7.70 (s, 1H), 7.18 (dd, J=2.4, 9.7 Hz, 1H), 6.97 (dt, J=2.5, 9.2 Hz, 1H), 4.75 (d, J=6.5 Hz, 1H), 3.75 (dt, J=2.6, 6.8 Hz, 2H), 3.07 (t, J=6.9 Hz, 2H), 1.64 (d, J=6.3 Hz, 3H); LC-MS: m/z 428.9 (M+H)$^+$, $[α]^{20}_D$ +5.63° (c=0.0015 g/mL, methanol).

Example 135: 5-(6-fluoro-1H-indol-3-yl)-3-methyl-benzo[d]isothiazole 1,1-dioxide

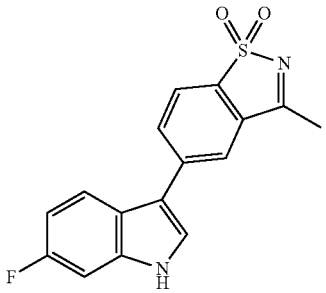 [SMILES: CC1=NS(=O)(=O)c2ccc(-c3c[nH]c4cc(F)ccc34)cc21]

Step 1: 5-bromo-3-methylbenzo[d]isothiazole 1,1-dioxide

To a solution of 5-bromobenzo[d]isothiazol-3(2H)-one 1,1-dioxide (10 g, 38 mmol) in anhydrous THF (191 mL) was added dropwise methylmagnesium bromide (3 M in Et$_2$O, 38.2 mL) at 0° C. The reaction was warmed to room temperature and stirred for 4 h then cooled to 0° C. 6 M HCl (65 mL) was added slowly and the mixture was stirred at room temperature for 30 min then concentrated. The resulting solid was diluted with water (200 mL) and filtered. The filter cake was washed with water (200 mL) then dried to give 5-bromo-3-methylbenzo[d]isothiazole 1,1-dioxide (7.5 g, 76%) as a yellow solid. $^1$H NMR (400 MHz, DMSO-d$_6$) δ [ppm] 8.32 (s, 1H), 8.14-8.07 (m, 2H), 2.71 (s, 3H).

Step 2: 5-(6-fluoro-1H-indol-3-yl)-3-methylbenzo[d]isothiazole 1,1-dioxide

A mixture of 5-bromo-3-methylbenzo[d]isothiazole 1,1-dioxide (200 mg, 0.54 mmol), tert-butyl 6-fluoro-3-(4,4,5,5-tetramethyl-1,3,2-dioxaborolan-2-yl)-1H-indole-1-carboxylate (194 mg, 0.538 mmol), PdCl$_2$(dppf)CH$_2$Cl$_2$ (20 mg, 0.03 mmol) and K$_3$PO$_4$ (228 mg, 1.08 mmol) in 1,4-dioxane (8 mL) and water (2 mL) was sparged with nitrogen for 1 minute. The reaction was stirred at 80° C. for 32 h then diluted with water (2 mL) and stirred for an additional 16 h at 80° C. The mixture was concentrated and purified by column chromatography followed by prep-HPLC purification to give tert-butyl 6-fluoro-3-(3-methyl-1,1-dioxido-benzo[d] isothiazol-5-yl)-1H-indole-1-carboxylate (17 mg, 10% yield) as a yellow solid. $^1$H NMR (400 MHz, acetonitrile-d$_3$) δ [ppm] 9.81 (br s, 1H), 8.12-8.05 (m, 2H), 8.00-7.90 (m, 2H), 7.74 (d, J=2.5 Hz, 1H), 7.28 (dd, J=2.4, 9.9 Hz, 1H), 7.03 (dt, J=2.3, 9.3 Hz, 1H), 2.72 (s, 3H); LC-MS: m/z 315.0 (M+H)$^+$.

Example 136: 5-(6-fluoro-1H-indol-3-yl)-2H-spiro[benzo[d]-isothiazole-3,1'-cyclopropane] 1,1-dioxide

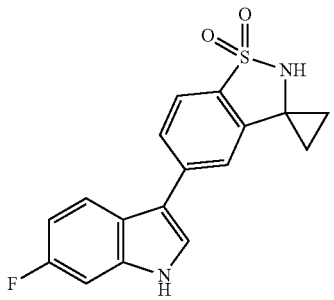 [SMILES: O=S1(=O)NC2(CC2)c2cc(-c3c[nH]c4cc(F)ccc34)ccc21]

Step 1: 1-(3-chlorophenyl)cyclopropanamine

To a solution of 3-bromobenzonitrile (10 g, 55 mmol) and Ti(O-iPr)$_4$ (17.2 g, 18 mL, 60.4 mmol) in THF (100 mL) was added dropwise EtMgBr (40.3 mL, 121 mmol, 3M in THF) at −78° C. The reaction was slowly warmed to room temperature for 1 h then BF$_3$·OEt$_2$ (13.9 mL, 110 mmol) was added. Stirring was continued for 16 h then the reaction was quenched with 1 N HCl (150 mL). The mixture was neutralized with 10% NaOH (200 mL) and extracted with EtOAc (300 mL). The organic solution was used for next step directly.

Step 2: tert-butyl (1-(3-chlorophenyl)cyclopropyl)carbamate

To a solution of 1-(3-bromophenyl)cyclopropanamine (12 g, 55 mmol) in EtOAc (300 mL) was added Boc$_2$O (18 g, 83 mmol) and TEA (17 g, 165 mmol). The reaction was stirred at 10° C. for 16 h then concentrated and purified by column chromatography to give tert-butyl (1-(3-bromophenyl)cyclopropyl)-carbamate (1.8 g, 11%) as a white solid. $^1$H NMR (400 MHz, CDCl$_3$) δ [ppm] 7.39-7.29 (m, 2H), 7.20-7.10 (m, 2H), 5.25 (br s, 1H), 1.52-1.37 (m, 9H), 1.33-1.18 (m, 4H).

Step 3: 2-(1-aminocyclopropyl)-4-chlorobenzene-1-sulfonyl chloride

To a cooled (ice bath) solution of tert-butyl (1-(3-bromophenyl)cyclopropyl)carbamate (1.8 g, 5.8 mmol) in chloroform (20 mL) was added chlorosulfonic acid (4.0 g, 35 mmol). The reaction was stirred in an ice bath for 16 h then quenched with ice-water (50 mL) and filtered. The filter cake was washed with water (15 mL) and DCM (20 mL) to give the by-product 2-(1-aminocyclopropyl)-4-bromobenzene-sulfonic acid (900 mg, 53%) as an off-white solid. The resulting filtrate was extracted with DCM (50 mL×2) and the combined organic layers were dried over Na$_2$SO$_4$, filtered and concentrated to give 2-(1-aminocyclopropyl)-4-bromobenzene-1-sulfonyl chloride (1 g, 56%) as black oil which was used directly for next step without purification. $^1$H NMR (400 MHz, DMSO-d$_6$) δ [ppm] 8.60 (br s, 3H), 7.88 (d, J=8.0 Hz, 1H), 7.62 (d, J=1.5 Hz, 1H), 7.36-7.21 (m, 1H), 1.40-1.17 (m, 4H); LCMS, m/z, 292.1 (M+H)$^+$.

Step 4: 5-chloro-2H-spiro[benzo[d]isothiazole-3,1'-cyclopropane] 1,1-dioxide A mixture of 2-(1-aminocyclopropyl)-4-chlorobenzene-1-sulfonyl chloride (1.0 g, 3.2 mmol) and Na$_2$CO$_3$ (1.0 g, 9.7 mmol) in acetone (30 mL) and water (30 mL) was stirred at 10° C. for 2 h. The reaction was concentrated to remove acetone and the aqueous solution was extracted with EtOAc (50 mL×2). The combined organic layers were washed with brine (10 mL) then dried over anhydrous Na$_2$SO$_4$, filtered and concentrated. The crude residue was purified by column chromatography to give 5-bromo-2H-spiro[benzo [d]isothiazole-3,1'-cyclopropane] 1,1-dioxide (40 mg, 0.3%) as a white solid. $^1$H NMR (400 MHz, CDCl$_3$) δ [ppm] 7.65-7.55 (m, 2H), 7.08 d, J=0.8 Hz, 1H), 5.03 (br s, 1H), 1.64-1.59 (m, 2H), 1.33 (d, J=2.0 Hz, 2H).

Step 5: tert-butyl 3-(1,1-dioxido-2H-spiro[benzo[d]isothiazole-3,1'-cyclopropan]-5-yl)-6-fluoro-1H-indole-1-carboxylate A mixture of 5-bromo-2H-spiro[benzo[d]isothiazole-3,1'-cyclopropane] 1,1-dioxide (40 mg, 0.15 mmol), tert-butyl 6-fluoro-3-(4,4,5,5-tetramethyl-1,3,2-dioxaborolan-2-yl)-1H-indole-1-carboxylate (79 mg, 0.22 mmol), PdCl$_2$(dppf) CH$_2$Cl$_2$ (5 mg, 0.01 mmol), and K$_3$PO$_4$ (62 mg, 0.29 mmol) in 1,4-dioxane (3 mL) and water (1 mL) was sparged with nitrogen for 1 minute. The reaction was stirred at 80° C. for 2 h then diluted with water (5 mL) and extracted with EtOAc (15 mL×2). The combined organic layers were washed with brine (15 mL) then dried over anhydrous Na$_2$SO$_4$, filtered and concentrated. The crude residue was purified by column chromatography to give tert-butyl 3-(1,1-dioxido-2H-spiro [benzo[d]isothiazole-3,1'-cyclopropan]-5-yl)-6-fluoro-1H-indole-1-carboxylate (20 mg, 32%) as yellow oil.

Step 6: 5-(6-fluoro-1H-indol-3-yl)-2H-spiro[benzo[d]-isothiazole-3,1'-cyclopropane] 1,1-dioxide A solution of tert-butyl 3-(1,1-dioxido-2H-spiro[benzo[d]isothiazole-3,1'-cyclopropan]-5-yl)-6-fluoro-1H-indole-1-carboxylate (20 mg, 0.05 mmol) and TFA (2 mL) in DCM (4 mL) was stirred at 5° C. for 1 h. The reaction was concentrated and neutralized with NaHCO$_3$ (sat) (5 mL) then extracted with EtOAc (15 mL×2). The combined organic layers were washed with brine (5 mL) then dried over anhydrous Na$_2$SO$_4$, filtered and concentrated. The crude residue was purified by column chromatography to give 5-(6-fluoro-1H-indol-3-yl)-2H-spiro[benzo[d]isothiazole-3,1'-cyclopropane] 1,1-dioxide (10 mg, 65%) as an off-white solid. $^1$H NMR (400 MHz, acetonitrile-d$_3$) δ [ppm] 9.70 (br s, 1H), 7.86 (dd, J=5.3, 8.8 Hz, 1H), 7.81-7.74 (m, 2H), 7.63 (d, J=2.8 Hz, 1H), 7.31 (s, 1H), 7.25 (dd, J=2.4, 9.9 Hz, 1H), 6.98 (dt, J=2.5, 9.3 Hz, 1H), 6.12 (s, 1H), 1.50-1.46 (m, 2H), 1.44-1.40 (m, 2H); LC-MS: m/z 329.0 (M+H)$^+$.

Example 137: 5-(6-fluoro-1H-indol-3-yl)-3-((methylamino)methyl)-2,3-dihydrobenzo[d]isothiazole 1,1-dioxide

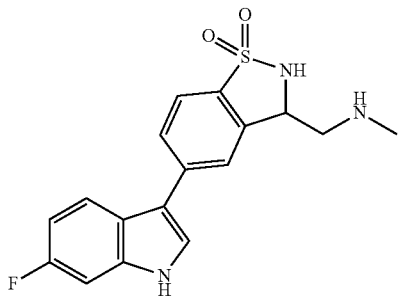 [SMILES: CNCC1NS(=O)(=O)c2ccc(-c3c[nH]c4cc(F)ccc34)cc21]

Step 1: 5-(6-fluoro-1H-indol-3-yl)-N-methyl-2,3-dihydrobenzo[d]thiophene-3-carboxamide 1,1-dioxide A solution of methyl 5-(1-(tert-butoxycarbonyl)-6-fluoro-1H-indol-3-yl)-2,3-dihydrobenzo[d]isothiazole-3-carboxylate 1,1-dioxide (200 mg, 0.43 mmol) in MeNH$_2$/EtOH (10 mL, 27% MeNH$_2$ in EtOH) was stirred at room temperature for 2 h then concentrated and purified by column chromatography to give 5-(6-fluoro-1H-indol-3-yl)-N-methyl-2,3-dihydrobenzo[d]isothiazole-3-carboxamide 1,1-dioxide (140 mg, 89%) as an off-white solid.

Step 2: (−)-5-(6-fluoro-1H-indol-3-yl)-3-((methylamino) methyl)-2,3-dihydrobenzo[d]isothiazole 1,1-dioxide To a solution of 5-(6-fluoro-1H-indol-3-yl)-N-methyl-2,3-dihydrobenzo [d]isothiazole-3-carboxamide 1,1-dioxide (120 mg, 0.334 mmol) in dry THF (12 mL) was added BH$_3$-Me$_2$S (0.334 mL, 3.34 mmol) at 10° C. The reaction was stirred 40° C. for 4 h then 1 M HCl (15 mL) was added dropwise and stirring was continued at 50° C. for 2 h. The crude reaction was neutralized with solid NaHCO$_3$ and extracted with EtOAc (30 mL×2). The combined organic layers were washed with brine (10 mL) then dried over anhydrous Na$_2$SO$_4$, filtered and concentrated to give the title compound as a racemic mixture. The enantiomers were separated by prep-chiral SFC to give (−)-2-(tert-butyl)-5-(6-fluoro-1H-indol-3-yl)-3-((methylamino)methyl)-2,3-dihydrobenzo[d]isothiazole 1,1-dioxide as the first eluting peak (12 mg, 10%) as a white solid. $^1$H NMR (400 MHz, MeOD) δ [ppm] 8.00-7.89 (m, 3H), 7.85 (d, J=8.0 Hz, 1H), 7.73 (s, 1H), 7.18 (dd, J=2.3, 9.5 Hz, 1H), 6.96 (dt, J=2.5, 9.2 Hz, 1H), 5.14-5.07 (m, 1H), 3.64 (d, J=12.5 Hz, 1H), 3.27 (br s, 1H), 2.81 (s, 3H); LC-MS: m/z 346.0 (M+H)$^+$, $[α]^{20}_D$ −74° (c=0.002 g/mL, MeOH).

Example 138: (+)-5-(6-fluoro-1H-indol-3-yl)-3-((methylamino)methyl)-2,3-dihydrobenzo[d]isothiazole 1,1-dioxide

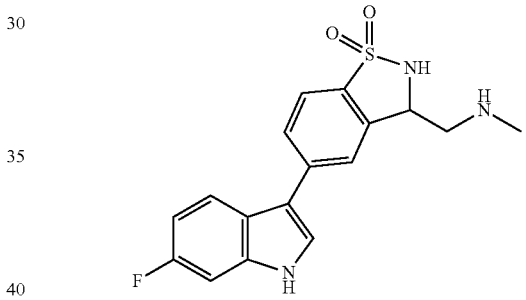

The title compound was obtained as the second eluting peak from the chiral separation described for Example 137 (9 mg, 8% yield) as a white solid. $^1$H NMR (400 MHz, MeOD) δ [ppm] 8.03-7.89 (m, 3H), 7.85 (d, J=8.0 Hz, 1H), 7.75 (s, 1H), 7.20 (dd, J=2.4, 9.7 Hz, 1H), 6.98 (dt, J=2.4, 9.2 Hz, 1H), 5.14 (dd, J=3.5, 9.5 Hz, 1H), 3.67 (dd, J=3.5, 13.1 Hz, 1H), 3.32-3.26 (m, 1H), 2.83 (s, 3H); LC-MS: m/z 346.0 (M+H)$^+$, $[α]^{20}_D$=+60.75° (c=0.004 g/mL, MeOH).

Example 139: (−)-N-((5-(6-fluoro-1H-indol-3-yl)-1,1-dioxido-2,3-dihydrobenzo[d]isothiazol-3-yl) methyl)methanesulfonamide

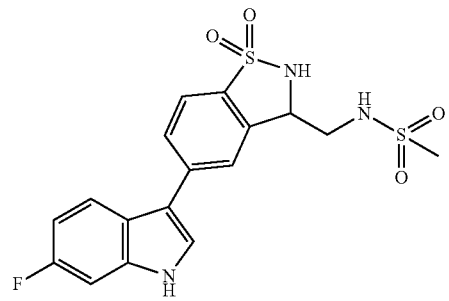

Step 1: chiral N-((2-(tert-butyl)-5-(6-fluoro-1H-indol-3-yl)-1,1-dioxido-2,3-dihydrobenzo[d]isothiazol-3-yl)methyl)methanesulfonamide To a cooled (ice bath) solution of 3-(aminomethyl)-2-(tert-butyl)-5-(6-fluoro-1H-indol-3-yl)-2,3-dihydrobenzo[d]isothiazole 1,1-dioxide (250 mg, 0.645 mmol) and DIPEA (0.213 ml, 1.29 mmol) in DCM (15 ml) was added dropwise MsCl (0.06 ml, 0.62 mmol). The reaction was stirred at 20° C. for 8 h then diluted with water (15 ml). The layers were separated and the organic layer was dried over anhydrous $Na_2SO_4$, filtered and concentrated to give the title compound as a racemic mixture (290 mg, 97%). Racemic N-((2-(tert-butyl)-5-(6-fluoro-1H-indol-3-yl)-1,1-dioxido-2,3-dihydrobenzo[d]isothiazol-3-yl)methyl)methane sulfonamide was purified by prep-chiral SFC to give two enantiomers, peak 1 (146 mg) and peak 2 (146 mg).

Step 2: (−)N-((5-(6-fluoro-1H-indol-3-yl)-1,1-dioxido-2,3-dihydrobenzo[d]isothiazol-3-yl)methyl)methanesulfonamide To a solution of chiral N-((2-(tert-butyl)-5-(6-fluoro-1H-indol-3-yl)-1,1-dioxido-2,3-dihydrobenzo[d]isothiazol-3-yl)methyl)methanesulfonamide (Step 1, Peak 1, 146 mg, 0.314 mmol) in DCM (5 ml) was added HCl/MeOH (20 ml). The reaction was stirred at 30° C. for 16 h then concentrated and purified by prep-HPLC to give (−)-N-((5-(6-fluoro-1H-indol-3-yl)-1,1-dioxido-2,3-dihydrobenzo[d]isothiazol-3-yl) methyl)methanesulfonamide (70 mg, 55%) as a white solid. $^1$H NMR (400 MHz, DMSO-$d_6$) δ [ppm] 11.70 (br s, 1H), 8.05 (d, J=5.3 Hz, 1H), 7.98 (dd, J=5.3, 8.8 Hz, 1H), 7.95-7.89 (m, 3H), 7.85-7.81 (m, 1H), 7.39 (t, J=6.0 Hz, 1H), 7.27 (dd, J=2.4, 9.9 Hz, 1H), 6.99 (dt, J=2.5, 9.3 Hz, 1H), 4.76 (q, J=5.6 Hz, 1H), 3.46-3.40 (m, 1H), 3.34-3.28 (m, 1H), 2.96 (s, 3H); LCMS: m/z 409.8 [M+H]$^+$; [α]$^{20}_D$ −72.3° (c=4.64 mg/ml, DMF).

Example 140: (+)-N-((5-(6-fluoro-1H-indol-3-yl)-1,1-dioxido-2,3-dihydrobenzo[d]isothiazol-3-yl)methyl)methanesulfonamide

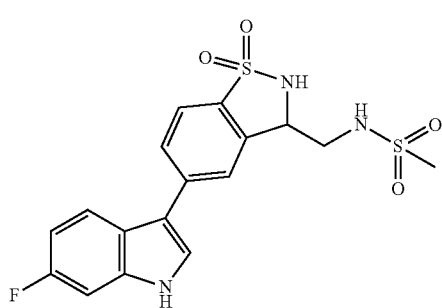 [SMILES: CS(=O)(=O)NCC1NS(=O)(=O)c2ccc(-c3c[nH]c4cc(F)ccc34)cc21]

To a solution of chiral N-((2-(tert-butyl)-5-(6-fluoro-1H-indol-3-yl)-1,1-dioxido-2,3-dihydrobenzo[d]isothiazol-3-yl)methyl)methanesulfonamide (Example 139, Step 1, Peak 2, 146 mg, 0.314 mmol) in DCM (5 ml) was added HCl/MeOH (20 ml). The reaction was stirred at 30° C. for 16 h then concentrated and purified by prep-HPLC to give (+)-N-((5-(6-fluoro-1H-indol-3-yl)-1,1-dioxido-2,3-dihydrobenzo[d]isothiazol-3-yl) methyl)methanesulfonamide (70 mg, 55%) as a white solid. $^1$H NMR (400 MHz, DMSO-$d_6$) δ [ppm] 11.70 (br s, 1H), 8.05 (d, J=5.0 Hz, 1H), 7.99 (dd, J=5.3, 8.8 Hz, 1H), 7.94 (s, 1H), 7.93-7.89 (m, 2H), 7.86-7.82 (m, 1H), 7.39 (t, J=6.1 Hz, 1H), 7.28 (dd, J=2.3, 9.8 Hz, 1H), 7.00 (dt, J=2.4, 9.2 Hz, 1H), 4.77 (q, J=5.9 Hz, 1H), 3.46-3.39 (m, 1H), 3.32 (d, J=7.0 Hz, 1H), 2.99-2.94 (m, 3H); LCMS: m/z 409.8 [M+H]$^+$; [α]$^{20}_D$ +37.3° (c=1.84 mg/ml, DMF).

Example 141: (+)-2-(2,3-dihydroxypropyl)-5-(6-fluoro-1H-indol-3-yl)-3-(hydroxymethyl)-2,3-dihydrobenzo[d]isothiazole 1,1-dioxide

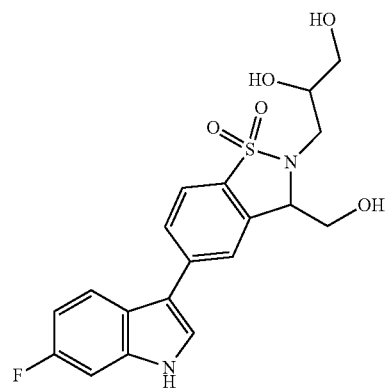 [SMILES: O=S1(=O)c2ccc(-c3c[nH]c4cc(F)ccc34)cc2C(CO)N1CC(O)CO]

Step 1: (5-bromo-1,1-dioxido-2,3-dihydrobenzo[d]isothiazol-3-yl)methyl acetate A solution of (5-bromo-2-(tert-butyl)-1,1-dioxido-2,3-dihydrobenzo[d]isothiazol-3-yl)methyl acetate (1.9 g, 5.1 mmol) in TFA (25 mL) was stirred at 30° C. for 24 h then concentrated and diluted with EtOAc (50 mL). The mixture was washed with NaHCO$_3$ (sat) (10 mL) and brine (10 mL×2) then dried over Na$_2$SO$_4$, filtered and concentrated to give crude 5-bromo-1,1-dioxido-2,3-dihydrobenzo[d]isothiazol-3-yl)methyl acetate (1.70 g, 100%) as yellow gum. $^1$H NMR (400 MHz, CDCl$_3$) δ [ppm] 7.75-7.62 (m, 3H), 5.33 (d, J=4.5 Hz, 1H), 4.98-4.86 (m, 1H), 4.57 (dd, J=4.3, 11.5 Hz, 1H), 4.27-4.21 (m, 1H), 2.14-2.08 (m, 3H).

Step 2: (2-allyl-5-bromo-1,1-dioxido-2,3-dihydrobenzo[d]isothiazol-3-yl)methyl acetate To a suspension of (5-bromo-1,1-dioxido-2,3-dihydrobenzo-[d]isothiazol-3-yl)methyl acetate (800 mg, 2.50 mmol) and K$_2$CO$_3$ (1.0 g, 7.5 mmol) in DMF (8 mL) was added 3-bromoprop-1-ene (363 mg, 3.0 mmol) at room temperature. The reaction was stirred at 25° C. for 1 h then poured into water (10 mL) and extracted with EtOAc (3×15 mL). The combined organic layers were dried over Na$_2$SO$_4$, filtered and concentrated. The crude residue was purified by column chromatography to give (2-allyl-5-bromo-1,1-dioxido-2,3-dihydrobenzo[d]isothiazol-3-yl)methyl acetate (620 mg, 69%) as a yellow gum. $^1$H NMR (400 MHz, CDCl$_3$) δ [ppm] 7.75-7.62 (m, 3H), 6.00-5.85 (m, 1H), 5.42 (s, 1H), 5.37 (s, 1H), 5.32 (d, J=1.0 Hz, 1H), 5.34 (s, 1H), 4.67-4.62 (m, 1H), 4.61-4.54 (m, 1H), 4.30 (d, J=4.5 Hz, 1H), 4.15-4.11 (m, 1H), 4.15-4.07 (m, 1H), 3.95 (dd, J=0.8, 8.0 Hz, 1H), 2.09-2.05 (m, 3H).

Step 3: (5-bromo-1,1-dioxido-2-(oxiran-2-ylmethyl)-2,3-dihydrobenzo[d]isothiazol-3-yl)methyl acetate To a solution of (2-allyl-5-bromo-1,1-dioxido-2,3-dihydrobenzo-[d]isothiazol-3-yl)methyl acetate (420 mg, 1.17 mmol) in DCM (15 mL) was added m-CPBA (947 mg, 4.66 mmol) in two portions. The reaction was stirred at 30° C. for 18 h then diluted with DCM (10 mL) and washed with NaHCO$_3$ (sat) (5 mL), Na$_2$SO$_3$ (5 mL) and brine(5 mL). The organic layer was dried over Na$_2$SO$_4$, filtered and concentrated then purified by column chromatography (0-40% EA/PE) to give (5-bromo-1,1-dioxido-2-(oxiran-2-ylmethyl)-2,3-dihydrobenzo[d]isothiazol-3-yl)methyl acetate (260 mg, 59%) as a white solid.

Step 4: (5-bromo-2-(2,3-dihydroxypropyl)-1,1-dioxido-2,3-dihydrobenzo[d]isothiazol-3-yl)methyl acetate To a solution of (5-bromo-1,1-dioxido-2-(oxiran-2-ylmethyl)-2,3-dihydrobenzo[d]isothiazol-3-yl)methyl acetate (260 mg, 0.55 mmol) in dioxane (4 mL) was added H$_2$SO$_4$ (4 mL) at 15° C. The reaction was heated to 60° C. and stirred for 6 h then quenched with NaHCO$_3$ (sat) (6 mL). The mixture was extracted with EA (15 mL×3) and the combined organic layers were dried over Na$_2$SO$_4$, filtered and concentrated to give the crude 5-bromo-2-(2,3-dihydroxypropyl)-1,1-dioxido-2,3-dihydrobenzo[d]isothiazol-3-yl) methyl acetate (230 mg) as a yellow gum, which was used directly in the next step.

Step 5: tert-butyl 3-(3-(acetoxymethyl)-2-(2,3-dihydroxypropyl)-1,1-dioxido-2,3-dihydrobenzo[d]isothiazol-5-yl)-6-fluoro-1H-indole-1-carboxylate To a solution of tert-butyl 6-fluoro-3-(4,4,5,5-tetramethyl-1,3,2-dioxaborolan-2-yl)-1H-indole-1-carboxylate (211 mg, 0.583 mmol), (5-bromo-2-(2,3-dihydroxypropyl)-1,1-dioxido-2,3-dihydrobenzo-[d]isothiazol-3-yl)methyl acetate (230 mg, 0.583 mmol) and K$_3$PO$_4$ (248 mg, 1.17 mmol) in dioxane/H$_2$O (8 ml/2 mL) was added Pd(dppf)Cl$_2$ (43 mg, 0.06 mmol) at 20° C. The reaction was stirred at 90° C. for 6 h then diluted with H$_2$O (5 mL) and extracted with EtOAc (10 mL×3). The combined organic layers were dried over Na$_2$SO$_4$, filtered and concentrated to give tert-butyl 3-(3-(acetoxymethyl)-2-(2,3-dihydroxypropyl)-1,1-dioxido-2,3-dihydrobenzo[d]isothiazol-5-yl)-6-fluoro-1H-indole-1-carboxylate (376 mg) as yellow oil, which was used directly in the next step.

Step 6: 2-(2,3-dihydroxypropyl)-5-(6-fluoro-1H-indol-3-yl)-3-(hydroxymethyl)-2,3-dihydrobenzo[d] isothiazole 1,1-dioxide A solution of tert-butyl 3-(3-(acetoxymethyl)-2-(2,3-dihydroxypropyl)-1,1-dioxido-2,3-dihydrobenzo[d]isothiazol-5-yl)-6-fluoro-1H-indole-1-carboxylate (320 mg, 0.583 mmol) in MeNH$_2$/EtOH (30%, 10 mL) was stirred in a sealed tube at 60° C. for 4 h. The reaction was concentrated and purified by column chromatography to give the title compound as a mixture of diastereomers. The diastereomers were separated by prep-chiral SFC to give (+)-2-(2, 3-dihydroxypropyl)-5-(6-fluoro-1H-indol-3-yl)-3-(hydroxymethyl)-2,3-dihydrobenzo[d]isothiazole 1,1-dioxide as the first eluting peak (26 mg, 11%) as a brown solid. $^1$H NMR (400 MHz, MeOD) δ [ppm] 7.95-7.85 (m, 3H), 7.81 (s, 1H), 7.68 (s, 1H), 7.16 (dd, J=2.1, 9.7 Hz, 1H), 6.94 (dt, J=2.3, 9.2 Hz, 1H), 4.80 (s, 1H), 4.13-3.97 (m, 3H), 3.74-3.62 (m, 2H), 3.60-3.46 (m, 2H); LCMS: m/z 407.0 (M+H)$^+$, [α]$^{20}_D$ +12° (c=2.0 mg/ml, MeOH).

Example 142: (−)-2-(2,3-dihydroxypropyl)-5-(6-fluoro-1H-indol-3-yl)-3-(hydroxymethyl)-2,3-dihydrobenzo[d]isothiazole 1,1-dioxide

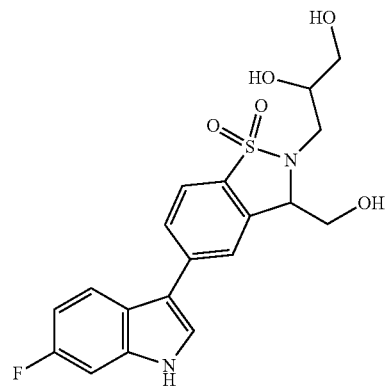 [SMILES: O=S1(=O)c2ccc(-c3c[nH]c4cc(F)ccc34)cc2C(CO)N1CC(O)CO]

The title compound was obtained as the second eluting peak from the chiral separation described for Example 141 (18 mg, 8%) as a yellow solid. $^1$H NMR (400 MHz, MeOD) δ [ppm] 7.94-7.85 (m, 3H), 7.81 (s, 1H), 7.68 (s, 1H), 7.19-7.13 (m, 1H), 6.99-6.90 (m, 1H), 4.69-4.63 (m, 1H), 4.14-4.00 (m, 3H), 3.81 (dd, J=3.5, 14.8 Hz, 1H), 3.68-3.58 (m, 2H), 3.29-3.22 (m, 1H); LCMS: m/z 407.0 (M+H)$^+$, [α]$^{20}_D$ −10° (c=2.2 mg/ml, MeOH).

Example 143: (−)-2-(2,3-dihydroxypropyl)-5-(6-fluoro-1H-indol-3-yl)-3-(hydroxymethyl)-2,3-dihydrobenzo[d]isothiazole 1,1-dioxide

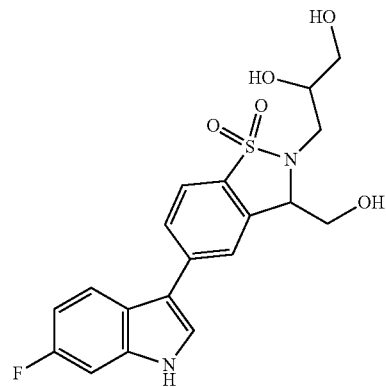 [SMILES: O=S1(=O)c2ccc(-c3c[nH]c4cc(F)ccc34)cc2C(CO)N1CC(O)CO]

The title compound was obtained as the third eluting peak from the chiral separation described for Example 141 (15 mg, 6%) as a gray solid. $^1$H NMR (400 MHz, MeOD) δ [ppm] 7.93-7.86 (m, 3H), 7.80 (d, J=8.0 Hz, 1H), 7.68 (s, 1H), 7.22-7.12 (m, 1H), 6.99-6.89 (m, 1H), 4.80 (t, J=4.1 Hz, 1H), 4.06 (d, J=4.0 Hz, 3H), 3.75-3.61 (m, 2H), 3.60-3.42 (m, 2H); LCMS: m/z 407.0 (M+H)$^+$, [α]$^{20}_D$ −15° (c=5.0 mg/ml, MeOH);

Example 144: (+)-2-(2,3-dihydroxypropyl)-5-(6-fluoro-1H-indol-3-yl)-3-(hydroxymethyl)-2,3-dihydrobenzo[d]isothiazole 1,1-dioxide

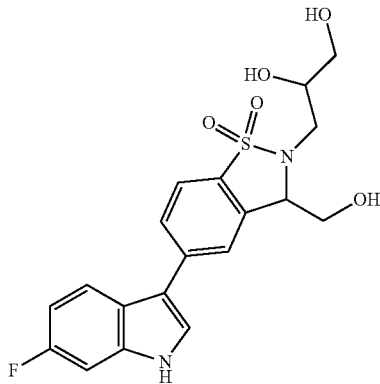 [SMILES: O=S1(=O)c2ccc(-c3c[nH]c4cc(F)ccc34)cc2C(CO)N1CC(O)CO]

The title compound was obtained as the fourth eluting peak from the chiral separation described for Example 141 (20 mg, 8%) as a gray solid. $^1$H NMR (400 MHz, MeOD) δ [ppm] 7.94-7.86 (m, 3H), 7.80 (d, J=8.3 Hz, 1H), 7.68 (s, 1H), 7.16 (dd, J=2.1, 9.7 Hz, 1H), 6.95 (dt, J=2.4, 9.2 Hz, 1H), 4.66 (t, J=4.3 Hz, 1H), 4.11-4.01 (m, 3H), 3.81 (dd, J=3.5, 15.1 Hz, 1H), 3.63 (dd, J=5.1, 11.2 Hz, 2H), 3.29-3.23 (m, 1H), LCMS: m/z 407.0 (M+H)$^+$, [α]$^{20}_D$ +19.5° (c=2.0 mg/ml, MeOH).

Example 145: (−)-2-(5-(6-fluoro-1H-indol-3-yl)-3-methyl-1,1-dioxidobenzo[d]isothiazol-2(3H)-yl)-N-methylpropanamide

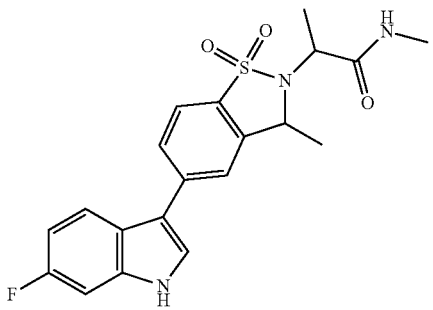 [SMILES: CNC(=O)C(C)N1C(C)c2cc(-c3c[nH]c4cc(F)ccc34)ccc2S1(=O)=O]

Step 1: ethyl 2-(5-bromo-3-methyl-1,1-dioxido-benzo-[d]isothiazol-2(3H)-yl)propanoate To a suspension of 5-bromo-3-methyl-2,3-dihydrobenzo [d]isothiazole 1,1-dioxide (1.2 g, 4.1 mmol) and K$_2$CO$_3$ (1.7 g, 12 mmol) in DMF (20 mL) was added ethyl 2-bromopropanoate (1.1 g, 6.2 mmol). The reaction was stirred for 1 h then diluted with EtOAc (60 mL) and washed with H$_2$O (10 mL×2) and brine (10 mL×2). The organic layer was dried over Na$_2$SO$_4$, filtered and concentrated then purified by column chromatography to give crude ethyl 2-(5-bromo-3-methyl-1,1-dioxidobenzo[d]isothiazol-2(3H)-yl)propanoate (1.2 g, 80%) as a yellow gum. $^1$H NMR (400 MHz, CDCl$_3$) δ [ppm] 7.69-7.61 (m, 2H), 7.54 (s, 1H), 4.85 (d, J=6.8 Hz, 1H), 4.34 (q, J=7.3 Hz, 1H), 4.20 (q, J=7.1 Hz, 2H), 1.74-1.68 (m, 3H), 1.57 (d, J=6.5 Hz, 3H), 1.23 (t, J=7.2 Hz, 3H); LCMS: m/z for 385.9 (M+Na)$^+$.

Step 2: tert-butyl 3-(2-(1-ethoxy-1-oxopropan-2-yl)-3-methyl-1,1-dioxido-2,3-dihydrobenzo[d]isothiazol-5-yl)-6-fluoro-1H-indole-1-carboxylate To a solution of tert-butyl 6-fluoro-3-(4,4,5,5-tetramethyl-1,3,2-dioxaborolan-2-yl)-1H-indole-1-carboxylate (1.2 g, 3.3 mmol), ethyl 2-(5-bromo-3-methyl-1,1-dioxidobenzo[d] isothiazol-2(3H)-yl)propanoate (1.2 g, 3.3 mmol) and K$_3$PO$_4$ (1.4 g, 6.6 mmol) in dioxane/H$_2$O(25 ml/5 mL) was added Pd(dppf)Cl$_2$ (240 mg, 0.328 mmol). The reaction was stirred at 90° C. for 16 h then diluted with H$_2$O (20 mL) and extracted with EtOAc (20 mL×3). The combined organic layers were dried over Na$_2$SO$_4$, filtered and concentrated to give crude tert-butyl 3-(2-(1-ethoxy-1-oxopropan-2-yl)-3-methyl-1,1-dioxido-2,3-dihydrobenzo[d]isothiazol-5-yl)-6-fluoro-1H-indole-1-carboxylate (1.8 g, >100%) as a light yellow oil, which was used directly in the next step.

Step 3: 2-(5-(6-fluoro-1H-indol-3-yl)-3-methyl-1,1-dioxidobenzo[d]isothiazol-2(3H)-yl)-N-methylpropanamide A solution of tert-butyl 3-(2-(1-ethoxy-1-oxopropan-2-yl)-3-methyl-1,1-dioxido-2,3-dihydrobenzo[d]isothiazol-5-yl)-6-fluoro-1H-indole-1-carboxylate (1.7 g, 3.3 mmol) in MeNH$_2$/EtOH(30%, 30 mL) was stirred at 60° C. for 4 h then concentrated. The crude residue was purified by column chromatography to give the title compound as a mixture of diastereomers. The diastereomers were separated by prep-chiral SFC to give (−)-2-(5-(6-fluoro-1H-indol-3-yl)-3-methyl-1,1-dioxidobenzo[d]isothiazol-2(3H)-yl)-N-methylpropanamide as the first eluting peak (106 mg, 8%) as a white solid. $^1$H NMR (400 MHz, DMSO-d$_6$) δ [ppm] 11.71-11.64 (m, 1H), 7.97-7.84 (m, 5H), 7.82-7.76 (m, 1H), 7.30-7.24 (m, 1H), 7.04-6.97 (m, 1H), 5.41-5.33 (m, 1H), 4.38-4.29 (m, 1H), 2.54 (d, J=4.8 Hz, 3H), 1.62-1.48 (m, 6H); LCMS: m/z 402.0 (M+H)$^+$, [α]$^{20}_D$ −13.5° (c=2.0 mg/ml, MeOH).

Example 146: (+)-2-(5-(6-fluoro-1H-indol-3-yl)-3-methyl-1,1-dioxidobenzo[d]isothiazol-2(3H)-yl)-N-methylpropanamide

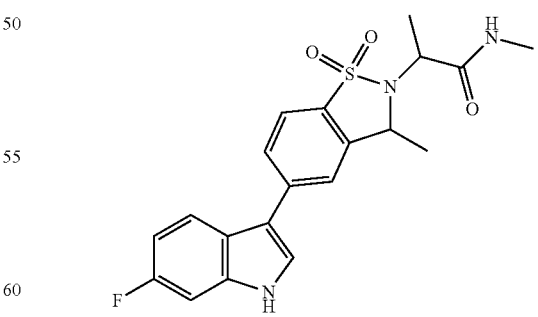

The title compound was obtained as the second eluting peak from the chiral separation described for Example 145 (60 mg, 5%) as a white solid. $^1$H NMR (400 MHz, DMSO-d$_6$) δ [ppm] 11.69 (br s, 1H), 7.98-7.83 (m, 6H), 7.30-7.24 (m, 1H), 7.05-6.98 (m, 1H), 4.94-4.87 (m, 1H), 4.35-4.28

(m, 1H), 2.64 (d, J=4.5 Hz, 3H), 1.50 (d, J=6.5 Hz, 3H), 1.40 (d, J=7.0 Hz, 3H); LCMS: m/z 402.0 (M+H)+, [α]$^{20}_D$ +13.5° (c=2.0 mg/ml, MeOH).

Example 147: 2-(5-(6-fluoro-1H-indol-3-yl)-3-methyl-1,1-dioxidobenzo[d]isothiazol-2(3H)-yl)-N-methylpropanamide

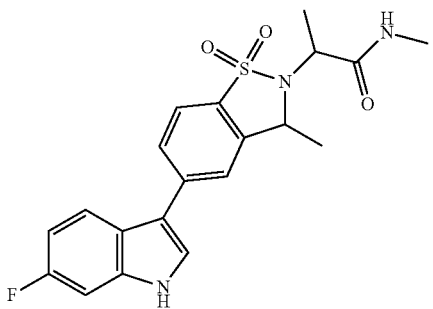 [SMILES: CNC(=O)C(C)N1C(C)c2cc(-c3c[nH]c4cc(F)ccc34)ccc2S1(=O)=O]

The title compound was obtained as the third eluting peak from the chiral separation described for Example 145 (93 mg, 7%) as a white solid. $^1$H NMR (400 MHz, DMSO-d$_6$) δ [ppm] 11.68 (br s, 1H), 7.97-7.85 (m, 5H), 7.82-7.76 (m, 1H), 7.27 (dd, J=2.3, 9.8 Hz, 1H), 7.01 (d, J=2.0 Hz, 1H), 5.37 (d, J=6.8 Hz, 1H), 4.34 (d, J=7.3 Hz, 1H), 2.54 (d, J=4.5 Hz, 3H), 1.55 (dd, J=7.0, 12.3 Hz, 6H); LCMS: m/z for 402.0 (M+H)+, [α]$^{20}_D$ +12.17° (c=2.0 mg/ml, MeOH).

Example 148: (−)-2-(5-(6-fluoro-1H-indol-3-yl)-3-methyl-1,1-dioxidobenzo[d]isothiazol-2(3H)-yl)-N-methylpropanamide

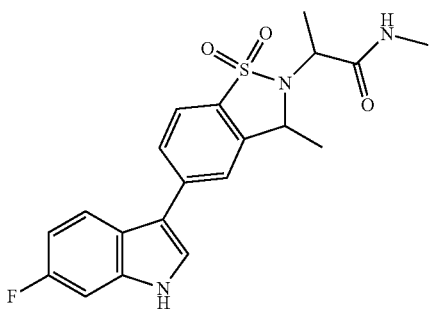 [SMILES: CNC(=O)C(C)N1C(C)c2cc(-c3c[nH]c4cc(F)ccc34)ccc2S1(=O)=O]

The title compound was obtained as the fourth eluting peak from the chiral separation described for Example 145 (215 mg, 16%) as a white solid. $^1$H NMR (400 MHz, DMSO-d$_6$) δ [ppm] 11.70 (br s, 1H), 8.00-7.83 (m, 6H), 7.27 (dd, J=1.9, 9.9 Hz, 1H), 7.01 (dt, J=2.1, 9.2 Hz, 1H), 4.91 (q, J=6.4 Hz, 1H), 4.32 (q, J=6.8 Hz, 1H), 2.64 (d, J=4.8 Hz, 3H), 1.50 (d, J=6.3 Hz, 3H), 1.40 (d, J=7.0 Hz, 3H); LCMS: m/z 402.0 (M+H)+, [α]$^{20}_D$ −9.33° (c=2.0 mg/ml, MeOH).

Example 149: 5-(6-fluoro-1H-indol-3-yl)-3-methyl-2-(pyridin-2-ylmethyl)-2,3-dihydrobenzo[d]isothiazole 1,1-dioxide

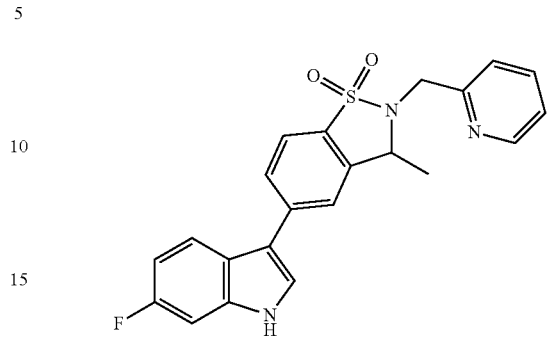

Step 1: tert-butyl 6-fluoro-3-(3-methyl-1,1-dioxido-2,3-dihydrobenzo[d]isothiazol-5-yl)-1H-indole-1-carboxylate To a mixture of 5-bromo-3-methyl-2,3-dihydrobenzo[d]isothiazole 1,1-dioxide (726 mg, 2.77 mmol), tert-butyl 6-fluoro-3-(4,4,5,5-tetramethyl-1,3,2-dioxaborolan-2-yl)-1H-indole-1-carboxylate (1000 mg, 2.77 mmol) and K$_3$PO$_4$ (1210 mg, 5.54 mmol) in 1,4-dioxane (13.8 mL, c=0.2 M) and water (4.6 mL, 0.6 M) was added Pd(dppf)Cl$_2$ (158 mg, 0.19 mmol) under N$_2$. After addition, the purple solution was stirred at 70° C. for 2 h. The reaction mixture was cooled to room temperature and diluted with EtOAc, washed with NH$_4$Cl (sat), dried over Na$_2$SO$_4$, filtered and concentrated. The residue was purified by column chromatography (15-60% EtOAc/heptane) to give tert-butyl 6-fluoro-3-(3-methyl-1,1-dioxido-2,3-dihydrobenzo[d]isothiazol-5-yl)-1H-indole-1-carboxylate (910 mg, 79%) as a yellow solid. $^1$H NMR (400 MHz, DMSO-d$_6$) δ [ppm] 8.11 (s, 1H), 7.83-7.98 (m, 6H), 7.18-7.32 (m, 1H), 4.79 (dd, J=6.42, 4.59 Hz, 1H), 1.68 (s, 9H), 1.55 (d, J=6.72 Hz, 3H); LC-MS: m/z 417 (M+H)+.

Step 2: tert-butyl 6-fluoro-3-(3-methyl-1,1-dioxido-2-(pyridin-2-ylmethyl)-2,3-dihydrobenzo[d]isothiazol-5-yl)-1H-indole-1-carboxylate To a mixture of tert-butyl 6-fluoro-3-(3-methyl-1,1-dioxido-2,3-dihydrobenzo[d]isothiazol-5-yl)-1H-indole-1-carboxylate (30.1 mg, 0.07 mmol), and 2-(chloromethyl)pyridine HCl (18.5 mg, 0.11 mmol) in dioxane (0.69 mL, 0.21 M) and DMF (0.69 mL, c=0.21 M) was added potassium t-butoxide (0.18 mL, 1.0 M) in THF drop-wise at room temperature. The mixture was stirred at room temperature for 5 min then heated to 80° C. and stirred for 1.5 h. The reaction mixture was filtered and purified by column chromatography to give tert-butyl 6-fluoro-3-(3-methyl-1,1-dioxido-2-(pyridin-2-ylmethyl)-2,3-dihydrobenzo[d]isothiazol-5-yl)-1H-indole-1-carboxylate (18 mg, 55% yield).

Step 3: 5-(6-fluoro-1H-indol-3-yl)-3-methyl-2-(pyridin-2-ylmethyl)-2,3-dihydrobenzo[d]isothiazole 1,1-dioxide To a solution of tert-butyl 6-fluoro-3-(3-methyl-1,1-dioxido-2-(pyridin-2-ylmethyl)-2,3-dihydrobenzo[d]isothiazol-5-yl)-1H-indole-1-carboxylate (18.0 mg, 0.036 mmol) in DCM (0.0709 mL, c=0.5 M) was added HCl (0.177 mL, 4.0 M) in dioxane. The reaction mixture was stirred at 30° C. overnight then concentrated to give 5-(6-fluoro-1H-indol-3-yl)-3-methyl-2-(pyridin-2-ylmethyl)-2,3-dihydrobenzo[d]isothiazole 1,1-dioxide (15.7 mg, 100% yield). $^1$H NMR (400 MHz, MeOD) δ [ppm] 8.83 (d, J=5.01 Hz, 1H), 8.60-8.70 (m, 1H), 8.26 (d, J=8.07 Hz, 1H), 8.05 (t, J=6.72 Hz, 1H), 7.94-7.99 (m, 1H), 7.84-7.91 (m, 3H), 7.73 (s, 1H), 7.18 (dd, J=9.66, 2.32 Hz, 1H), 6.96 (td, J=9.20, 2.38 Hz, 1H), 4.94-5.11 (m, 2H), 4.84 (d, J=6.60 Hz, 1H), 1.69 (d, J=6.48 Hz, 3H); LC-MS: m/z 408 (M+H)$^+$.

Example 150: 5-(6-fluoro-1H-indol-3-yl)-3-methyl-2-((6-methylpyridin-2-yl)methyl)-2,3-dihydrobenzo[d]isothiazole 1,1-dioxide

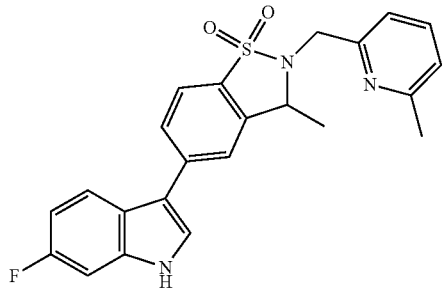 [SMILES: Cc1cccc(CN2C(C)c3cc(-c4c[nH]c5cc(F)ccc45)ccc3S2(=O)=O)n1]

Following the general method as outlined in Example 149, starting with 2-(chloromethyl)-6-methylpyridine, the title compound was obtained as white solid. $^1$H NMR (400 MHz, DMSO-d$_6$) δ [ppm] 11.72 (br. s., 1H), 8.12 (br. s., 1H), 7.89-8.00 (m, 5H), 7.66 (br. s., 1H), 7.55 (br. s., 1H), 7.28 (dd, J=9.84, 2.38 Hz, 1H), 7.02 (td, J=9.26, 2.38 Hz, 1H), 4.67-4.89 (m, 3H), 2.66 (br. s., 3H), 1.54 (d, J=6.48 Hz, 3H); LC-MS: m/z 422 (M+H)$^+$.

Example 151: (R)-5-(6-fluoro-1H-indol-3-yl)-3-methyl-2-(pyridin-2-ylmethyl)-2,3-dihydrobenzo[d]isothiazole 1,1-dioxide

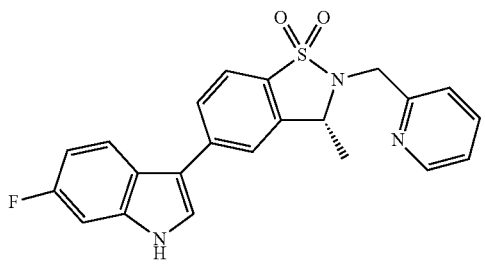 [SMILES: C[C@@H]1c2cc(-c3c[nH]c4cc(F)ccc34)ccc2S(=O)(=O)N1Cc1ccccn1]

Step 1: (3R)-5-bromo-3-methyl-2,3-dihydro-1,2-benzothiazole 1,1-dioxide

A solution of formic acid/triethylamine (10.0 mL, 5:2) was added to a solution of 5-bromo-1,2-benzothiazol-3(2H)-one 1,1-dioxide (5.0 g, 19.2 mmol) and RuCl(p-cymene)[(R,R)-Ts-DPEN] (122 mg, 0.19 mmol) at room temperature which gave a light amber solution. The reaction was stirred overnight. The solvent was removed and the amber oil was added to 200 mL of 50% saturated NaHCO$_3$. The aqueous layer was extracted with EtOAc (3×150 mL) and the combined organic extracts were washed with brine, dried over MgSO$_4$, filtered and concentrated to give a tan solid. The tan solid was triturated with 50 mL of MTBE to give the title compound (2 g, 40%, 96% ee) as white solid. The filtrate was concentrated and triturated again with 2 mL of MTBE to give an off white solid which was further purified by column chromatography (silica gel, 30% heptane-EtOAc) to give the title compound (1 g, 20%, 96% ee) as a white solid. $^1$H NMR (400 MHz, DMSO-d$_6$) δ [ppm] 8.01 (s, 1H), 7.93 (s, 1H), 7.68-7.81 (m, 2H), 4.70 (q, J=6.7 Hz, 1H), 1.47 (d, J=6.7 Hz, 3H); LC-MS: m/z 262/264 (M+H)$^+$; [γ]$^{20}_D$ +42.9° (c=0.2, MeOH), [α]$^{20}_D$ +30.3° (c=0.4, CHCl$_3$).

Step 2: tert-butyl (R)-6-fluoro-3-(3-methyl-1,1-dioxido-2,3-dihydrobenzo[d]isothiazol-5-yl)-1H-indole-1-carboxylate To a solution of (R)-5-bromo-3-methyl-2,3-dihydrobenzo[d]isothiazole 1,1-dioxide (890 mg, 3.4 mmol), tert-butyl 6-fluoro-3-(4,4,5,5-tetramethyl-1,3,2-dioxaborolan-2-yl)-1H-indole-1-carboxylate (1230 mg, 3.4 mmol) and K$_3$PO$_4$ (1340 mg, 6.1 mmol) in 1,4-dioxane (17.0 mL, 0.2 M) and de-ionized water (5.7 mL, 0.6 M) was added Pd(dppf)Cl$_2$ (194 mg, 0.24 mmol) under N$_2$. After addition, the red solution was stirred at 70° C. for 2.2 h. The reaction mixture was cooled to room temperature and diluted with EtOAc, washed with NH4Cl (sat), dried over Na$_2$SO$_4$, filtered and concentrated. The crude residue was purified by column chromatography (10-55% EtOAc/heptane) to give tert-butyl (R)-6-fluoro-3-(3-methyl-1,1-dioxido-2,3-dihydrobenzo[d]isothiazol-5-yl)-1H-indole-1-carboxylate (1213 mg, 84%) as a yellow solid. $^1$H NMR (400 MHz, DMSO-d$_6$) δ [ppm] 8.11 (s, 1H), 7.84-7.98 (m, 6H), 7.20-7.31 (m, 1H), 4.79 (dd, J=6.42, 4.46 Hz, 1H), 1.67 (s, 9H), 1.55 (d, J=6.72 Hz, 3H); LC-MS: m/z 417 (M+H)$^+$.

Step 3: tert-butyl (R)-6-fluoro-3-(3-methyl-1,1-dioxido-2-(pyridin-2-ylmethyl)-2,3-dihydrobenzo[d]isothiazol-5-yl)-1H-indole-1-carboxylate To a mixture of tert-butyl (R)-6-fluoro-3-(3-methyl-1,1-dioxido-2,3-dihydrobenzo[d]isothiazol-5-yl)-1H-indole-1-carboxylate (60.0 mg, 0.144 mmol), and 2-(chloromethyl)pyridine HCl (42.5 mg, 0.26 mmol)) in dioxane (0.69 mL, 0.21 M) and DMF (0.69 mL, c=0.21 M) was added potassium t-butoxide (0.26 mL) in THF (1.0 M) drop-wise at room temperature. The mixture was stirred at room temperature for 5 min and then heated to 80° C. for 1.5 h. The reaction mixture was filtered and purified by column chromatography to give tert-butyl (R)-6-fluoro-3-(3-methyl-1,1-dioxido-2-(pyridin-2-ylmethyl)-2,3-dihydrobenzo[d]isothiazol-5-yl)-1H-indole-1-carboxylate (30 mg, 40%).

Step 4

(R)-5-(6-fluoro-1H-indol-3-yl)-3-methyl-2-((6-methylpyridin-2-yl)methyl)-2,3-dihydrobenzo[d]isothiazole 1,1-dioxide tert-butyl (R)-6-fluoro-3-(3-methyl-1,1-dioxido-2-(pyridin-2-ylmethyl)-2,3-dihydrobenzo-[d]isothiazol-5-yl)-1H-indole-1-carboxylate (29 mg, 0.06 mmol) in EtOAc (0.2 mL) was treated with HCl (0.31 mL) in dioxane (4.0 M). The reaction was stirred at 30° C. overnight. The solvent was removed and the residue was purified by prep HPLC to give (R)-5-(6-fluoro-1H-indol-3-yl)-3-methyl-2-((6-methylpyridin-2-yl)methyl)-2,3-dihydrobenzo[d]isothiazole 1,1-dioxide (19 mg, 77%) as a white solid $^1$H NMR (400 MHz, MeOD)™ [ππμ] 8.54 (br. s., 1H), 7.76-7.96 (m, 5H), 7.63-

7.74 (m, 2H), 7.33-7.42 (m, 1H), 7.15 (dd, J=9.60, 2.26 Hz, 1H), 6.94 (td, J=9.23, 2.32 Hz, 1H), 4.65-4.74 (m, 2H), 4.55-4.65 (m, 1H), 1.53 (d, J=6.48 Hz, 3H); LC-MS: m/z 408 (M+H)$^+$.

Example 152: (R)-5-(6-fluoro-1H-indol-3-yl)-3-methyl-2-((6-methylpyridin-2-yl)methyl)-2,3-dihydrobenzo[d]isothiazole 1,1-dioxide

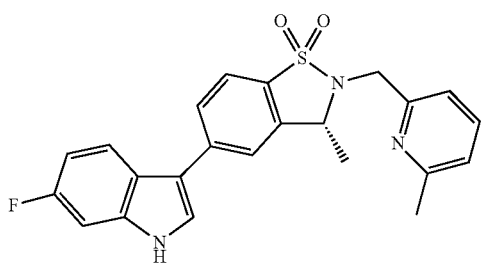 [SMILES: Cc1cccc(CN2[C@H](C)c3cc(-c4c[nH]c5cc(F)ccc45)ccc3S2(=O)=O)n1]

Following the general method as outlined in Example 151, starting with 2-(chloromethyl)-6-methylpyridine, the title compound was obtained as white solid. $^1$H NMR (400 MHz, MeOD)™ [πтμ] 7.95-8.01 (m, 1H), 7.87-7.94 (m, 2H), 7.85 (s, 1H), 7.71-7.81 (m, 2H), 7.54 (d, J=7.83 Hz, 1H), 7.27 (d, J=7.70 Hz, 1H), 7.21 (dd, J=9.72, 2.26 Hz, 1H), 6.99 (td, J=9.17, 2.32 Hz, 1H), 4.67-4.79 (m, 2H), 4.54-4.64 (m, 1H), 2.61 (s, 3H), 1.58 (d, J=6.48 Hz, 3H); LC-MS: m/z 422 (M+H)$^+$.

Example 153: (R)-5-(6-fluoro-1H-indol-3-yl)-3-methyl-2-((2-methyl-2H-tetrazol-5-yl)methyl)-2,3-dihydrobenzo[d]isothiazole 1,1-dioxide

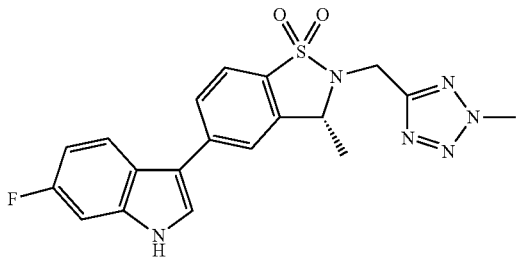 [SMILES: C[C@@H]1c2cc(-c3c[nH]c4cc(F)ccc34)ccc2S(=O)(=O)N1Cc1nnn(C)n1]

Following the general method as outlined in Example 151, starting with 5-(chloromethyl)-2-methyl-2H-tetrazole, the title compound was obtained as white solid. $^1$H NMR (400 MHz, MeOD)™ [πтμ] 7.76-7.95 (m, 4H), 7.68 (s, 1H), 7.16 (dd, J=9.66, 2.32 Hz, 1H), 6.95 (td, J=9.20, 2.38 Hz, 1H), 4.84-4.91 (m, 1H), 4.81 (s, 2H), 4.37 (s, 3H), 1.66 (d, J=6.48 Hz, 3H); LC-MS: m/z 413 (M+H)$^+$.

I. Biology Examples

II.1. Assay for TDO2 Enzymatic Activity Determination

The compounds of formula I, its subformulae, and enantiomers, salts and solvates thereof, are useful to inhibit the enzymatic activity of human TDO2.

To measure the TDO2 activity, the procedure described in Dolusic et al. *J. Med. Chem.*; 2011, 54, 5320-533 is adapted: the reaction mixture contains (final concentrations) potassium phosphate buffer (50 mM, pH 7.5), ascorbic acid (0.25 M), methylene blue (0.125 μM), catalase (40 units/mL, from bovine liver, Sigma), and human recombinant TDO2 enzyme (prepared as described in Dolusic et al. *J. Med. Chem.*; 2011, 54, 5320-5334; 0.9 μg) without or with the compounds of the present invention at the test concentrations (total volume 112.5 μL). The reaction was initiated by the addition of 37.5 μL of L-Trp (final concentration 1 mM) at room temperature. The reaction is conducted at room temperature during one hour and stopped by the addition of 30 μL of 30% (w/v) trichloroacetic acid.

To convert N-formylkynurenine into kynurenine, the reaction mixture is incubated at 65° C. for 30 min. Then 150 μL of the reaction mixture is mixed with 120 μL of 2.5% (w/v) 4-(dimethylamino)-benzaldehyde in acetic acid and incubated for 5 min at room temperature. Kynurenine concentrations are determined by measuring the absorbance at 480 nm. A standard curve was made with pure kynurenine. The TDO activity is measured as described above using ten serial concentrations of the compounds of the present invention. Data were fitted using the Prism™ software (Graph Pad Software, Inc.) using standard parameters.

In one embodiment, compounds having an $IC_{50}$<2000 nM, preferably compound having an $IC_{50}$<1000 nM are selected.

11.2. Cellular Assay for TDO2 Activity Determination

II.2.a A172 Cells

The compounds of formula I inhibit the activity of human TDO2 in cells that constitutively express TDO2, such as A172 cells. A172 is a cell line derived from human brain glioblastoma cells. The cells are available from the American Type Culture Collection (ATCC®) as CRL-1620™.

The assay (adapted from Pilotte L et al., Proc Natl Acad Sci USA, 2012, 109(7), 2497-502) was performed in 96-well flat bottom plates seeded with human glioblastoma A172 cells, naturally expressing hTDO2 (prepared as described in Tilman et al., *Mol Cancer*, 2007, 17(6), 80), at a concentration of $1.25 \times 10^4$ cells/well in a final volume of 200 μL. To determine TDO, the cells were incubated overnight at 37° C. at 5% $CO_2$ in IMDM (Invitrogen) supplemented with 2% FBS and 2% penicillin/streptomycin in the presence of the compounds of the present invention, at different concentrations.

The plates were then centrifuged 5 min at 1000 rpm, and 100 μL of the supernatant were collected in a conical plate, 30 μL of TCA 30% were added and a further centrifuged at 3000×g for 10 minutes. 100 μL of the supernatant were collected in a flat bottomed plate and 100 μL of 2% (w/v) 4-(dimethylamino)-benzaldehyde in acetic acid and incubated for 5 min at room temperature. Kynurenine concentrations were determined by measuring the absorbance at 480 nm. A standard curve was made with pure kynurenine. The TDO activity was measured as described above using ten serial concentrations of the compounds of the present invention. Data were fitted using the Prism™ software (GraphPad Software, Inc.) using standard parameters.

The biological activity of representative compounds in human brain glioblastoma cells as determined in the above-referenced assay is summarized in the following table:

| Example | hTDO2 A172 IC$_{50}$ (nM) |
|---|---|
| 1 | 27 |
| 2 | 110 |
| 3 | 64 |
| 4 | 272 |
| 5 | 96 |
| 6 | 367 |
| 7 | 1448 |
| 8 | 47 |
| 9 | 82 |
| 10 | 240 |
| 11 | 103 |
| 12 | 74 |
| 13 | 43 |
| 14 | 8087 |
| 15 | 2070 |
| 16 | 1377 |
| 17 | 10000 |
| 18 | 4995 |
| 19 | 311 |
| 20 | 430 |
| 21 | 156 |
| 22 | 647 |
| 23 | 1018 |
| 24 | 255 |
| 25 | 4975 |
| 26 | 437 |
| 27 | 226 |
| 28 | 505 |
| 29 | 126 |
| 30 | 34 |
| 31 | 221 |
| 32 | 230 |
| 33 | 89 |
| 34 | 103 |
| 35 | 119 |
| 36 | 192 |
| 37 | 196 |
| 38 | 380 |
| 39 | 342 |
| 40 | 859 |
| 41 | 433 |
| 42 | 142 |
| 43 | 136 |
| 44 | 255 |
| 45 | 71 |
| 46 | 328 |
| 47 | 199 |
| 48 | 77 |
| 49 | 91 |
| 50 | 336 |
| 51 | 186 |
| 52 | 563 |
| 53 | 70 |
| 54 | 233 |
| 55 | 76 |
| 56 | 306 |
| 57 | 61 |
| 58 | 267 |
| 59 | 425 |
| 60 | 133 |
| 61 | 309 |
| 62 | 67 |
| 63 | 70 |
| 64 | 322 |
| 65 | 546 |
| 66 | 244 |
| 67 | 9505 |
| 68 | 3455 |
| 69 | 264 |
| 70 | 50 |
| 71 | 342 |
| 72 | 64 |
| 73 | 246 |
| 74 | 254 |
| 75 | 49 |
| 76 | 61 |
| 77 | 415 |
| 78 | 174 |
| 79 | 258 |
| 80 | 56 |
| 81 | 473 |
| 82 | 61 |
| 83 | 152 |
| 84 | 389 |
| 85 | 57 |
| 86 | 97 |
| 87 | 313 |
| 88 | 68 |
| 89 | 58 |
| 90 | 358 |
| 91 | 260 |
| 92 | 27 |
| 93 | 269 |
| 94 | 39 |
| 95 | 114 |
| 96 | 30 |
| 97 | 33 |
| 98 | 115 |
| 99 | 180 |
| 100 | 33 |
| 101 | 366 |
| 102 | 114 |
| 103 | 413 |
| 104 | 120 |
| 105 | 188 |
| 106 | 507 |
| 107 | 499 |
| 108 | 93 |
| 109 | 345 |
| 110 | 157 |
| 111 | 45 |
| 112 | 142 |
| 113 | 59 |
| 114 | 239 |
| 115 | 88 |
| 116 | 26 |
| 117 | 308 |
| 118 | 191 |
| 119 | 390 |
| 120 | 91 |
| 121 | 348 |
| 122 | 54 |
| 123 | 501 |
| 124 | 68 |
| 125 | 505 |
| 126 | 77 |
| 127 | 87 |
| 128 | 79 |
| 129 | 39 |
| 130 | 112 |
| 131 | 182 |
| 132 | 81 |
| 133 | 383 |
| 134 | 53 |
| 135 | 183 |
| 136 | 233 |
| 137 | 66 |
| 138 | 234 |
| 139 | 520 |
| 140 | 285 |
| 141 | 830 |
| 142 | 124 |
| 143 | 342 |
| 144 | 190 |
| 145 | 92 |
| 146 | 54 |
| 147 | 59 |
| 148 | 265 |
| 149 | 397 |

In one embodiment, compounds having an IC$_{50}$<1000 nM are selected. In another embodiment, compounds having an IC$_{50}$<300 nM are selected.

II.3. Pharmacodynamic Assay for TDO2 In Vivo Activity Determination: Increase of Blood Tryptophan Levels in Mice The compounds of the present invention can be assessed for their ability to increase the amount of Tryptophan in mouse blood. Briefly, female BALB/c mice (7-8 weeks old) are treated with either a suspension of one of the compounds of the present invention in 0.5% hydroxypropyl methyl cellulose (HPMC) K4M (4000 mPa·s (cPs), Methocell™, Dow chemical)/0.25% Tween® (Sigma Aldrich) at different doses (30, 60 and 100 mg/kg), or with a vehicle control (0.5% HPMC K4M/0.25% Tween 20), by the oral route by gavage (dosing volume 5 mL/kg, 10 mice per group). After two hours, blood is harvested, plasma prepared and the amount of Tryptophan present determined by LC-MS-MS (HPLC column Unison UK-Phenyl, 75×4.6, 3 μm, flow rate 0.8 mL/min, 8 minutes gradient from 95% water+0.1% formic acid/5% Acetonitrile+0.1% formic acid to 5% water+0.1% formic acid/95% Acetonitrile+0.1% formic acid, retention time 2.4 min; API4000 MS-MS system from AB Sciex, ESI+ mode, parent ion 205.1, daughter ion 146.1).

All documents cited in this specification, as well as priority applications PCT/IB2015/051957, filed Mar. 17, 2015 and U.S. Provisional Application No. 62/203,032, filed Aug. 10, 2015, are incorporated herein by reference. While the invention has been described with reference to particular embodiments, it will be appreciated that modifications can be made without departing from the spirit of the invention. Such modifications are intended to fall within the scope of the appended claims.

The invention claimed is:
1. A compound of formula I:

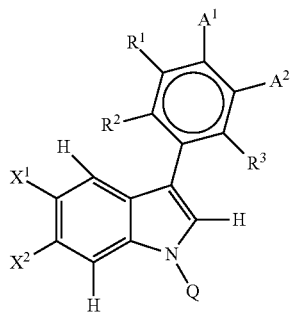

I or a pharmaceutically acceptable enantiomer, salt, or solvate thereof, wherein:
$X^1$ and $X^2$ represent each independently H, halogen, OH, $OR^7$; or C1-C4 alkyl;
$R^1$, $R^2$, and $R^3$ are independently: H, halogen, cyano, $R^7$, $OR^7$, $NR^7R^8$, $CONR^7$, $N(R^7)COR^8$, $SO_2R^7$, or alkyl$NR^7R^8$;
Q is H or $COR^7$ or $CONR^7R^8$;
$R^7$ and $R^8$ are independently (i) H, (ii) $NH_2$, (iii) C1 to C6 branched or unbranched alkyl, optionally substituted with one to three substituents selected from one or more of oxo, amino, OH, halogen, or C1 to C4 alkyl, (iv) a C1-C3 alkyl-heterocycle or (v) a heterocycle, wherein the heterocycle of (iv) or (v) is an optionally substituted five or six-membered heterocycle in which the substituent is oxo, OH, $NH_2$, or a C1 to C3 alkyl which is optionally substituted with one to three substituents selected from one or more of a halogen, alkyl, OH, oxo, or amino;
$A^1$ and $A^2$ together form a 5-membered fused ring structure comprising $SO_2NR^5CR^{9'}R^9$, wherein $R^{9'}$ is H, or $R^{9'}$ and $R^9$ are each methyl, wherein when $R^{9'}$ is H, $R^9$ is a hydrogen atom, cyclopropyl, or a group, optionally substituted, selected from C1-C6 alkyl, aryl, arylalkyl, alkylaryl, heteroaryl, heteroarylalkyl, or alkylheteroaryl, wherein the optionally substituted group has one, two or three substituents selected from one or more of a halogen, C1-C4 alkyl, OH, oxo, or amino;
$R^5$ is: (i') H, (ii') oxo, (iii') amino, or (iv') a group, optionally substituted, selected from:
(v') C1-C6 alkyl, linear or branched, optionally substituted with up to three substituents selected from one or more of halogen, hydroxyl, $OR^9$, $COOR^9$, $CONR^9R^{10}$, $NR^9COR^{10}$, $NR^9R^{10}$, $SO_2R^9$, $SO_2NR^9R^{10}$, $NR^9SO_2R^{10}$, $SOR^9$, aryl, or CO-alkyl,
(vi') heterocyclyl or C1-C3 alkyl-heterocyclyl, the heterocyclyl being optionally substituted with up to three substituents which are selected from one or more of halogen, hydroxyl, oxo, $OR^9$, $COOR^9$, $CONR^9R^{10}$, $NR^9COR^{10}$, $NR^9R^{10}$, $SO_2R^9$, $SO_2NR^9R^{10}$, $NR^9SO_2R^{10}$, $SO_2R^9$, aryl, CO-alkyl, a five or six membered heterocycle having 2 N atoms in its backbone; a piperidine substituted with F and three OH, or alkyl, the alkyl group being optionally substituted by one to three groups selected from one or more of halogen, hydroxyl, oxo, amino or COOH;
(vii') cycloalkyl, optionally substituted with up to three substituents selected from halogen, hydroxyl, $OR^9$, $COOR^9$, $CONR^9R^{10}$, $NR^9COR^{10}$, $NR^9R^{10}$, $SO_2R^9$, $SO_2NR^9R^{10}$, $NR^9SO_2R^{19}$, $SO_2R^9$, aryl, CO-alkyl, or C1-C6 alkyl which is optionally substituted by one or more groups selected from halogen, hydroxyl, amino or COOH;
$R^9$ and $R^{10}$ represent each independently a hydrogen atom or a group, optionally substituted, selected from C1-C6 alkyl, wherein when substituted, the C1-C6 alkyl has one, two or three groups selected from one or more halogen, hydroxyl, oxo, amino or COOH, heterocyclyl, aryl, arylalkyl, alkylaryl, heteroaryl, heteroarylalkyl, or alkylheteroaryl, wherein when substituted, the aryl, arylalkyl, alkylaryl, heteroaryl, heteroarylalkyl, alkylheteroaryl has up to three substituents which are one or more of halogen, hydroxyl, oxo, $OR^9$, $COOR^9$, $CONR^9R^{10}$, $NR^9COR^{10}$, $NR^9R^{10}$, $SO_2R^9$, $SO_2NR^9R^{10}$, $NR^9SO_2R^{10}$, $SO_2R^9$, CO-alkyl, or amino.

2. The compound according to claim 1, wherein Q is H.
3. The compound according to claim 1, wherein $X^1$ and $X^2$ are independently H, F or Cl.
4. The compound according to claim 3, wherein $X^1$ is H and $X^2$ is F.
5. The compound according to claim 1, wherein $R^5$ is the C1-C3 alkyl-heterocyclyl optionally substituted with up to three substituents which are independently halogen, C1-C6 alkyl, hydroxyl, oxo, $OR^9$, $COOR^9$, $CONR^9R^{10}$, $NR^9COR^{10}$, $NR^9R^{10}$, $SO_2R^9$, $SO_2NR^9R^{10}$, $NR^9SO_2R^{10}$, $SO_2R^9$.

6. The compound according to claim 1, wherein $R^9$ is a C1-C4 alkyl which is optionally substituted with OH or halogen.

7. The compound according to claim 1, wherein the compound is not in salt form.

8. The compound according to claim 1, wherein the compound is selected from the group consisting of:
- (+)-5-(6-fluoro-1H-indol-3-yl)-3-methyl-2,3-dihydro-1,2-benzothiazole 1,1-dioxide, or
- (−)-5-(6-fluoro-1H-indol-3-yl)-3-methyl-2,3-dihydro-1,2-benzothiazole 1,1-dioxide,
- (+)-3-ethyl-5-(6-fluoro-1H-indol-3-yl)-2,3-dihydrobenzo[d]isothiazole 1,1-dioxide,
- (−)-3-ethyl-5-(6-fluoro-1H-indol-3-yl)-2,3-dihydrobenzo[d]isothiazole 1,1-dioxide,
- 5-(6-fluoro-1H-indol-3-yl)-3,3-dimethyl-2,3-dihydrobenzo[d]-isothiazole 1,1-dioxide,
- (+)-5-(6-fluoro-1H-indol-3-yl)-3-propyl-2,3-dihydrobenzo[d]isothiazole 1,1-dioxide,
- (−)-5-(6-fluoro-1H-indol-3-yl)-3-propyl-2,3-dihydrobenzo[d]isothiazole 1,1-dioxide,
- (+)-5-(6-fluoro-1H-indol-3-yl)-3-isopropyl-2,3-dihydrobenzo[d]-isothiazole 1,1-dioxide,
- (−)-5-(6-fluoro-1H-indol-3-yl)-3-isopropyl-2,3-dihydrobenzo[d]-isothiazole 1,1-dioxide,
- (+)-3-cyclopropyl-5-(6-fluoro-1H-indol-3-yl)-2,3-dihydrobenzo[d]isothiazole 1,1-dioxide,
- (−)-3-cyclopropyl-5-(6-fluoro-1H-indol-3-yl)-2,3-dihydrobenzo[d]iso-thiazole 1,1-dioxide,
- (−)-5-(6-fluoro-1H-indol-3-yl)-3-(hydroxymethyl)-2,3-dihydrobenzo[d]-isothiazole 1,1-dioxide,
- (+)-5-(6-fluoro-1H-indol-3-yl)-3-(hydroxymethyl)-2,3-dihydrobenzo[d]-isothiazole 1,1-dioxide,
- methyl 5-(6-fluoro-1H-indol-3-yl)-2,3-dihydrobenzo[d]isothiazole-3-carboxylate 1,1-dioxide,
- (−)-5-(6-fluoro-1H-indol-3-yl)-2,3-dihydrobenzo[d]isothiazole-3-carboxamide 1,1-dioxide,
- (+)-5-(6-fluoro-1H-indol-3-yl)-2,3-dihydrobenzo[d]isothiazole-3-carboxamide 1,1-dioxide,
- (−)-5-(6-fluoro-1H-indol-3-yl)-N-methyl-2,3-dihydrobenzo[d]-isothiazole-3-carboxamide 1,1-dioxide,
- (+)-5-(6-fluoro-1H-indol-3-yl)-N-methyl-2,3-dihydrobenzo[d]-isothiazole-3-carboxamide 1,1-dioxide,
- (+)-3-(aminomethyl)-5-(6-fluoro-1H-indol-3-yl)-2,3-dihydrobenzo[d]-isothiazole 1,1-dioxide,
- (−)-3-(aminomethyl)-5-(6-fluoro-1H-indol-3-yl)-2,3-dihydrobenzo[d]-isothiazole 1,1-dioxide,
- (−)-methyl((5-(6-fluoro-1H-indol-3-yl)-1,1-dioxido-2,3-dihydro-benzo[d]isothiazol-3-yl)methyl)carbamate,
- (+)-methyl((5-(6-fluoro-1H-indol-3-yl)-1,1-dioxido-2,3-dihydro-benzo[d]isothiazol-3-yl)methyl)carbamate,
- (−)-N-((5-(6-fluoro-1H-indol-3-yl)-1,1-dioxido-2,3-dihydro-benzo[d]isothiazol-3-yl)methyl)acetamide,
- (+)-N-((5-(6-fluoro-1H-indol-3-yl)-1,1-dioxido-2,3-dihydro-benzo[d]isothiazol-3-yl)methyl)acetamide,
- (−)-3-((dimethylamino)methyl)-5-(6-fluoro-1H-indol-3-yl)-2,3-dihydro-benzo[d]isothiazole 1,1-dioxide,
- (+)-3-((dimethylamino)methyl)-5-(6-fluoro-1H-indol-3-yl)-2,3-dihydro-benzo[d]isothiazole 1,1-dioxide,
- (+)-N-((5-(6-fluoro-1H-indol-3-yl)-1,1-dioxido-2,3-dihydro-benzo[d]isothiazol-3-yl)methyl)-N-methylacetamide,
- (−)-N-((5-(6-fluoro-1H-indol-3-yl)-1,1-dioxido-2,3-dihydro-benzo[d]isothiazol-3-yl)methyl)-N-methylacetamide,
- (−)-5-(6-fluoro-1H-indol-3-yl)-3-(2-hydroxyethyl)-2,3-dihydro-benzo[d]isothiazole 1,1-dioxide,
- (+)-5-(6-fluoro-1H-indol-3-yl)-3-(2-hydroxyethyl)-2,3-dihydro-benzo[d]isothiazole 1,1-dioxide,
- 2-(2-aminoethyl)-5-(6-fluoro-1H-indol-3-yl)-2,3-dihydrobenzo[d]isothiazole 1,1-dioxide,
- 2-(2-(dimethylamino)ethyl)-5-(6-fluoro-1H-indol-3-yl)-2,3-dihydro-benzo[d]isothiazole 1,1-dioxide,
- 5-(6-fluoro-1H-indol-3-yl)-2-(2-hydroxyethyl)-2,3-dihydro-benzo[d]isothiazole 1,1-dioxide,
- (S)-2-(2,3-dihydroxypropyl)-5-(6-fluoro-1H-indol-3-yl)-2,3-dihydro-benzo[d]isothiazole 1,1-dioxide,
- (R)-2-(2,3-dihydroxypropyl)-5-(6-fluoro-1H-indol-3-yl)-2,3-dihydro-benzo[d]isothiazole 1,1-dioxide,
- 5-(6-fluoro-1H-indol-3-yl)-2-(piperidin-4-yl)-2,3-dihydrobenzo[d]isothiazole 1,1-dioxide,
- 5-(6-fluoro-1H-indol-3-yl)-2-(1-methylpiperidin-4-yl)-2,3-dihydro-benzo[d]isothiazole 1,1-dioxide,
- (R)-5-(6-fluoro-1H-indol-3-yl)-2-(tetrahydrofuran-3-yl)-2,3-dihydro-benzo[d]isothiazole 1,1-dioxide,
- (S)-5-(6-fluoro-1H-indol-3-yl)-2-(tetrahydrofuran-3-yl)-2,3-dihydro-benzo[d]isothiazole 1,1-dioxide,
- 2-(azetidin-3-yl)-5-(6-fluoro-1H-indol-3-yl)-2,3-dihydro-benzo[d]isothiazole 1,1-dioxide,
- 5-(6-fluoro-1H-indol-3-yl)-2-(1-methylazetidin-3-yl)-2,3-dihydrobenzo[d]isothiazole 1,1-dioxide,
- (+)-5-(6-fluoro-1H-indol-3-yl)-2-(2-(methylsulfinyl)ethyl)-2,3-dihydrobenzo[d]-isothiazole 1,1-dioxide,
- 3-(5-(6-fluoro-1H-indol-3-yl)-1,1-dioxidobenzo[d]isothiazol-2(3H)-yl)-N-methyl-propanamide,
- 3-(5-(6-fluoro-1H-indol-3-yl)-1,1-dioxidobenzo[d]isothiazol-2(3H)-yl)propanamide,
- (+)-3-(5-(6-fluoro-1H-indol-3-yl)-3-methyl-1,1-dioxidobenzo[d]isothiazol-2(3H)-yl)-N-methylpropanamide,
- (−)-3-(5-(6-fluoro-1H-indol-3-yl)-3-methyl-1,1-dioxidobenzo[d]isothiazol-2(3H)-yl)-N-methylpropanamide,
- (+)-3-(5-(6-fluoro-1H-indol-3-yl)-3-methyl-1,1-dioxidobenzo[d]isothiazol-2(3H)-yl)propanamide,
- (−)-3-(5-(6-fluoro-1H-indol-3-yl)-3-methyl-1,1-dioxidobenzo[d]isothiazol-2(3H)-yl)propanamide,
- (+)-3-(5-(6-fluoro-1H-indol-3-yl)-3-methyl-1,1-dioxidobenzo[d]isothiazol-2(3H)-yl)-1-(piperazin-1-yl)propan-1-one,
- (−)3-(5-(6-fluoro-1H-indol-3-yl)-3-methyl-1,1-dioxidobenzo[d]isothiazol-2(3H)-yl)-1-(piperazin-1-yl)propan-1-one,
- (−)-5-(6-fluoro-1H-indol-3-yl)-3-methyl-2-(piperidin-4-yl)-2,3-dihydrobenzo[d]isothiazole 1,1-dioxide,
- (+)-5-(6-fluoro-1H-indol-3-yl)-3-methyl-2-(piperidin-4-yl)-2,3-dihydrobenzo[d] isothiazole 1,1-dioxide,
- (+)-5-(6-fluoro-1H-indol-3-yl)-3-methyl-2-(2-(methylsulfonyl)ethyl)-2,3-dihydrobenzo[d]isothiazole 1,1-dioxide,
- (−)-5-(6-fluoro-1H-indol-3-yl)-3-methyl-2-(2-(methylsulfonyl)ethyl)-2,3-dihydrobenzo[d]isothiazole 1,1-dioxide,
- (+)-5-(6-fluoro-1H-indol-3-yl)-3-methyl-2-(2-(methylsulfinyl)ethyl)-2,3-dihydrobenzo[d]isothiazole 1,1-dioxide,
- (−)-5-(6-fluoro-1H-indol-3-yl)-3-methyl-2-(2-(methylsulfinyl)ethyl)-2,3-dihydrobenzo[d]isothiazole 1,1-dioxide,
- (+)-5-(6-fluoro-1H-indol-3-yl)-3-methyl-2-(2-(methylsulfinyl)ethyl)-2,3-dihydrobenzo[d]isothiazole 1,1-dioxide,
- (−)-2-(5-(6-fluoro-1H-indol-3-yl)-3-methyl-1,1-dioxidobenzo[d]isothiazol-(3H)-yl)-N-methylethane-1-sulfonamide, (+)-2-(5-(6-fluoro-1H-indol-3-yl)-3-methyl-1,1-dioxidobenzo[d]isothiazol-2(3H)-yl)-N-methylethane-1-sulfonamide, (−)-2-(5-(6-fluoro-1H-indol-3-yl)-3-methyl-1,1-dioxidobenzo[d]isothiazol-2(3H)-yl)ethane-1-sulfonamide, (+)-5-(6-fluoro-1H-indol-3-yl)-2-(2-hydroxyethyl)-3-methyl-2,3-dihydrobenzo[d]isothiazole 1,1-dioxide, (−)-5-(6-fluoro-1H-indol-3-yl)-2-(2-hydroxyethyl)-3-methyl-2,3-dihydrobenzo-[d]isothiazole 1,1-dioxide, (−)1-(2-(5-(6-fluoro-1H-indol-3-yl)-3-methyl-1,1-dioxidobenzo[d]isothiazol-2(3H)-yl)ethyl)piperazin-2-one, (+)1-(2-(5-(6-fluoro-1H-indol-3-yl)-3-methyl-1,1-dioxidobenzo[d]isothiazol-2(3H)-yl)ethyl)piperazin-2-one, (+)-5-(6-fluoro-1H-indol-3-yl)-2-(2-(5-hydroxy-3-methyl-1H-pyrazol-1-yl)ethyl)-3-methyl-2,3-dihydrobenzo[d]isothiazole 1,1-dioxide, (−)-5-(6-fluoro-1H-indol-3-yl)-2-(2-(5-hydroxy-3-methyl-1H-pyrazol-1-yl)ethyl)-3-methyl-2,3-dihydrobenzo[d]isothiazole 1,1-dioxide, (+)-3-(2-(5-(6-fluoro-1H-indol-3-yl)-3-methyl-1,1-dioxidobenzo[d]isothiazol-2(3H)-yl)ethyl)oxazolidin-2-one, (−)-3-(2-(5-(6-fluoro-1H-indol-3-yl)-3-methyl-1,1-dioxidobenzo[d]isothiazol-2(3H)-yl)ethyl)oxazolidin-2-one, (+)-1-(4-(5-(6-fluoro-1H-indol-3-yl)-3-methyl-1,1-dioxidobenzo[d]isothiazol-2(3H)-yl)piperidin-1-yl)ethanone, (−)-1-(4-(5-(6-fluoro-1H-indol-3-yl)-3-methyl-1,1-dioxidobenzo[d]isothiazol-2(3H)-yl)piperidin-1-yl)ethanone, (+)-1-(3-(5-(6-fluoro-1H-indol-3-yl)-3-methyl-1,1-dioxidobenzo[d]isothiazol-2(3H)-yl)pyrrolidin-1-yl)ethanone, (−)-1-(3-(5-(6-fluoro-1H-indol-3-yl)-3-methyl-1,1-dioxidobenzo[d]isothiazol-2(3H)-yl)pyrrolidin-1-yl)ethanone, 5-(6-fluoro-1H-indol-3-yl)-3-methyl-2-(piperidin-4-ylmethyl)-2,3-dihydrobenzo-[d]isothiazole 1,1-dioxide, (+)-5-(6-fluoro-1H-indol-3-yl)-3-methyl-2-(piperidin-4-ylmethyl)-2,3-dihydrobenzo[d]isothiazole 1,1-dioxide, (−)-5-(6-fluoro-1H-indol-3-yl)-3-methyl-2-((1-methylpiperidin-4-yl)methyl)-2,3-dihydrobenzo[d]isothiazole 1,1-dioxide, (+)-5-(6-fluoro-1H-indol-3-yl)-3-methyl-2-((1-methylpiperidin-4-yl)methyl)-2,3-dihydrobenzo[d]isothiazole 1,1-dioxide, (+)-(5S)-5-((5-(6-fluoro-1H-indol-3-yl)-3-methyl-1,1-dioxidobenzo[d]isothiazol-2(3H)-yl)methyl)-5-methylpyrrolidin-2-one, (−)-(5R)-5-((5-(6-fluoro-1H-indol-3-yl)-3-methyl-1,1-dioxidobenzo[d]isothiazol-2(3H)-yl)methyl)-5-methylpyrrolidin-2-one, (−)-5-(6-fluoro-1H-indol-3-yl)-3-methyl-2-((1-methyl-1H-1,2,4-triazol-3-yl)-methyl)-2,3-dihydrobenzo[d]isothiazole 1,1-dioxide, (+)-5-(6-fluoro-1H-indol-3-yl)-3-methyl-2-((1-methyl-1H-1,2,4-triazol-3-yl)-methyl)-2,3-dihydrobenzo[d]isothiazole 1,1-dioxide, (−)-4-((5-(6-fluoro-1H-indol-3-yl)-3-methyl-1,1-dioxidobenzo[d]isothiazol-2(3H)-yl)methyl)-4-methyloxazolidin-2-one, (+)-4-((5-(6-fluoro-1H-indol-3-yl)-3-methyl-1,1-dioxidobenzo[d]isothiazol-2(3H)-yl)methyl)-4-methyloxazolidin-2-one, (+)-4-((5-(6-fluoro-1H-indol-3-yl)-3-methyl-1,1-dioxidobenzo[d]isothiazol-2(3H)-yl)methyl)-4-methyloxazolidin-2-one, (−)-2-(azetidin-3-yl)-5-(6-fluoro-1H-indol-3-yl)-3-methyl-2,3-dihydrobenzo-[d]isothiazole 1,1-dioxide, (+)-2-(azetidin-3-yl)-5-(6-fluoro-1H-indol-3-yl)-3-methyl-2,3-dihydrobenzo-[d]isothiazole 1,1-dioxide, (−)-2-((R)-2,3-dihydroxypropyl)-5-(6-fluoro-1H-indol-3-yl)-3-methyl-2,3-dihydrobenzo[d]isothiazole 1,1-dioxide, (+)-2-((R)-2,3-dihydroxypropyl)-5-(6-fluoro-1H-indol-3-yl)-3-methyl-2,3-dihydrobenzo[d]isothiazole 1,1-dioxide, (−)2-((S)-2,3-dihydroxypropyl)-5-(6-fluoro-1H-indol-3-yl)-3-methyl-2,3-dihydrobenzo[d]isothiazole 1,1-dioxide, (+)-2-((S)-2,3-dihydroxypropyl)-5-(6-fluoro-1H-indol-3-yl)-3-methyl-2,3-dihydrobenzo[d]isothiazole 1,1-dioxide, (+)-3-(5-(6-fluoro-1H-indol-3-yl)-3-methyl-1,1-dioxidobenzo[d]isothiazol-2(3H)-yl)-2-hydroxy-N-methylpropanamide, (−)-3-(5-(6-fluoro-1H-indol-3-yl)-3-methyl-1,1-dioxidobenzo[d]isothiazol-2(3H)-yl)-2-hydroxy-N-methylpropanamide, (−)-2-amino-3-(5-(6-fluoro-1H-indol-3-yl)-3-methyl-1,1-dioxidobenzo[d]-isothiazol-2(3H)-yl)-N-methylpropanamide, (+)-2-amino-3-(5-(6-fluoro-1H-indol-3-yl)-3-methyl-1,1-dioxidobenzo[d]-isothiazol-2(3H)-yl)-N-methylpropanamide, 2-amino-3-(5-(6-fluoro-1H-indol-3-yl)-3-methyl-1,1-dioxidobenzo[d]isothiazol-2(3H)-yl)-N-methylpropanamide, (+)-3-(5-(6-fluoro-1H-indol-3-yl)-3-methyl-1,1-dioxidobenzo[d]isothiazol-2(3H)-yl)-2-methoxy-N-methylpropanamide, (−)-3-(5-(6-fluoro-1H-indol-3-yl)-3-methyl-1,1-dioxidobenzo[d]isothiazol-2(3H)-yl)-2-methoxy-N-methylpropanamide, (+)-3-(5-(6-fluoro-1H-indol-3-yl)-3-methyl-1,1-dioxidobenzo[d]isothiazol-2(3H)-yl)-2-methoxy-N-methylpropanamide, (−)-3-(5-(6-fluoro-1H-indol-3-yl)-3-methyl-1,1-dioxidobenzo[d]isothiazol-2(3H)-yl)-2-methoxy-N-methylpropanamide, (−)-ethyl (2-(5-(6-fluoro-1H-indol-3-yl)-3-methyl-1,1-dioxidobenzo[d]-isothiazol-2(3H)-yl)ethyl)carbamate, (+)-ethyl (2-(5-(6-fluoro-1H-indol-3-yl)-3-methyl-1,1-dioxidobenzo[d]-isothiazol-2(3H)-yl)ethyl)carbamate, (−)-2-(5-(6-fluoro-1H-indol-3-yl)-3-methyl-1,1-dioxidobenzo[d]isothiazol-2(3H)-yl)-N-methylacetamide, (+)-2-(5-(6-fluoro-1H-indol-3-yl)-3-methyl-1,1-dioxidobenzo[d]isothiazol-2(3H)-yl)-Nmethylacetamide, (−)-2-(5-(6-fluoro-1H-indol-3-yl)-3-methyl-1,1-dioxidobenzo[d]isothiazol-2(3H)-yl)-N,N-dimethylacetamide, (+)2-(5-(6-fluoro-1H-indol-3-yl)-3-methyl-1,1-dioxidobenzo[d]isothiazol-2(3H)-yl)-N,N-dimethylacetamide, (+)2-(5-(6-fluoroindolin-3-yl)-3-methyl-1,1-dioxidobenzo[d]isothiazol-2(3H)-yl)acetamide, (−)-2-(5-(6-fluoroindolin-3-yl)-3-methyl-1,1-dioxidobenzo[d]isothiazol-2(3H)-yl)acetamide, (−)-5-(6-fluoro-1H-indol-3-yl)-3-methyl-2-(2-morpholinoethyl)-2,3-dihydro-benzo[d] isothiazole 1,1-dioxide, (+)-5-(6-fluoro-1H-indol-3-yl)-3-methyl-2-(2-morpholinoethyl)-2,3-dihydro-benzo[d] isothiazole 1,1-dioxide, (−)-4-(-5-(6-fluoro-1H-indol-3-yl)-3-methyl-1,1-dioxido-benzo[d]isothiazol-2(3H)-yl)piperidin-2-one,
(+)-4-((S)-5-(6-fluoro-1H-indol-3-yl)-3-methyl-1,1-dioxidobenzo[d]isothiazol-2(3H)-yl)piperidin-2-one,
(+)-4-((R)-5-(6-fluoro-1H-indol-3-yl)-3-methyl-1,1-dioxidobenzo[d]isothiazol-2(3H)-yl)piperidin-2-one,
(−)-4-(-5-(6-fluoro-1H-indol-3-yl)-3-methyl-1,1-dioxido-benzo[d]isothiazol-2(3H)-yl)piperidin-2-one,
(+)4-(5-(6-fluoro-1H-indol-3-yl)-3-methyl-1,1-dioxido-benzo[d]isothiazol-2(3H)-yl)pyrrolidin-2-one,
(−)-4-(5-(6-fluoro-1H-indol-3-yl)-3-methyl-1,1-dioxido-benzo[d]isothiazol-2(3H)-yl)pyrrolidin-2-one,
(−)-2-(5-(6-fluoro-1H-indol-3-yl)-3-(hydroxymethyl)-1,1-dioxidobenzo[d]-isothiazol-2(3H)-yl)-N-methylacetamide,
(+)-2-(5-(6-fluoro-1H-indol-3-yl)-3-(hydroxymethyl)-1,1-dioxidobenzo[d]-isothiazol-2(3H)-yl)-N-methylacetamide,
(−)-5-(6-fluoro-1H-indol-3-yl)-3-(hydroxymethyl)-2-((1-methyl-1H-1,2,4-triazol-3-yl)methyl)-2,3-dihydrobenzo[d]isothiazole 1,1-dioxide,
(+)-5-(6-fluoro-1H-indol-3-yl)-3-(hydroxymethyl)-2-((1-methyl-1H-1,2,4-triazol-3-yl)methyl)-2,3-dihydrobenzo[d]isothiazole 1,1-dioxide,
(+)-5-(6-fluoro-1H-indol-3-yl)-2-(2-hydroxyethyl)-3-(hydroxymethyl)-2,3-dihydrobenzo[d]isothiazole 1,1-dioxide,
(−)-5-(6-fluoro-1H-indol-3-yl)-2-(2-hydroxyethyl)-3-(hydroxymethyl)-2,3-dihydrobenzo[d]isothiazole 1,1-dioxide,
(−)-5-(2-(5-(6-fluoro-1H-indol-3-yl)-3-methyl-1,1-dioxidobenzo[d]isothiazol-2(3H)-yl)ethyl)-1,3,4-oxadiazol-2(3H)-one,
(+)-5-(2-(5-(6-fluoro-1H-indol-3-yl)-3-methyl-1,1-dioxidobenzo[d]isothiazol-2(3H)-yl)ethyl)-1,3,4-oxadiazol-2(3H)-one,
5-(6-fluoro-1H-indol-3-yl)-3-methylbenzo[d]isothiazole 1,1-dioxide,
5-(6-fluoro-1H-indol-3-yl)-2H-spiro[benzo[d]isothiazole-3,1'-cyclopropane]1,1-dioxide,
5-(6-fluoro-1H-indol-3-yl)-3-((methylamino)methyl)-2,3-dihydrobenzo[d]isothiazole 1,1-dioxide,
(+)-5-(6-fluoro-1H-indol-3-yl)-3-((methylamino)methyl)-2,3-dihydrobenzo[d]-isothiazole 1,1-dioxide,
(−)-N-((5-(6-fluoro-1H-indol-3-yl)-1,1-dioxido-2,3-dihydrobenzo[d]isothiazol-3-yl)methyl)methanesulfonamide,
(+)-N-((5-(6-fluoro-1H-indol-3-yl)-1,1-dioxido-2,3-dihydrobenzo[d]isothiazol-3-yl)methyl)methanesulfonamide,
(+)-2-(2,3-dihydroxypropyl)-5-(6-fluoro-1H-indol-3-yl)-3-(hydroxymethyl)-2,3-dihydrobenzo[d]isothiazole 1,1-dioxide,
(−)-2-(2,3-dihydroxypropyl)-5-(6-fluoro-1H-indol-3-yl)-3-(hydroxymethyl)-2,3-dihydrobenzo[d]isothiazole 1,1-dioxide,
(−)-2-(2,3-dihydroxypropyl)-5-(6-fluoro-1H-indol-3-yl)-3-(hydroxymethyl)-2,3-dihydrobenzo[d]isothiazole 1,1-dioxide,
(+)-2-(2, 3-di hydroxypropyl)-5-(6-fluoro-1H-indol-3-yl)-3-(hydroxymethyl)-2,3-dihydrobenzo[d]isothiazole 1,1-dioxide,
(−)-2-(5-(6-fluoro-1H-indol-3-yl)-3-methyl-1,1-dioxido-benzo[d]isothiazol-2(3H)-yl)-N-methylpropanamide,
(+)-2-(5-(6-fluoro-1H-indol-3-yl)-3-methyl-1,1-dioxido-benzo[d]isothiazol-2(3H)-yl)-N-methylpropanamide,
2-(5-(6-fluoro-1H-indol-3-yl)-3-methyl-1,1-dioxido-benzo[d]isothiazol-2(3H)-yl)-N-methylpropanamide,
(−)-2-(5-(6-fluoro-1H-indol-3-yl)-3-methyl-1,1-dioxido-benzo[d]isothiazol-2(3H)-yl)-N-methylpropanamide,
5-(6-fluoro-1H-indol-3-yl)-3-methyl-2-(pyridin-2-ylmethyl)-2,3-dihydrobenzo-[d]isothiazole 1,1-dioxide,
5-(6-fluoro-1H-indol-3-yl)-3-methyl-2-((6-methylpyridin-2-yl)methyl)-2,3-dihydrobenzo[d]isothiazole 1,1-dioxide,
(R)-5-(6-fluoro-1H-indol-3-yl)-3-methyl-2-(pyridin-2-ylmethyl)-2,3-dihydro-benzo[d]isothiazole 1,1-dioxide,
(R)-5-(6-fluoro-1H-indol-3-yl)-3-methyl-2-((6-methylpyridin-2-yl)methyl)-2,3-dihydrobenzo[d]isothiazole 1,1-dioxide, or
(R)-5-(6-fluoro-1H-indol-3-yl)-3-methyl-2-((2-methyl-2H-tetrazol-5-yl)-methyl)-2,3-dihydrobenzo[d]isothiazole 1,1-dioxide.

9. A pharmaceutical composition comprising a compound according to claim 1, or a pharmaceutically acceptable enantiomer, salt or solvate thereof, and at least one pharmaceutically acceptable carrier, diluent, excipient and/or adjuvant.

* * * * *